(12) United States Patent
Candia, III et al.

(10) Patent No.: US 12,378,255 B2
(45) Date of Patent: *Aug. 5, 2025

(54) TOLL-LIKE RECEPTOR ANTAGONIST COMPOUNDS AND METHODS OF USE

(71) Applicant: Dynavax Technologies Corporation, Berkeley, CA (US)

(72) Inventors: Albert Frederick Candia, III, San Mateo, CA (US); Richard Thomas Beresis, San Francisco, CA (US); Robert L. Coffman, Portola Valley, CA (US)

(73) Assignee: DYNAVAX TECHNOLOGIES CORPORATION, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/484,588

(22) Filed: Oct. 11, 2023

(65) Prior Publication Data

US 2024/0182478 A1    Jun. 6, 2024

Related U.S. Application Data

(63) Continuation of application No. 17/664,305, filed on May 20, 2022, now Pat. No. 11,827,641, which is a continuation of application No. 16/348,816, filed as application No. PCT/US2017/060946 on Nov. 9, 2017, now Pat. No. 11,370,794.

(60) Provisional application No. 62/421,140, filed on Nov. 11, 2016, provisional application No. 62/421,144, filed on Nov. 11, 2016.

(51) Int. Cl.
| | | |
|---|---|---|
| *C07D 487/04* | (2006.01) | |
| *A61K 45/06* | (2006.01) | |
| *C07D 231/56* | (2006.01) | |
| *C07D 235/18* | (2006.01) | |
| *C07D 519/00* | (2006.01) | |

(52) U.S. Cl.
CPC ............ *C07D 487/04* (2013.01); *A61K 45/06* (2013.01); *C07D 231/56* (2013.01); *C07D 235/18* (2013.01); *C07D 519/00* (2013.01)

(58) Field of Classification Search
CPC .. C07D 487/04; C07D 231/56; C07D 235/18; C07D 519/00
See application file for complete search history.

(56) References Cited

U.S. PATENT DOCUMENTS

| | | |
|---|---|---|
| 8,759,305 B2 | 6/2014 | Barrat |
| 8,853,375 B2 | 10/2014 | Kandimalla |
| 9,228,184 B2 | 1/2016 | Guiducci |
| 11,370,794 B2 | 6/2022 | Candia, III |
| 11,827,641 B2 | 11/2023 | Candia, III |
| 2014/0221646 A1 | 8/2014 | Lipford |
| 2017/0174653 A1 | 6/2017 | Sherer |
| 2018/0037570 A1 | 2/2018 | Sherer |
| 2019/0270281 A1 | 9/2019 | Hirose |
| 2019/0345161 A1 | 11/2019 | Candia, III |
| 2022/0298162 A1 | 9/2022 | Candia |

FOREIGN PATENT DOCUMENTS

| | | |
|---|---|---|
| JP | 2013166770 A | 8/2013 |
| WO | 2011152485 A1 | 12/2011 |
| WO | 2012167046 A1 | 12/2012 |

OTHER PUBLICATIONS

Chemical Abstracts STN Registry Database, record for 894535-39-8, entered into STN on Jul. 19, 2006. 1 page.
Chemical Abstracts STN Registry Database, record for 894535-99-0, entered into STN on Jul. 19, 2006, 1 page.
Chemical Abstracts STN Registry Database, record for 894537-55-4, entered into STN on Jul. 19, 2006, 1 page.
Chemical Abstracts STN Registry Database, record for 894544-21-9, entered into STN on Jul. 19, 2006. 1 page.
Chemical Abstracts STN Registry Database, record for 894555-38-5, entered into STN on Jul. 19, 2006. 1 page.
Czarniecki, M. (Nov. 13, 2008, e-pub. Oct. 2, 2008). "Small Molecule Modulators of Toll-Like Receptors," J. Med. Chem. 51(21):6621-6626.

(Continued)

*Primary Examiner* — Daniel R Carcanague
(74) *Attorney, Agent, or Firm* — MORRISON & FOERSTER LLP

(57) ABSTRACT

The invention relates to compounds of formula (I):

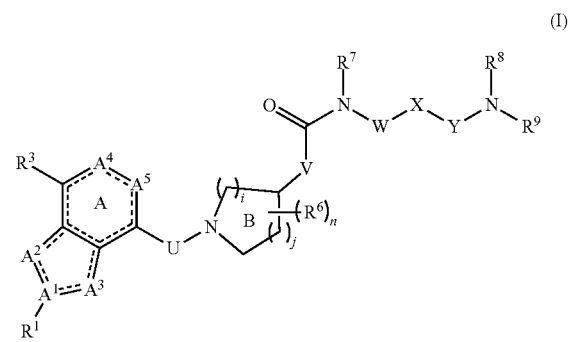

or a salt or solvate thereof, wherein the variables are as described herein. Compounds of formula (I) and pharmaceutical compositions thereof are antagonists of toll-like receptors such as TLR7, TLR8 and/or TLR9 that are useful for inhibiting immune response and treating diseases associated with undesirable immune response.

17 Claims, 1 Drawing Sheet

(56) References Cited

OTHER PUBLICATIONS

Gosu, V. et al. (Nov. 14, 2012). "Therapeutic Applications of Nucleic Acids and Their Analogues in Toll-like Receptor Signaling," Molecules 17:13503-13529.

Imberdis, T. et al. (Dec. 9, 2016). "Identification of Anti-Prion Compounds Using a Novel Cellular Assay," J. Biol. Chem. 291(50):26164-26176.

International Preliminary Report on Patentability, issued on May 14, 2019, for PCT Application No. PCT/US2017/060946, filed on Nov. 9, 2017, 7 pages.

International Search Report and Written Opinion mailed on Apr. 3, 2018, for PCT Application No. PCT/US2017/060946, filed on Nov. 9, 2017, 9 pages.

Kandimalla, E.R. et al. (Apr. 1, 2013, e-pub. Feb. 8, 2013). "Design, Synthesis and Biological Evaluation of Novel Antagonist Compounds of Toll-Like Receptors 7, 8 and 9," Nucleic Acids Res. 41(6):3947-3961.

National Center for Biotechnology Information. PubChem Substance Record for SID 34321357, Deposit Date Dec. 5, 2007, 5 pages.

National Center for Biotechnology Information. PubChem Substance Record for SID 34321364, Deposit Date Dec. 5, 2007, 5 pages.

Patra; M.C. et al. (2016). "Recent Progress in the Development of Toll-Like Receptor (TLR) Antagonists," Expert Opinion on Therapeutic Patents 26(6):719-730.

TOLL-LIKE RECEPTOR ANTAGONIST COMPOUNDS AND METHODS OF USE

CROSS REFERENCE TO RELATED APPLICATIONS

This application is a continuation of, and claims priority to, U.S. application Ser. No. 17/664,305, filed May 20, 2022, which is a continuation of, and claims priority to U.S. application Ser. No. 16/348,816, filed May 9, 2019, now U.S. Pat. No. 11,370,794, issued Jul. 5, 2022, which is a 35 U.S.C. § 371 national phase application of, and claims priority to, International Application No. PCT/US2017/060946, filed Nov. 9, 2017, which claims priority under 35 U.S.C. § 119(e) to U.S. Provisional Patent Application Nos. 62/421,140, filed Nov. 11, 2016, and 62/421,144, filed Nov. 11, 2016, the disclosures of each of which are hereby incorporated by reference in their entireties.

STATEMENT OF RIGHTS TO INVENTIONS MADE UNDER FEDERALLY SPONSORED RESEARCH

This invention was made with government support under NIH SBIR grants R43AI00376-02 and R44AI00376-03 awarded by the National Institutes of Health (NIH). The United States government has certain rights in the invention.

BACKGROUND OF THE INVENTION

Toll-like receptors (TLRs) are a family of transmembrane proteins that recognize conserved microbial molecules, referred to as pathogen-associated molecular patterns (PAMPs), which are distinguishable from host molecules. As such TLRs play important roles in innate immune responses. TLRs 7, 8 and 9 are nucleic acid sensing TLRs. In addition to recognizing PAMPs, these receptors also recognize endogenous immune complexes containing self-nucleic acids as well as self-antigens referred to as damage-associated molecular patterns (DAMPs). By recognizing and responding to self-nucleic acids and DAMPs these receptors have been implicated in certain autoimmune disease conditions, including lupus, psoriasis, arthritis and multiple sclerosis, and noninfectious inflammatory disorders including non-alcoholic liver disease, non-alcoholic steatohepatitis, acetaminophen-induced hepatotoxicity, and pancreatitis, which induce pro-inflammatory cytokines that contribute to the pathogenesis of disease. Activation of TLRs 7, 8 and 9 by immune complexes and DAMPs leads to the expression of inflammatory cytokines such as interleukin (IL)-12, IL-6, tumor necrosis factor alpha (TNF-α), IL-1β, interferon (IFN)-α, and to the induction of IFN-inducible genes (Kandimalla, et al. *Nucleic Acids Res.* 2013 41:3947-3961).

Agonists and antagonists of TLRs find use in modulating immune responses. TLR agonists are typically employed to stimulate immune responses, whereas TLR antagonists are typically employed to inhibit immune responses (Gosu et al., *Molecules*, 2012, 17:13503-13529). Immunoregulatory nucleic acids, synthetic oligodeoxyribonucleotides, and oligoribonucleotides have been reported as antagonists for TLRs 7, 8 and 9. See, e.g., U.S. Pat. Nos. 8,759,305; 8,853,375; and 9,228,184. However, there remains a need for orally bioavailable TLR antagonists for therapeutic or prophylactic treatment of TLR-mediated immune responses.

BRIEF SUMMARY OF THE INVENTION

Disclosed are heterocyclic compounds that are antagonists of toll-like receptors such as TLR8 and/or TLR9, compositions containing these compounds and methods for inhibiting an immune response such as a TLR8- and/or TLR9-dependent immune response, and methods of treating diseases associated with an undesirable immune response.

In one aspect, provided is a compound of formula (I), or any variation thereof, or a salt thereof (e.g., a pharmaceutically acceptable salt thereof), as detailed herein. Also provided is a compound of formula (A-I), (Ia), (I$^0$), (I$^0$a), (I$^0$a-1), (I$^0$a-2), (II), (IIa), (IIa-1), (IIa-1a), (IIa-1a-1), (IIa-1a-2), (IIa-1a-3), (IIa-1b), (IIa-1b-1), (IIa-1b-2), (IIa-1b-3), (IIa-1c), (IIa-1c-1), (IIa-1d), (IIa-1d-1), (IIa-1d-2), (IIa-1d-3), (IIa-1e), (IIa-1e-1), (IIa-1e-2), (IIa-1e-3), (IIa-1f), (IIa-1f-1), (IIa-1f-2), (IIa-1f-3), (III), (IIIa), (IV), (IV-a), (IV-a-1), (IV-a-2), (V), (V-a), (V-a-1), (V-a-2), (VI), (VI-a), (VI-a-1), (VI-a-2), (VII), (VII-a), (VII-a-1), (VII-a-2), (VIII), (VIII-a), (VIII-a-1), or (VIII-a-2), or a salt thereof (e.g., a pharmaceutically acceptable salt thereof), as detailed herein.

Further provided is a pharmaceutical composition comprising a compound of formula (I), or any variation thereof detailed herein, or a salt thereof (e.g., a pharmaceutically acceptable salt thereof), and a pharmaceutically acceptable excipient.

In another aspect, provided is a method of inhibiting an immune response in an individual (such as a human) in need thereof comprising administering to the individual a therapeutically effective amount of a compound of formula (I), or any variation thereof detailed herein, or a pharmaceutically acceptable salt thereof. In some embodiments, the immune response is TLR8-dependent. In some embodiments, the immune response is TLR9-dependent. In some embodiments, the immune response is TLR8- and TLR9-dependent. In some embodiments, the immune response is associated with chronic pathogen stimulation or acute pathogen stimulation (e.g., acute pathogen stimulation due to sepsis). In some embodiments, the immune response is associated with an immunological disorder.

Also provided is a method of treating or ameliorating one or more symptoms of an immunological disorder in an individual (such as a human) in need thereof comprising administering to the individual a therapeutically effective amount of a compound of formula (I), or any variation thereof detailed herein, or a pharmaceutically acceptable salt thereof. In some embodiments, the immunological disorder is an autoimmune disease (e.g., systemic lupus erythematosus, type I diabetes mellitus, multiple sclerosis, rheumatoid arthritis, inflammatory bowel disease, Sjogren's syndrome, scleroderma and dermatomyositis). In some embodiments, the immunological disorder is an inflammatory disease (e.g., pancreatitis, kidney fibrosis, liver fibrosis, lung fibrosis, chronic kidney disease, alcohol-related fatty liver disease, non-alcoholic fatty liver disease, and liver cirrhosis).

Further provided is a method of treating cancer in an individual (such as a human) in need thereof comprising administering to the individual a therapeutically effective amount of a compound of formula (I), or any variation thereof detailed herein, or a pharmaceutically acceptable salt thereof. In some embodiments, the cancer is dependent upon activation of one or both of TLR8 and TLR9. In some embodiments, the cancer is Waldenstrom's macroglobulinemia. In some embodiments, the cancer possesses an oncogenic mutation in a myeloid differentiation primary response gene 88 (MYD88). In some embodiments, the cancer is hepatocellular carcinoma (HCC).

Also provided is a compound of formula (I), or any variation thereof detailed herein, or a pharmaceutical composition thereof, for inhibiting an immune response, for the treatment of an immunological disorder (e.g., autoimmune disease, inflammatory disease, chronic or acute pathogen stimulation, etc.), or for the treatment of cancer.

Also provided is use of a compound of formula (I), or any variation thereof detailed herein, or a pharmaceutically acceptable salt thereof, in the manufacture of a medicament for inhibiting an immune response, for treating an immunological disorder, or for treating cancer.

Further provided is a kit comprising a compound of formula (I), or any variation thereof detailed herein, or a pharmaceutically acceptable salt thereof. In some embodiments, the kit comprises instructions for use according to a method described herein, such as a method of inhibiting immune response, a method of treating an immunological disorder, or a method of treating cancer.

In another aspect, provided is a method of making a compound of formula (I) or any variation thereof. Also provided are compound intermediates useful in synthesis of a compound of formula (I), or any variation thereof.

DETAILED DESCRIPTION OF THE INVENTION

Figure 1:
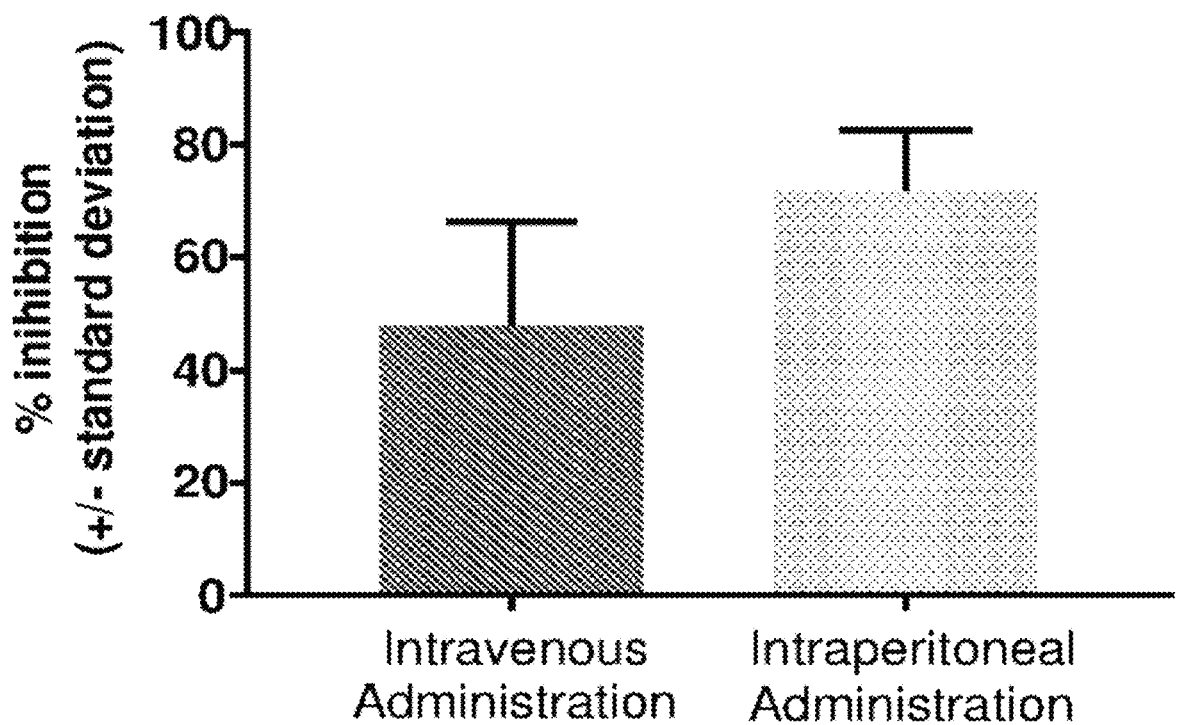
FIG. 1 shows inhibition of TLR9 activity in mice using Compound No. 5 at 5 mg/Kg.

The invention provides, inter alia, compounds of formula (A-I) or (I), and variations thereof, pharmaceutical compositions comprising compounds of formula (A-I) or (I), and methods of using such compounds and compositions for inhibiting TLR8- and/or TLR9-dependent responses, particularly for inhibiting pathological immune responses, or for treating an immunological disorder or cancer.

Definitions

For use herein, unless clearly indicated otherwise, the terms "a", "an" and "the" refer to one or more. For example, "an excipient" includes one or more excipients.

Reference to "about" a value or parameter herein encompasses from 90% to 110% of the value or parameter, and includes (and describes) embodiments that are directed to that value or parameter per se. For example, a description referring to "about X" includes description of "X", as well as a range of 0.9X to 1.1X.

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_1$-$C_{20}$ alkylene"), having 1 to 10 carbon atoms (a "$C_1$-$C_{10}$ alkylene"), having 6 to 10 carbon atoms (a "$C_6$-$C_{10}$ alkylene"), having 1 to 6 carbon atoms (a "$C_1$-$C_6$ alkylene"), 1 to 5 carbon atoms (a "$C_1$-$C_8$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), isopropylene (—$CH_2CH(CH_3)$—), butylene (—$CH_2(CH_2)_2CH_2$—), isobutylene (—$CH_2CH(CH_3)CH_2$—), pentylene (—$CH_2(CH_2)_3CH_2$—), hexylene (—$CH_2(CH_2)_4CH_2$—), heptylene (—$CH_2(CH_2)_5CH_2$—), octylene (—$CH_2(CH_2)_6CH_2$—), and the like.

"Alkenyl" as used herein refers to and includes, unless otherwise stated, an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). An alkenyl group may have "cis" or "trans" configurations, or alternatively have "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, for example, pent-1-enyl, pent-2-enyl, hex-1-enyl, hex-2-enyl, hex-3-enyl, and the like.

"Alkenylene" as used herein refers to the same residues as alkenyl, but having bivalency. Particular alkylene groups are those having 2 to 20 carbon atoms (a "$C_2$-$C_{20}$ alkenylene"), having 2 to 10 carbon atoms (a "$C_2$-$C_{10}$ alkenylene"), having 2 to 6 carbon atoms (a "$C_2$-$C_6$ alkenylene"), 2 to 4 carbon atoms (a "$C_2$-$C_4$ alkenylene") or 2 to 3 carbon atoms (a "$C_2$-$C_3$ alkenylene"). Examples of alkenylene include, but are not limited to, groups such as ethenylene (or vinylene) (—CH=CH—), propenylene (—CH=CHCH$_2$—), 1,4-but-1-enylene (—CH=CH—CH$_2$CH$_2$—), 1,4-but-2-enylene (—CH$_2$CH=CHCH$_2$—), 1,6-hex-1-enylene (—CH=CH—(CH$_2$)$_3$CH$_2$—), and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Alkynylene" as used herein refers to the same residues as alkynyl, but having bivalency. Particular alkylene groups are those having 2 to 20 carbon atoms (a "$C_2$-$C_{20}$ alkynylene"), having 2 to 10 carbon atoms (a "$C_2$-$C_{10}$ alkynylene"), having 2 to 6 carbon atoms (a "$C_2$-$C_6$ alkynylene"), 2 to 4 carbon atoms (a "$C_2$-$C_4$ alkynylene") or 2 to 3 carbon atoms (a "$C_2$-$C_3$ alkynylene"). Examples of alkynylene include, but are not limited to, groups such as ethynylene (or acetylenylene) (—C≡C—), propynylene (—C≡CCH$_2$—), and the like.

"Cycloalkyl" as used herein refers to and includes, unless otherwise stated, saturated cyclic univalent hydrocarbon structures, having the number of carbon atoms designated (i.e., C$_3$-C$_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "C$_3$-C$_8$ cycloalkyl"), having 3 to 6 annular carbon atoms (a "C$_3$-C$_6$ cycloalkyl"), or having from 3 to 4 annular carbon atoms (a "C$_3$-C$_4$ cycloalkyl"). Examples of cycloalkyl include, but are not limited to, cyclopropyl, cyclobutyl, cyclopentyl, cyclohexyl, cycloheptyl, norbornyl, and the like.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "C$_3$-C$_8$ cycloalkylene"), having 3 to 6 annular carbon atoms (a "C$_3$-C$_6$ cycloalkylene"), or having from 3 to 4 annular carbon atoms (a "C$_3$-C$_4$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the parent structure twice via the same ring carbon atom or via two different ring carbon atoms. When a cycloalkylene attaches to the remaining structures via two different ring carbon atoms, the connecting bonds may be cis- or trans- to each other. For example, cyclobutylene may include 1,1-cyclobutylene, 1,2-cyclobutylene and 1,3-cyclobutylene (e.g., cis-1,3-cyclobutylene or trans-1,3-cyclobutylene), or mixture thereof.

"Cycloalkenyl" refers to and includes, unless otherwise stated, an unsaturated cyclic non-aromatic univalent hydrocarbon structures, having at least one site of olefinic unsaturation (i.e., having at least one moiety of the formula C=C) and having the number of carbon atoms designated (i.e., C$_2$-C$_{10}$ means two to ten carbon atoms). Cycloalkenyl can consist of one ring, such as cyclohexenyl, or multiple rings, such as norbornenyl. A preferred cycloalkenyl is an unsaturated cyclic hydrocarbon having from 3 to 8 annular carbon atoms (a "C$_3$-C$_8$ cycloalkenyl"). Examples of cycloalkenyl groups include, but are not limited to, cyclopropenyl, cyclobutenyl, cyclopentenyl, cyclohexenyl, norbornenyl, and the like.

"Cycloalkenylene" as used herein refers to the same residues as cycloalkenyl, but having bivalency.

"Aryl" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "C$_6$-C$_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Arylene" as used herein refers to the same residues as aryl, but having bivalency. Particular arylene groups are those having from 6 to 14 annular carbon atoms (a "C$_6$-C$_{14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, imidazolyl) or multiple condensed rings (e.g., indolizinyl, pyrazolo-pyridazinyl) where at least one of the condensed rings is aromatic. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, heteroaryl includes monocyclic aromatic 5-, 6- or 7-membered rings having from 1 to 6 annular carbon atoms and 1 to 4 annular heteroatoms independently selected from nitrogen, oxygen and sulfur. In another variation, heteroaryl includes polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Heteroarylene" as used herein refers to the same residues as heteroaryl, but having bivalency.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof. In fused ring systems, one or more of the fused rings can be cycloalkyl or cycloalkenyl. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5 or 1 to 6 annular carbon atoms and 1 to 2, 1 to 3 or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Heterocyclylene" as used herein refers to the same residues as heterocyclyl, but having bivalency.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached. For example, dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Thiocarbonyl" refers to the group C=S.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4 or 1 to 5 substituents.

Unless a specific isotope of an element is indicated in a formula, the invention includes all isotopologues of the compounds disclosed herein, such as, for example, deuterated derivatives of the compounds (where H can be $^2H$, i.e., D). Isotopologues can have isotopic replacements at any or at all locations in a structure, or can have atoms present in natural abundance at any or all locations in a structure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such subcombination of chemical groups was individually and explicitly disclosed herein.

It is understood that aspects and embodiments described herein as "comprising" include "consisting of" and "consisting essentially of" embodiments.

As used herein and in the appended claims, the singular forms "a", "an", and "the" include plural referents unless otherwise indicated or clear from context.

Unless clearly indicated otherwise, the term "about" is used to indicate that a value includes the standard deviation of error for the device or method being employed to determine the value. Reference to "about" a value or parameter herein includes (and describes) embodiments that are directed to that value or parameter per se. For example, description referring to "about X" includes description of "X."

The term "individual" as used herein refers to a mammal, including but not limited to a human, non-human primate, cow, horse, cat, dog, or rodent. In one variation, the individual is a human.

As used herein, "treatment" or "treating" is an approach for obtaining beneficial or desired results including clinical results. For purposes of this invention, beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. Thus, "treating" or "treatment" does not require complete alleviation of signs or symptoms, does not require a cure, and specifically includes protocols that have only a palliative effect on the individual. Further, "treating" and "treatment" do not necessarily occur by administration of one dose, but often occur upon administration of a series of doses.

As used herein, the term "effective amount" refers to an amount of a compound of the invention sufficient to carry out a specifically stated purpose. As is understood in the art, an effective amount of a given therapeutic form may be in one or more doses, i.e., a single dose or multiple doses may be required to achieve the desired treatment endpoint. An effective amount may be considered in the context of administering one or more therapeutic agents (e.g., a compound, or pharmaceutically acceptable salt thereof), and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical excipient. Unit dosage forms may contain a single or a combination therapy.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

The term "immune response" as used herein refers to a reaction by cells (e.g., dendritic cells, monocytes, B cells, etc.) of the immune system to a stimulus (e.g., injury, infection, vaccination, etc.). An exemplary TLR7-dependent immune response is characterized by secretion of interferon-alpha by plasmacytoid dendritic cells in reaction to heat-inactivated influenza virus. An exemplary TLR8-dependent immune response is characterized by secretion of one or both of tumor-necrosis factor-alpha and interleukin-1 beta by monocytes in reaction to RNA (e.g., ORN8L or released from damaged joint tissue in rheumatoid arthritis). An exemplary TLR9-dependent immune response is characterized by secretion of interleukin-6 by B cells in reaction to CpG containing DNA (e.g., 1018 ISS or bacterially-derived DNA during infection). A further exemplary TLR9-dependent immune response is characterized by secretion of interleukin-12 by various immune cells in reaction to CpG containing DNA (e.g., 1018 ISS or bacterially-derived DNA during infection).

The terms "disease" and "disorder" are used interchangeably herein to refer to an abnormal physical condition, which is typically characterized by distinguishing signs and symptoms. For instance, signs and symptoms of diabetes mellitus type 1 include but are not limited to hyperglycemia, frequent urination, and increased thirst.

The terms "immunological disorder" and "immune disorder" are used interchangeably herein to refer to a dysfunction of the immune system. In some embodiments of the present disclosure, the immunological disorder is characterized by an overactive and/or misdirected immune response.

As used herein, the term "autoimmune disease" refers to a disorder in which the immune system overreacts to a self antigen of an individual. For example, Graves' disease is an autoimmune disease characterized by development of autoantibodies to thyroid stimulating hormone.

As used herein, the term "inflammatory disease" refers to a disorder in which the immune system overreacts in the absence of an identifiable autoimmune or infectious stimulus. For example, atherosclerosis is an inflammatory disease characterized by thickening of artery walls as a result of accumulation of white blood cells.

The terms "immunostimulatory sequence" and "ISS" refer to a nucleic acid sequence that stimulates a measurable immune response (e.g., measured in vitro, in vivo, and/or ex vivo). For the purpose of the present disclosure, the term ISS refers to a nucleic acid sequence comprising an unmethylated CG dinucleotide. Examples of measurable immune responses include, but are not limited to, antigen-specific antibody production, cytokine secretion, lymphocyte activation and lymphocyte proliferation.

"Stimulation" of a response includes eliciting and/or enhancing the response when compared to an otherwise identical condition except for a parameter of interest or as compared to another condition (e.g., increase in TLR-signaling in the presence of a TLR agonist as compared to the absence of the TLR agonist). For example, "stimulation" of an immune response means a measurable increase in the immune response.

"Inhibition" of a response includes blocking and/or suppressing the response when compared to an otherwise identical condition except for a parameter of interest or as compared to another condition (e.g., decrease in TLR-signaling in the presence of a TLR agonist and a TLR antagonist as compared to the presence of the TLR agonist in the absence of the TLR antagonist). For example, "inhibition" of an immune response means a measurable decrease in the immune response.

Compounds

The present disclosure provides a compound of formula (A-I):

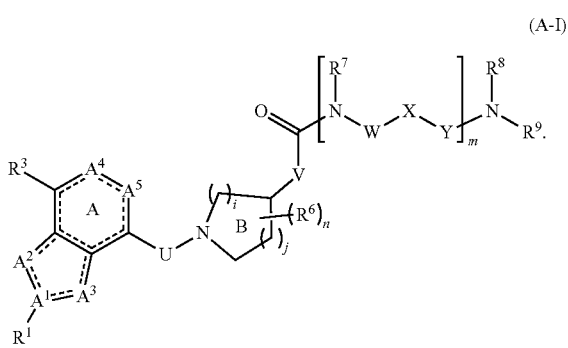

or a salt or solvate thereof, wherein $A^1$, $A^2$, $A^3$, $A^4$, $A^5$, $R^1$, $R^3$, $R^6$, $R^7$, $R^8$, $R^9$, U, V, W, X, Y, Z, i, j, m, and n are as detailed herein. In the compound of formula (A-I), ring A is a bicyclic heteroaryl containing 2 to 4 ring nitrogen atoms, and ring B is a 3- to 7-membered heterocycle containing 1 or 2 ring nitrogen atoms. One ring nitrogen atom of ring B is attached to ring A via an optional linker U. In one embodiment, U is a bond or absent. A compound of formula (A-I) further comprises a moiety —C(O)—[N($R^7$)—W—X—Y]$_m$—N($R^8$)$R^9$, which is attached to ring B at a carbon atom or a second optional ring nitrogen atom via an optional linker V, and includes a basic nitrogen (e.g., an amine or a ring nitrogen of a heterocycle or heteroaryl group). The —[N($R^7$)—W—X—Y]$_m$—N($R^8$)$R^9$ moiety may be a linear chain, a ring or multiple rings, or a combination thereof. For example, $R^7$ and $R^8$ may be combined, $R^8$ and $R^9$ may be combined, or any one of the side chains of W (where present), X and Y may be combined with $R^7$, $R^8$, or a side chain of another one of W (where present), X and Y to form a ring. The —N($R^8$)$R^9$ moiety may also be combined with Y, with Y and X, or with Y, X and W (where present) to form a heteroaryl group (e.g., an imidazole or a pyridyl group). In some preferred embodiments, the terminal nitrogen atom (attached to $R^8$, $R^9$ and Y) is not attached to an electron-withdrawing group (e.g., a carbonyl group, an aryl or heteroaryl group) that diminishes the basicity of the basic nitrogen atom, which may be important for the biological activities for the compound.

In one aspect, provided is a compound of formula (A-I):

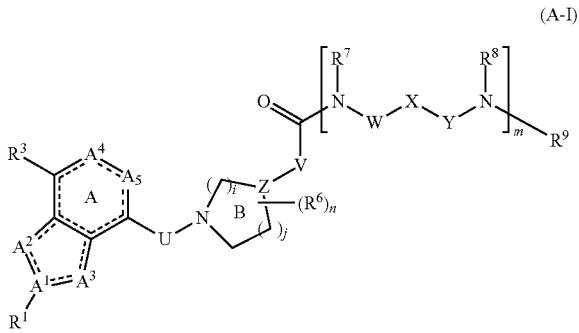

or a salt or solvate thereof, wherein:
$A^1$ is C or N;
$A^2$ is $CR^2$, N or $NR^{2a}$,
$A^3$ is $CR^{30}$, N or $NR^{3a}$;
$A^4$ is N or $CR^4$;
$A^5$ is N or $CR^5$;

provided that two, three or four of $A^1$, $A^2$, $A^3$, $A^4$ and $A^5$ are N; wherein the dashed lines indicate partial or delocalized bonds in an aromatic ring;
i and j are independently 0, 1 or 2;
Z is CH or N;
m is 0 or 1;
$R^1$ is $C_1$-$C_6$ alkyl, $C_3$-$C_8$ cycloalkyl, $C_6$-$C_{14}$ aryl, 5-10-membered heteroaryl or 3-12-membered heterocyclyl; wherein the $C_1$-$C_6$ alkyl, $C_3$-$C_8$ cycloalkyl, $C_6$-$C_{14}$ aryl, 5-10-membered heteroaryl and 3-12-membered heterocyclyl are independently optionally substituted by $R^{10A}$;
each $R^2$, $R^3$, $R^{30}$, $R^4$ and $R^5$ is independently hydrogen, halogen, $C_1$-$C_6$ alkyl, $C_3$-$C_8$ cycloalkyl, $C_6$-$C_{14}$ aryl, 5-10-membered heteroaryl or 3-12-membered heterocyclyl; wherein the $C_1$-$C_6$ alkyl, $C_3$-$C_8$ cycloalkyl, $C_6$-$C_{14}$ aryl, 5-10-membered heteroaryl and 3-12-membered heterocyclyl are independently optionally substituted by $R^{10A}$,
each $R^{2a}$ and $R^{3a}$ is independently hydrogen, $C_1$-$C_6$ alkyl, $C_3$-$C_8$ cycloalkyl, $C_6$-$C_{14}$ aryl, 5-10-membered heteroaryl or 3-12-membered heterocyclyl; wherein the $C_1$-$C_6$ alkyl, $C_3$-$C_8$ cycloalkyl, $C_6$-$C_{14}$ aryl, 5-10-membered heteroaryl and 3-12-membered heterocyclyl are independently optionally substituted by $R^{10A}$;
each $R^6$, where present, is independently $C_1$-$C_6$ alkyl optionally substituted by $R^{10A}$,
n is 0, 1, 2, 3 or 4;
U is a bond or methylene optionally substituted by $R^{10}$;
V is a bond or $C_1$-$C_2$ alkylene optionally substituted by $R^{10}$;
W is a bond or $C_1$-$C_4$ alkylene optionally substituted by one or both of $R^{W1}$ and $R^{W2}$;
X is —$CR^{X1}R^{X2}$—;
Y is —$CR^{Y1}R^{Y2}$—;
$R^7$ is hydrogen, $C_1$-$C_6$ alkyl, or taken together with $R^8$ to form an ethylene optionally substituted by $R^{10}$, or taken together with $R^{Y1}$, $R^{X1}$ or $R^{W1}$, where present, to form a $C_1$-$C_6$ alkylene optionally substituted by $R^{10}$;
$R^8$ is hydrogen, $C_1$-$C_6$ alkyl optionally substituted by $R^{10}$, $C_6$-$C_{14}$ aryl, 5-10-membered heteroaryl, or taken together with $R^7$ to form an ethylene optionally substituted by $R^{10}$, or taken together with $R^{Y1}$, $R^{Y2}$, $R^{X1}$, $R^{X2}$ or $R^{W1}$, where present, to form a $C_1$-$C_6$ alkylene optionally substituted by $R^{10}$, or taken together with $R^{10}$, where present, to form a $C_1$-$C_6$ alkylene, or taken together with $R^9$ and the nitrogen atom to which they are attached to form a 3-12-membered heterocyclyl optionally substituted by $R^{10}$ or a 5-10-membered heteroaryl optionally substituted by $R^{10}$, or taken together with $R^{Y1}$, $R^{Y2}$, $R^9$ and the atoms to which they are attached to form a 5-10-membered heteroaryl optionally substituted by $R^{10}$, or taken together with $R^{X1}$, $R^{X2}$, $R^{Y1}$, $R^{Y2}$, $R^9$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y1}$, $R^{Y2}$, $R^9$ and the atoms to which they are attached to form a 5-10-membered heteroaryl optionally substituted by $R^{10}$,
$R^9$ is hydrogen, $C_1$-$C_6$ alkyl optionally substituted by $R^{10}$, or taken together with $R^8$ and the nitrogen atom to which they are attached to form a 3-12-membered heterocyclyl optionally substituted by $R^{10}$ or a 5-10-membered heteroaryl optionally substituted by $R^{10}$, or taken together with $R^{Y1}$, $R^{Y2}$, $R^8$ and the atoms to which they are attached to form a 5-10-membered heteroaryl optionally substituted by $R^{10}$, or taken together with $R^{X1}$, $R^{X2}$, $R^{Y1}$, $R^{Y2}$, $R^8$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y1}$, $R^{Y2}$, $R^8$ and the atoms to which they are attached to form a 5-10-membered heteroaryl optionally substituted by $R^{10}$;

$R^{W1}$, where present, is $C_1$-$C_6$ alkyl optionally substituted by $R^{10A}$, or taken together with $R^7$, $R^8$, $R^{X1}$ or $R^{Y1}$ to form a $C_1$-$C_6$ alkylene optionally substituted by $R^{10}$, or taken together with $R^{W2}$, $R^{X1}$, $R^{X2}$, $R^{Y1}$, $R^{Y2}$, $R^8$, $R_9$ and the atoms to which they are attached to form a 5-10-membered heteroaryl optionally substituted by $R^{10}$;

$R^{W2}$, where present, is $C_1$-$C_6$ alkyl optionally substituted by $R^{10A}$, or taken together with $R^{W1}$, $R^{X1}$, $R^{X2}$, $R^{Y1}$, $R^{Y2}$, $R_8$, $R_9$ and the atoms to which they are attached to form a 5-10-membered heteroaryl optionally substituted by $R^{10}$;

$R^{X1}$ is hydrogen, $C_1$-$C_6$ alkyl optionally substituted by $R^{10A}$, or taken together with $R^7$, $R^8$, $R^{Y1}$ or $R^{W1}$, where present, to form a $C_1$-$C_6$ alkylene optionally substituted by $R^{10}$, or taken together with $R^{X2}$, $R^{Y1}$, $R^{Y2}$, $R^8$, $R_9$ and the atoms to which they are attached to form a 5-10-membered heteroaryl optionally substituted by $R^{10}$, or taken together with $R^{W1}$, $R^{W2}$, where present, $R^{X2}$, $R^{Y1}$, $R^{Y2}$, $R^8$, $R^9$ and the atoms to which they are attached to form a 5-10-membered heteroaryl optionally substituted by $R^{10}$;

$R^{X2}$ is hydrogen or $C_1$-$C_6$ alkyl optionally substituted by $R^{10A}$, or taken together with $R^{X1}$, $R^{Y1}$, $R^{Y2}$, $R^8$, $R_9$ and the atoms to which they are attached to form a 5-10-membered heteroaryl optionally substituted by $R^{10}$, or taken together with $R^{W1}$, $R^{W2}$, where present, $R^{X1}$, $R^{Y1}$, $R^{Y2}$, $R^8$, $R^9$ and the atoms to which they are attached to form a 5-10-membered heteroaryl optionally substituted by $R^{10}$, or taken together with $R^8$ to form a $C_1$-$C_6$ alkylene optionally substituted by $R^{10}$;

$R^{Y1}$ is hydrogen, $C_1$-$C_6$ alkyl optionally substituted by $R^{10A}$, or taken together with $R^7$, $R^8$, $R^{X1}$ or $R^{W1}$, where present, to form a $C_1$-$C_6$ alkylene optionally substituted by $R^{10}$, or taken together with $R^{Y2}$, $R^8$, $R^9$ and the atoms to which they are attached to form a 5-10-membered heteroaryl optionally substituted by $R^{10}$, or taken together with $R^{X1}$, $R^{X2}$, $R^{Y2}$, $R^8$, $R^9$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y2}$, $R^8$, $R^9$ and the atoms to which they are attached to form a 5-10-membered heteroaryl optionally substituted by $R^{10}$;

$R^{Y2}$ is hydrogen, $C_1$-$C_6$ alkyl optionally substituted by $R^{10A}$, or taken together with $R^{Y1}$, $R^8$, $R^9$ and the atoms to which they are attached to form a 5-10-membered heteroaryl optionally substituted by $R^{10}$, or taken together with $R^{X1}$, $R^{X2}$, $R^{Y1}$, $R^8$, $R^9$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y1}$, $R^8$, $R^9$ and the atoms to which they are attached to form a 5-10-membered heteroaryl optionally substituted by $R^{10}$, or taken together with $R^8$ to form a $C_1$-$C_6$ alkylene optionally substituted by $R^{10}$;

each $R^{10}$ is independently $C_1$-$C_6$ alkyl, $C_2$-$C_6$ alkenyl, $C_2$-$C_6$ alkynyl, $C_3$-$C_8$ cycloalkyl, 3-12-membered heterocyclyl, 5-10-membered heteroaryl, $C_6$-$C_{14}$ aryl, halogen, —CN, —$OR^{11}$, —$SR^{11}$, —$NR^{12}R^{13}$, —$NO_2$, —C=$NH(OR^{11})$, —$C(O)R^{11}$, —$OC(O)R^{11}$, —$C(O)OR^{11}$, —$C(O)NR^{12}R^{13}$, —$NR^{11}C(O)R^{12}$, —$NR^1C(O)$ $OR^{12}$, —$NR^{11}C(O)NR^{12}R^{13}$, —$S(O)R^{11}$, —$S(O)_2R^{11}$, —$NR^{11}S(O)R^{12}$, —$NR^{11}S(O)_2R^{12}$, —$S(O)NR^{12}R^{13}$, —$S(O)_2NR^{12}R^{13}$, or —$P(O)(OR^{12})(OR^{13})$; wherein the $C_1$-$C_6$ alkyl, $C_2$-$C_6$ alkenyl, $C_2$-$C_6$ alkynyl, $C_3$-$C_8$ cycloalkyl, 3-12-membered heterocyclyl, 5-10-membered heteroaryl and $C_6$-$C_{14}$ aryl of $R^{10}$ are independently optionally substituted by halogen, —CN, oxo, —$OR^{14}$, —$SR^{14}$, —NR 1+$R^{15}$, —$C(O)R^{14}$, —$C(O)OR^{14}$, —$S(O)R^{14}$, —$S(O)_2R^{14}$, —$P(O)(OR^{14})(OR^{15})$, 3-12-membered heterocyclyl, 5-10-membered heteroaryl, $C_6$-$C_{14}$ aryl, $C_3$-$C_8$ cycloalkyl, or $C_1$-$C_6$ alkyl optionally substituted by oxo, —OH or halogen, or is taken together with $R^8$ to form a $C_1$-$C_6$ alkylene;

each $R^{10A}$ is independently oxo or $R^{10}$;

$R^{11}$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6-membered heterocyclyl of $R^{11}$ are independently optionally substituted by halogen, oxo, —CN, —$OR^{16}$, —$NR^{16}R^{17}$, —$P(O)(OR^{16})(OR^{17})$, or $C_1$-$C_6$ alkyl optionally substituted by halogen, —OH or oxo;

$R^{12}$ and $R^{13}$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6 membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6 membered heterocyclyl of $R^{12}$ and $R^{13}$ are independently optionally substituted by halogen, oxo, —CN, —$OR^{16}$, —$NR^{16}R^{17}$ or $C_1$-$C_6$ alkyl optionally substituted by halogen, —OH or oxo;

or $R^{12}$ and $R^{13}$ are taken together with the atom to which they attached to form a 3-6 membered heterocyclyl optionally substituted by halogen, oxo, —$OR^{16}$, —$NR^{16}R^{17}$ or $C_1$-$C_6$ alkyl optionally substituted by halogen, oxo or —OH;

$R^{14}$ and $R^{15}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^{14}$ and $R^{15}$ are taken together with the atom to which they attached to form a 3-6 membered heterocyclyl optionally substituted by halogen, oxo or $C_1$-$C_6$ alkyl optionally substituted by halogen or oxo; and $R^{16}$ and $R^{17}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^{16}$ and $R^{17}$ are taken together with the atom to which they attached to form a 3-6 membered heterocyclyl optionally substituted by halogen, oxo or $C_1$-$C_6$ alkyl optionally substituted by oxo or halogen.

In some embodiments of the compound of formula (A-I), Z is C. In one variation, ring B is a piperidine ring. In other embodiments of the compound of formula (A-I), Z is N. In one variation, ring B is a piperazine ring.

In some embodiments of the compound of formula (A-I), m is 1. In other embodiments, m is 0. In some embodiments, m is 0 and the —$[N(R^7)—W—X—Y]_m$—$N(R^8)R^9$ moiety is —$NH(R^8)$ or $NH(R^9)$. In one variation, —$NH(R^8)$ or $NH(R^9)$ is

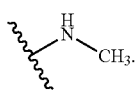

In one aspect, the present disclosure provides a compound of formula (I):

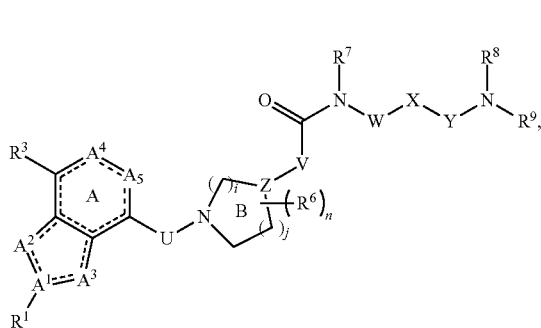

or a salt or solvate thereof, wherein $A^1$, $A^2$, $A^3$, $A^4$, $A^5$, $R^1$, $R^3$, $R^6$, $R^7$, $R^8$, $R^9$, U, V, W, X, Y, i, j, and n are as detailed herein. In the compound of formula (I), ring A is a bicyclic heteroaryl containing 2 to 4 ring nitrogen atoms, and ring B is a 3- to 7-membered heterocycle containing one ring nitrogen atom. The ring nitrogen atom of ring B is attached to ring A via an optional linker U. In one embodiment, U is a bond or absent. A compound of formula (I) further comprises a carboxy amide moiety, the carboxy end of which is attached to ring B via an optional linker V, and the amide end of which is tethered to a basic nitrogen (e.g., an amine or a ring nitrogen of a heterocycle or heteroaryl group) via a linking moiety of the formula "—W—X—Y—". The —N($R^7$)—W—X—Y—N($R^8$)$R^9$ moiety may be a linear chain, a ring or multiple rings, or a combination thereof. For example, $R^7$ and $R^8$ may be combined, $R^8$ and $R^9$ may be combined, or any one of the side chains of W (where present), X and Y may be combined with $R^7$, $R^8$, or a side chain of another one of W (where present), X and Y to form a ring. The —N($R^8$)$R^9$ moiety may also be combined with Y, with Y and X, or with Y, X and W (where present) to form a heteroaryl group (e.g., an imidazole or a pyridyl group). In some preferred embodiments, the terminal nitrogen atom (attached to $R^8$, $R^9$ and Y) is not attached to an electron-withdrawing group (e.g., a carbonyl group, an aryl or heteroaryl group) that diminishes the basicity of the basic nitrogen atom, which may be important for the biological activities for the compound.

In one aspect, the compound of formula (A-I) is a compound of formula (I):

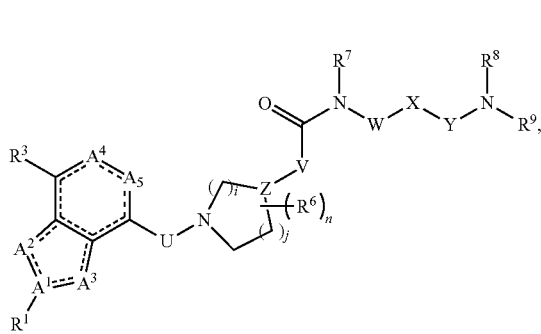

or a salt or solvate thereof, wherein:
$A^1$ is C or N;
$A^2$ is $CR^2$, N or $NR^{2a}$;
$A^3$ is $CR^{30}$, N or $NR^{3a}$;
$A^4$ is N or $CR^4$;
$A^5$ is N or $CR^5$;
provided that two, three or four of $A^1$, $A^2$, $A^3$, $A^4$ and $A^5$ are N; wherein the dashed lines indicate partial or delocalized bonds in an aromatic ring;
i and j are independently 0, 1 or 2;
$R^1$ is $C_1$-$C_6$ alkyl, $C_3$-$C_8$ cycloalkyl, $C_6$-$C_{14}$ aryl, 5-10-membered heteroaryl or 3-12-membered heterocyclyl; wherein the $C_1$-$C_6$ alkyl, $C_3$-$C_8$ cycloalkyl, $C_6$-$C_{14}$ aryl, 5-10-membered heteroaryl and 3-12-membered heterocyclyl are independently optionally substituted by $R^{10A}$;
each $R^2$, $R^3$, $R^{30}$, $R^4$ and $R^5$ is independently hydrogen, halogen, $C_1$-$C_6$ alkyl, $C_3$-$C_8$ cycloalkyl, $C_6$-$C_{14}$ aryl, 5-10-membered heteroaryl or 3-12-membered heterocyclyl; wherein the $C_1$-$C_6$ alkyl, $C_3$-$C_8$ cycloalkyl, $C_6$-$C_{14}$ aryl, 5-10-membered heteroaryl and 3-12-membered heterocyclyl are independently optionally substituted by $R^{10A}$;
each $R^{2a}$ and $R^{3a}$ is independently hydrogen, $C_1$-$C_6$ alkyl, $C_3$-$C_8$ cycloalkyl, $C_6$-$C_{14}$ aryl, 5-10-membered heteroaryl or 3-12-membered heterocyclyl; wherein the $C_1$-$C_6$ alkyl, $C_3$-$C_8$ cycloalkyl, $C_6$-$C_{14}$ aryl, 5-10-membered heteroaryl and 3-12-membered heterocyclyl are independently optionally substituted by $R^{10A}$;
each $R^6$, where present, is independently $C_1$-$C_6$ alkyl optionally substituted by $R^{10A}$;
n is 0, 1, 2, 3 or 4;
U is a bond or methylene optionally substituted by $R^{10}$;
V is a bond or $C_1$-$C_2$ alkylene optionally substituted by $R^{10}$;
W is a bond or $C_1$-$C_4$ alkylene optionally substituted by one or both of $R^{W1}$ and $R^{W2}$;
X is —$CR^{X1}R^{X2}$—;
Y is —$CR^{Y1}R^{Y2}$—;
$R^7$ is hydrogen, $C_1$-$C_6$ alkyl, or taken together with $R^8$ to form an ethylene optionally substituted by $R^{10}$, or taken together with $R^{Y1}$, $R^{X1}$ or $R^{W1}$, where present, to form a $C_1$-$C_6$ alkylene optionally substituted by $R^{10}$;
$R^8$ is hydrogen, $C_1$-$C_6$ alkyl optionally substituted by $R^{10}$, $C_6$-$C_{14}$ aryl, 5-10-membered heteroaryl, or taken together with $R^7$ to form an ethylene optionally substituted by $R^{10}$, or taken together with $R^{Y1}$, $R^{Y2}$, $R^{X1}$, $R^{X2}$ or $R^{W1}$, where present, to form a $C_1$-$C_6$ alkylene optionally substituted by $R^{10}$, or taken together with $R^{10}$, where present, to form a $C_1$-$C_6$ alkylene, or taken together with $R^9$ and the nitrogen atom to which they are attached to form a 3-12-membered heterocyclyl optionally substituted by $R^{10}$ or a 5-10-membered heteroaryl optionally substituted by $R^{10}$, or taken together with $R^{Y1}$, $R^{Y2}$, $R^9$ and the atoms to which they are attached to form a 5-10-membered heteroaryl optionally substituted by $R^{10}$, or taken together with $R^{X1}$, $R^{X2}$, $R^{Y1}$, $R^{Y2}$, $R^9$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y1}$, $R^{Y2}$, $R^9$ and the atoms to which they are attached to form a 5-10-membered heteroaryl optionally substituted by $R^{10}$,
$R^9$ is hydrogen, $C_1$-$C_6$ alkyl optionally substituted by $R^{10}$, or taken together with $R^8$ and the nitrogen atom to which they are attached to form a 3-12-membered heterocyclyl optionally substituted by $R^{10}$ or a 5-10- membered heteroaryl optionally substituted by $R^{10}$, or taken together with $R^{Y1}$, $R^{Y2}$, $R^8$ and the atoms to which they are attached to form a 5-10-membered heteroaryl optionally substituted by $R^{10}$, or taken together with $R^{X1}$, $R^{X2}$, $R^{Y1}$, $R^{Y2}$, $R^8$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y1}$, $R^{Y2}$, $R^8$ and the atoms to which they are attached to form a 5-10-membered heteroaryl optionally substituted by $R^{10}$;

$R^{W1}$, where present, is $C_1$-$C_6$ alkyl optionally substituted by $R^{10A}$, or taken together with $R^7$, $R^8$, $R^{X1}$ or $R^{Y1}$ to form a $C_1$-$C_6$ alkylene optionally substituted by $R^{10}$, or taken together with $R^{W2}$, $R^{X1}$, $R^{X2}$, $R^{Y1}$, $R^{Y2}$, $R^8$, $R^9$ and the atoms to which they are attached to form a 5-10-membered heteroaryl optionally substituted by $R^{10}$;

$R^{W2}$, where present, is $C_1$-$C_6$ alkyl optionally substituted by $R^{10A}$, or taken together with $R^{W1}$, $R^{X1}$, $R^{X2}$, $R^{Y1}$, $R^{Y2}$, $R^8$, $R^9$ and the atoms to which they are attached to form a 5-10-membered heteroaryl optionally substituted by $R^{10}$;

$R^{X1}$ is hydrogen, $C_1$-$C_6$ alkyl optionally substituted by $R^{10A}$, or taken together with $R^7$, $R^8$, $R^{Y1}$ or $R^{W1}$, where present, to form a $C_1$-$C_6$ alkylene optionally substituted by $R^{10}$, or taken together with $R^{X2}$, $R^{Y1}$, $R^{Y2}$, $R^8$, $R^9$ and the atoms to which they are attached to form a 5-10-membered heteroaryl optionally substituted by $R^{10}$, or taken together with $R^{W1}$, $R^{W2}$, where present, $R^{X2}$, $R^{Y1}$, $R^{Y2}$, $R^8$, $R^9$ and the atoms to which they are attached to form a 5-10-membered heteroaryl optionally substituted by $R^{10}$;

$R^{X2}$ is hydrogen or $C_1$-$C_6$ alkyl optionally substituted by $R^{10A}$, or taken together with $R^{X1}$, $R^{Y1}$, $R^{Y2}$, $R^8$, $R^9$ and the atoms to which they are attached to form a 5-10-membered heteroaryl optionally substituted by $R^{10}$, or taken together with $R^{W1}$, $R^{W2}$, where present, $R^{X1}$, $R^{Y1}$, $R^{Y2}$, $R^8$, $R^9$ and the atoms to which they are attached to form a 5-10-membered heteroaryl optionally substituted by $R^{10}$, or taken together with $R^8$ to form a $C_1$-$C_6$ alkylene optionally substituted by $R^{10}$;

$R^{Y1}$ is hydrogen, $C_1$-$C_6$ alkyl optionally substituted by $R^{10A}$, or taken together with $R^7$, $R^8$, $R^{X1}$ or $R^{W1}$, where present, to form a $C_1$-$C_6$ alkylene optionally substituted by $R^{10}$, or taken together with $R^{Y2}$, $R^8$, $R^9$ and the atoms to which they are attached to form a 5-10-membered heteroaryl optionally substituted by $R^{10}$, or taken together with $R^{X1}$, $R^{X2}$, $R^{Y2}$, $R^8$, $R^9$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y2}$, $R^8$, $R^9$ and the atoms to which they are attached to form a 5-10-membered heteroaryl optionally substituted by $R^{10}$;

$R^{Y2}$ is hydrogen, $C_1$-$C_6$ alkyl optionally substituted by $R^{10A}$, or taken together with $R^{Y1}$, $R^8$, $R^9$ and the atoms to which they are attached to form a 5-10-membered heteroaryl optionally substituted by $R^{10}$, or taken together with $R^{X1}$, $R^{X2}$, $R^{Y1}$, $R^8$, $R^9$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y1}$, $R^8$, $R^9$ and the atoms to which they are attached to form a 5-10-membered heteroaryl optionally substituted by $R^{10}$, or taken together with $R^8$ to form a $C_1$-$C_6$ alkylene optionally substituted by $R^{10}$;

each $R^{10}$ is independently $C_1$-$C_6$ alkyl, $C_2$-$C_6$ alkenyl, $C_2$-$C_6$ alkynyl, $C_3$-$C_8$ cycloalkyl, 3-12-membered heterocyclyl, 5-10-membered heteroaryl, $C_6$-$C_{14}$ aryl, halogen, —CN, —OR$^{11}$, —SR$^{11}$, —NR$^{12}$R$^{13}$, —NO$_2$, —C=NH(OR$^{11}$), —C(O)R$^{11}$, —OC(O)R$^{11}$, —C(O)OR$^{11}$, —C(O)NR$^{12}$R$^{13}$, —NR$^{11}$C(O)R$^{12}$, —NR$^{11}$C(O)OR$^{12}$, —NR$^{1}$C(O)NR$^{12}$R$^{13}$, —S(O)R$^{11}$, —S(O)$_2$R$^{11}$, —NR$^{11}$S(O)R$^{12}$, —NR$^{11}$S(O)$_2$R$^{12}$, —S(O)NR$^{12}$R$^{13}$, —S(O)$_2$NR$^{12}$R$^{13}$, or —P(O)(OR$^{12}$)(OR$^{13}$); wherein the $C_1$-$C_6$ alkyl, $C_2$-$C_6$ alkenyl, $C_2$-$C_6$ alkynyl, $C_3$-$C_8$ cycloalkyl, 3-12-membered heterocyclyl, 5-10-membered heteroaryl and $C_6$-$C_{14}$ aryl of $R^{10}$ are independently optionally substituted by halogen, —CN, oxo, —OR$^{14}$, —SR$^{14}$, —NR$^{14}$R$^{15}$, —C(O)R$^{14}$, —C(O)OR$^{14}$, —S(O)R$^{14}$, —S(O)$_2$R$^{14}$, —P(O)(OR$^{14}$)(OR$^{15}$), 3-12-membered heterocyclyl, 5-10-membered heteroaryl, $C_6$-$C_{14}$ aryl, $C_3$-$C_8$ cycloalkyl, or $C_1$-$C_6$ alkyl optionally substituted by oxo, —OH or halogen, or is taken together with $R^8$ to form a $C_1$-$C_6$ alkylene;

each $R^{10A}$ is independently oxo or $R^{10}$;

$R^{11}$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6-membered heterocyclyl of $R^{11}$ are independently optionally substituted by halogen, oxo, —CN, —OR$^{16}$, —NR$^{16}$R$^{17}$, —P(O)(OR$^{16}$)(OR$^{17}$), or $C_1$-$C_6$ alkyl optionally substituted by halogen, —OH or oxo;

$R^{12}$ and $R^{13}$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6 membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6 membered heterocyclyl of $R^{12}$ and $R^{13}$ are independently optionally substituted by halogen, oxo, —CN, —OR$^{16}$, —NR$^{16}$R$^{17}$ or $C_1$-$C_6$ alkyl optionally substituted by halogen, —OH or oxo;

or $R^{12}$ and $R^{13}$ are taken together with the atom to which they attached to form a 3-6 membered heterocyclyl optionally substituted by halogen, oxo, —OR$^{16}$, —NR$^{16}$R$^{17}$ or $C_1$-$C_6$ alkyl optionally substituted by halogen, oxo or —OH;

$R^{14}$ and $R^{15}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^{14}$ and $R^{15}$ are taken together with the atom to which they attached to form a 3-6 membered heterocyclyl optionally substituted by halogen, oxo or $C_1$-$C_6$ alkyl optionally substituted by halogen or oxo; and $R^{16}$ and $R^{17}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^{16}$ and $R^{17}$ are taken together with the atom to which they attached to form a 3-6 membered heterocyclyl optionally substituted by halogen, oxo or $C_1$-$C_6$ alkyl optionally substituted by oxo or halogen.

In some embodiments, where $R^8$ and $R^9$ are taken together with the nitrogen atom to which they are attached to form a 3-12-membered heterocyclyl optionally substituted by $R^{10}$ or a 5-10-membered heteroaryl optionally substituted by $R^{10}$, and the 5-10-membered heteroaryl is a fused ring heteroaryl comprising an aryl moiety fused to a heterocycle containing the nitrogen atom to which $R^8$ and $R^9$ are attached, the aryl moiety is not adjacent to the nitrogen atom to which $R^8$ and $R^9$ are attached. For example, in some embodiments, the 5-10-membered heteroaryl formed by $R^8$ and $R^9$ taken together with the nitrogen atom to which they are attached is other than indolin-1-yl and 3,4-dihydroquinolin-1(2H)-yl.

In some embodiments, the compound is other than a compound in Table 1X and salts thereof. In some embodiments, the compound herein, such as a compound of formula (A-I) or (I), is other than a compound selected from one or more of Compound Nos. 1x-83x in Table 1X. In some embodiments, the compounds of the disclosure, and methods of using the compounds detailed herein, encompass any of the compounds of formula (A-I) or (I), including one or more of Compound Nos. 1x-83x listed in Table 1X and salts thereof.

TABLE 1X

| Compound No. | Structure | Chemical Name [1] |
|---|---|---|
| 1x | 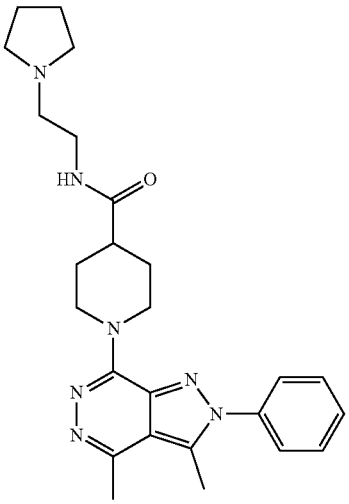 [SMILES: Cc1nnc(N2CCC(C(=O)NCCN3CCCC3)CC2)c2nn(-c3ccccc3)c(C)c12] | 1-(3,4-dimethyl-2-phenyl-2H-pyrazolo[3,4-d]pyridazin-7-yl)-N-(2-(pyrrolidin-1-yl)ethyl)piperidine-4-carboxamide; 4-Piperidinecarboxamide, 1-(3,4-dimethyl-2-phenyl-2H-pyrazolo[3,4-d]pyridazin-7-yl)-N-[2-(1-pyrrolidinyl)ethyl]- |
| 2x | 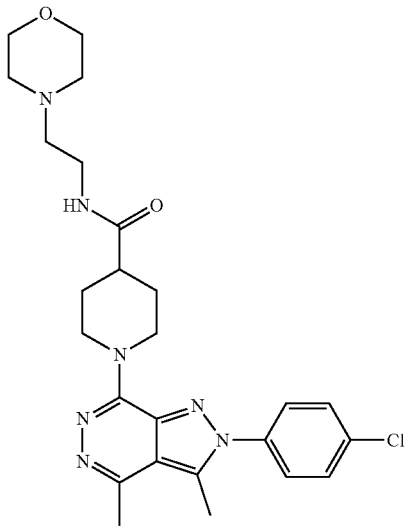 [SMILES: Cc1nnc(N2CCC(C(=O)NCCN3CCOCC3)CC2)c2nn(-c3ccc(Cl)cc3)c(C)c12] | 1-(2-(4-chlorophenyl)-3,4-dimethyl-2H-pyrazolo[3,4-d]pyridazin-7-yl)-N-(2-morpholinoethyl)piperidine-4-carboxamide; 4-Piperidinecarboxamide, 1-[2-(4-chlorophenyl)-3,4-dimethyl-2H-pyrazolo[3,4-d]pyridazin-7-yl]-N-[2-(4-morpholinyl)ethyl]- |

TABLE 1X-continued

| Compound No. | Structure | Chemical Name [1] |
|---|---|---|
| 3x | 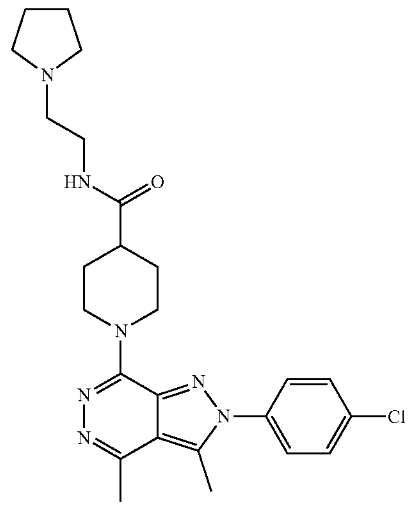 [SMILES: Cc1nnc(N2CCC(C(=O)NCCN3CCCC3)CC2)c2nn(-c3ccc(Cl)cc3)c(C)c12] | 1-(2-(4-chlorophenyl)-3,4-dimethyl-2H-pyrazolo[3,4-d]pyridazin-7-yl)-N-(2-(pyrrolidin-1-yl)ethyl)piperidine-4-carboxamide; 4-Piperidinecarboxamide, 1-[2-(4-chlorophenyl)-3,4-dimethyl-2H-pyrazolo[3,4-d]pyridazin-7-yl]-N-[2-(1-pyrrolidinyl)ethyl]- |
| 4x | 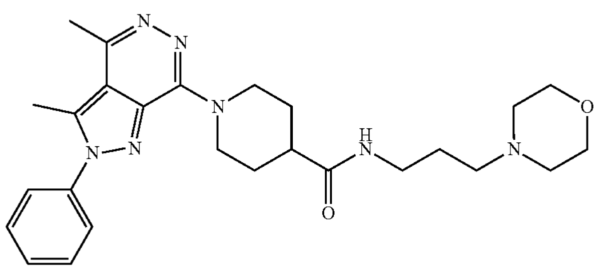 [SMILES: Cc1nnc(N2CCC(C(=O)NCCCN3CCOCC3)CC2)c2nn(-c3ccccc3)c(C)c12] | 1-(3,4-dimethyl-2-phenyl-2H-pyrazolo[3,4-d]pyridazin-7-yl)-N-(3-morpholinopropyl)piperidine-4-carboxamide; 4-Piperidinecarboxamide, 1-(3,4-dimethyl-2-phenyl-2H-pyrazolo[3,4-d]pyridazin-7-yl)-N-[3-(4-morpholinyl)propyl]- |
| 5x | 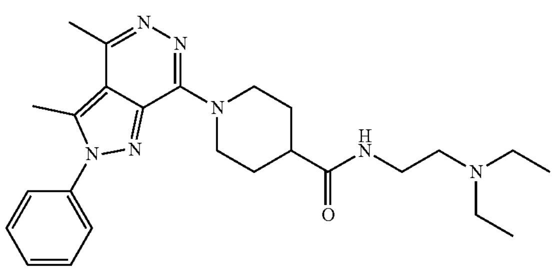 [SMILES: CCN(CC)CCNC(=O)C1CCN(c2nnc(C)c3c(C)n(-c4ccccc4)nc23)CC1] | N-(2-(diethylamino)ethyl)-1-(3,4-dimethyl-2-phenyl-2H-pyrazolo[3,4-d]pyridazin-7-yl)piperidine-4-carboxamide; N-(2-Diethylaminoethyl)-1-(3,4-dimethyl-2-phenylpyrazolo[3,4-d]pyridazin-7-yl)piperidine-4-carboxamide |
| 6x | 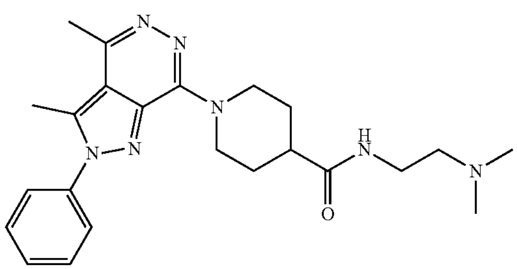 [SMILES: Cc1nnc(N2CCC(C(=O)NCCN(C)C)CC2)c2nn(-c3ccccc3)c(C)c12] | 1-(3,4-dimethyl-2-phenyl-2H-pyrazolo[3,4-d]pyridazin-7-yl)-N-(2-(dimethylamino)ethyl)piperidine-4-carboxamide; N-(2-Dimethylaminoethyl)-1-(3,4-dimethyl-2-phenylpyrazolo[3,4-d]pyridazin-7-yl)piperidine-4-carboxamide |
| 7x | 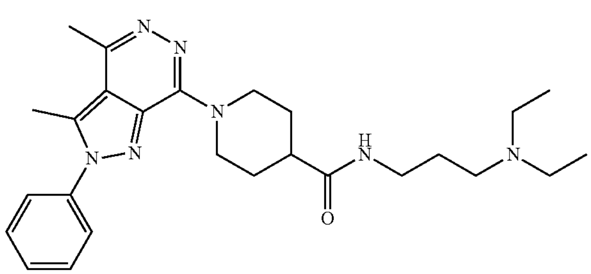 [SMILES: CCN(CC)CCCNC(=O)C1CCN(c2nnc(C)c3c(C)n(-c4ccccc4)nc23)CC1] | N-(3-(diethylamino)propyl)-1-(3,4-dimethyl-2-phenyl-2H-pyrazolo[3,4-d]pyridazin-7-yl)piperidine-4-carboxamide; N-(3-Diethylaminopropyl)-1-(3,4-dimethyl-2-phenylpyrazolo[3,4-d]pyridazin-7-yl)piperidine-4-carboxamide |

TABLE 1X-continued

| Compound No. | Structure | Chemical Name [1] |
|---|---|---|
| 8x | 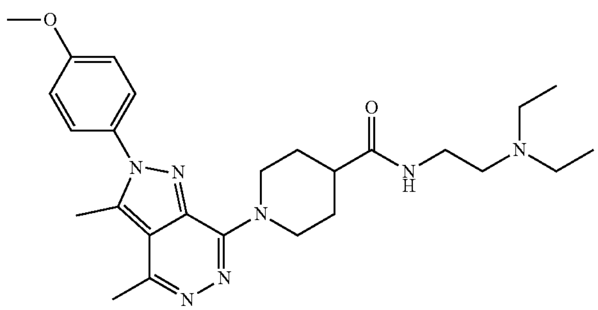 [SMILES: CCN(CC)CCNC(=O)C1CCN(c2nnc(C)c3c(C)n(-c4ccc(OC)cc4)nc23)CC1] | N-(2-(diethylamino)ethyl)-1-(2-(4-methoxyphenyl)-3,4-dimethyl-2H-pyrazolo[3,4-d]pyridazin-7-yl)piperidine-4-carboxamide; 4-Piperidinecarboxamide, N-[2-(diethylamino)ethyl]-1-[2-(4-methoxyphenyl)-3,4-dimethyl-2H-pyrazolo[3,4-d]pyridazin-7-yl]- |
| 9x | 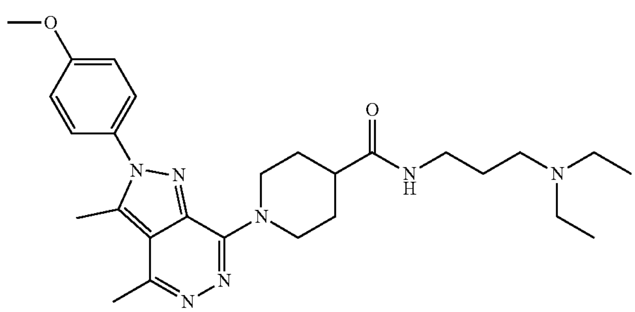 [SMILES: CCN(CC)CCCNC(=O)C1CCN(c2nnc(C)c3c(C)n(-c4ccc(OC)cc4)nc23)CC1] | N-(3-(diethylamino)propyl)-1-(2-(4-methoxyphenyl)-3,4-dimethyl-2H-pyrazolo[3,4-d]pyridazin-7-yl)piperidine-4-carboxamide; 4-Piperidinecarboxamide, N-[3-(diethylamino)propyl]-1-[2-(4-methoxyphenyl)-3,4-dimethyl-2H-pyrazolo[3,4-d]pyridazin-7-yl]- |
| 10x | 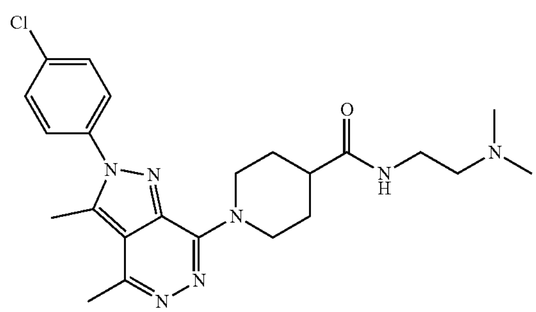 [SMILES: Cc1nnc(N2CCC(C(=O)NCCN(C)C)CC2)c2nn(-c3ccc(Cl)cc3)c(C)c12] | 1-(2-(4-chlorophenyl)-3,4-dimethyl-2H-pyrazolo[3,4-d]pyridazin-7-yl)-N-(2-(dimethylamino)ethyl)piperidine-4-carboxamide; 4-Piperidinecarboxamide, 1-[2-(4-chlorophenyl)-3,4-dimethyl-2H-pyrazolo[3,4-d]pyridazin-7-yl]-N-[2-(dimethylamino)ethyl]- |
| 11x | 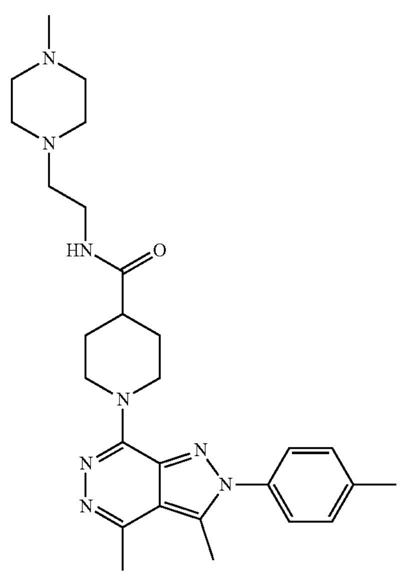 [SMILES: Cc1ccc(-n2nc3c(N4CCC(C(=O)NCCN5CCN(C)CC5)CC4)nnc(C)c3c2C)cc1] | 1-(3,4-dimethyl-2-(p-tolyl)-2H-pyrazolo[3,4-d]pyridazin-7-yl)-N-(2-(4-methylpiperazin-1-yl)ethyl)piperidine-4-carboxamide; 4-Piperidinecarboxamide, 1-[3,4-dimethyl-2-(4-methylphenyl)-2H-pyrazolo[3,4-d]pyridazin-7-yl]-N-[2-(4-methyl-1-piperazinyl)ethyl]- |

TABLE 1X-continued

| Compound No. | Structure | Chemical Name [1] |
|---|---|---|
| 12x | 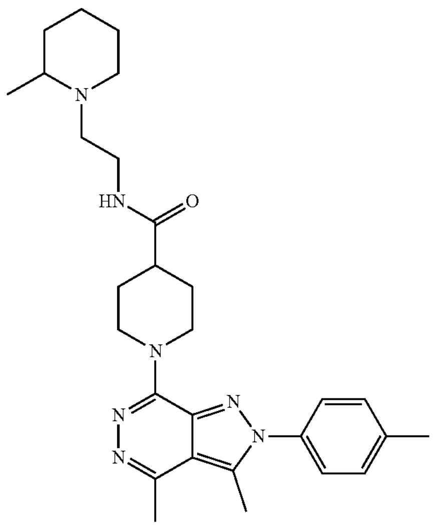 | 1-(3,4-dimethyl-2-(p-tolyl)-2H-pyrazolo[3,4-d]pyridazin-7-yl)-N-(2-(2-methylpiperidin-1-yl)ethyl)piperidine-4-carboxamide; 1-[3,4-Dimethyl-2-(4-methylphenyl)pyrazolo[3,4-d]pyridazin-7-yl]-N-[2-(2-methylpiperidin-1-yl)ethyl]piperidine-4-carboxamide |
| 13x | 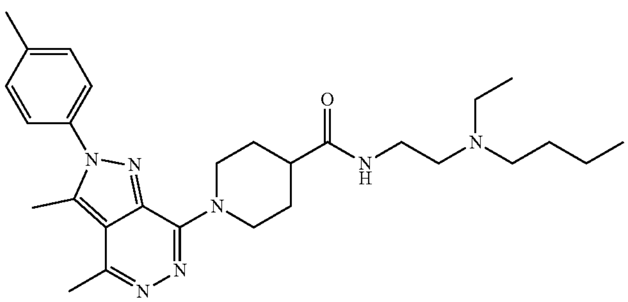 [SMILES: CCCCN(CC)CCNC(=O)C1CCN(c2nnc(C)c3c(C)n(-c4ccc(C)cc4)nc23)CC1] | N-(2-(butyl(ethyl)amino)ethyl)-1-(3,4-dimethyl-2-(p-tolyl)-2H-pyrazolo[3,4-d]pyridazin-7-yl)piperidine-4-carboxamide; 4-Piperidinecarboxamide, N-[2-(butylethylamino)ethyl]-1-[3,4-dimethyl-2-(4-methylphenyl)-2H-pyrazolo[3,4-d]pyridazin-7-yl]- |
| 14x | 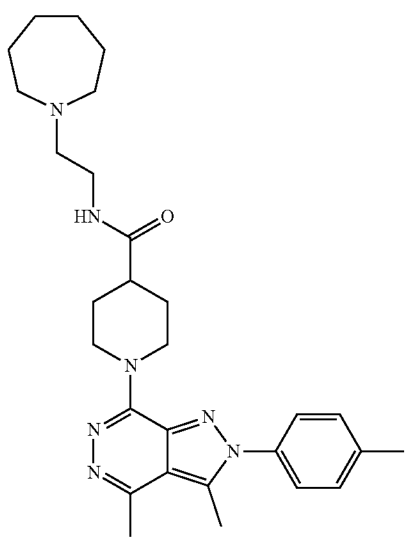 [SMILES: Cc1ccc(-n2nc3c(N4CCC(C(=O)NCCN5CCCCCC5)CC4)nnc(C)c3c2C)cc1] | N-(2-(azepan-1-yl)ethyl)-1-(3,4-dimethyl-2-(p-tolyl)-2H-pyrazolo[3,4-d]pyridazin-7-yl)piperidine-4-carboxamide; 4-Piperidinecarboxamide, 1-[3,4-dimethyl-2-(4-methylphenyl)-2H-pyrazolo[3,4-d]pyridazin-7-yl]-N-[2-(hexahydro-1H-azepin-1-yl)ethyl]- |

TABLE 1X-continued

| Compound No. | Structure | Chemical Name [1] |
|---|---|---|
| 15x | 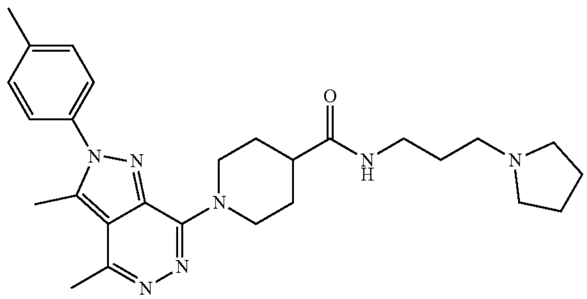 [SMILES: Cc1ccc(-n2nc3c(N4CCC(C(=O)NCCCN5CCCC5)CC4)nnc(C)c3c2C)cc1] | 1-(3,4-dimethyl-2-(p-tolyl)-2H-pyrazolo[3,4-d]pyridazin-7-yl)-N-(3-(pyrrolidin-1-yl)propyl)piperidine-4-carboxamide; 4-Piperidinecarboxamide, 1-[3,4-dimethyl-2-(4-methylphenyl)-2H-pyrazolo[3,4-d]pyridazin-7-yl]-N-[3-(1-pyrrolidinyl)propyl]- |
| 16x | 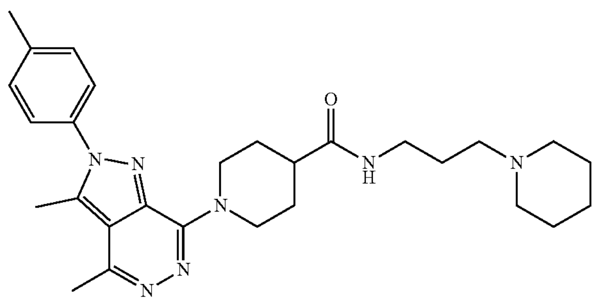 [SMILES: Cc1ccc(-n2nc3c(N4CCC(C(=O)NCCCN5CCCCC5)CC4)nnc(C)c3c2C)cc1] | 1-(3,4-dimethyl-2-(p-tolyl)-2H-pyrazolo[3,4-d]pyridazin-7-yl)-N-(3-piperidin-1-yl)propyl)piperidine-4-carboxamide; 4-Piperidinecarboxamide, 1-[3,4-dimethyl-2-(4-methylphenyl)-2H-pyrazolo[3,4-d]pyridazin-7-yl]-N-[3-(1-piperidinyl)propyl]- |
| 17x | 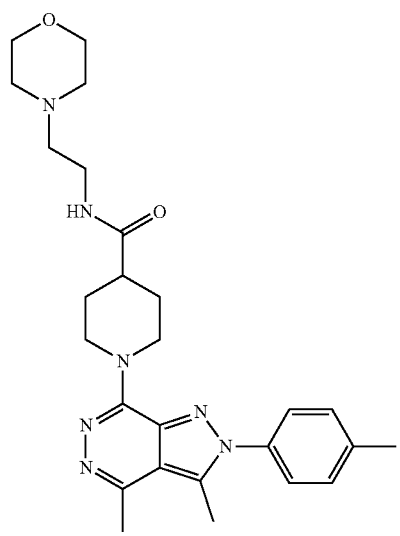 [SMILES: Cc1ccc(-n2nc3c(N4CCC(C(=O)NCCN5CCOCC5)CC4)nnc(C)c3c2C)cc1] | 1-(3,4-dimethyl-2-(p-tolyl)-2H-pyrazolo[3,4-d]pyridazin-7-yl)-N-(2-morpholinoethyl)piperidine-4-carboxamide; 4-Piperidinecarboxamide, 1-[3,4-dimethyl-2-(4-methylphenyl)-2H-pyrazolo[3,4-d]pyridazin-7-yl]-N-[2-(4-morpholinyl)ethyl]- |
| 18x | 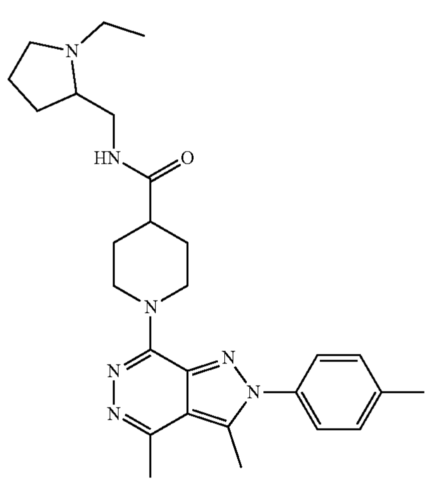 [SMILES: CCN1CCCC1CNC(=O)C1CCN(c2nnc(C)c3c(C)n(-c4ccc(C)cc4)nc23)CC1] | 1-(3,4-dimethyl-2-(p-tolyl)-2H-pyrazolo[3,4-d]pyridazin-7-yl)-N-((1-ethylpyrrolidin-2-yl)methyl)piperidine-4-carboxamide; 1-[3,4-Dimethyl-2-(4-methylphenyl)pyrazolo[3,4-d]pyridazin-7-yl]-N-[(1-ethylpyrrolidin-2-yl)methyl]piperidine-4-carboxamide |

TABLE 1X-continued

| Compound No. | Structure | Chemical Name [1] |
|---|---|---|
| 19x | 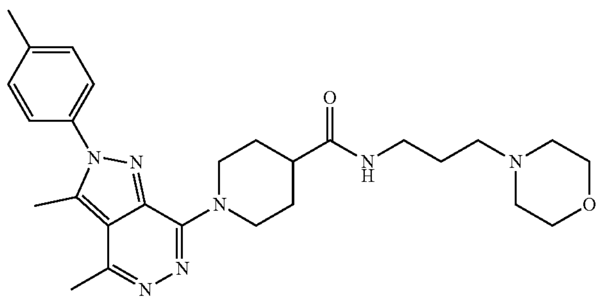 [SMILES: Cc1ccc(-n2nc3c(N4CCC(C(=O)NCCCN5CCOCC5)CC4)nnc(C)c3c2C)cc1] | 1-(3,4-dimethyl-2-(p-tolyl)-2H-pyrazolo[3,4-d]pyridazin-7-yl)-N-(3-morpholinopropyl)piperidine-4-carboxamide; 4-Piperidinecarboxamide, 1-[3,4-dimethyl-2-(4-methylphenyl)-2H-pyrazolo[3,4-d]pyridazin-7-yl]-N-[3-(4-morpholinyl)propyl]- |
| 20x | 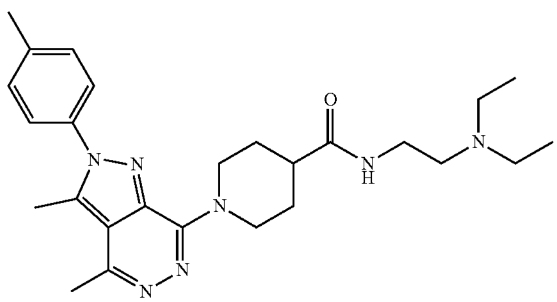 [SMILES: CCN(CC)CCNC(=O)C1CCN(c2nnc(C)c3c(C)n(-c4ccc(C)cc4)nc23)CC1] | N-(2-(diethylamino)ethyl)-1-(3,4-dimethyl-2-(p-tolyl)-2H-pyrazolo[3,4-d]pyridazin-7-yl)piperidine-4-carboxamide; 4-Piperidinecarboxamide, N-[2-(diethylamino)ethyl]-1-[3,4-dimethyl-2-(4-methylphenyl)-2H-pyrazolo[3,4-d]pyridazin-7-yl]- |
| 21x | 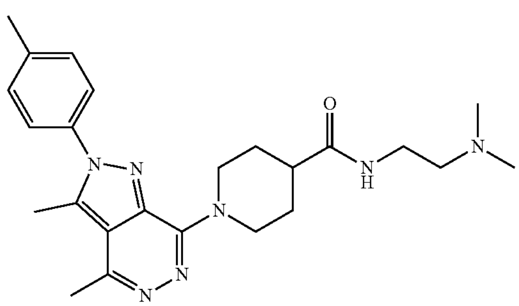 | 1-(3,4-dimethyl-2-(p-tolyl)-2H-pyrazolo[3,4-d]pyridazin-7-yl)-N-(2-(dimethylamino)ethyl)piperidine-4-carboxamide; 4-Piperidinecarboxamide, N-[2-(dimethylamino)ethyl]-1-[3,4-dimethyl-2-(4-methylphenyl)-2H-pyrazolo[3,4-d]pyridazin-7-yl]- |
| 22x | 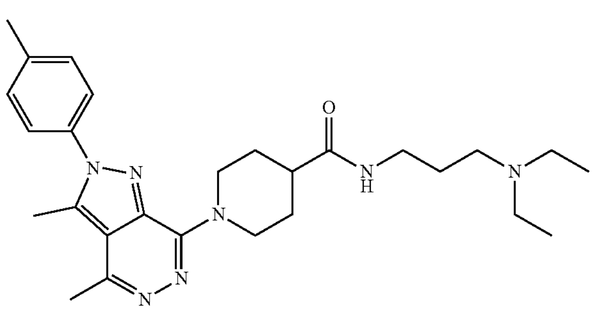 [SMILES: CCN(CC)CCCNC(=O)C1CCN(c2nnc(C)c3c(C)n(-c4ccc(C)cc4)nc23)CC1] | N-(3-(diethylamino)propyl)-1-(3,4-dimethyl-2-(p-tolyl)-2H-pyrazolo[3,4-d]pyridazin-7-yl)piperidine-4-carboxamide; 4-Piperidinecarboxamide, N-[3-(diethylamino)propyl]-1-[3,4-dimethyl-2-(4-methylphenyl)-2H-pyrazolo[3,4-d]pyridazin-7-yl]- |

TABLE 1X-continued

| Compound No. | Structure | Chemical Name [1] |
|---|---|---|
| 23x | 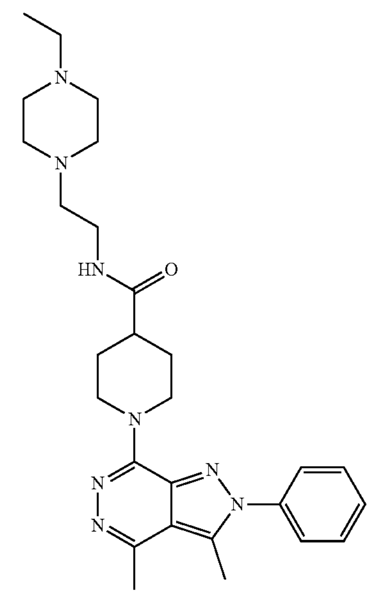 [SMILES: CCN1CCN(CCNC(=O)C2CCN(c3nnc(C)c4c(C)n(-c5ccccc5)nc34)CC2)CC1] | 1-(3,4-dimethyl-2-phenyl-2H-pyrazolo[3,4-d]pyridazin-7-yl)-N-(2-(4-ethylpiperazin-1-yl)ethyl)piperidine-4-carboxamide; 1-(3,4-Dimethyl-2-phenyl-2H-pyrazolo[3,4-d]pyridazin-7-yl)-N-[2-(4-ethylpiperazin-1-yl)ethyl]piperidine-4-carboxamide |
| 24x | 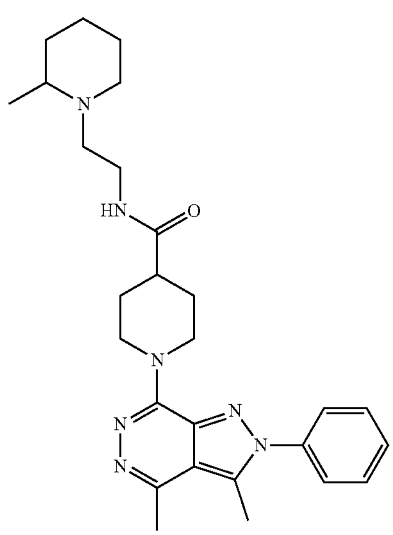 [SMILES: Cc1nnc(N2CCC(C(=O)NCCN3CCCCC3C)CC2)c2nn(-c3ccccc3)c(C)c12] | 1-(3,4-dimethyl-2-phenyl-2H-pyrazolo[3,4-d]pyridazin-7-yl)-N-(2-(2-methylpiperidin-1-yl)ethyl)piperidine-4-carboxamide; 1-(3,4-Dimethyl-2-phenyl-2H-pyrazolo[3,4-d]pyridazin-7-yl)-N-[2-(2-methylpiperidin-1-yl)ethyl]piperidine-4-carboxamide |
| 25x | 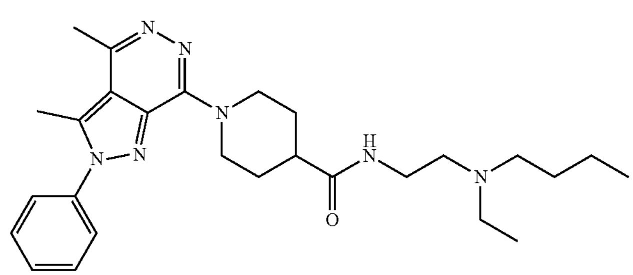 [SMILES: CCCCN(CC)CCNC(=O)C1CCN(c2nnc(C)c3c(C)n(-c4ccccc4)nc23)CC1] | N-(2-(butyl(ethyl)amino)ethyl)-1-(3,4-dimethyl-2-phenyl-2H-pyrazolo[3,4-d]pyridazin-7-yl)piperidine-4-carboxamide; N-[2-(Butyl-ethylamino)ethyl]-1-(3,4-dimethyl-2-phenylpyrazolo[3,4-d]pyridazin-7-yl)piperidine-4-carboxamide |

TABLE 1X-continued

| Compound No. | Structure | Chemical Name [1] |
|---|---|---|
| 26x | 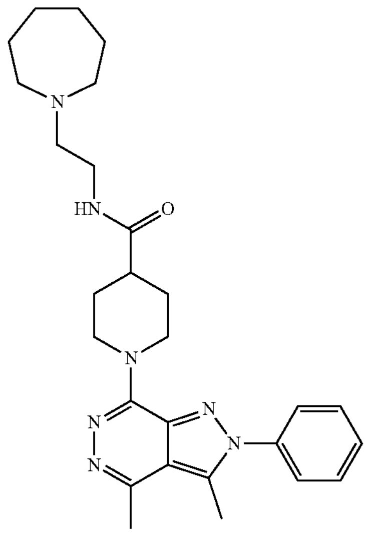 [SMILES: Cc1nnc(N2CCC(C(=O)NCCN3CCCCCC3)CC2)c2nn(-c3ccccc3)c(C)c12] | N-(2-(azepan-1-yl)ethyl)-1-(3,4-dimethyl-2-phenyl-2H-pyraozlo[3,4-d]pyridazin-7-yl)piperidine-4-carboxamide; 4-Piperidinecarboxamide, 1-(3,4-dimethyl-2-phenyl-2H-pyrazolo[3,4-d]pyridazin-7-yl)-N-[2-(hexahydro-1H-azepin-1-yl)ethyl]- |
| 27x | 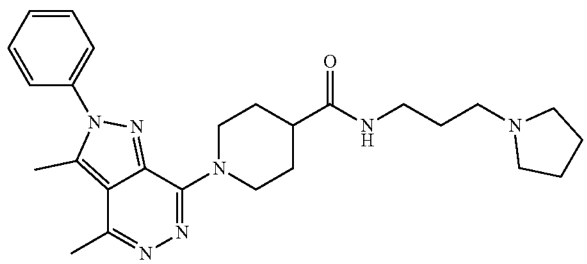 [SMILES: Cc1nnc(N2CCC(C(=O)NCCCN3CCCC3)CC2)c2nn(-c3ccccc3)c(C)c12] | 1-(3,4-dimethyl-2-phenyl-2H-pyrazolo[3,4-d]pyridazin-7-yl)-N-(3-(pyrrolidin-1-yl)propyl)piperidine-4-carboxamide; 4-Piperidinecarboxamide, 1-(3,4-dimethyl-2-phenyl-2H-pyrazolo[3,4-d]pyridazin-7-yl)-N-[3-(1-pyrrolidinyl)propyl]- |
| 28x | 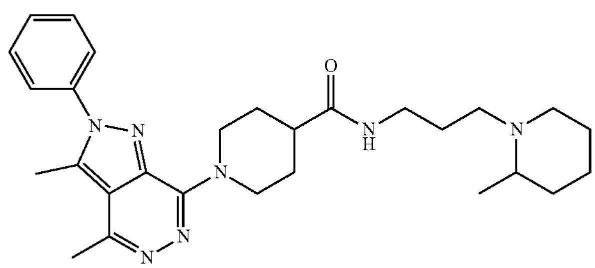 [SMILES: Cc1nnc(N2CCC(C(=O)NCCCN3CCCCC3C)CC2)c2nn(-c3ccccc3)c(C)c12] | 1-(3,4-dimethyl-2-phenyl-2H-pyrazolo[3,4-d]pyridazin-7-yl)-N-(3-(2-methylpiperidin-1-yl)propyl)piperidine-4-carboxamide; 4-Piperidinecarboxamide, 1-(3,4-dimethyl-2-phenyl-2H-pyrazolo[3,4-d]pyridazin-7-yl)-N-[3-(2-methyl-1-piperidinyl)propyl]- |
| 29x | 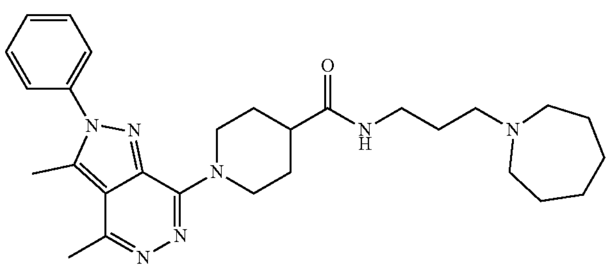 [SMILES: Cc1nnc(N2CCC(C(=O)NCCCN3CCCCCC3)CC2)c2nn(-c3ccccc3)c(C)c12] | N-(3-(azepan-1-yl)propyl)-1-(3,4-dimethyl-2-phenyl-2H-pyrazolo[3,4-d]pyridazin-7-yl)piperidine-4-carboxamide; 4-Piperidinecarboxamide, 1-(3,4-dimethyl-2-phenyl-2H-pyrazolo[3,4-d]pyridazin-7-yl)-N-[3-(hexahydro-1H-azepin-1-yl)propyl]- |
| 30x | 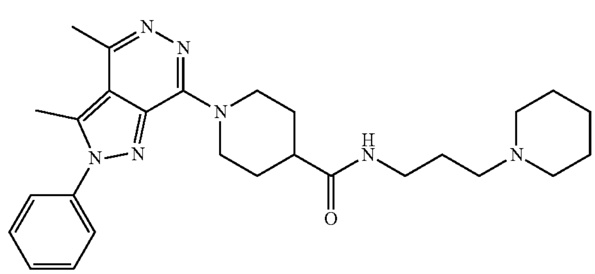 [SMILES: Cc1nnc(N2CCC(C(=O)NCCCN3CCCCC3)CC2)c2nn(-c3ccccc3)c(C)c12] | 1-(3,4-dimethyl-2-phenyl-2H-pyrazolo[3,4-d]pyridazin-7-yl)-N-(3-piperidin-1-yl)propyl)piperidine-4-carboxamide; 4-Piperidinecarboxamide, 1-(3,4-dimethyl-2-phenyl-2H-pyrazolo[3,4-d]pyridazin-7-yl)-N-[3-(1-piperidinyl)propyl]- |

TABLE 1X-continued

| Compound No. | Structure | Chemical Name [1] |
|---|---|---|
| 31x | 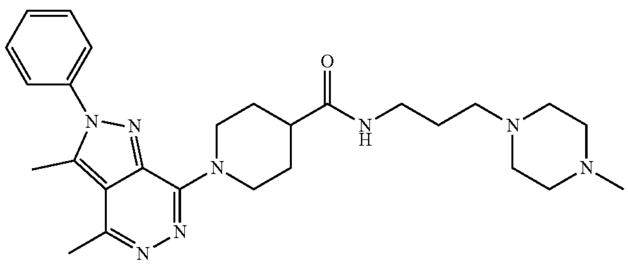 [SMILES: Cc1nnc(N2CCC(C(=O)NCCCN3CCN(C)CC3)CC2)c2nn(-c3ccccc3)c(C)c12] | 1-(3,4-dimethyl-2-phenyl-2H-pyrazolo[3,4-d]pyridazin-7-yl)-N-(3-(4-methylpiperazin-1-yl)propyl)piperidine-4-carboxamide; 4-Piperidinecarboxamide, 1-(3,4-dimethyl-2-phenyl-2H-pyrazolo[3,4-d]pyridazin-7-yl)-N-[3-(4-methyl-1-piperazinyl)propyl]- |
| 32x | 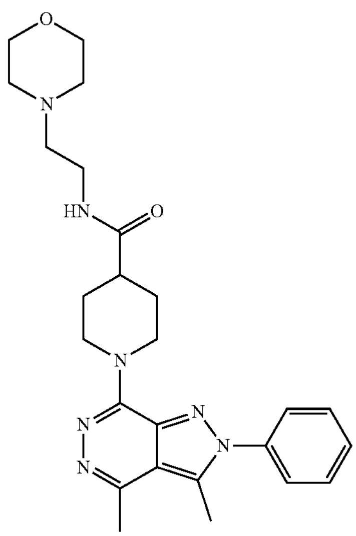 [SMILES: Cc1nnc(N2CCC(C(=O)NCCN3CCOCC3)CC2)c2nn(-c3ccccc3)c(C)c12] | 1-(3,4-dimethyl-2-phenyl-2H-pyrazolo[3,4-d]pyridazin-7-yl)-N-(2-morpholinoethyl)piperidine-4-carboxamide; 4-Piperidinecarboxamide, 1-(3,4-dimethyl-2-phenyl-2H-pyrazolo[3,4-d]pyridazin-7-yl)-N-[2-(4-morpholinyl)ethyl]- |
| 33x | 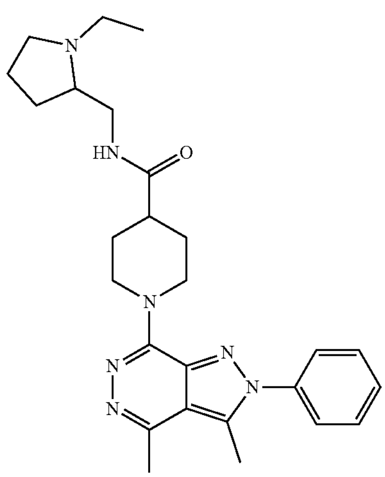 [SMILES: CCN1CCCC1CNC(=O)C1CCN(c2nnc(C)c3c(C)n(-c4ccccc4)nc23)CC1] | 1-(3,4-dimethyl-2-phenyl-2H-pyrazolo[3,4-d]pyridazin-7-yl)-N-((1-ethylpyrrolidin-2-yl)methyl)piperidine-4-carboxamide; 1-(3,4-Dimethyl-2-phenyl-2H-pyrazolo[3,4-d]pyridazin-7-yl)-N-[(1-ethylpyrrolidin-2-yl)methyl]piperidine-4-carboxamide |

TABLE 1X-continued

| Compound No. | Structure | Chemical Name [1] |
|---|---|---|
| 34x | 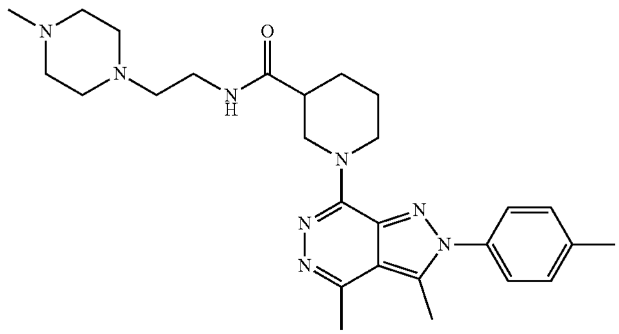 | 1-(3,4-dimethyl-2-(p-tolyl)-2H-pyrazolo[3,4-d]pyridazin-7-yl)-N-(2-(4-methylpiperazin-1-yl)ethyl)piperidine-3-carboxamide; 3-Piperidinecarboxamide, 1-[3,4-dimethyl-2-(4-methylphenyl)-2H-pyrazolo[3,4-d]pyridazin-7-yl]-N-[2-(4-methyl-1-piperazinyl)ethyl]- |
| 35x | 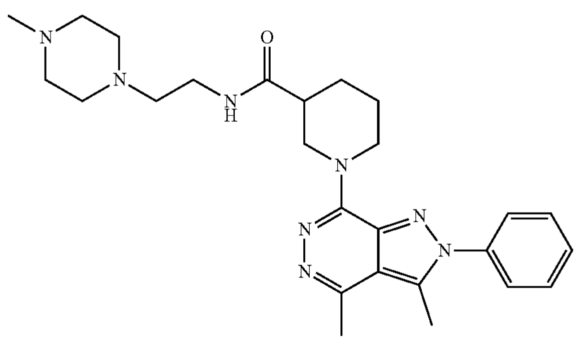 [SMILES: Cc1nnc(N2CCCC(C(=O)NCCN3CCN(C)CC3)C2)c2nn(-c3ccccc3)c(C)c12] | 1-(3,4-dimethyl-2-phenyl-2H-pyrazolo[3,4-d]pyridazin-7-yl)-N-(2-(4-methylpiperazin-1-yl)ethyl)piperidine-3-carboxamide; 3-Piperidinecarboxamide, 1-(3,4-dimethyl-2-phenyl-2H-pyrazolo[3,4-d]pyridazin-7-yl)-N-[2-(4-methyl-1-piperazinyl)ethyl]- |
| 36x | 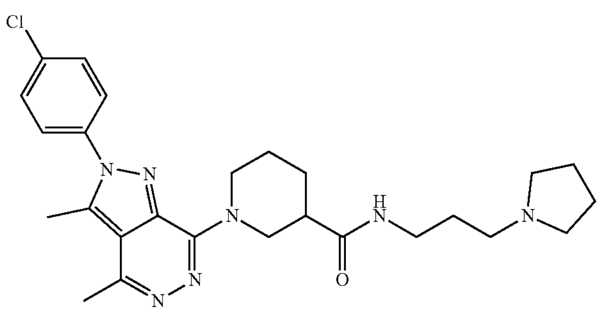 [SMILES: Cc1nnc(N2CCCC(C(=O)NCCCN3CCCC3)C2)c2nn(-c3ccc(Cl)cc3)c(C)c12] | 1-(2-(4-chlorophenyl)-3,4-dimethyl-2H-pyrazolo[3,4-d]pyridazin-7-yl)-N-(3-(pyrrolidin-1-yl)propyl)piperidine-3-carboxamide; 3-Piperidinecarboxamide, 1-[2-(4-chlorophenyl)-3,4-dimethyl-2H-pyrazolo[3,4-d]pyridazin-7-yl]-N-[3-(1-pyrrolidinyl)propyl]- |
| 37x | 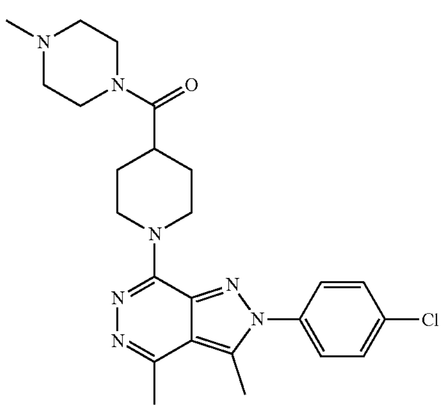 [SMILES: Cc1nnc(N2CCC(C(=O)N3CCN(C)CC3)CC2)c2nn(-c3ccc(Cl)cc3)c(C)c12] | (1-(2-(4-chlorophenyl)-3,4-dimethyl-2H-pyrazolo[3,4-d]pyridazin-7-yl)piperidin-4-yl)(4-methylpiperazin-1-yl)methanone; Methanone, [1-[2-(4-chlorophenyl)-3,4-dimethyl-2H-pyrazolo[3,4-d]pyridazin-7-yl]-4-piperidinyl](4-methyl-1-piperazinyl)- |

TABLE 1X-continued

| Compound No. | Structure | Chemical Name [1] |
|---|---|---|
| 38x | 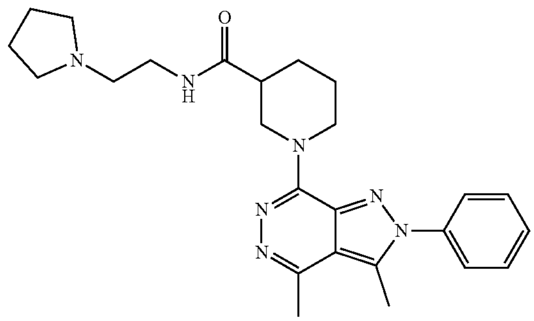 [SMILES: Cc1nnc(N2CCCC(C(=O)NCCN3CCCC3)C2)c2nn(-c3ccccc3)c(C)c12] | 1-(3,4-dimethyl-2-phenyl-2H-pyrazolo[3,4-d]pyridazin-7-yl)-N-(2-(pyrrolidin-1-yl)ethyl)piperidine-3-carboxamide; 3-Piperidinecarboxamide, 1-(3,4-dimethyl-2-phenyl-2H-pyrazolo[3,4-d]pyridazin-7-yl)-N-[2-(1-pyrrolidinyl)ethyl]- |
| 39x | 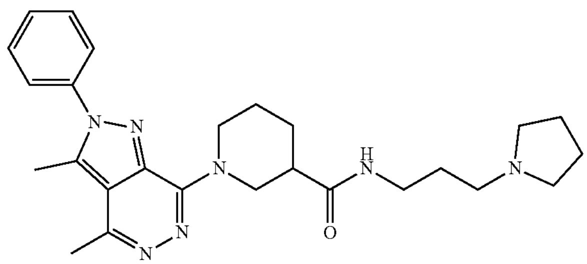 [SMILES: Cc1nnc(N2CCCC(C(=O)NCCCN3CCCC3)C2)c2nn(-c3ccccc3)c(C)c12] | 1-(3,4-dimethyl-2-phenyl-2H-pyrazolo[3,4-d]pyridazin-7-yl)-N-(3-(pyrrolidin-1-yl)propyl)piperidine-3-carboxamide; 3-Piperidinecarboxamide, 1-(3,4-dimethyl-2-phenyl-2H-pyrazolo[3,4-d]pyridazin-7-yl)-N-[3-(1-pyrrolidinyl)propyl]- |
| 40x | 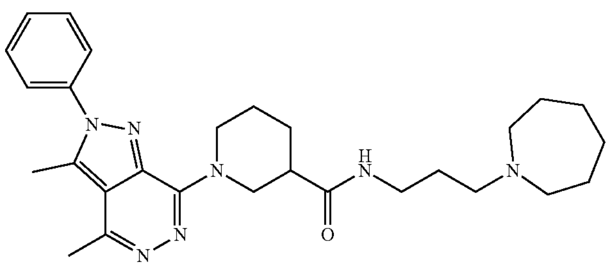 [SMILES: Cc1nnc(N2CCCC(C(=O)NCCCN3CCCCCC3)C2)c2nn(-c3ccccc3)c(C)c12] | N-(3-(azepan-1-yl)propyl)-1-(3,4-dimethyl-2-phenyl-2H-pyrazolo[3,4-d]pyridazin-7-yl)piperidine-3-carboxamide; 3-Piperidinecarboxamide, 1-(3,4-dimethyl-2-phenyl-2H-pyrazolo[3,4-d]pyridazin-7-yl)-N-[3-(hexahydro-1H-azepin-1-yl)propyl]- |
| 41x | 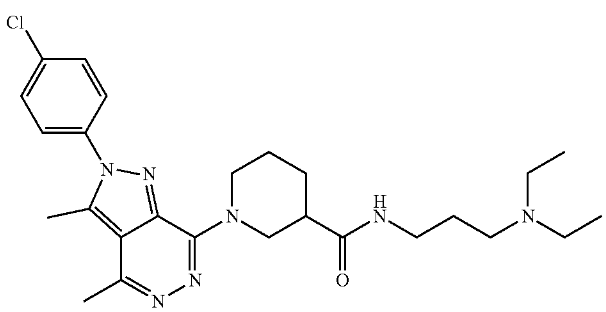 [SMILES: CCN(CC)CCCNC(=O)C1CCCN(c2nnc(C)c3c(C)n(-c4ccc(Cl)cc4)nc23)C1] | 1-(2-(4-chlorophenyl)-3,4-dimethyl-2H-pyrazolo[3,4-d]pyridazin-7-yl)-N-(3-(diethylamino)propyl)piperidine-3-carboxamide; 3-Piperidinecarboxamide, 1-[2-(4-chlorophenyl)-3,4-dimethyl-2H-pyrazolo[3,4-d]pyridazin-7-yl]-N-[3-(diethylamino)propyl]- |
| 42x | 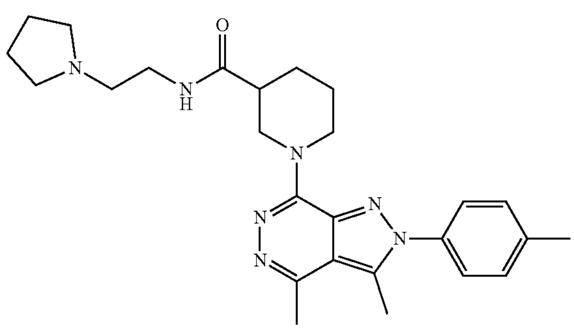 [SMILES: Cc1ccc(-n2nc3c(N4CCCC(C(=O)NCCN5CCCC5)C4)nnc(C)c3c2C)cc1] | 1-(3,4-dimethyl-2-(p-tolyl)-2H-pyrazolo[3,4-d]pyridazin-7-yl)-N-(2-(pyrrolidin-1-yl)ethyl)piperidine-3-carboxamide; 3-Piperidinecarboxamide, 1-[3,4-dimethyl-2-(4-methylphenyl)-2H-pyrazolo[3,4-d]pyridazin-7-yl]-N-[2-(1-pyrrolidinyl)ethyl]- |

TABLE 1X-continued

| Compound No. | Structure | Chemical Name [1] |
|---|---|---|
| 43x | 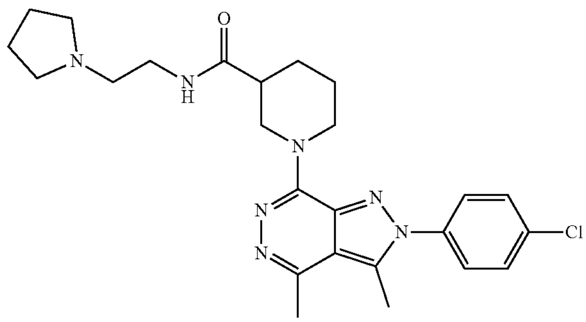 [SMILES: Cc1nnc(N2CCCC(C(=O)NCCN3CCCC3)C2)c2nn(-c3ccc(Cl)cc3)c(C)c12] | 1-(2-(4-chlorophenyl)-3,4-dimethyl-2H-pyrazolo[3,4-d]pyridazin-7-yl)-N-(2-(pyrrolidin-1-yl)ethyl)piperidine-3-carboxamide; 3-Piperidinecarboxamide, 1-[2-(4-chlorophenyl)-3,4-dimethyl-2H-pyrazolo[3,4-d]pyridazin-7-yl]-N-[2-(1-pyrrolidinyl)ethyl]- |
| 44x | 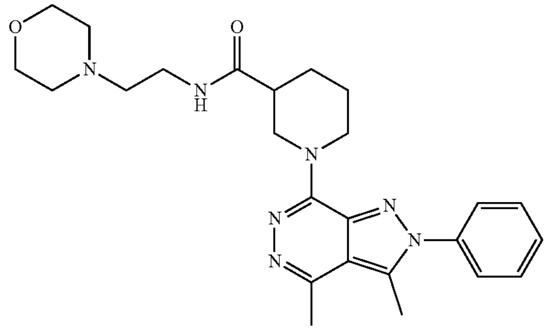 [SMILES: Cc1nnc(N2CCCC(C(=O)NCCN3CCOCC3)C2)c2nn(-c3ccccc3)c(C)c12] | 1-(3,4-dimethyl-2-phenyl-2H-pyrazolo[3,4-d]pyridazin-7-yl)-N-(2-morpholinoethyl)piperidine-3-carboxamide; 3-Piperidinecarboxamide, 1-(3,4-dimethyl-2-phenyl-2H-pyrazolo[3,4-d]pyridazin-7-yl)-N-[2-(4-morpholinyl)ethyl]- |
| 45x | 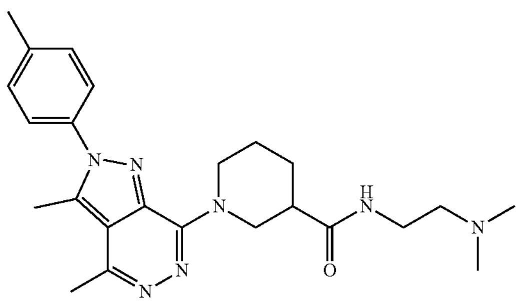 | 1-(3,4-dimethyl-2-(p-tolyl)-2H-pyrazolo[3,4-d]pyridazin-7-yl)-N-(2-(dimethylamino)ethyl)piperidine-3-carboxamide; 3-Piperidinecarboxamide, N-[2-(dimethylamino)ethyl]-1-[3,4-dimethyl-2-(4-methylphenyl)-2H-pyrazolo[3,4-d]pyridazin-7-yl]- |
| 46x | 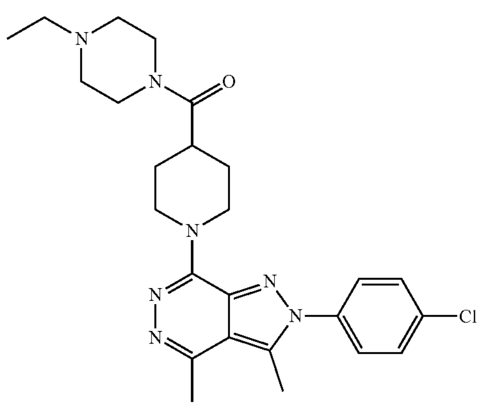 [SMILES: CCN1CCN(C(=O)C2CCN(c3nnc(C)c4c(C)n(-c5ccc(Cl)cc5)nc34)CC2)CC1] | (1-(2-(4-chlorophenyl)-3,4-dimethyl-2H-pyrazolo[3,4-d]pyridazin-7-yl)piperidin-4-yl)(4-ethylpiperazin-1-yl)methanone; Methanone, [1-[2-(4-chlorophenyl)-3,4-dimethyl-2H-pyrazolo[3,4-d]pyridazin-7-yl]-4-piperidinyl](4-ethyl-1-piperazinyl)- |

TABLE 1X-continued

| Compound No. | Structure | Chemical Name [1] |
|---|---|---|
| 47x | 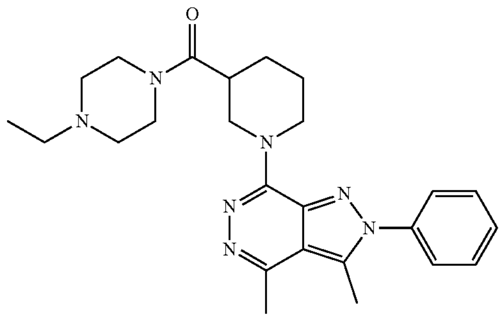 [SMILES: CCN1CCN(C(=O)C2CCCN(c3nnc(C)c4c(C)n(-c5ccccc5)nc34)C2)CC1] | (1-(3,4-dimethyl-2-phenyl-2H-pyrazolo[3,4-d]pyridazin-7-yl)piperidin-3-yl)(4-ethylpiperazin-1-yl)methanone; Methanone, [1-(3,4-dimethyl-2-phenyl-2H-pyrazolo[3,4-d]pyridazin-7-yl)-3-piperidinyl](4-ethyl-1-piperazinyl)- |
| 48x | 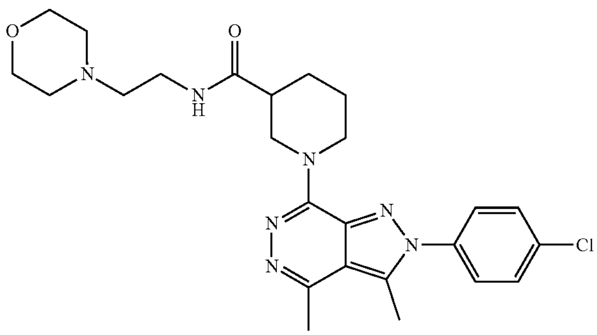 [SMILES: Cc1nnc(N2CCCC(C(=O)NCCN3CCOCC3)C2)c2nn(-c3ccc(Cl)cc3)c(C)c12] | 1-(2-(4-chlorophenyl)-3,4-dimethyl-2H-pyrazolo[3,4-d]pyridazin-7-yl)-N-(2-morpholinoethyl)piperidine-3-carboxamide; 3-Piperidinecarboxamide, 1-[2-(4-chlorophenyl)-3,4-dimethyl-2H-pyrazolo[3,4-d]pyridazin-7-yl]-N-[2-(4-morpholinyl)ethyl]- |
| 49x | 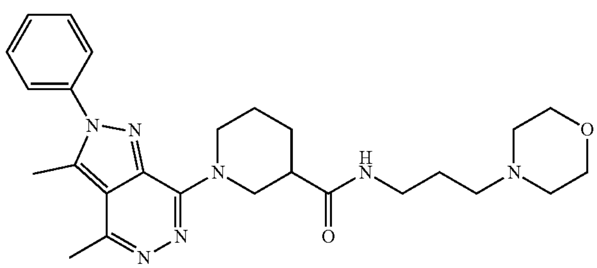 [SMILES: Cc1nnc(N2CCCC(C(=O)NCCCN3CCOCC3)C2)c2nn(-c3ccccc3)c(C)c12] | 1-(3,4-dimethyl-2-phenyl-2H-pyrazolo[3,4-d]pyridazin-7-yl)-N-(3-morpholinopropyl)piperidine-3-carboxamide; 3-Piperidinecarboxamide, 1-(3,4-dimethyl-2-phenyl-2H-pyrazolo[3,4-d]pyridazin-7-yl)-N-[3-(4-morpholinyl)propyl]- |
| 50x | 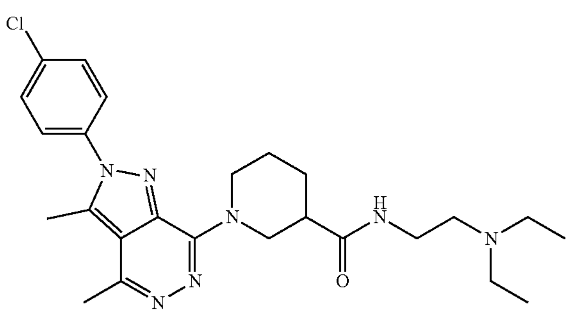 [SMILES: CCN(CC)CCNC(=O)C1CCCN(c2nnc(C)c3c(C)n(-c4ccc(Cl)cc4)nc23)C1] | 1-(2-(4-chlorophenyl)-3,4-dimethyl-2H-pyrazolo[3,4-d]pyridazin-7-yl)-N-(2-(diethylamino)ethyl)piperidine-3-carboxamide; 3-Piperidinecarboxamide, 1-[2-(4-chlorophenyl)-3,4-dimethyl-2H-pyrazolo[3,4-d]pyridazin-7-yl]-N-[2-(diethylamino)ethyl]- |

TABLE 1X-continued

| Compound No. | Structure | Chemical Name [1] |
|---|---|---|
| 51x | 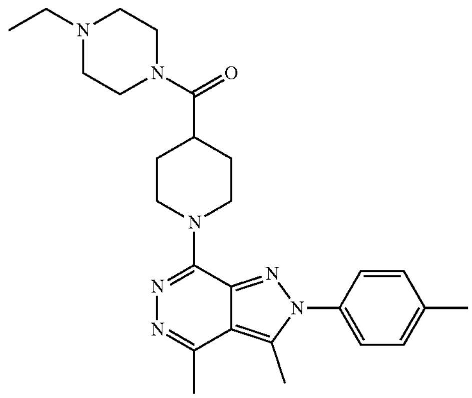 [SMILES: CCN1CCN(C(=O)C2CCN(c3nnc(C)c4c(C)n(-c5ccc(C)cc5)nc34)CC2)CC1] | (1-(3,4-dimethyl-2-(p-tolyl)-2H-pyrazolo[3,4-d]pyridazin-7-yl)piperidin-4-yl)(4-ethylpiperazin-1-yl)methanone; Methanone, [1-[3,4-dimethyl-2-(4-methylphenyl)-2H-pyrazolo[3,4-d]pyridazin-7-yl]-4-piperidinyl](4-ethyl-1-piperazinyl)- |
| 52x | 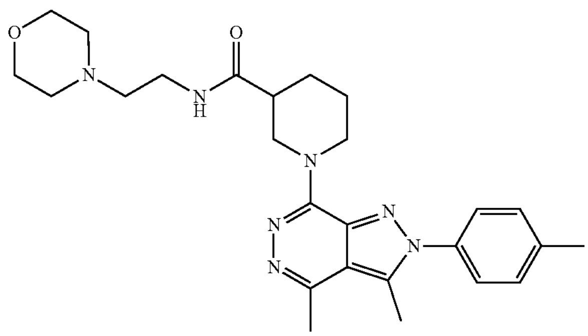 [SMILES: Cc1ccc(-n2nc3c(N4CCCC(C(=O)NCCN5CCOCC5)C4)nnc(C)c3c2C)cc1] | 1-(3,4-dimethyl-2-(p-tolyl)-2H-pyrazolo[3,4-d]pyridazin-7-yl)-N-(2-morpholinoethyl)piperidine-3-carboxamide; 3-Piperidinecarboxamide, 1-[3,4-dimethyl-2-(4-methylphenyl)-2H-pyrazolo[3,4-d]pyridazin-7-yl]-N-[2-(4-morpholinyl)ethyl]- |
| 53x | 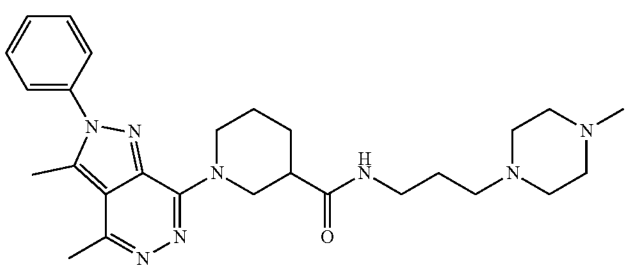 [SMILES: Cc1nnc(N2CCCC(C(=O)NCCCN3CCN(C)CC3)C2)c2nn(-c3ccccc3)c(C)c12] | 1-(3,4-dimethyl-2-phenyl-2H-pyrazolo[3,4-d]pyridazin-7-yl)-N-(3-(4-methylpiperazin-1-yl)propyl)piperidine-3-carboxamide; 3-Piperidinecarboxamide, 1-(3,4-dimethyl-2-phenyl-2H-pyrazolo[3,4-d]pyridazin-7-yl)-N-[3-(4-methyl-1-piperazinyl)propyl]- |
| 54x | 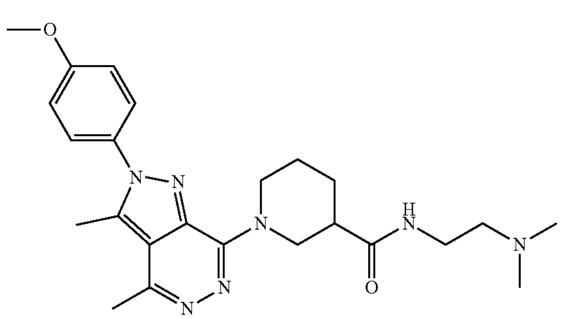 | N-(2-(dimethylamino)ethyl)-1-(2-(4-methoxyphenyl)-3,4-dimethyl-2H-pyrazolo[3,4-d]pyridazin-7-yl)piperidine-3-carboxamide; 3-Piperidinecarboxamide, N-[2-(dimethylamino)ethyl]-1-[2-(4-methoxyphenyl)-3,4-dimethyl-2H-pyrazolo[3,4-d]pyridazin-7-yl]- |

TABLE 1X-continued

| Compound No. | Structure | Chemical Name [1] |
|---|---|---|
| 55x | 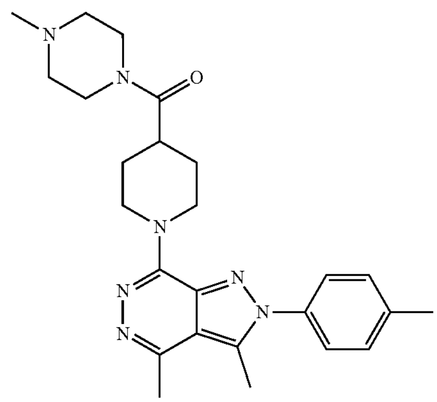 | (1-(3,4-dimethyl-2-(p-tolyl)-2H-pyrazolo[3,4-d]pyridazin-7-yl)piperidin-4-yl)(4-methylpiperazin-1-yl)methanone; Methanone, [1-[3,4-dimethyl-2-(4-methylphenyl)-2H-pyrazolo[3,4-d]pyridazin-7-yl]-4-piperidinyl](4-methyl-1-piperazinyl)- |
| 56x | 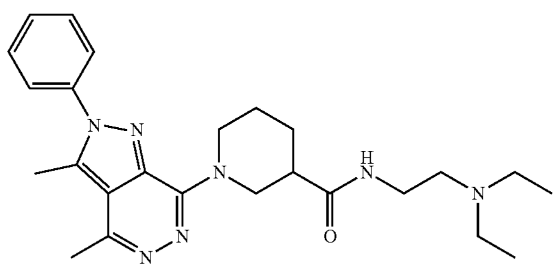 [SMILES: CCN(CC)CCNC(=O)C1CCCN(c2nnc(C)c3c(C)n(-c4ccccc4)nc23)C1] | N-(2-(diethylamino)ethyl)-1-(3,4-dimethyl-2-phenyl-2H-pyrazolo[3,4-d]pyridazin-7-yl)piperidine-3-carboxamide; N-(2-(diethylamino)ethyl)-1-(3,4-dimethyl-2-phenyl-2H-pyrazolo[3,4-d]pyridazin-7-yl)piperidine-3-carboxamide |
| 57x | 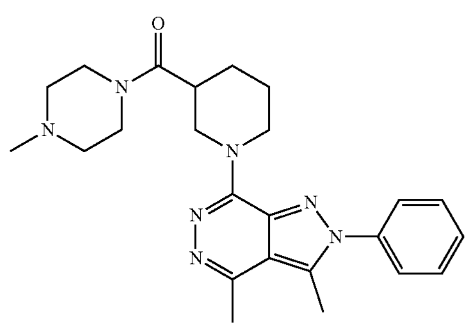 [SMILES: Cc1nnc(N2CCCC(C(=O)N3CCN(C)CC3)C2)c2nn(-c3ccccc3)c(C)c12] | (1-(3,4-dimethyl-2-phenyl-2H-pyrazolo[3,4-d]pyridazin-7-yl)piperidin-3-yl)(4-methylpiperazin-1-yl)methanone; (1-(3,4-dimethyl-2-phenyl-2H-pyrazolo[3,4-d]pyridazin-7-yl)piperidin-3-yl)(4-methylpiperazin-1-yl)methanone |
| 58x | 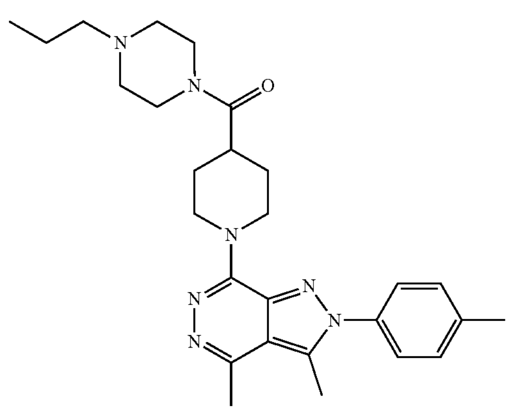 [SMILES: CCCN1CCN(C(=O)C2CCN(c3nnc(C)c4c(C)n(-c5ccc(C)cc5)nc34)CC2)CC1] | (1-(3,4-dimethyl-2-(p-tolyl)-2H-pyrazolo[3,4-d]pyridazin-7-yl)piperidin-4-yl)(4-propylpiperazin-1-yl)methanone; (1-(3,4-dimethyl-2-(p-tolyl)-2H-pyrazolo[3,4-d]pyridazin-7-yl)piperidin-4-yl)(4-propylpiperazin-1-yl)methanone |

TABLE 1X-continued

| Compound No. | Structure | Chemical Name [1] |
|---|---|---|
| 59x | 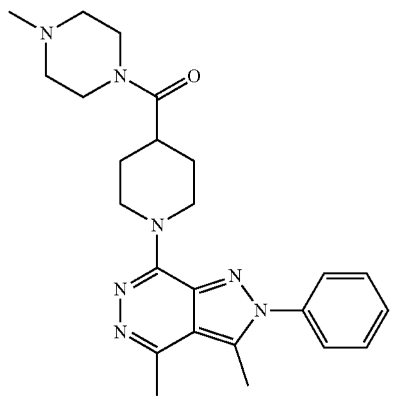 [SMILES: Cc1nnc(N2CCC(C(=O)N3CCN(C)CC3)CC2)c2nn(-c3ccccc3)c(C)c12] | (1-(3,4-dimethyl-2-phenyl-2H-pyrazolo[3,4-d]pyridazin-7-yl)piperidin-4-yl)(4-methylpiperazin-1-yl)methanone; (1-(3,4-dimethyl-2-phenyl-2H-pyrazolo[3,4-d]pyridazin-7-yl)piperidin-4-yl)(4-methylpiperazin-1-yl)methanone |
| 60x | 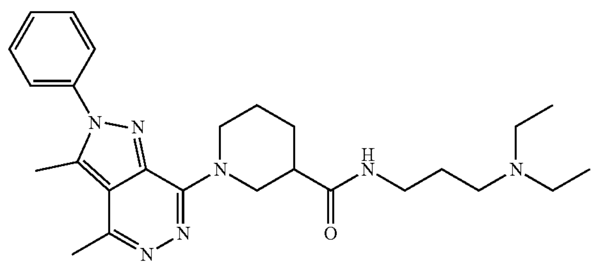 [SMILES: CCN(CC)CCCNC(=O)C1CCCN(c2nnc(C)c3c(C)n(-c4ccccc4)nc23)C1] | N-(3-(diethylamino)propyl)-1-(3,4-dimethyl-2-phenyl-2H-pyrazolo[3,4-d]pyridazin-7-yl)piperidine-3-carboxamide; N-(3-(diethylamino)propyl)-1-(3,4-dimethyl-2-phenyl-2H-pyrazolo[3,4-d]pyridazin-7-yl)piperidine-3-carboxamide |
| 61x | 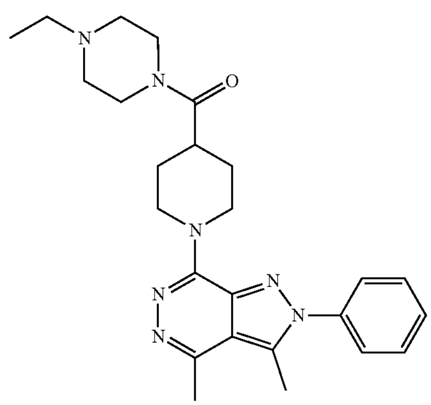 [SMILES: CCN1CCN(C(=O)C2CCN(c3nnc(C)c4c(C)n(-c5ccccc5)nc34)CC2)CC1] | (1-(3,4-dimethyl-2-phenyl-2H-pyrazolo[3,4-d]pyridazin-7-yl)piperidin-4-yl)(4-ethylpiperazin-1-yl)methanone; (1-(3,4-dimethyl-2-phenyl-2H-pyrazolo[3,4-d]pyridazin-7-yl)piperidin-4-yl)(4-ethylpiperazin-1-yl)methanone |
| 62x | 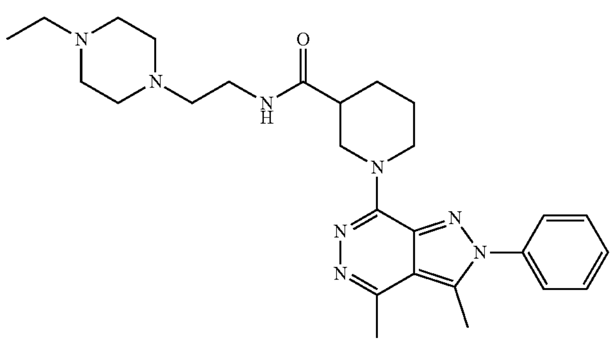 [SMILES: CCN1CCN(CCNC(=O)C2CCCN(c3nnc(C)c4c(C)n(-c5ccccc5)nc34)C2)CC1] | 1-(3,4-dimethyl-2-phenyl-2H-pyrazolo[3,4-d]pyridazin-7-yl)-N-(2-(4-ethylpiperazin-1-yl)ethyl)piperidine-3-carboxamide; 1-(3,4-dimethyl-2-phenyl-2H-pyrazolo[3,4-d]pyridazin-7-yl)-N-(2-(4-ethylpiperazin-1-yl)ethyl)piperidine-3-carboxamide |

TABLE 1X-continued

| Compound No. | Structure | Chemical Name [1] |
|---|---|---|
| 63x | 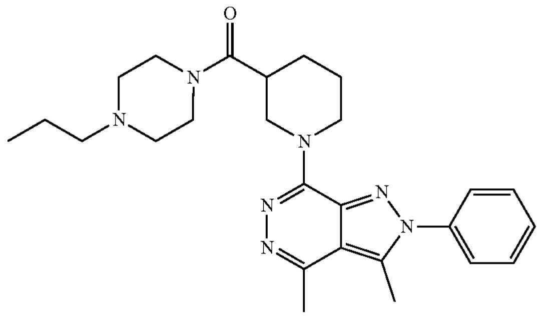 [SMILES: CCCN1CCN(C(=O)C2CCCN(c3nnc(C)c4c(C)n(-c5ccccc5)nc34)C2)CC1] | (1-(3,4-dimethyl-2-phenyl-2H-pyrazolo[3,4-d]pyridazin-7-yl)piperidin-3-yl)(4-propylpiperazin-1-yl)methanone; (1-(3,4-dimethyl-2-phenyl-2H-pyrazolo[3,4-d]pyridazin-7-yl)piperidin-3-yl)(4-propylpiperazin-1-yl)methanone |
| 64x | 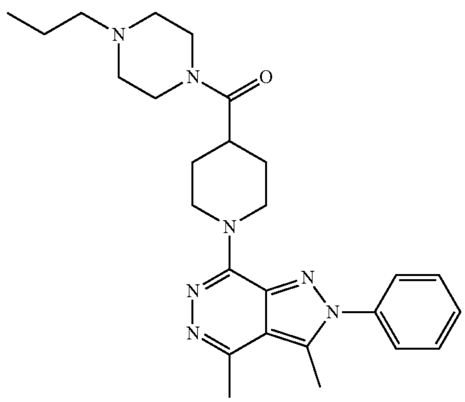 [SMILES: CCCN1CCN(C(=O)C2CCN(c3nnc(C)c4c(C)n(-c5ccccc5)nc34)CC2)CC1] | (1-(3,4-dimethyl-2-phenyl-2H-pyrazolo[3,4-d]pyridazin-7-yl)piperidin-4-yl)(4-propylpiperazin-1-yl)methanone; (1-(3,4-dimethyl-2-phenyl-2H-pyrazolo[3,4-d]pyridazin-7-yl)piperidin-4-yl)(4-propylpiperazin-1-yl)methanone |
| 65x | 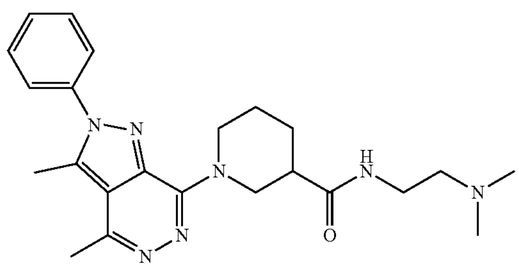 [SMILES: Cc1nnc(N2CCCC(C(=O)NCCN(C)C)C2)c2nn(-c3ccccc3)c(C)c12] | 1-(3,4-dimethyl-2-phenyl-2H-pyrazolo[3,4-d]pyridazin-7-yl)-N-(2-(dimethylamino)ethyl)piperidine-3-carboxamide; 1-(3,4-dimethyl-2-phenyl-2H-pyrazolo[3,4-d]pyridazin-7-yl)-N-(2-(dimethylamino)ethyl)piperidine-3-carboxamide |
| 66x | 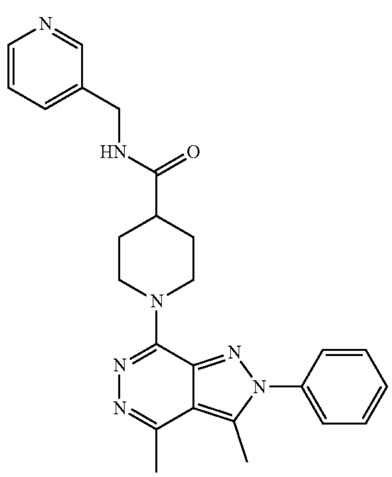 [SMILES: Cc1nnc(N2CCC(C(=O)NCc3cccnc3)CC2)c2nn(-c3ccccc3)c(C)c12] | 1-(3,4-dimethyl-2-phenyl-2H-pyrazolo[3,4-d]pyridazin-7-yl)-N-(pyridin-3-ylmethyl)piperidine-4-carboxamide; 4-Piperidinecarboxamide, 1-(3,4-dimethyl-2-phenyl-2H-pyrazolo[3,4-d]pyridazin-7-yl)-N-(3-pyridinylmethyl)- |

TABLE 1X-continued

| Compound No. | Structure | Chemical Name [1] |
|---|---|---|
| 67x | 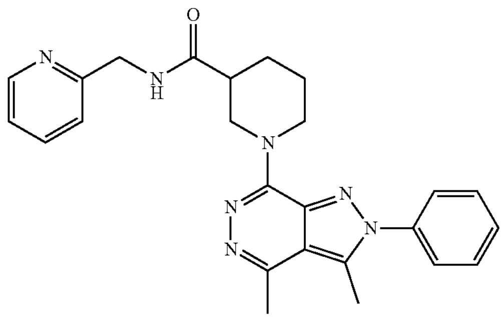 [SMILES: Cc1nnc(N2CCCC(C(=O)NCc3ccccn3)C2)c2nn(-c3ccccc3)c(C)c12] | 1-(3,4-dimethyl-2-phenyl-2H-pyrazolo[3,4-d]pyridazin-7-yl)-N-(pyridin-2-ylmethyl)piperidine-3-carboxamide; 3-Piperidinecarboxamide, 1-(3,4-dimethyl-2-phenyl-2H-pyrazolo[3,4-d]pyridazin-7-yl)-N-(2-pyridinylmethyl)- |
| 68x | 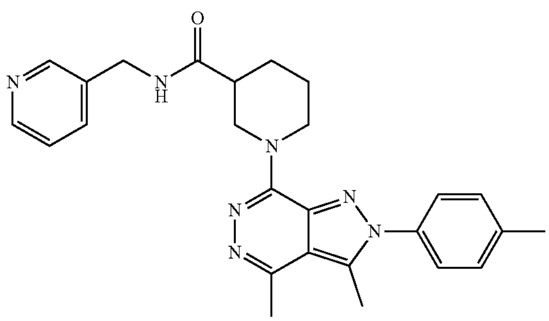 [SMILES: Cc1ccc(-n2nc3c(N4CCCC(C(=O)NCc5cccnc5)C4)nnc(C)c3c2C)cc1] | 1-(3,4-dimethyl-2-(p-tolyl)-2H-pyrazolo[3,4-d]pyridazin-7-yl)-N-(pyridin-3-ylmethyl)piperidine-3-carboxamide; 3-Piperidinecarboxamide, 1-[3,4-dimethyl-2-(4-methylphenyl)-2H-pyrazolo[3,4-d]pyridazin-7-yl]-N-(3-pyridinylmethyl)- |
| 69x | 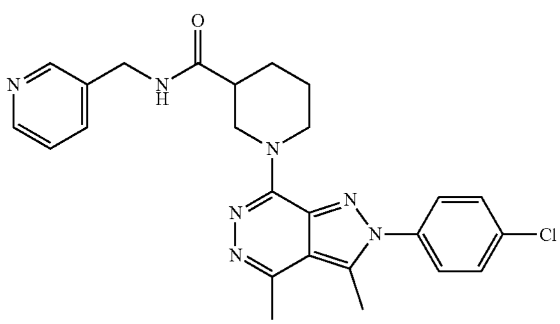 [SMILES: Cc1nnc(N2CCCC(C(=O)NCc3cccnc3)C2)c2nn(-c3ccc(Cl)cc3)c(C)c12] | 1-(2-(4-chlorophenyl)-3,4-dimethyl-2H-pyrazolo[3,4-d]pyridazin-7-yl)-N-(pyridin-3-ylmethyl)piperidine-3-carboxamide; 3-Piperidinecarboxamide, 1-[2-(4-chlorophenyl)-3,4-dimethyl-2H-pyrazolo[3,4-d]pyridazin-7-yl]-N-(3-pyridinylmethyl)- |
| 70x | 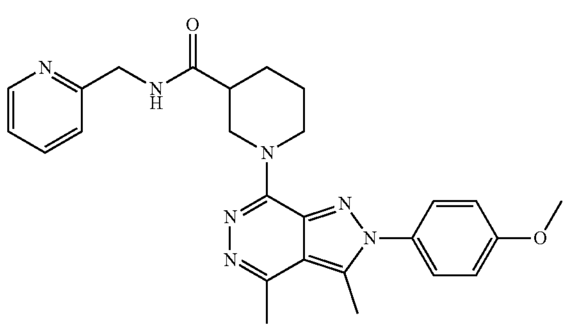 [SMILES: COc1ccc(-n2nc3c(N4CCCC(C(=O)NCc5ccccn5)C4)nnc(C)c3c2C)cc1] | 1-(2-(4-methoxyphenyl)-3,4-dimethyl-2H-pyrazolo[3,4-d]pyridazin-7-yl)-N-(pyridin-2-ylmethyl)piperidine-3-carboxamide; 3-Piperidinecarboxamide, 1-[2-(4-methoxyphenyl)-3,4-dimethyl-2H-pyrazolo[3,4-d]pyridazin-7-yl]-N-(2-pyridinylmethyl)- |

TABLE 1X-continued

| Compound No. | Structure | Chemical Name [1] |
|---|---|---|
| 71x | 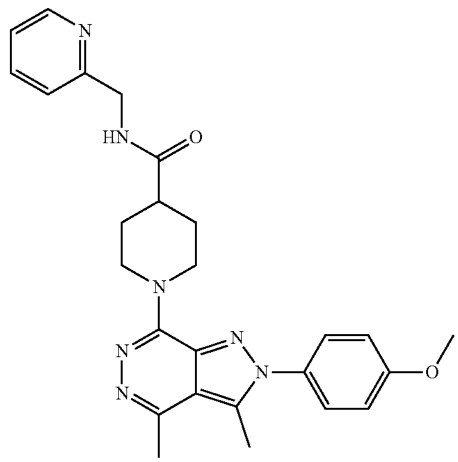 [SMILES: COc1ccc(-n2nc3c(N4CCC(C(=O)NCc5ccccn5)CC4)nnc(C)c3c2C)cc1] | 1-(2-(4-methoxyphenyl)-3,4-dimethyl-2H-pyrazolo[3,4-d]pyridazin-7-yl)-N-(pyridin-2-ylmethyl)piperidine-4-carboxamide; 4-Piperidinecarboxamide, 1-[2-(4-methoxyphenyl)-3,4-dimethyl-2H-pyrazolo[3,4-d]pyridazin-7-yl]-N-(2-pyridinylmethyl)- |
| 72x | 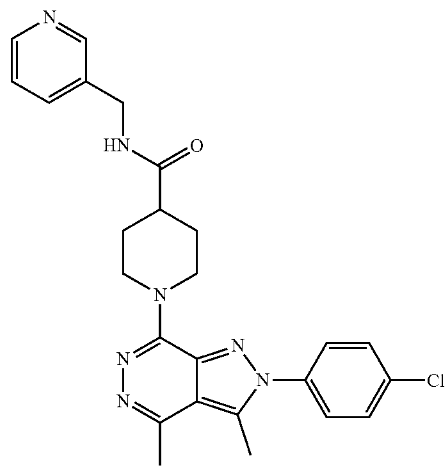 [SMILES: Cc1nnc(N2CCC(C(=O)NCc3cccnc3)CC2)c2nn(-c3ccc(Cl)cc3)c(C)c12] | 1-(2-(4-chlorophenyl)-3,4-dimethyl-2H-pyrazolo[3,4-d]pyridazin-7-yl)-N-(pyridin-3-ylmethyl)piperidine-4-carboxamide; 4-Piperidinecarboxamide, 1-[2-(4-chlorophenyl)-3,4-dimethyl-2H-pyrazolo[3,4-d]pyridazin-7-yl]-N-(3-pyridinylmethyl)- |
| 73x | 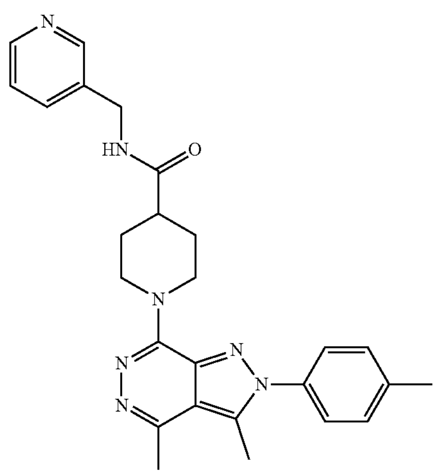 [SMILES: Cc1ccc(-n2nc3c(N4CCC(C(=O)NCc5cccnc5)CC4)nnc(C)c3c2C)cc1] | 1-(3,4-dimethyl-2-(p-tolyl)-2H-pyrazolo[3,4-d]pyridazin-7-yl)-N-(pyridin-3-ylmethyl)piperidine-4-carboxamide; 4-Piperidinecarboxamide, 1-[3,4-dimethyl-2-(4-methylphenyl)-2H-pyrazolo[3,4-d]pyridazin-7-yl]-N-(3-pyridinylmethyl)- |

TABLE 1X-continued

| Compound No. | Structure | Chemical Name [1] |
|---|---|---|
| 74x | 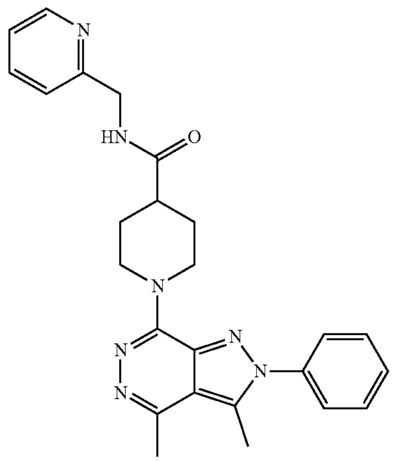 [SMILES: Cc1nnc(N2CCC(C(=O)NCc3ccccn3)CC2)c2nn(-c3ccccc3)c(C)c12] | 1-(3,4-dimethyl-2-phenyl-2H-pyrazolo[3,4-d]pyridazin-7-yl)-N-(pyridin-2-ylmethyl)piperidine-4-carboxamide; 4-Piperidinecarboxamide, 1-(3,4-dimethyl-2-phenyl-2H-pyrazolo[3,4-d]pyridazin-7-yl)-N-(2-pyridinylmethyl)- |
| 75x | 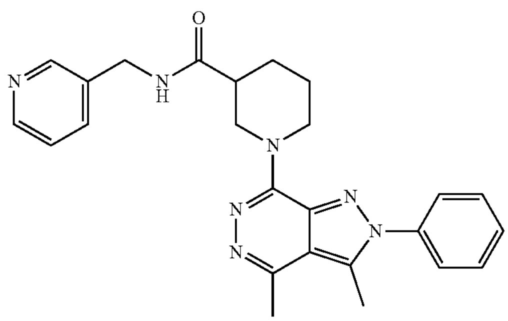 [SMILES: Cc1nnc(N2CCCC(C(=O)NCc3cccnc3)C2)c2nn(-c3ccccc3)c(C)c12] | 1-(3,4-dimethyl-2-phenyl-2H-pyrazolo[3,4-d]pyridazin-7-yl)-N-(pyridin-3-ylmethyl)piperidine-3-carboxamide; 3-Piperidinecarboxamide, 1-(3,4-dimethyl-2-phenyl-2H-pyrazolo[3,4-d]pyridazin-7-yl)-N-(3-pyridinylmethyl)- |
| 76x | 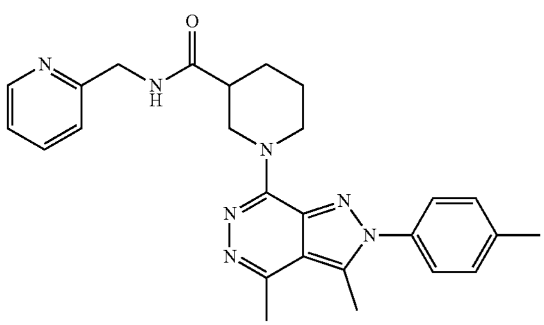 [SMILES: Cc1ccc(-n2nc3c(N4CCCC(C(=O)NCc5ccccn5)C4)nnc(C)c3c2C)cc1] | 1-(3,4-dimethyl-2-(p-tolyl)-2H-pyrazolo[3,4-d]pyridazin-7-yl)-N-(pyridin-2-ylmethyl)piperidine-3-carboxamide; 3-Piperidinecarboxamide, 1-[3,4-dimethyl-2-(4-methylphenyl)-2H-pyrazolo[3,4-d]pyridazin-7-yl]-N-(2-pyridinylmethyl)- |
| 77x | 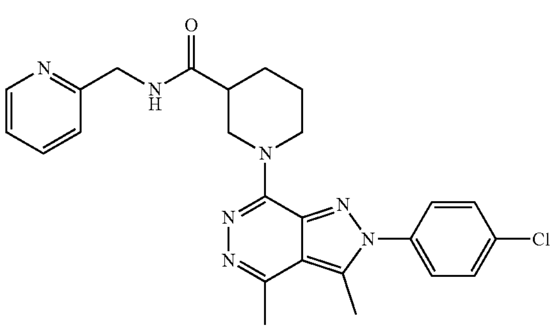 [SMILES: Cc1nnc(N2CCCC(C(=O)NCc3ccccn3)C2)c2nn(-c3ccc(Cl)cc3)c(C)c12] | 1-(2-(4-chlorophenyl)-3,4-dimethyl-2H-pyrazolo[3,4-d]pyridazin-7-yl)-N-(pyridin-2-ylmethyl)piperidine-3-carboxamide; 3-Piperidinecarboxamide, 1-[2-(4-chlorophenyl)-3,4-dimethyl-2H-pyrazolo[3,4-d]pyridazin-7-yl]-N-(2-pyridinylmethyl)- |

TABLE 1X-continued

| Compound No. | Structure | Chemical Name [1] |
|---|---|---|
| 78x | 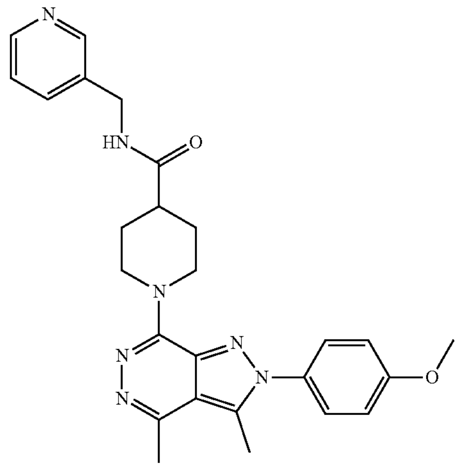 [SMILES: COc1ccc(-n2nc3c(N4CCC(C(=O)NCc5cccnc5)CC4)nnc(C)c3c2C)cc1] | 1-(2-(4-methoxyphenyl)-3,4-dimethyl-2H-pyrazolo[3,4-d]pyridazin-7-yl)-N-(pyridin-3-ylmethyl)piperidine-4-carboxamide; 4-Piperidinecarboxamide, 1-[2-(4-methoxyphenyl)-3,4-dimethyl-2H-pyrazolo[3,4-d]pyridazin-7-yl]-N-(3-pyridinylmethyl)- |
| 79x | 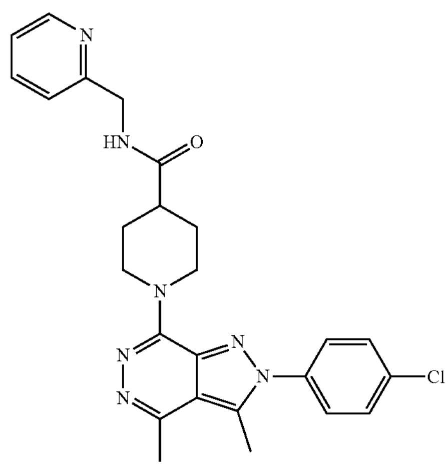 [SMILES: Cc1nnc(N2CCC(C(=O)NCc3ccccn3)CC2)c2nn(-c3ccc(Cl)cc3)c(C)c12] | 1-(2-(4-chlorophenyl)-3,4-dimethyl-2H-pyrazolo[3,4-d]pyridazin-7-yl)-N-(pyridin-2-ylmethyl)piperidine-4-carboxamide; 4-Piperidinecarboxamide, 1-[2-(4-chlorophenyl)-3,4-dimethyl-2H-pyrazolo[3,4-d]pyridazin-7-yl]-N-(2-pyridinylmethyl)- |
| 80x | 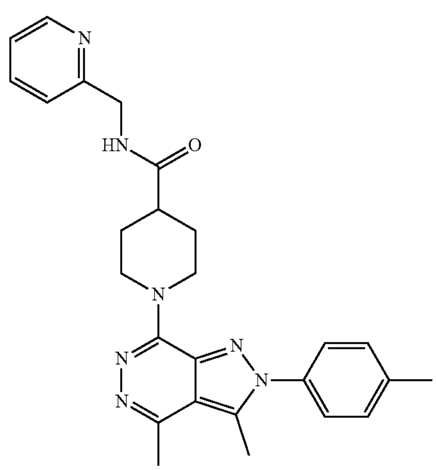 [SMILES: Cc1ccc(-n2nc3c(N4CCC(C(=O)NCc5ccccn5)CC4)nnc(C)c3c2C)cc1] | 1-(3,4-dimethyl-2-(p-tolyl)-2H-pyrazolo[3,4-d]pyridazin-7-yl)-N-(pyridin-2-ylmethyl)piperidine-4-carboxamide; 4-Piperidinecarboxamide, 1-[3,4-dimethyl-2-(4-methylphenyl)-2H-pyrazolo[3,4-d]pyridazin-7-yl]-N-(2-pyridinylmethyl)- |

TABLE 1X-continued

| Compound No. | Structure | Chemical Name [1] |
|---|---|---|
| 81x | 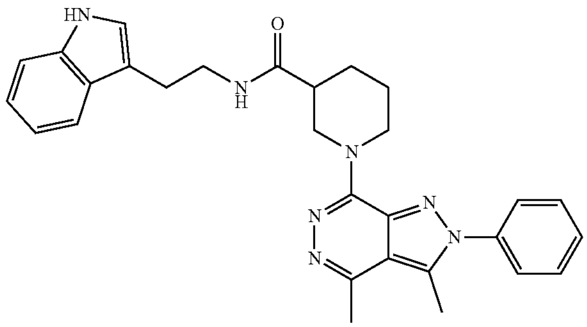 [SMILES: Cc1nnc(N2CCCC(C(=O)NCCc3c[nH]c4ccccc34)C2)c2nn(-c3ccccc3)c(C)c12] | N-(2-(1H-indol-3-yl)ethyl)-1-(3,4-dimethyl-2-phenyl-2H-pyrazolo[3,4-d]pyridazin-7-yl)piperidine-3-carboxamide; 3-Piperidinecarboxamide, 1-(3,4-dimethyl-2-phenyl-2H-pyrazolo[3,4-d]pyridazin-7-yl)-N-[2-(1H-indol-3-yl)ethyl]- |
| 82x | 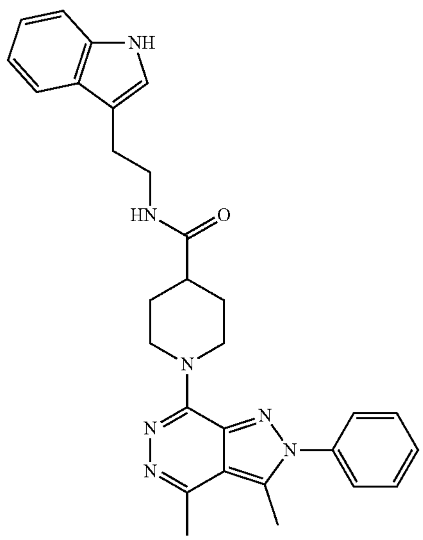 [SMILES: Cc1nnc(N2CCC(C(=O)NCCc3c[nH]c4ccccc34)CC2)c2nn(-c3ccccc3)c(C)c12] | N-(2-(1H-indol-3-yl)ethyl)-1-(3,4-dimethyl-2-phenyl-2H-pyrazolo[3,4-d]pyridazin-7-yl)piperidine-4-carboxamide; 4-Piperidinecarboxamide, 1-(3,4-dimethyl-2-phenyl-2H-pyrazolo[3,4-d]pyridazin-7-yl)-N-[2-(1H-indol-3-yl)ethyl]- |
| 83x | 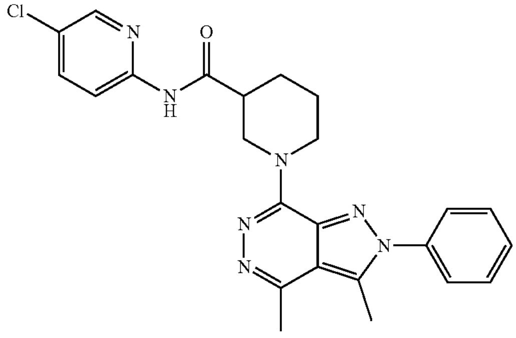 [SMILES: Cc1nnc(N2CCCC(C(=O)Nc3ccc(Cl)cn3)C2)c2nn(-c3ccccc3)c(C)c12] | N-(5-chloropyridin-2-yl)-1-(3,4-dimethyl-2-phenyl-2H-pyrazolo[3,4-d]pyridazin-7-yl)piperidine-3-carboxamide; 3-Piperidinecarboxamide, N-(5-chloro-2-pyridinyl)-1-(3,4-dimethyl-2-phenyl-2H-pyrazolo[3,4-d]pyridazin-7-yl)- |

[1] Chemical names are either index names (IN) or chemical names (CN) for the compound as in CAS Registry ® database, and generated using the ChemBioDraw ® Ultra version 14.0.0.117 or 16.0.0.82 (68) software.

In one embodiment of the compound of the formula (I), U is a bond (ring A is directly attached to the ring nitrogen of ring B), the compound having the formula (I⁰):

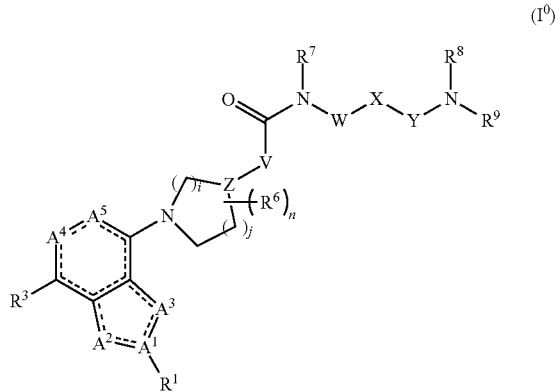

or a salt or solvate thereof, wherein $A^1$, $A^2$, $A^3$, $A^4$, $A^5$, $R^1$, $R^3$, $R^6$, $R^7$, $R^8$, $R^9$, V, W, X, Y, i, j, and n are as defined for formula (I).

In some embodiments of the compound of formula (A-I), (I) or (I⁰), or a salt or solvate thereof, ring A contains 2 to 4 ring nitrogen atoms. In some embodiments, at least two of $A^1$, $A^2$, $A^3$, $A^4$ and $A^5$ are N (or $NR^{2a}$ for $A^2$, or $NR^{3a}$ for $A^3$). In some embodiments, at least three of $A^1$, $A^2$, $A^3$, $A^4$ and $A^5$ are N (or $NR^{2a}$ for $A^2$, or $NR^{3a}$ for $A^3$). In some embodiments, two of $A^1$, $A^2$, $A^3$, $A^4$ and $A^5$ are N (or $NR^{2a}$ for $A^2$, or $NR^{3a}$ for $A^3$). In some embodiments, three of $A^1$, $A^2$, $A^3$, $A^4$ and $A^5$ are N (or $NR^{2a}$ for $A^2$, or $NR^{3a}$ for $A^3$). In some embodiments, four of $A^1$, $A^2$, $A^3$, $A^4$ and $A^5$ are N (or $NR^{2a}$ for $A^2$, or $NR^{3a}$ for $A^3$).

In some embodiments, $A^1$ is N, $A^2$ is $CR^2$ and $A^3$ is N. In some of these embodiments, $R^2$ is hydrogen. In some of these embodiments, $R^2$ is $C_1$-$C_6$ alkyl optionally substituted by $R^{10A}$. In some of these embodiments, $R^2$ is $C_1$-$C_6$ alkyl (e.g., methyl). In some of these embodiments, $R^2$ is $C_6$-$C_{14}$ aryl optionally substituted by $R^{10A}$. In some of these embodiments, $R^2$ is $C_6$-$C_{14}$ aryl (e.g., phenyl).

In some embodiments, $A^1$ is N, $A^2$ is N and $A^3$ is $CR^{30}$. In some of these embodiments, $R^{30}$ is hydrogen. In some of these embodiments, $R^{30}$ is $C_1$-$C_6$ alkyl optionally substituted by $R^{10A}$. In some of these embodiments, $R^{30}$ is $C_1$-$C_6$ alkyl (e.g., methyl).

In some embodiments, $A^1$ is C, $A^2$ is $CR^2$ and $A^3$ is NH. In some of these embodiments, $R^2$ is hydrogen. In some of these embodiments, $R^2$ is $C_1$-$C_6$ alkyl optionally substituted by $R^{10A}$. In some of these embodiments, $R^2$ is $C_1$-$C_6$ alkyl (e.g., methyl).

In some embodiments, $A^1$ is C, $A^2$ is $NR^{2a}$ and $A^3$ is N. In some of these embodiments, $R^{2a}$ is hydrogen. In some of these embodiments, $R^{2a}$ is $C_1$-$C_6$ alkyl optionally substituted by $R^{10A}$. In some of these embodiments, $R^{2a}$ is $C_1$-$C_6$ alkyl (e.g., methyl).

In some embodiments, $A^4$ is $CR^4$ and $A^5$ is $CR^5$. In some embodiments, $A^4$ is $CR^4$ and $A^5$ is N. In some embodiments, $A^4$ is N and $A^5$ is $CR^5$. In some embodiments, $A^4$ is N and $A^5$ is N. In some of these embodiments, $R^4$ is hydrogen. In some of these embodiments, $R^5$ is hydrogen.

In some embodiments, $A^1$ is C, $A^2$ is $CR^2$, $A^3$ is $NR^{3a}$, $A^4$ is N, and $A^5$ is N. In some of these embodiments, $R^2$ is hydrogen. In some of these embodiments, $R^{3a}$ is hydrogen.

In some embodiments, $A^1$ is N, $A^2$ is $CR^2$, $A^3$ is N, $A^4$ is N, and $A^5$ is $CR^5$. In some of these embodiments, $R^2$ is hydrogen. In some of these embodiments, $R^5$ is hydrogen.

In some embodiments, $A^1$ is N, $A^2$ is $CR^2$, $A^3$ is N, $A^4$ is $CR^4$, and $A^5$ is $CR^5$. In some of these embodiments, $R^2$ is hydrogen. In some of these embodiments, $R^4$ is hydrogen. In some of these embodiments, $R^5$ is hydrogen.

In some embodiments, $A^1$ is C, $A^2$ is $NR^2$, $A^3$ is N, $A^4$ is $CR^4$, and $A^5$ is $CR^5$. In some of these embodiments, $R^2$ is $C_1$-$C_6$ alkyl (e.g., methyl). In some of these embodiments, $R^4$ is hydrogen. In some of these embodiments, $R^5$ is hydrogen.

It is intended and understood that each and every variation of $A^1$, $A^2$ and $A^3$, described herein, may be combined with each and every variation of $A^4$ and $A^5$ described herein, the same as if each and every combination is individually and specifically described. For example, in some embodiments, $A^1$ is N, $A^2$ is $CR^2$, $A^3$ is N, $A^4$ is $CR^4$, and $A^5$ is $CR^5$. In some embodiments, $A^1$ is N, $A^2$ is $CR^2$, $A^3$ is NH, $A^4$ is N, and $A^5$ is $CR^5$. In some embodiments, $A^1$ is C, $A^2$ is $NR^{2a}$, $A^3$ is N, $A^4$ is $CR^4$, and $A^5$ is $CR^5$. In some embodiments, $A^1$ is N, $A^2$ is $CR^2$, $A^3$ is N, $A^4$ is N, and $A^5$ is $CR^5$. In some embodiments, $A^1$ is N, $A^2$ is $CR^2$, $A^3$ is N, $A^4$ is N, and $A^5$ is N. In some of these embodiments, $R^2$ is hydrogen. In some of these embodiments, $R^{2a}$ is methyl. In some of these embodiments, $R^4$ is hydrogen. In some of these embodiments, $R^5$ is hydrogen.

In some embodiments, the compound of the formula (I) is a pyrazolo[3,4-d]pyridazine compound having the formula (Ia):

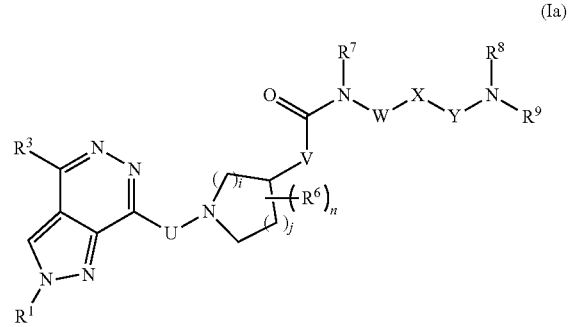

or a salt or solvate thereof, wherein $R^1$, $R^2$, $R^3$, $R^6$, $R^7$, $R^8$, $R^9$, U, V, W, X, Y, i, j, and n are as defined for formula (I).

In some embodiments, the compound of the formula (I), where ring A is pyrazolo[3,4-d]pyridazine and is directly attached to the ring nitrogen of ring B, has the formula (I⁰a):

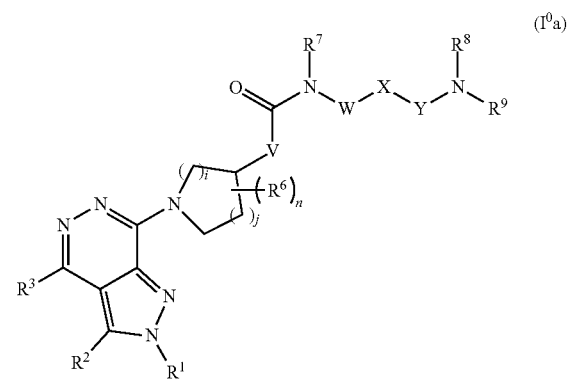

or a salt or solvate thereof, wherein $R^1$, $R^2$, $R^3$, $R^6$, $R^7$, $R^8$, $R^9$, V, W, X, Y, i, j, and n are as defined for formula (I) or (I°).

In some embodiments of the compound of formula (A-I), (I), (Ia), (I°) or (I°a), or a salt or solvate thereof, ring B is a 3- to 7-membered heterocycle containing one ring nitrogen atom. In some embodiments, ring B is a 4- to 6-membered heterocycle containing one ring nitrogen atom. In some embodiments, ring B is a 5- or 6-membered heterocycle containing one ring nitrogen atom. In some embodiments, ring B is a pyrrolidine ring. In some embodiments, ring B is a piperidine ring.

In some embodiments, i is 2 and j is 1 or 2 (ring B is 1-piperdin-4-yl or 1-azepan-4-yl). In some embodiments, i is 1 and j is 2 (ring B is 1-piperdin-3-yl). In some embodiments, i is 1 and j is 1 (ring B is 1-pyrrolidin-3-yl). In some embodiments, i is 1 and j is 0 (ring B is 1-azetidin-3-yl). In some embodiments, i is 0 and j is 0 (ring B is 1-aziridin-2-yl). In some preferred embodiments, i is 2 and j is 1 (ring B is 1-piperdin-4-yl).

It is intended and understood that each and every variation of ring A (e.g., $A^1$, $A^2$, $A^3$, $A^4$ and $A^5$) described herein, may be combined with each and every variation of ring B (e.g., i and j) described herein, the same as if each and every combination is individually and specifically described. For example, in some embodiments, $A^1$ is N, $A^2$ is $CR^2$, $A^3$ is N, $A^4$ is N, $A^5$ is N; i is 2 and j is 1, or i is 1 and j is 2. In some embodiments, $A^1$ is N, $A^2$ is $CR^2$, $A^3$ is N, $A^4$ is N, $A^5$ is N, i is 2 and j is 1.

In some embodiments, the compound of formula (I°a) is of the formula (I°a-1):

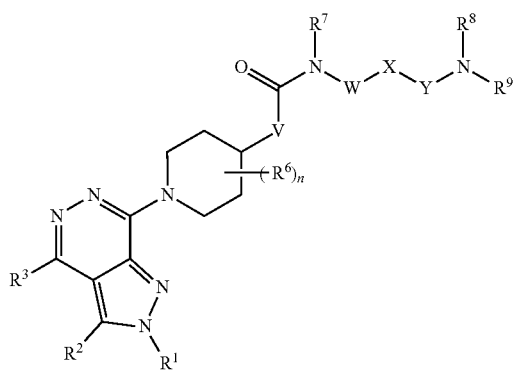

(I°a-1)

or a salt or solvate thereof, wherein $R^1$, $R^2$, $R^3$, $R^6$, $R^7$, $R^8$, $R^9$, V, W, X, Y, and n are as defined for formula (I).

In some embodiments, the compound of formula (I°a-1) is of the formula (I°a-2):

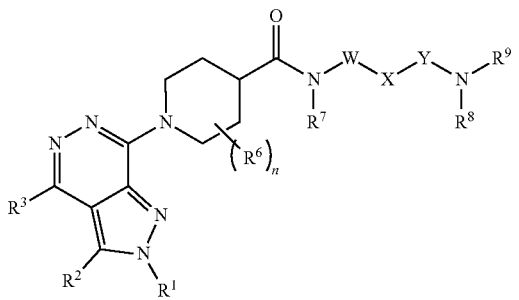

(I°a-2)

or a salt or solvate thereof, wherein $R^1$, $R^2$, $R^3$, $R^6$, $R^7$, $R^8$, $R^9$, W, X, Y, and n are as defined for formula (I).

It is intended and understood that each and every variation of formula (I°) described herein applies to each and every variation of formula (I°a), (I°a-1), and (I°a-2) the same as if each and every variation is individually and specifically described. Similarly, it is intended and understood that each and every variation of formula (I°a) described herein applies to each and every variation of formula (I°a-1) and (I°a-2) the same as if each and every variation is individually and specifically described.

In some embodiments, the compound of the formula (I) is of the formula (II):

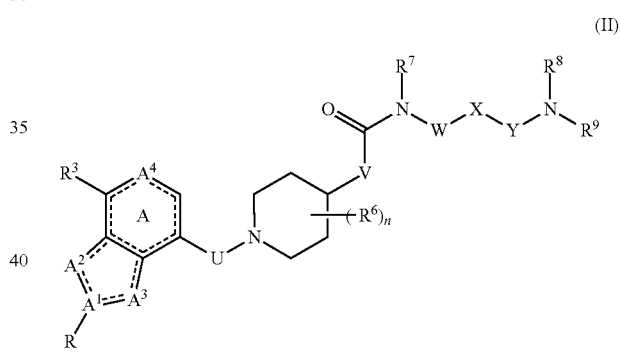

(II)

or a salt or solvate thereof, wherein $A^1$, $A^2$, $A^3$, $A^4$, $A^5$, $R^1$, $R^3$, $R^6$, $R^7$, $R^8$, $R^9$, U, V, W, X, Y, and n are as defined for formula (I).

In some embodiments, the compound of the formula (II) is a pyrazolo[3,4-d]pyridazine compound having the formula (IIa):

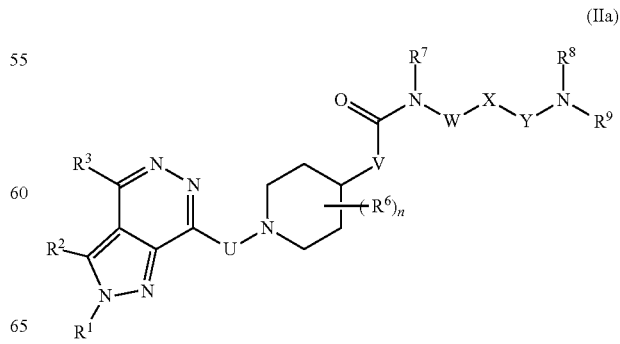

(IIa)

or a salt or solvate thereof, wherein $R^1$, $R^2$, $R^3$, $R^6$, $R^7$, $R^8$, $R^9$, U, V, W, X, Y, and n are as defined for formula (I) or (II), provided that the compound is other than any applicable compound in Table 1X (e.g., Compound Nos. 1x-33x, 37x, 46x, 51x, 55x, 58x, 59x, 61x, 64x, 66x, 71x-74x, 78x-80x, or 82x in Table 1X) and salts thereof.

In some embodiments, the compound of formula (IIa) is of the formula (IIa-1):

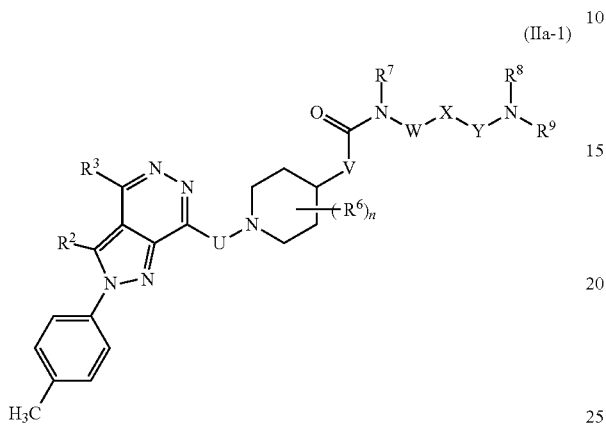

(IIa-1)

or a salt or solvate thereof, wherein $R^2$, $R^3$, $R^6$, $R^7$, $R^8$, $R^9$, U, V, W, X, Y, and n are as defined for formula (I) or any embodiment or variation thereof, provided that the compound is other than any applicable compound in Table 1X (e.g., Compound Nos. 11x-22x, 51x, 55x, 58x, 73x, or 80x in Table 1X) and salts thereof.

In some embodiments, the compound of formula (IIa-1) is of the formula (IIa-1a):

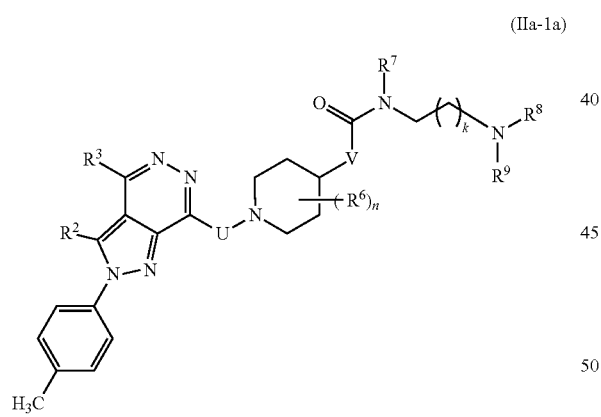

(IIa-1a)

or a salt or solvate thereof, wherein $R^2$, $R^3$, $R^6$, $R^7$, $R^8$, $R^9$, U, V, and n are as defined for formula (I) or any embodiment or variation thereof, k is 1, 2, 3, 4, or 5, provided that the compound is other than any applicable compound in Table 1X (e.g., Compound Nos. 11x-17x or 19x-22x in Table 1X) and salts thereof. In some embodiments, k is 1 or 2. In some embodiments, $R^7$ is hydrogen. In some embodiments, $R^8$ and $R^9$ are each independently hydrogen or $C_1$-$C_6$ alkyl optionally substituted by $R^{10}$. In some embodiments, $R^8$ is methyl and $R^9$ is methyl optionally substituted by $C_6$-$C_{14}$ aryl. In some embodiments, $R^8$ and $R^9$ are each methyl. In some embodiments, $R^8$ is methyl and $R^9$ is benzyl.

In some embodiments, the compound of formula (IIa-1a) is of the formula (IIa-1a-1):

(IIa-1a-1)

or a salt or solvate thereof, wherein $R^2$, $R^3$, $R^6$, $R^7$, U, V, and n are as defined for formula (I) or any embodiment or variation thereof, $R^8$ is hydrogen or methyl optionally substituted by $C_6$-$C_{14}$ aryl, k is 1, 2, 3, 4, or 5, provided that the compound is other than Compound No. 21x in Table 1X and salts thereof. In one embodiment, k is 1 or 2. In some embodiments, $R^7$ is hydrogen. In some embodiments, $R^8$ is methyl optionally substituted by $C_6$-$C_{14}$ aryl. In some embodiments, $R^8$ is methyl. In some embodiments, $R^8$ is benzyl.

In some embodiments, the compound of formula (IIa-1a) is of the formula (IIa-1a-2):

(IIa-1a-2)

or a salt or solvate thereof, wherein $R^2$, $R^3$, $R^6$, $R^8$, $R^9$, V, and n are as defined for formula (I) or any embodiment or variation thereof, k is 1, 2, 3, 4, or 5, provided that the compound is other than any applicable compound in Table 1X (e.g., Compound Nos. 11x-17x or 19x-22x in Table 1X) and salts thereof. In some embodiments, k is 1 or 2. In some embodiments, n is 0. In some embodiments, n is 1 or 2, and each $R^6$ is independently $C_1$-$C_6$ alkyl optionally substituted by $R^{10A}$. In some embodiments, n is 1 and $R^6$ is $C_1$-$C_6$ alkyl (e.g., methyl). In some embodiments, $R^2$ and $R^3$ are each hydrogen. In some embodiments, $R^2$ and $R^3$ are each methyl.

In some embodiments, the compound of formula (IIa-1a-1) is of the formula (IIa-1a-3):

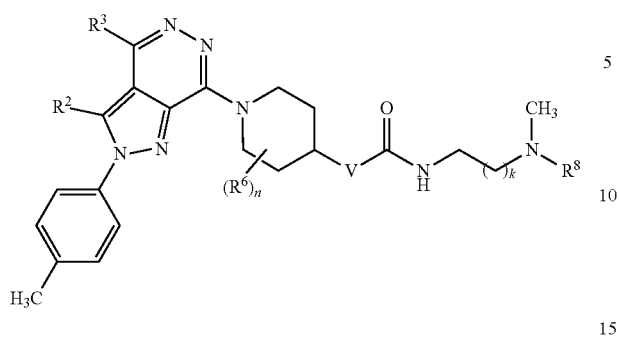

(IIa-1a-3)

or a salt or solvate thereof, wherein $R^2$, $R^3$, $R^6$, V, and n are as defined for formula (I) or any embodiment or variation thereof, $R^8$ is hydrogen or methyl optionally substituted by $C_6$-$C_{14}$ aryl, k is 1, 2, 3, 4, or 5, provided that the compound is other than Compound No. 21x in Table 1X and salts thereof. In some embodiments, k is 1 or 2. In some embodiments, n is 0 or 1. In some embodiments, $R^2$ and $R^3$ are each hydrogen. In some embodiments, $R^2$ and $R^3$ are each methyl. In some embodiments, $R^8$ is methyl optionally substituted by $C_6$-$C_{14}$ aryl. In some embodiments, $R^8$ is methyl. In some embodiments, $R^8$ is benzyl.

In a preferred embodiment, the compound of formula (IIa-1a-3) is Compound No. 1:

Compound No. 1

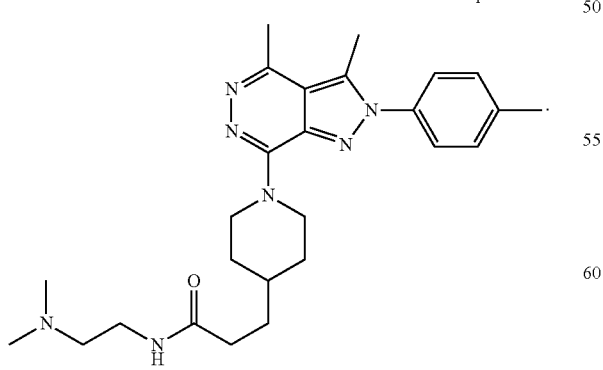

In a preferred embodiment, the compound of formula (IIa-1a-3) is Compound No. 20:

Compound No. 20

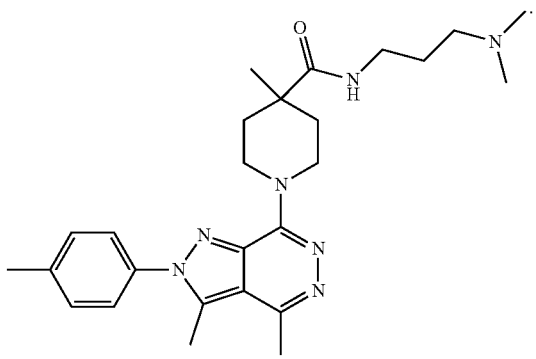

In a preferred embodiment, the compound of formula (IIa-1a-3) is Compound No. 22:

Compound No. 22

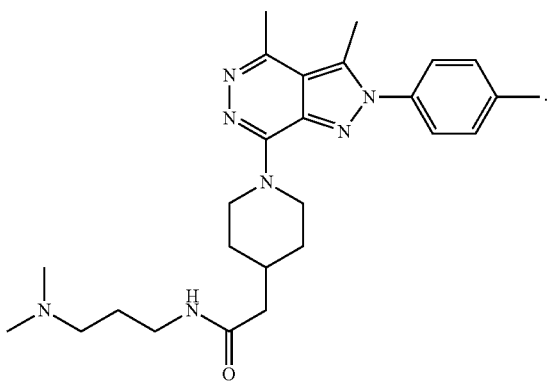

In a preferred embodiment, the compound of formula (IIa-1a-3) is Compound No. 29:

Compound No. 29

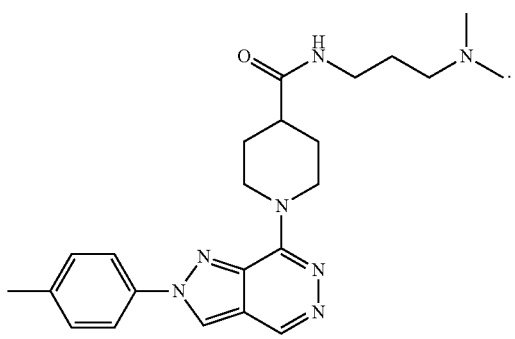

In a preferred embodiment, the compound of formula (IIa-1a-3) is Compound No. 46:

Compound No. 46

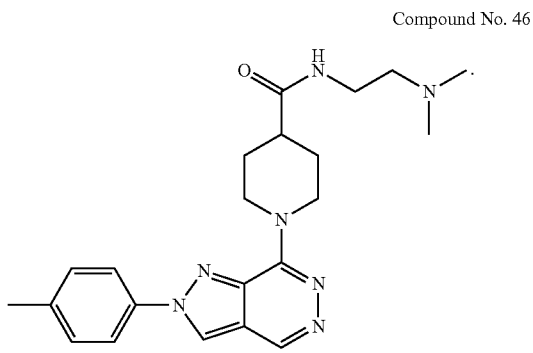

In a preferred embodiment, the compound of formula (IIa-1a-3) is Compound No. 61:

Compound No. 61

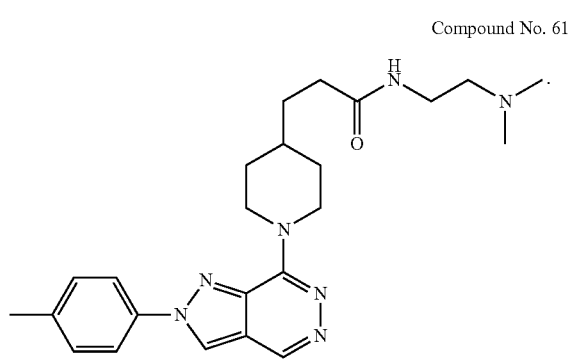

In some embodiments, the compound of formula (IIa-1) is of the formula (IIa-1b):

(IIa-1b)

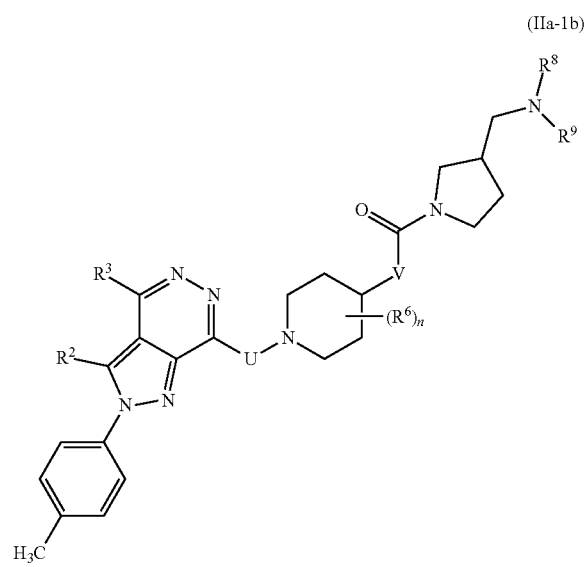

or a salt or solvate thereof, wherein $R^2$, $R^3$, $R^6$, $R^8$, $R^9$, U, V, and n are as defined for formula (I) or any embodiment or variation thereof. In one embodiment, $R^2$ and $R^3$ are each hydrogen. In another embodiment, $R^2$ and $R^3$ are each methyl. In some embodiments, U is a bond. In some embodiments, V is bond. In some embodiments, n is 0. In some embodiments, $R^8$ and $R^9$ are independently $C_1$-$C_6$ alkyl optionally substituted by $R^{10}$. In some embodiments, $R^8$ and $R^9$ are each methyl.

In some embodiments, the compound of formula (IIa-1b) is of the formula (IIa-1b-1):

(IIa-1b-1)

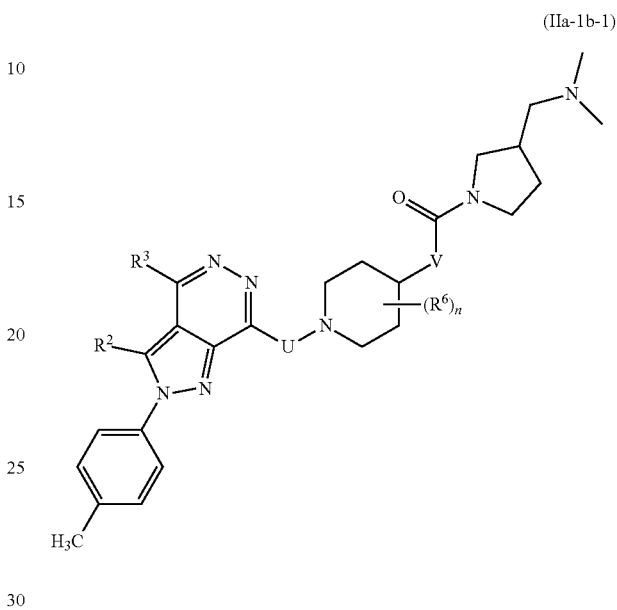

or a salt or solvate thereof, wherein $R^2$, $R^3$, $R^6$, U, V, and n are as defined for formula (I) or any embodiment or variation thereof. In some embodiments, $R^2$ and $R^3$ are each hydrogen. In some embodiments, $R^2$ and $R^3$ are each methyl. In some embodiments, U is a bond. In some embodiments, V is bond. In some embodiments, n is 0.

In some embodiments, the compound of formula (IIa-1b) is of the formula (IIa-1b-2):

(IIa-1b-2)

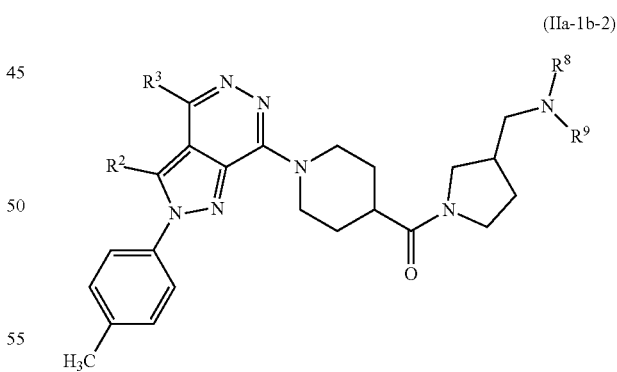

or a salt or solvate thereof, wherein $R^2$, $R^3$. $R^8$, and $R^9$ are as defined for formula (I) or any embodiment or variation thereof. In some embodiments, $R^2$ and $R^3$ are each hydrogen. In some embodiments, $R^2$ and $R^3$ are each methyl. In some embodiments, $R^8$ and $R^9$ are independently $C_1$-$C_6$ alkyl optionally substituted by $R^{10}$. In some embodiments, $R^8$ and $R^9$ are each methyl.

In some embodiments, the compound of formula (IIa-1b) is of the formula (IIa-1b-3):

(IIa-1b-3)

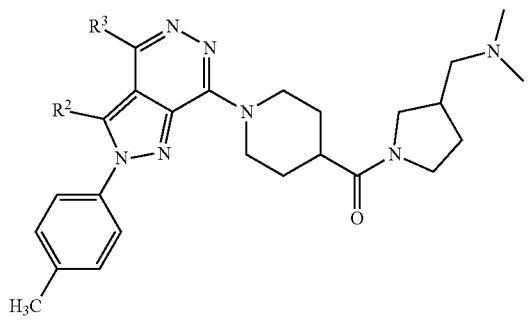

or a salt or solvate thereof, wherein $R^2$ and $R^3$ are as defined for formula (I) or any embodiment or variation thereof. In one embodiment, $R^2$ and $R^3$ are each hydrogen. In another embodiment, $R^2$ and $R^3$ are each methyl.

In a preferred embodiment, the compound of formula (IIa-1b-3) is Compound No. 45:

Compound No. 45

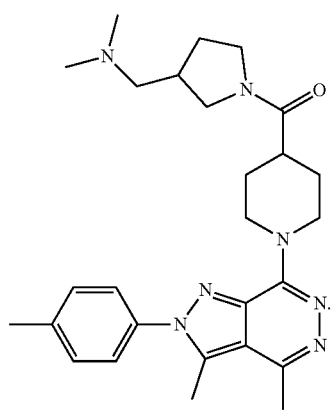

In a preferred embodiment, the compound of formula (IIa-1b-3) is Compound No. 60:

Compound No. 60

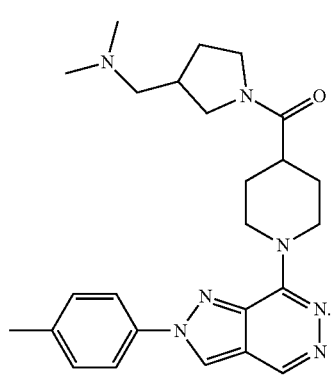

In some embodiments, the compound of formula (IIa-1) is of the formula (IIa-1c):

(IIa-1c)

or a salt or solvate thereof, wherein $R^2$, $R^3$, $R^6$, $R^8$, $R^9$, U, V, and n are as defined for formula (I) or any embodiment or variation thereof. In some embodiments, $R^2$ and $R^3$ are each hydrogen. In some embodiments, $R^2$ and $R^3$ are each methyl. In some embodiments, U is a bond. In some embodiments, V is bond. In some embodiments, n is 0. In some embodiments, $R^8$ and $R^9$ are independently $C_1$-$C_6$ alkyl optionally substituted by $R^{10}$. In some embodiments, $R^8$ and $R^9$ are each ethyl. In some embodiments, $R^8$ and $R^9$ are taken together with the nitrogen atom to which they are attached to form a 3- to 12-membered heterocyclyl optionally substituted by $R^{10}$. In some embodiments, $R^8$ and $R^9$ are taken together with the nitrogen atom to which they are attached to form azetanyl.

In some embodiments, the compound of formula (IIa-1c) is of the formula (IIa-1c-1):

(IIa-1c-1)

or a salt or solvate thereof, wherein $R^2$ and $R^3$ are as defined for formula (I) or any embodiment or variation thereof. In some embodiments, $R^2$ and $R^3$ are each hydrogen. In some embodiments, $R^2$ and $R^3$ are each methyl. In some embodiments, $R^8$ and $R^9$ are independently $C_1$-$C_6$ alkyl optionally substituted by $R^{10}$. In some embodiments, $R^8$ and $R^9$ are each ethyl. In some embodiments, $R^8$ and $R^9$ are taken together with the nitrogen atom to which they are attached to form a 3- to 12-membered heterocyclyl optionally substituted by $R^{10}$. In some embodiments, $R^8$ and $R^9$ are taken together with the nitrogen atom to which they are attached to form azetanyl.

In a preferred embodiment, the compound of formula (IIa-1c-1) is Compound No. 43:

Compound No. 43

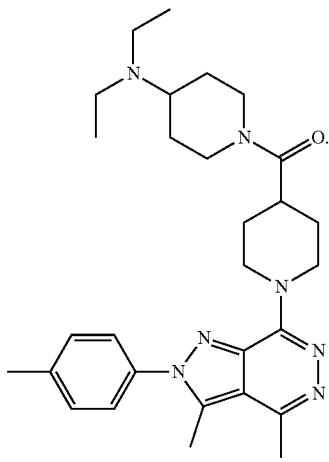

In a preferred embodiment, the compound of formula (IIa-1c-1) is Compound No. 59:

Compound No. 59

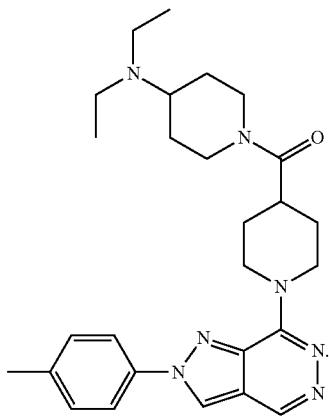

In a preferred embodiment, the compound of formula (IIa-1c-1) is Compound No. 65:

Compound No. 65

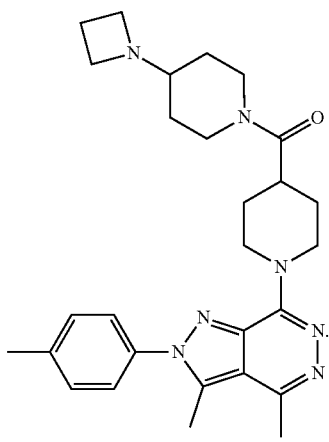

In some embodiments, the compound of formula (IIa-1) is of the formula (IIa-1d):

(IIa-1d)

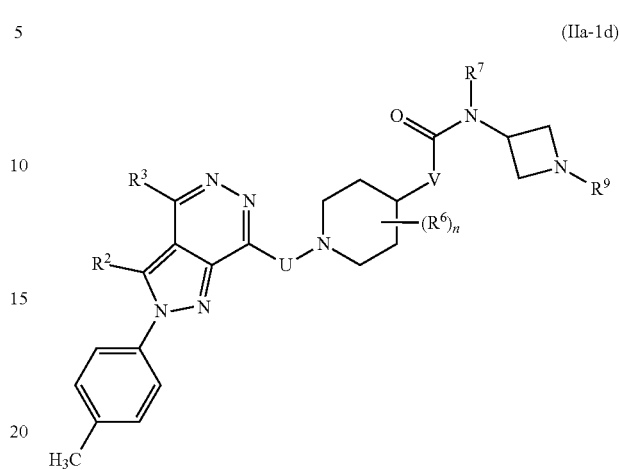

or a salt or solvate thereof, wherein $R^2$, $R^3$, $R^6$, $R^7$, $R^9$, U, V, and n are as defined for formula (I) or any embodiment or variation thereof. In some embodiments, $R^2$ and $R^3$ are each hydrogen. In some embodiments, $R^2$ and $R^3$ are each methyl. In some embodiments, $R^7$ is hydrogen. In some embodiments, U is a bond. In some embodiments, V is bond. In some embodiments, n is 0. In some embodiments, $R^9$ is $C_1$-$C_6$ alkyl optionally substituted by $R^{10}$. In some embodiments, $R^9$ is methyl.

In some embodiments, the compound of formula (IIa-1d) is of the formula (IIa-1d-1):

(IIa-1d-1)

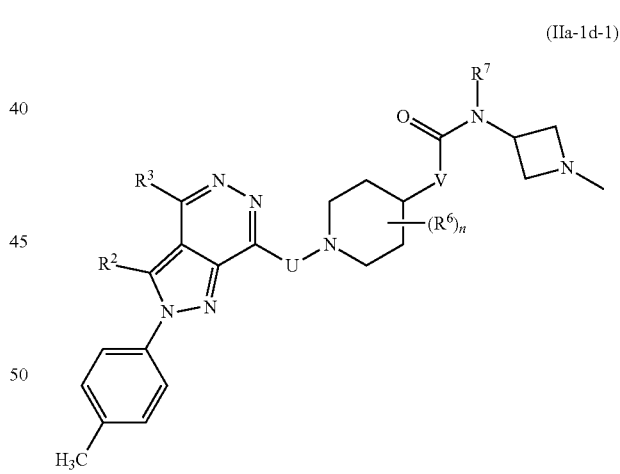

or a salt or solvate thereof, wherein $R^2$, $R^3$, $R^6$, $R^7$, U, V, and n are as defined for formula (I) or any embodiment or variation thereof. In some embodiments, $R^2$ and $R^3$ are each hydrogen. In some embodiments, $R^2$ and $R^3$ are each methyl. In some embodiments, $R^7$ is hydrogen. In some embodiments, U is a bond. In some embodiments, V is bond. In some embodiments, n is 0.

In some embodiments, the compound of formula (IIa-1d) is of the formula (IIa-1d-2):

(IIa-1d-2)

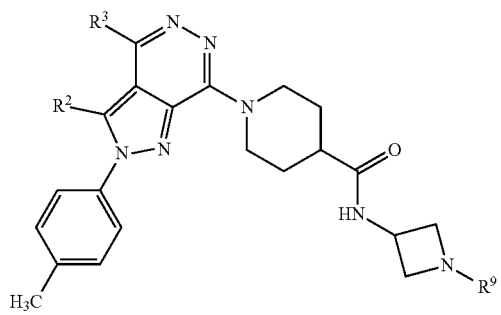

or a salt or solvate thereof, wherein $R^2$, $R^3$, and $R^9$ are as defined for formula (I) or any embodiment or variation thereof. In some embodiments, $R^2$ and $R^3$ are each hydrogen. In some embodiments, $R^2$ and $R^3$ are each methyl. In some embodiments, $R^9$ is $C_1$-$C_6$ alkyl optionally substituted by $R^{10}$. In some embodiments, $R^9$ is methyl.

In some embodiments, the compound of formula (IIa-1d) is of the formula (IIa-1d-3):

(IIa-1d-3)

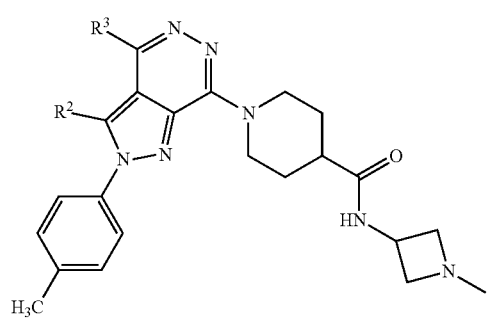

or a salt or solvate thereof, wherein $R^2$ and $R^3$ are as defined for formula (I) or any embodiment or variation thereof. In some embodiments, $R^2$ and $R^3$ are each hydrogen. In some embodiments, $R^2$ and $R^3$ are each methyl.

In a preferred embodiment, the compound of formula (IIa-1d-3) is Compound No. 62:

Compound No. 62

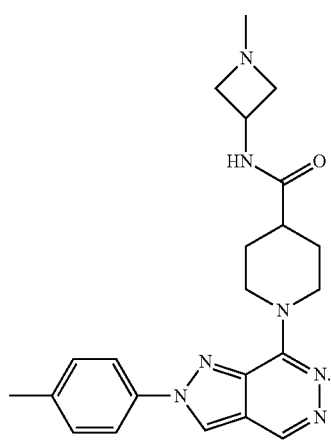

In some embodiments, the compound of formula (IIa-1) is of the formula (IIa-1e):

(IIa-1e)

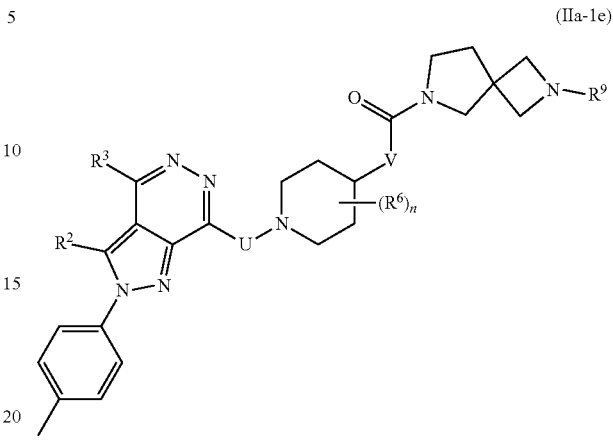

or a salt or solvate thereof, wherein $R^2$, $R^3$, $R^6$, $R^9$, U, V, and n are as defined for formula (I) or any embodiment or variation thereof. In some embodiments, $R^2$ and $R^3$ are each hydrogen. In some embodiments, $R^2$ and $R^3$ are each methyl. In some embodiments, U is a bond. In some embodiments, V is bond. In some embodiments, n is 0. In some embodiments, $R^9$ is $C_1$-$C_6$ alkyl optionally substituted by $R^{10}$. In some embodiments, $R^9$ is methyl.

In some embodiments, the compound of formula (IIa-1e) is of the formula (IIa-1e-1):

(IIa-1e-1)

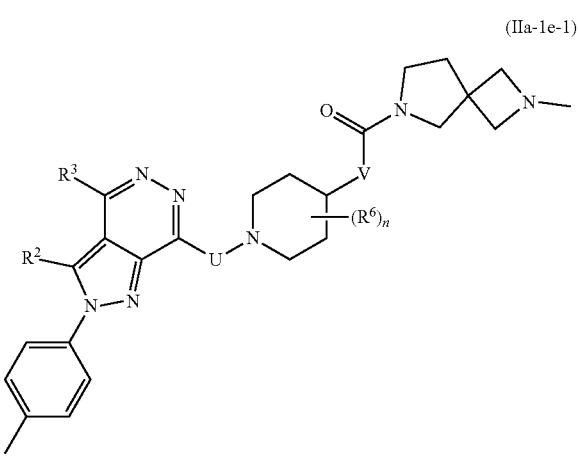

or a salt or solvate thereof, wherein $R^2$, $R^3$, $R^6$, U, V, and n are as defined for formula (I) or any embodiment or variation thereof. In some embodiments, $R^2$ and $R^3$ are each hydrogen. In some embodiments, $R^2$ and $R^3$ are each methyl. In some embodiments, U is a bond. In some embodiments, V is bond. In some embodiments, n is 0.

In some embodiments, the compound of formula (IIa-1e) is of the formula (IIa-1e-2):

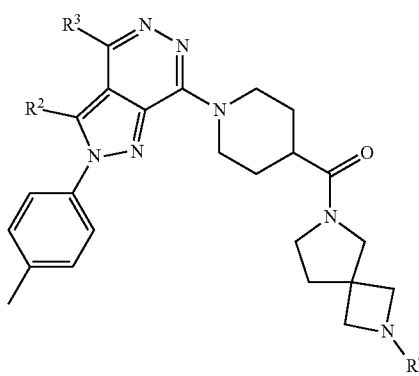

(IIa-1e-2)

or a salt or solvate thereof, wherein $R^2$, $R^3$, and $R^9$ are as defined for formula (I) or any embodiment or variation thereof. In some embodiments, $R^2$ and $R^3$ are each hydrogen. In some embodiments, $R^2$ and $R^3$ are each methyl. In some embodiments, $R^9$ is $C_1$-$C_6$ alkyl optionally substituted by $R^{10}$. In some embodiments, $R^9$ is methyl.

In some embodiments, the compound of formula (IIa-1e) is of the formula (IIa-1e-3):

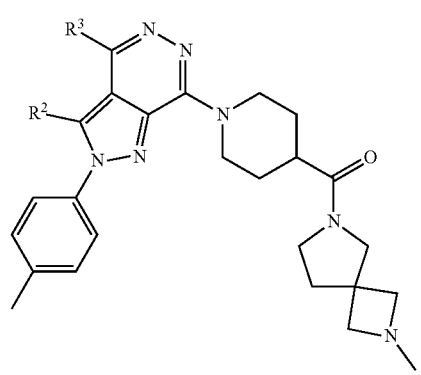

(IIa-1e-3)

or a salt or solvate thereof, wherein $R^2$ and $R^3$ are as defined for formula (I) or any embodiment or variation thereof. In some embodiments, $R^2$ and $R^3$ are each hydrogen. In some embodiments, $R^2$ and $R^3$ are each methyl.

In a preferred embodiment, the compound of formula (IIa-1e-3) is Compound No. 75:

Compound No. 75

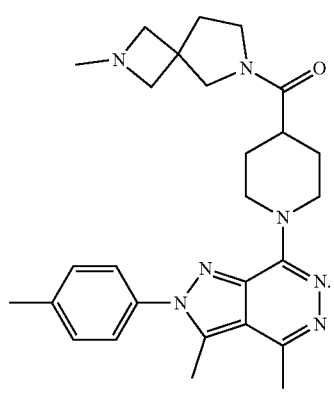

In some embodiments, the compound of formula (IIa-1) is of the formula (IIa-1f):

(IIa-1f)

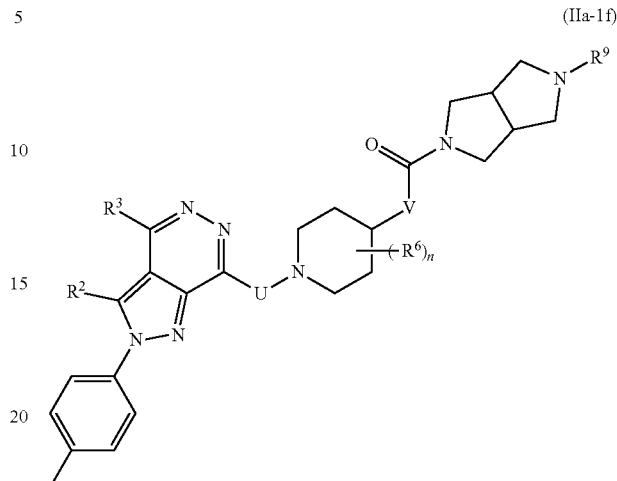

or a salt or solvate thereof, wherein $R^2$, $R^3$, $R^6$, $R^9$, U, V, and n are as defined for formula (I) or any embodiment or variation thereof. In some embodiments, $R^9$ is $C_1$-$C_6$ alkyl optionally substituted by $R^{10}$. In some embodiments, $R^9$ is methyl.

In some embodiments, the compound of formula (IIa-1f) is of the formula (IIa-1f-1):

(IIa-1f-1)

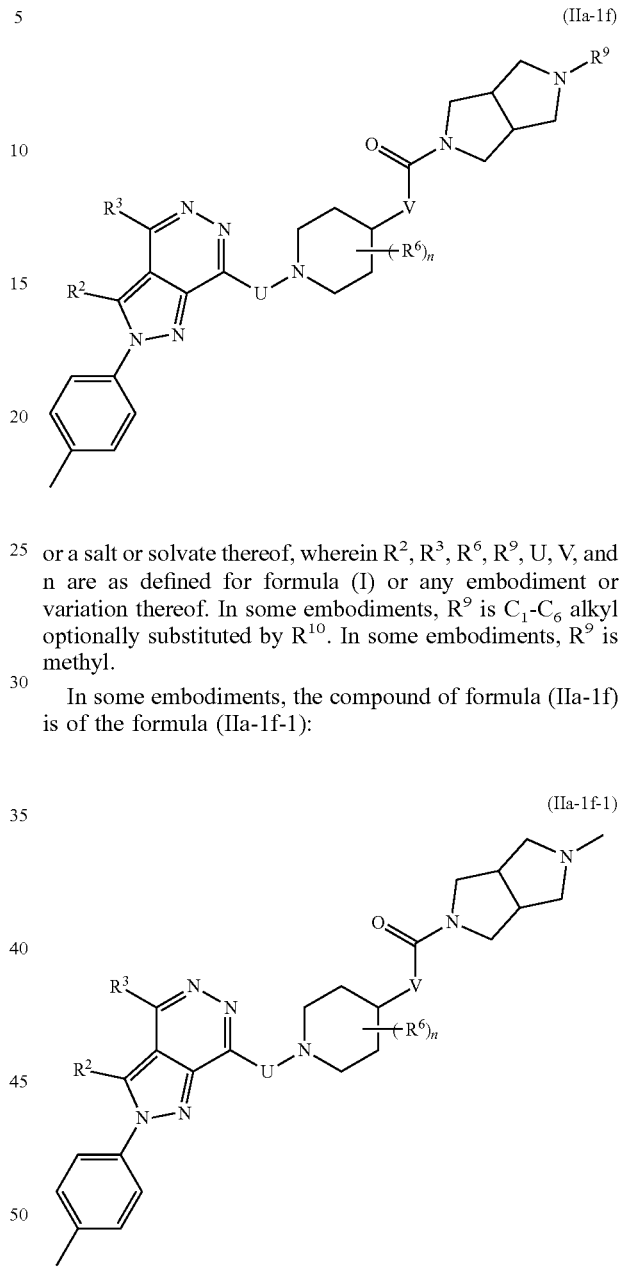

or a salt or solvate thereof, wherein $R^2$, $R^3$, $R^6$, U, V, and n are as defined for formula (I) or any embodiment or variation thereof. In some embodiments, $R^2$ and $R^3$ are each hydrogen. In some embodiments, $R^2$ and $R^3$ are each methyl. In some embodiments, U is a bond. In some embodiments, V is bond. In some embodiments, n is 0.

In some embodiments, the compound of formula (IIa-1f) is of the formula (IIa-1f-2):

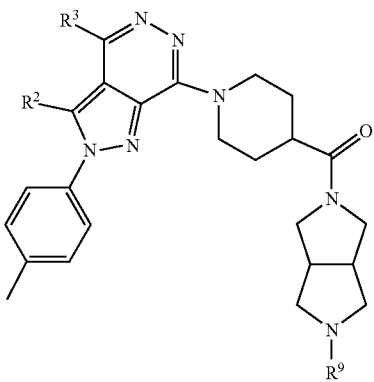

(IIa-1f-2)

or a salt or solvate thereof, wherein $R^2$, $R^3$, and $R^9$ are as defined for formula (I) or any embodiment or variation thereof. In some embodiments, $R^2$ and $R^3$ are each hydrogen. In some embodiments, $R^2$ and $R^3$ are each methyl. In some embodiments, $R^9$ is $C_1$-$C_6$ alkyl optionally substituted by $R^{10}$. In some embodiments, $R^9$ is methyl.

In some embodiments, the compound of formula (IIa-1f) is of the formula (IIa-1f-3):

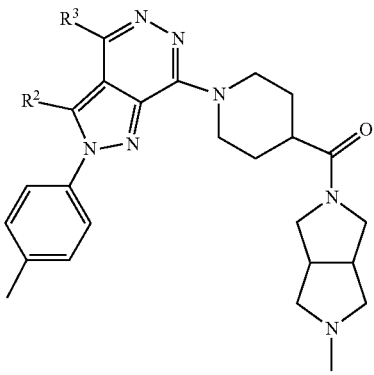

(IIa-1f-3)

or a salt or solvate thereof, wherein $R^2$ and $R^3$ are as defined for formula (I) or any embodiment or variation thereof. In some embodiments, $R^2$ and $R^3$ are each hydrogen. In some embodiments, $R^2$ and $R^3$ are each methyl.

In a preferred embodiment, the compound of formula (IIa-1f-3) is Compound No. 72:

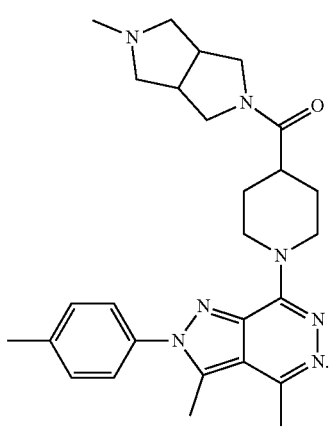

Compound No. 72

It is intended and understood that each and every variation of formula (II) described herein applies to each and every variation of formula (IIa), (IIa-1), (IIa-1a), (IIa-1a-1), (IIa-1a-2), (IIa-1a-3), (IIa-1b), (IIa-1b-1), (IIa-1b-2), (IIa-1b-3), (IIa-1c), (IIa-1c-1), (IIa-d), (IIa-1d-1), (IIa-1d-2), (IIa-1d-3), (IIa-1e), (IIa-1e-1), (IIa-1e-2), (IIa-1e-3), (IIa-1f), (IIa-1f-1), (IIa-1f-2), and (IIa-1f-3) the same as if each and every variation is individually and specifically described. Similarly, it is intended and understood that each and every variation of formula (IIa) described herein applies to each and every variation of formula (IIa-1), (IIa-1a), (IIa-1a-1), (IIa-1a-2), (IIa-1a-3), (IIa-1b), (IIa-1b-1), (IIa-1b-2), (IIa-1b-3), (IIa-1c), (IIa-1c-1), (IIa-d), (IIa-1d-1), (IIa-1d-2), (IIa-1d-3), (IIa-1e), (IIa-1e-1), (IIa-1e-2), (IIa-1e-3), (IIa-1f), (IIa-1f-1), (IIa-1f-2), and (IIa-1f-3) the same as if each and every variation is individually and specifically described.

In some embodiments of the compound of formula (A-I), (I), (Ia), (II), (IIa), or any variation thereof, or a salt or solvate thereof, U is a bond (or absent) or an optionally substituted methylene. In some embodiments, U is a bond. In some embodiments, U is methylene optionally substituted by $R^{10}$. In some embodiments, U is methylene (—$CH_2$—).

In some embodiments of the compound of formula (A-I), (I), (Ia), (I°), (I°a), (II), (IIa), or any variation thereof, or a salt or solvate thereof, V is a bond (or absent) or an optionally substituted methylene or ethylene. In some embodiments, V is a bond. In some embodiments, V is $C_1$-$C_2$ alkylene optionally substituted by $R^{10}$. In some embodiments, V is methylene (—$CH_2$—). In some embodiments, V is ethylene (—$CH_2CH_2$—). In some embodiments, U is a bond and V is a bond, methylene (—$CH_2$—) or ethylene (—$CH_2CH_2$—).

It is intended and understood that each and every variation of ring A (e.g., $A^1$, $A^2$, $A^3$, $A^4$ and $A^5$) and ring B (e.g., i and j) described herein, may be combined with each and every variation of linkers U and V described herein, the same as if each and every combination is individually and specifically described. For example, in some embodiments, $A^1$ is N, $A^2$ is $CR^2$, $A^3$ is N, $A^4$ is N, $A^5$ is N, i is 2, is 1, U is a bond, and V is a bond or ethylene (—$CH_2CH_2$—). In some of these embodiments, $R^2$ is hydrogen or methyl. In some of these embodiments, V is a bond.

In some embodiments of the compound of the formula (II), both U and V are absent, the compound is of the formula (III):

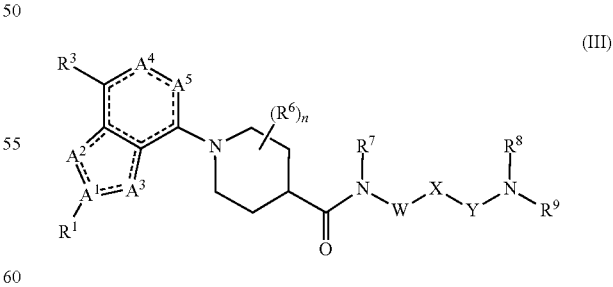

(III)

or a salt or solvate thereof, wherein $A^1$, $A^2$, $A^3$, $A^4$, $A^5$, $R^1$, $R^3$, $R^6$, $R^7$, $R^8$, $R^9$, W, X, Y, and n are as defined for formula (I) or (II).

In some embodiments, the compound of the formula (III) is a pyrazolo[3,4-d]pyridazine compound having the formula (IIIa):

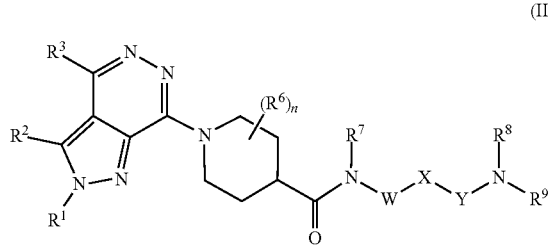

(IIIa)

or a salt or solvate thereof, wherein $R^1$, $R^2$, $R^3$, $R^6$, $R^7$, $R^8$, $R^9$, W, X, Y, and n are as defined for formula (I), (II) or (III).

In some embodiments, the compound of the formula (I) is a pyrazolo[3,4-d]pyridazine compound having the formula (IV):

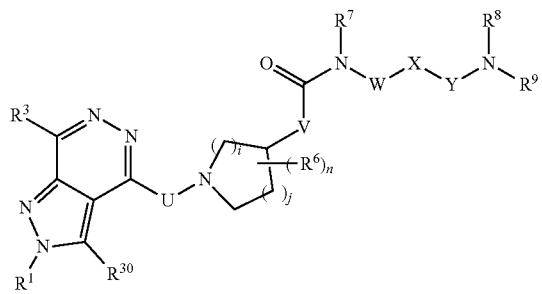

(IV)

or a salt or solvate thereof, wherein $R^1$, $R^3$, $R^{30}$, $R^6$, $R^7$, $R^8$, $R^9$, U, V, W, X, Y, i, j, and n are as defined for formula (I).

In some embodiments, the compound of the formula (IV), where ring A is pyrazolo[3,4-d]pyridazin-4-yl and is directly attached to the ring nitrogen of ring B, has the formula (IV-a):

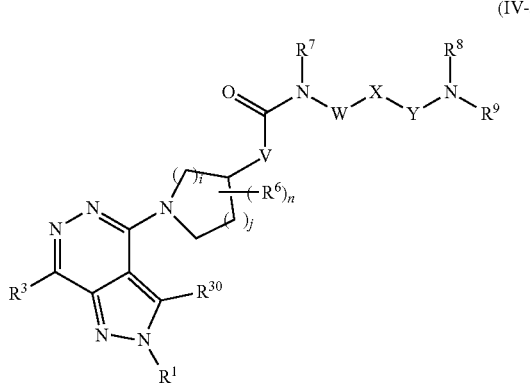

(IV-a)

or a salt or solvate thereof, wherein $R^1$, $R^3$, $R^{30}$, $R^6$, $R^7$, $R^8$, $R^9$, V, W, X, Y, i, j, and n are as defined for formula (I).

In some embodiments, the compound of the formula (IV-a) is of the formula (IV-a-1):

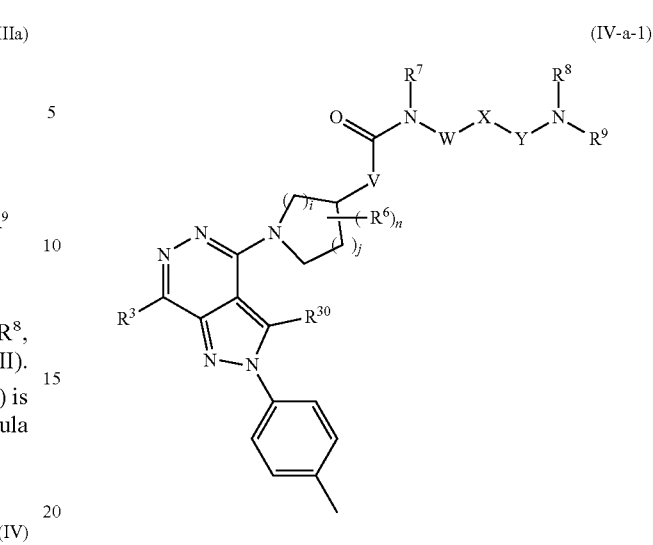

(IV-a-1)

or a salt or solvate thereof, wherein $R^6$, $R^7$, $R^8$, $R^9$, V, W, X, Y, i, j, and n are as defined for formula (I). In some embodiments, $R^3$ is halogen. In some embodiments, $R^{30}$ is $C_1$-$C_6$ alkyl. In some embodiments, $R^3$ is halogen and $R^{30}$ is $C_1$-$C_6$ alkyl.

In some embodiments, the compound of formula (IV-a-1) is of the formula (IV-a-2):

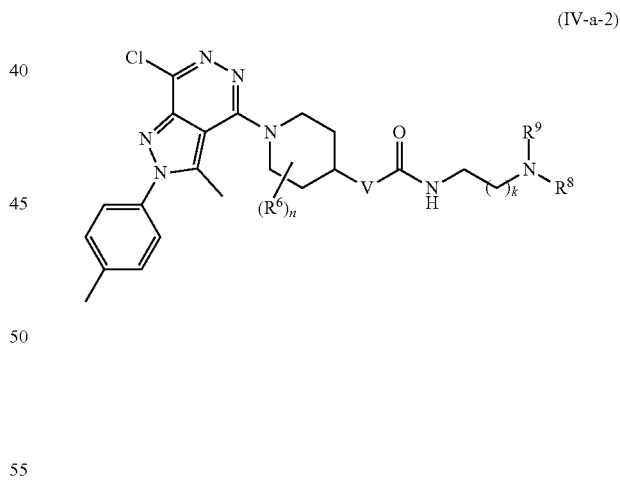

(IV-a-2)

or a salt or solvate thereof, wherein $R^6$, $R^8$, $R^9$, V, and n are as defined for formula (I) or any embodiment or variation thereof, and k is 1, 2, 3, 4, or 5. In some embodiments, V is a bond. In some embodiments, V is $C_1$-$C_6$ alkylene (e.g., ethylene). In some embodiments, k is 1 or 2. In some embodiments, n is 0. In some embodiments, $R^8$ and $R_9$ are independently $C_1$-$C_6$ alkyl optionally substituted by $R^{10}$. In some embodiments, $R^8$ and $R_9$ are each methyl.

In one embodiment, the compound of formula (IV-a-2) is Compound No. 48:

Compound No. 48

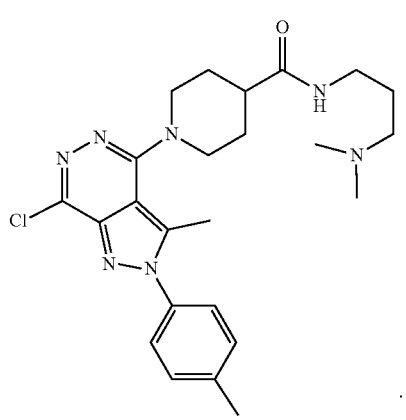

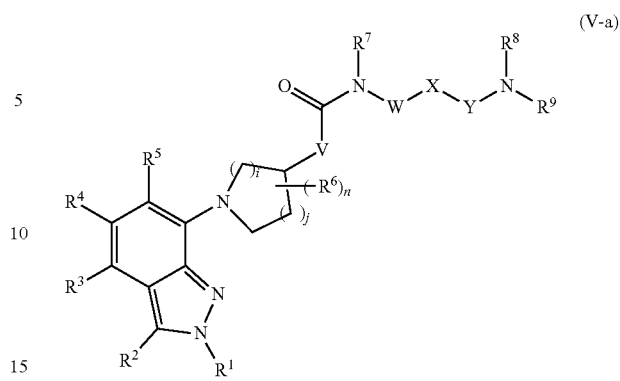

or a salt or solvate thereof, wherein $R^1$, $R^2$, $R^3$, $R^4$, $R^5$, $R^6$, $R^7$, $R^8$, $R^9$, V, W, X, Y, i, j, and n are as defined for formula (I).

In some embodiments, the compound of the formula (V-a) is of the formula (V-a-1):

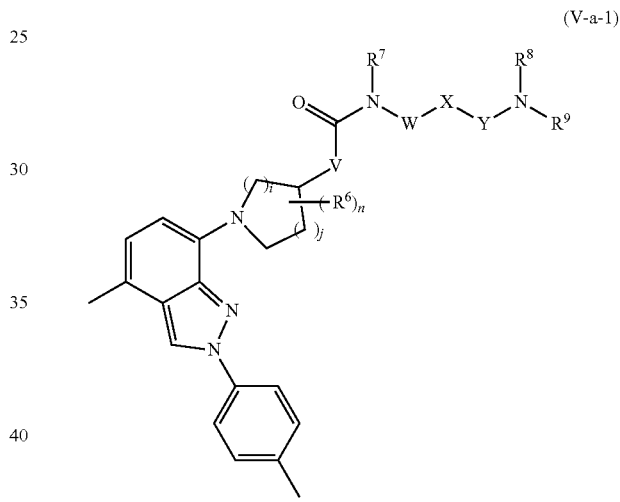

or a salt or solvate thereof, wherein $R^6$, $R^7$, $R^8$, $R^9$, V, W, X, Y, i, j, and n are as defined for formula (I).

In some embodiments, the compound of formula (V-a-1) is of the formula (V-a-2):

It is intended and understood that each and every variation of formula (IV) described herein applies to each and every variation of formula (IV-a), (IV-a-1), and (IV-a-2) the same as if each and every variation is individually and specifically described. Similarly, it is intended and understood that each and every variation of formula (IV-a) described herein applies to each and every variation of formula (IV-a-1) and (IV-a-2) the same as if each and every variation is individually and specifically described.

In some embodiments, the compound of the formula (I) is an indazole compound having the formula (V):

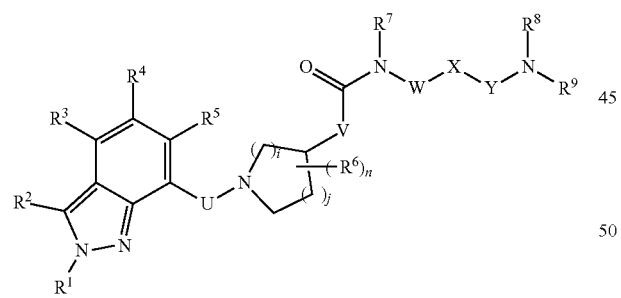

or a salt or solvate thereof, wherein $R^1$, $R^2$, $R^3$, $R^4$, $R^5$, $R^6$, $R^7$, $R^8$, $R^9$, U, V, W, X, Y, i, j, and n are as defined for formula (I).

In some embodiments, the compound of the formula (V), where ring A is an indazol-7-yl and is directly attached to the ring nitrogen of ring B, has the formula (V-a):

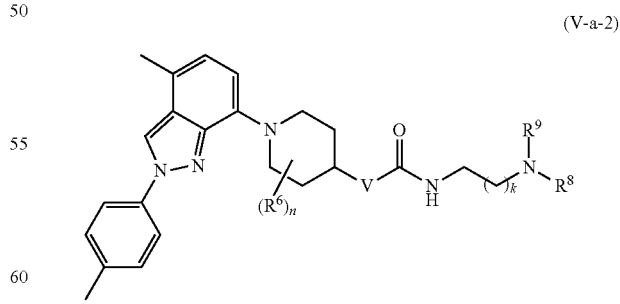

or a salt or solvate thereof, wherein $R^6$, $R^8$, $R^9$, V, and n are as defined for formula (I) or any embodiment or variation thereof, and k is 1, 2, 3, 4, or 5. In some embodiments, V is a bond. In some embodiments, V is $C_1$-$C_6$ alkylene (e.g., ethylene). In some embodiments, k is 1 or 2. In some embodiments, n is 0. In some embodiments, $R^8$ and $R^9$ are independently $C_1$-$C_6$ alkyl optionally substituted by $R^{10}$. In some embodiments, $R^8$ and $R^9$ are each methyl.

In one embodiment, the compound of formula (V-a-2) is Compound No. 49:

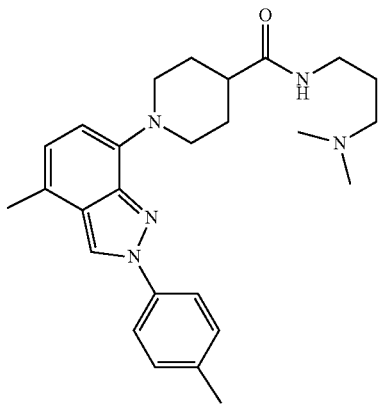

Compound No. 49

In one embodiment, the compound of formula (V-a-2) is Compound No. 50:

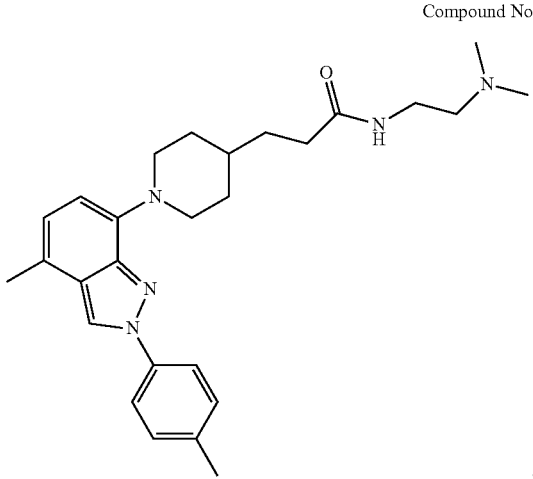

Compound No. 50

It is intended and understood that each and every variation of formula (V) described herein applies to each and every variation of formula (V-a), (V-a-1), and (V-a-2) the same as if each and every variation is individually and specifically described. Similarly, it is intended and understood that each and every variation of formula (V-a) described herein applies to each and every variation of formula (V-a-1) and (V-a-2) the same as if each and every variation is individually and specifically described.

In some embodiments, the compound of the formula (I) is a pyrrolo[2,3-d]pyridazine compound having the formula (VI):

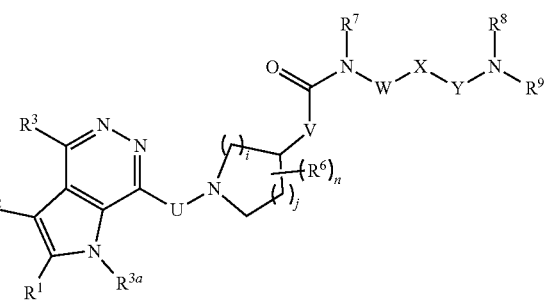

(VI)

or a salt or solvate thereof, wherein $R^1$, $R^2$, $R^3$, $R^{3a}$, $R^6$, $R^7$, $R^8$, $R^9$, U, V, W, X, Y, i, j, and n are as defined for formula (I).

In some embodiments, the compound of the formula (VI), where ring A is pyrrolo[2,3-d]pyridazin-7-yl and is directly attached to the ring nitrogen of ring B, has the formula (VI-a):

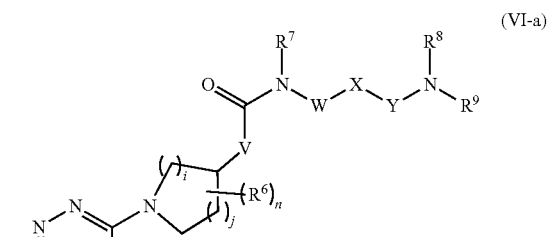

(VI-a)

or a salt or solvate thereof, wherein $R^1$, $R^2$, $R^3$, $R^{3a}$, $R^6$, $R^7$, $R^8$, $R^9$, V, W, X, Y, i, j, and n are as defined for formula (I).

In some embodiments, the compound of the formula (VI-a) is of the formula (VI-a-1):

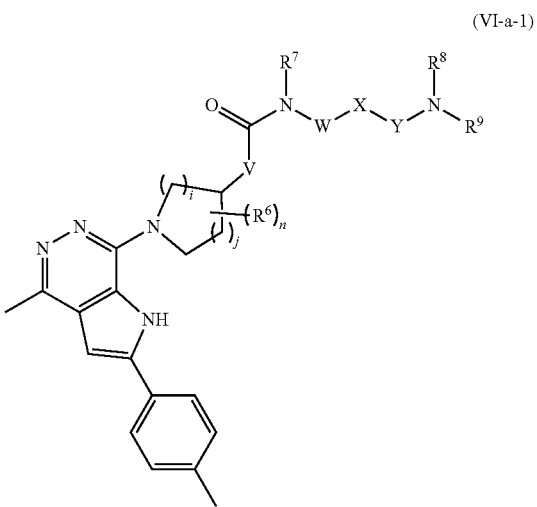

(VI-a-1)

or a salt or solvate thereof, wherein R⁶, R⁷, R⁸, R⁹, V, W, X, Y, i, j, and n are as defined for formula (I).

In some embodiments, the compound of formula (VI-a-1) is of the formula (VI-a-2):

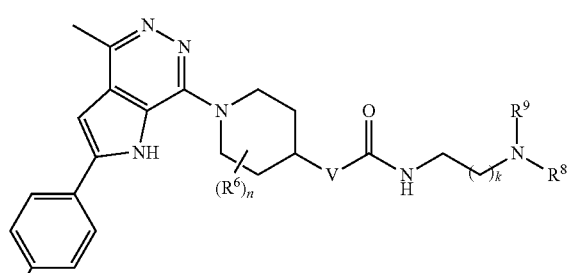

(VI-a-2)

or a salt or solvate thereof, wherein $R^6$, $R^8$, $R^9$, V, and n are as defined for formula (I) or any embodiment or variation thereof, and k is 1, 2, 3, 4, or 5. In some embodiments, V is a bond. In some embodiments, V is $C_1$-$C_6$ alkylene (e.g., ethylene). In some embodiments, k is 1 or 2. In some embodiments, n is 0. In some embodiments, $R^8$ and $R^9$ are independently $C_1$-$C_6$ alkyl optionally substituted by $R^{10}$. In some embodiments, $R^8$ and $R_9$ are each methyl.

In one embodiment, the compound of formula (VI-a-2) is Compound No. 51:

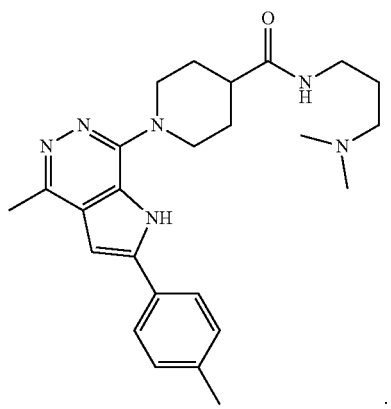

Compound No. 51

In one embodiment, the compound of formula (VI-a-2) is Compound No. 52:

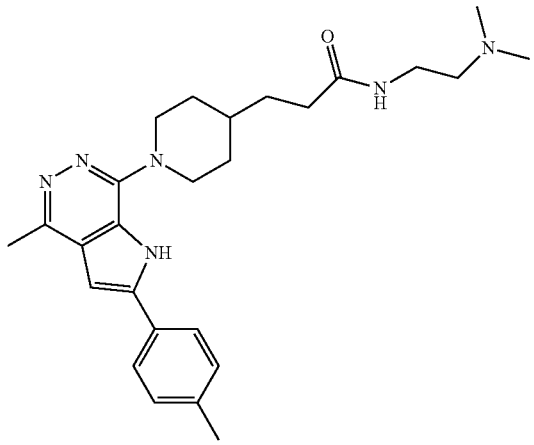

Compound No. 52

It is intended and understood that each and every variation of formula (VI) described herein applies to each and every variation of formula (VI-a), (VI-a-1), and (VI-a-2) the same as if each and every variation is individually and specifically described. Similarly, it is intended and understood that each and every variation of formula (VI-a) described herein applies to each and every variation of formula (VI-a-1) and (VI-a-2) the same as if each and every variation is individually and specifically described.

In some embodiments, the compound of the formula (I) is a benzo[d]imidazole compound having the formula (VII):

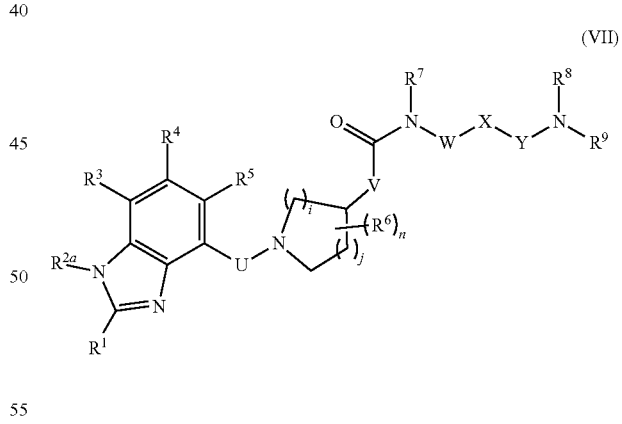

(VII)

or a salt or solvate thereof, wherein $R^1$, $R^{2a}$, $R^3$, $R^4$, $R^5$, $R^6$, $R^7$, $R^8$, $R^9$, U, V, W, X, Y, i, j, and n are as defined for formula (I).

In some embodiments, the compound of the formula (VII), where ring A is benzo[d]imidazole-4-yl and is directly attached to the ring nitrogen of ring B, has the formula (VII-a):

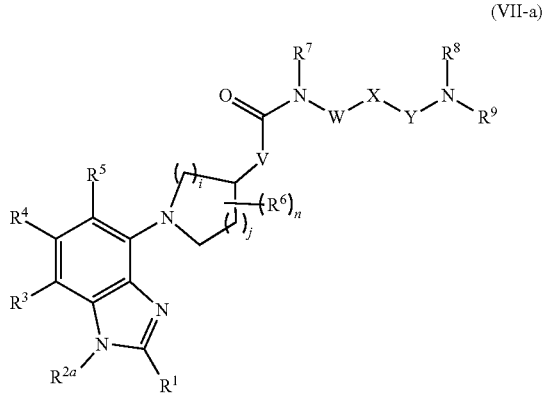

(VII-a)

or a salt or solvate thereof, wherein $R^1$, $R^{2a}$, $R^3$, $R^4$, $R^5$, $R^6$, $R^7$, $R^8$, $R^9$, V, W, X, Y, i, j, and n are as defined for formula (I).

In some embodiments, the compound of the formula (VII-a) is of the formula (VII-a-1):

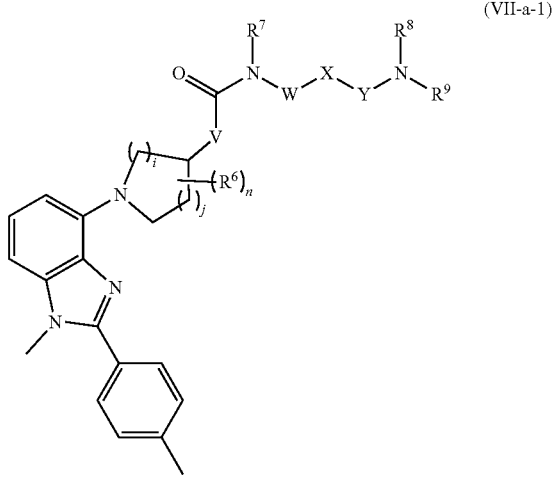

(VII-a-1)

or a salt or solvate thereof, wherein $R^6$, $R^7$, $R^8$, $R^9$, V, W, X, Y, i, j, and n are as defined for formula (I).

In some embodiments, the compound of formula (VII-a-1) is of the formula (VII-a-2):

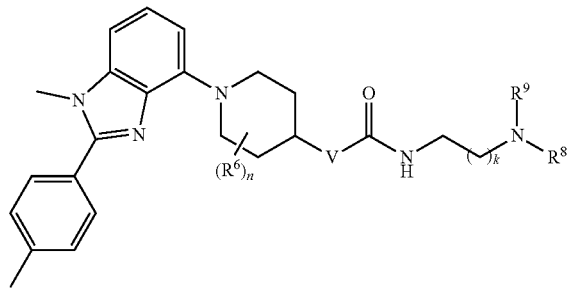

(VII-a-2)

or a salt or solvate thereof, wherein $R^6$, $R^8$, $R^9$, V, and n are as defined for formula (I) or any embodiment or variation thereof, and k is 1, 2, 3, 4, or 5. In some embodiments, V is a bond. In some embodiments, V is $C_1$-$C_6$ alkylene (e.g., ethylene). In some embodiments, k is 1 or 2. In some embodiments, n is 0. In some embodiments, $R^8$ and $R^9$ are independently $C_1$-$C_6$ alkyl optionally substituted by $R^{10}$. In some embodiments, $R^8$ and $R^9$ are each methyl.

In one embodiment, the compound of formula (VII-a-2) is Compound No. 53:

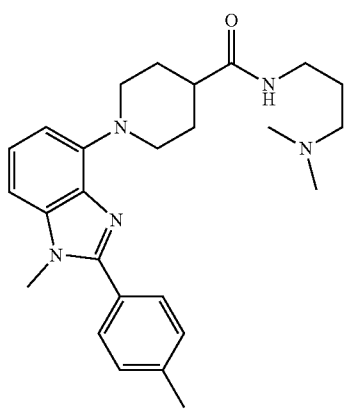

Compound No. 53

In one embodiment, the compound of formula (VII-a-2) is Compound No. 54:

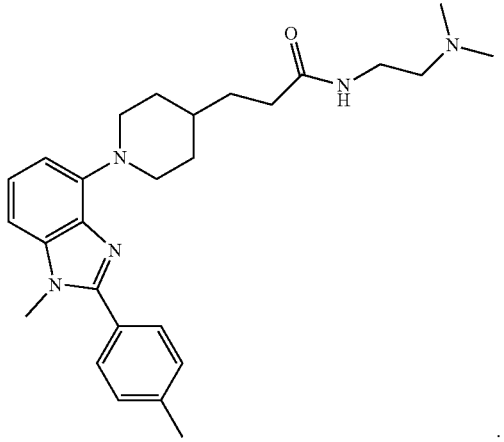

Compound No. 54

It is intended and understood that each and every variation of formula (VII) described herein applies to each and every variation of formula (VII-a), (VII-a-1), and (VII-a-2) the same as if each and every variation is individually and specifically described. Similarly, it is intended and understood that each and every variation of formula (VII-a) described herein applies to each and every variation of formula (VII-a-1) and (VII-a-2) the same as if each and every variation is individually and specifically described.

In some embodiments, the compound of the formula (I) is a pyrazolo[4,3-c]pyridine compound having the formula (VIII):

(VIII)

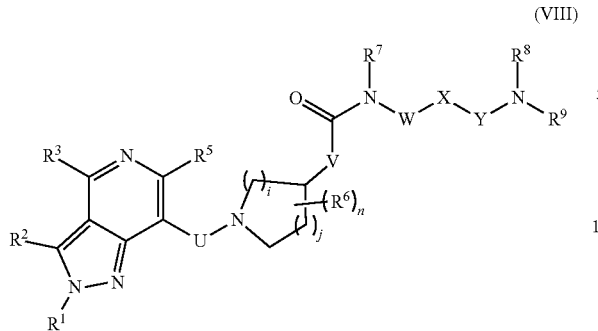

or a salt or solvate thereof, wherein $R^1$, $R^2$, $R^3$, $R^5$, $R^6$, $R^7$, $R^8$, $R^9$, U, V, W, X, Y, i, j, and n are as defined for formula (I).

In some embodiments, the compound of the formula (VIII), where ring A is pyrazolo[4,3-c]pyridine-7-yl and is directly attached to the ring nitrogen of ring B, has the formula (VIII-a):

(VIII-a)

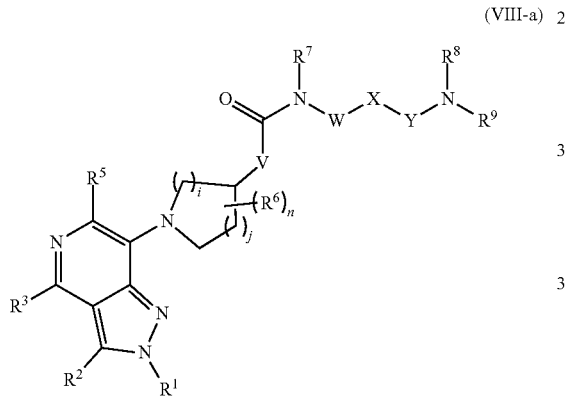

or a salt or solvate thereof, wherein $R^1$, $R^2$, $R^3$, $R^5$, $R^6$, $R^7$, $R^8$, $R^9$, V, W, X, Y, i, j, and n are as defined for formula (I).

In some embodiments, the compound of the formula (VIII-a) is of the formula (VIII-a-1):

(VIII-a-1)

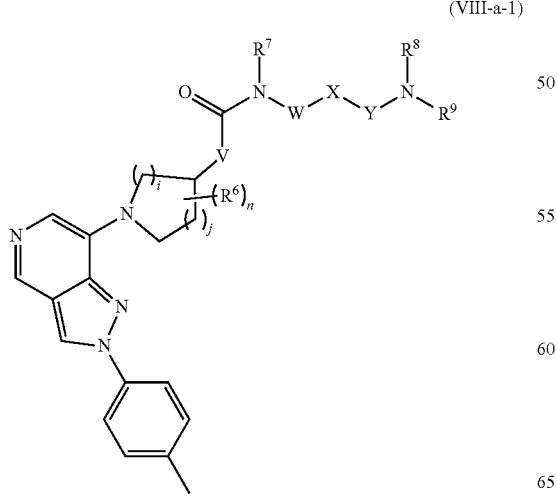

or a salt or solvate thereof, wherein $R^6$, $R^7$, $R^8$, $R^9$, V, W, X, Y, i, j, and n are as defined for formula (I).

In some embodiments, the compound of formula (VIII-a-1) is of the formula (VIII-a-2):

(VIII-a-2)

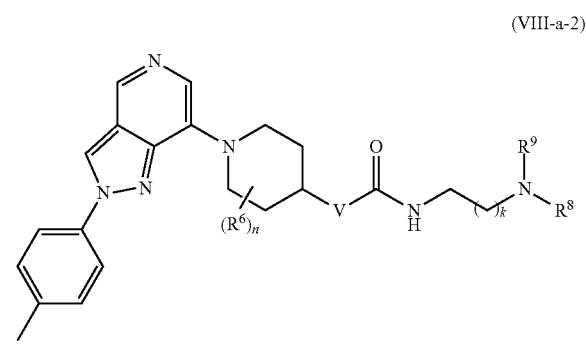

or a salt or solvate thereof, wherein $R^6$, $R^8$, $R^9$, V, and n are as defined for formula (I) or any embodiment or variation thereof, and k is 1, 2, 3, 4, or 5. In some embodiments, V is a bond. In some embodiments, V is $C_1$-$C_6$ alkylene (e.g., ethylene). In some embodiments, k is 1 or 2. In some embodiments, n is 0. In some embodiments, $R^8$ and $R^9$ are independently $C_1$-$C_6$ alkyl optionally substituted by $R^{10}$. In some embodiments, $R^8$ and $R^9$ are each methyl.

In a preferred embodiment, the compound of formula (VIII-a-2) is Compound No. 55:

Compound No. 55

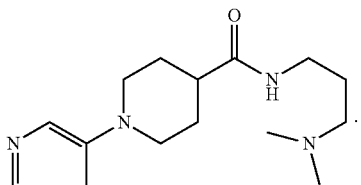

In one embodiment, the compound of formula (VIII-a-2) is Compound No. 56:

Compound No. 56

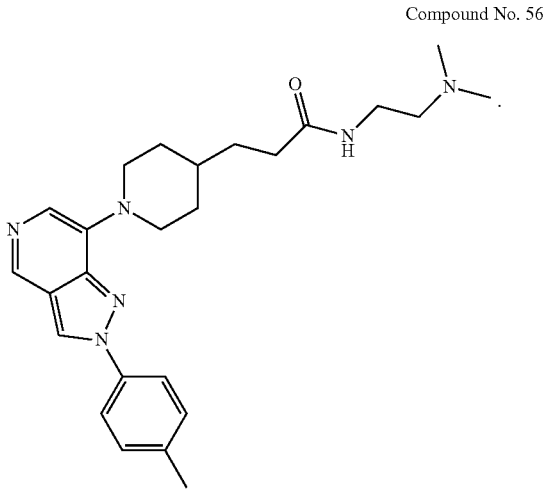 [SMILES: Cc1ccc(-n2cc3cncc(N4CCC(CCC(=O)NCCN(C)C)CC4)c3n2)cc1]

It is intended and understood that each and every variation of formula (VIII) described herein applies to each and every variation of formula (VIII-a), (VIII-a-1), and (VIII-a-2) the same as if each and every variation is individually and specifically described. Similarly, it is intended and understood that each and every variation of formula (VIII-a) described herein applies to each and every variation of formula (VIII-a-1) and (VIII-a-2) the same as if each and every variation is individually and specifically described.

In some embodiments of the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a) or any variation thereof, or a salt or solvate thereof, ring B may be optionally substituted with up to 4 additional substituents. In some embodiments, n is 0. In some embodiments, n is 1 or 2, and each $R^6$ is independently $C_1$-$C_6$ alkyl optionally substituted by $R^{10A}$. In some embodiments, n is 1 and $R^6$ is $C_1$-$C_6$ alkyl (e.g., methyl).

In some embodiments of the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a) or any variation thereof, or a salt or solvate thereof, $R^1$ is $C_1$-$C_6$ alkyl, $C_3$-$C_8$ cycloalkyl, $C_6$-$C_{14}$ aryl, 5-10-membered heteroaryl or 3-12-membered heterocyclyl; each of which may be optionally independently substituted by up to five $R^{10A}$ groups. In some embodiments, $R^1$ is phenyl optionally substituted by $R^{10A}$. In some embodiments, $R^1$ is phenyl optionally substituted by $C_1$-$C_6$ alkyl or halo (e.g., 4-methylphenyl or 4-chlorophenyl). In some embodiments, $R^1$ is $C_1$-$C_6$ alkyl optionally substituted by $R^{10A}$. In some embodiments, $R^1$ is $C_1$-$C_6$ alkyl (e.g., 2-propyl). In some embodiments, $R^1$ is 3-12-membered heterocyclyl optionally substituted by $R^{10A}$. In some embodiments, $R^1$ is 3-12-membered heterocyclyl (e.g., tetrahydropyran-4-yl). In some embodiments, $R^1$ is 5-10-membered heteroaryl optionally substituted by $R^{10A}$. In some embodiments, $R^1$ is 5-10-membered heteroaryl (e.g., pyridyl, thiophenyl, or oxazolyl).

In some embodiments, $R^2$ is $C_1$-$C_6$ alkyl optionally substituted by $R^{10A}$. In some embodiments, $R^2$ is $C_1$-$C_6$ alkyl (e.g., methyl). In some embodiments, $R^2$ is hydrogen. In some embodiments, $R^2$ is $C_6$-$C_{14}$ aryl optionally substituted by $R^{10A}$. In some embodiments, $R^2$ is $C_6$-$C_{14}$ aryl (e.g., phenyl). In some embodiments, $R^2$ is halogen (e.g., F, Cl, Br or I). In some embodiments, $R^2$ is $C_3$-$C_8$ cycloalkyl optionally substituted by $R^{10A}$. In some embodiments, $R^2$ is 5-10-membered heteroaryl optionally substituted by $R^{10A}$. In some embodiments, $R^2$ is 3-12-membered heterocyclyl optionally substituted by $R^{10A}$.

In some embodiments, $R^3$ is $C_1$-$C_6$ alkyl optionally substituted by $R^{10A}$. In some embodiments, $R^3$ is $C_1$-$C_6$ alkyl (e.g., methyl). In some embodiments, $R^3$ is $C_1$-$C_6$ alkyl substituted independently by 1 to 5 halogen atoms (e.g., $CF_3$). In some embodiments, $R^3$ is hydrogen. In some embodiments, $R^3$ is $C_6$-$C_{14}$ aryl optionally substituted by $R^{10A}$. In some embodiments, $R^3$ is $C_6$-$C_{14}$ aryl (e.g., phenyl). In some embodiments, $R^3$ is halogen (e.g., F, Cl, Br or I). In some embodiments, $R^3$ is $C_3$-$C_8$ cycloalkyl optionally substituted by $R^{10A}$. In some embodiments, $R^3$ is 5-10-membered heteroaryl optionally substituted by $R^{10A}$. In some embodiments, $R^3$ is 3-12-membered heterocyclyl optionally substituted by $R^{10A}$.

In some embodiments of the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a) or any variation thereof, or a salt or solvate thereof, $R^7$ is hydrogen, $C_1$-$C_6$ alkyl, or taken together with $R^8$ to form an ethylene optionally substituted by $R^{10}$, or taken together with $R^{Y1}$, $R^{X1}$ or $R^{W1}$, where present, to form a $C_1$-$C_6$ alkylene optionally substituted by $R^{10}$. In some embodiments, $R^7$ is hydrogen or $C_1$-$C_6$ alkyl. In some embodiments, $R^7$ is hydrogen. In some embodiments, $R^7$ is $C_1$-$C_6$ alkyl. In some embodiments, $R^7$ is taken together with $R^{Y1}$, $R^{X1}$ or $R^{W1}$, where present, to form a $C_1$-$C_6$ alkylene optionally substituted by $R^{10}$. In some embodiments, $R^7$ is taken together with $R^{Y1}$, $R^{X1}$ or $R^{W1}$, where present, to form a $C_1$-$C_4$ alkylene optionally substituted by $R^{10}$. In some embodiments, $R^7$ is taken together with $R^{Y1}$, $R^{X1}$ or $R^{W1}$, where present, to form a propylene, ethylene, or methylene optionally substituted by $R^{10}$.

In some embodiments of the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a) or any variation thereof, or a salt or solvate thereof, $R^8$ is hydrogen, $C_1$-$C_6$ alkyl optionally substituted by $R^{10}$, $C_6$-$C_{14}$ aryl, 5-10-membered heteroaryl, or taken together with $R^7$ to form an ethylene optionally substituted by $R^{10}$, or taken together with $R^{Y1}$, $R^{Y2}$, $R^{X1}$, $R^{X2}$, or $R^{W1}$, where present, to form a $C_1$-$C_6$ alkylene optionally substituted by $R^{10}$, or taken together with $R^{10}$, where present, to form a $C_1$-$C_6$ alkylene, or taken together with $R^9$ and the nitrogen atom to which they are attached to form a 3-12-membered heterocyclyl optionally substituted by $R^{10}$ or a 5-10-membered heteroaryl optionally substituted by $R^{10}$, or taken together with $R^{Y1}$, $R^{Y2}$, $R^9$ and the atoms to which they are attached to form a 5-10-membered heteroaryl (e.g., 4-imidazolyl or 2-pyridyl) optionally substituted by $R^{10}$, or taken together with $R^{X1}$, $R^{X2}$, $R^{Y1}$, $R^{Y2}$, $R^9$ and the atoms to which they are attached to form a 5-10-membered heteroaryl (e.g., 3-pyridyl) optionally substituted by $R^{10}$, or taken together with $R^{W1}$, $R^{W2}$, where present, $R^{X1}$, $R^{X2}$, $R^{Y1}$, $R^{Y2}$, $R^9$ and the atoms to which they are attached to form a 5-10-membered heteroaryl (e.g., 4-pyridyl) optionally substituted by $R^{10}$. In some embodiments, $R^8$ is hydrogen or $C_1$-$C_6$ alkyl optionally substituted by $R^{10}$. In some embodiments, $R^8$ is hydrogen or $C_1$-$C_6$ alkyl. In some embodiments, $R^8$ is hydrogen. In some embodiments, $R^8$ is $C_1$-$C_6$ alkyl optionally substituted by $R^{10}$ (e.g., benzyl). In some embodiments, $R^8$ is $C_1$-$C_6$ alkyl (e.g., methyl or 2-propyl). In some embodiments, $R^8$ is taken together with $R^{Y1}$, $R^{Y2}$, $R^{X1}$, $R^{X2}$, or $R^{W1}$, where present, to form a $C_1$-$C_6$ alkylene optionally substituted by $R^{10}$. In some embodiments, $R^8$ is taken together with $R^{10}$, where present, to form a $C_1$-$C_6$ alkylene. In some embodiments, $R^8$ is $C_6$-$C_{14}$ aryl. In some embodiments, $R^8$ is phenyl. In some embodiments, when $R^8$ is phenyl, $R^9$ is hydrogen or $C_1$-$C_6$ alkyl optionally substituted by $R^{10}$. In some embodiments, $R^8$ is 5-10-membered heteroaryl.

In some embodiments of the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a) or any variation thereof, or a salt or solvate thereof, $R^9$ is hydrogen, $C_1$-$C_6$ alkyl optionally substituted by $R^{10}$, or taken together with $R^8$ and the nitrogen atom to which they are attached to form a 3-12-membered heterocyclyl optionally substituted by $R^{10}$ or a 5-10-membered heteroaryl optionally substituted by $R^{10}$, or taken together with $R^{Y1}$, $R^{Y2}$, $R^8$ and the atoms to which they are attached to form a 5-10-membered heteroaryl optionally substituted by $R^{10}$, or taken together with $R^{X1}$, $R^{X2}$, $R^{Y1}$, $R^{Y2}$, $R^8$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y1}$, $R^{Y2}$, $R^8$ and the atoms to which they are attached to form a 5-10-membered heteroaryl optionally substituted by $R^{10}$. In some embodiments, $R^9$ is hydrogen or $C_1$-$C_6$ alkyl optionally substituted by $R^{10}$. In some embodiments, $R^9$ is hydrogen. In some embodiments, $R^9$ is $C_1$-$C_6$ alkyl optionally substituted by $R^{10}$. In some embodiments, $R^9$ is $C_1$-$C_6$ alkyl substituted by phenyl (e.g., benzyl). In some embodiments, $R^9$ is $C_1$-$C_6$ alkyl (e.g., methyl or 2-propyl).

In some embodiments, each $R^8$ and $R^9$ is independently hydrogen or $C_1$-$C_6$ alkyl optionally substituted by $R^{10}$. In some embodiments, each $R^8$ and $R^9$ is independently $C_1$-$C_6$ alkyl optionally substituted by $R^{10}$. In some embodiments, each $R^8$ and $R_9$ is methyl. In some embodiments, $R^8$ is methyl and $R^9$ is benzyl. In some embodiments, $R^8$ is hydrogen and $R^9$ is methyl, 2-propyl or benzyl.

In some embodiments, $R^7$ and $R^8$ are taken together to form an ethylene optionally substituted by $R^{10}$. In some embodiments, $R^7$ and $R^8$ are taken together to form an ethylene ($-CH_2CH_2-$).

In some embodiments, $R^8$ and $R^9$ are taken together with the nitrogen atom to which they are attached to form a 3-12-membered heterocyclyl optionally substituted by $R^{10}$ or a 5-10-membered heteroaryl optionally substituted by $R^{10}$. In some embodiments, $R^8$ and $R^9$ are taken together with the nitrogen atom to which they are attached to form a 3-12-membered heterocyclyl optionally substituted by $R^{10}$. In some embodiments, $R^8$ and $R^9$ are taken together with the nitrogen atom to which they are attached to form a 3-7-membered heterocyclyl (e.g., azetidinyl, pyrrolidinyl and morpholinyl) optionally substituted by $R^{10}$. In some embodiments, $R^8$ and $R^9$ are taken together with the nitrogen atom to which they are attached to form a 5-10-membered heteroaryl optionally substituted by $R^{10}$. In some embodiments, the 5-10-membered heteroaryl is a monocyclic 5- or 6-membered heteroaryl (e.g., 1-imidazolyl). In some embodiments, the 5-10-membered heteroaryl is a fused ring heteroaryl comprising an aryl moiety fused to a heterocycle containing the nitrogen atom to which $R^8$ and $R^9$ are attached. In some embodiments, the 5-10-membered heteroaryl is a fused ring heteroaryl comprising an aryl moiety fused to a heterocycle containing the nitrogen atom to which $R^8$ and $R^9$ are attached and the aryl moiety is not adjacent to the nitrogen atom to which $R^8$ and $R^9$ are attached. In some embodiments, $R^8$ and $R^9$ are taken together with the nitrogen atom to which they are attached to form a 5-6-membered heterocyclyl (e.g., pyrrolidinyl or piperidinyl) fused with an aryl or heteroaryl optionally substituted by $R^{10}$. In some embodiments, $R^8$ and $R^9$ are taken together with the nitrogen atom to which they are attached to form a 5-10-membered heteroaryl optionally substituted by $R^{10}$, wherein the 5-10-membered heteroaryl is other than indolin-1-yl and 3,4-dihydroquinolin-1(2H)-yl.

In some embodiments, $R^8$ is taken together with $R^{Y1}$, $R^{Y2}$, $R^{X1}$, $R^{X2}$, or $R^{W1}$, where present, to form a $C_1$-$C_6$ alkylene optionally substituted by $R^{10}$. In some embodiments, $R^8$ is taken together with $R^{Y1}$, $R^{Y2}$, $R^{X1}$, $R^{X2}$, or $R^{W1}$, where present, to form a $C_1$-$C_4$ alkylene optionally substituted by $R^{10}$. In some embodiments, $R^8$ is taken together with $R^{Y1}$, $R^{Y2}$, $R^{X1}$, $R^{X2}$, or $R^{W1}$, where present, to form a methylene ($-CH_2-$), ethylene ($-CH_2CH_2-$), or propylene ($-CH_2CH_2CH_2-$).

In some embodiments, $R^8$ is taken together with $R^{10}$, where present, to form a $C_1$-$C_6$ alkylene. In some embodiments, $R^8$ is taken together with $R^{10}$, where present, to form a $C_1$-$C_4$ alkylene. In some embodiments, $R^8$ is taken together with $R^{10}$, where present, to form a methylene ($-CH_2-$), ethylene ($-CH_2CH_2-$), or propylene ($-CH_2CH_2CH_2-$).

In some embodiments of the compound of formula (A-I), (I), (Ia), (10), (I$^0$a), (II), (IIa), (III), (IIIa), (IV), (IV-a), (V), (V-a), (VI), (VI-a), (VII), (VII-a), (VIII), (VIII-a) or any variation thereof, or a salt or solvate thereof, W is a bond or $C_1$-$C_4$ alkylene optionally substituted by one or both of $R^{W1}$ and $R^{W2}$. $R^{W1}$, where present, is $C_1$-$C_6$ alkyl optionally substituted by $R^{10A}$, or taken together with $R^7$, $R^8$, $R^{X1}$ or $R^{Y1}$ to form a $C_1$-$C_6$ alkylene optionally substituted by $R^{10}$, or taken together with $R^{W2}$, $R^{X1}$, $R^{X2}$, $R^{Y1}$, $R^{Y2}$, $R^8$, $R^9$ and the atoms to which they are attached to form a 5-10-membered heteroaryl optionally substituted by $R^{10}$. $R^{W2}$, where present, is $C_1$-$C_6$ alkyl optionally substituted by $R^{10A}$, or taken together with $R^{W1}$, $R^{X1}$, $R^{X2}$, $R^{Y1}$, $R^{Y2}$, $R^8$, $R^9$ and the atoms to which they are attached to form a 5-10-membered heteroaryl optionally substituted by $R^{10}$. In some embodiments, W is a bond (or absent). In some embodiments, W is a bond or $C_1$-$C_4$ alkylene. In some embodiments, W is a $C_1$-$C_4$ alkylene. In some embodiments, W is methylene ($-CH_2-$), ethylene ($-CH_2CH_2-$), propylene ($-CH_2CH_2CH_2-$), or butylene ($-CH_2(CH_2)_2CH_2-$). In some embodiments, W is methylene ($-CH_2-$). In some embodiments, W is ethylene ($-CH_2CH_2-$). In some embodiments, W is propylene ($-CH_2CH_2CH_2-$).

In some embodiments, W is $C_1$-$C_4$ alkylene optionally substituted by one or both of $R^{W1}$ and $R^{W2}$.

In some embodiments, W is $C_1$-$C_4$ alkylene substituted by $R^{W1}$. In some embodiments, W is $-CHR^{W1}-$. In some embodiments, W is $-CH_2-CHR^{W1}-$. In some embodiments, W is $-CH_2CH_2-CHR^{W1}-$ In some of these embodiments, $R^{W1}$ is $C_1$-$C_6$ alkyl optionally substituted by $R^{10A}$. In some of these embodiments, $R^{W1}$ is $C_1$-$C_6$ alkyl (e.g., methyl). In some of these embodiments, $R^{W1}$ is taken together with $R^7$, $R^8$, $R^{X1}$ or $R^{Y1}$ to form a $C_1$-$C_6$ alkylene optionally substituted by $R^{10}$.

In some embodiments, W is $C_1$-$C_4$ alkylene substituted by $R^{W1}$ and $R^{W2}$, wherein $R^{W1}$ and $R^{W2}$ may be attached to the same or different carbon atoms of the $C_1$-$C_4$ alkylene. In some embodiments, W is $-CR^{W1}R^{W2}-$. In some embodiments, W is $-CH_2-CR^{W1}R^{W2}-$. In some embodiments, W is $-CH_2CH_2-CR^{W1}R^{W2}-$ In some of these embodiments, each $R^{W1}$ and $R^{W2}$ is independently $C_1$-$C_6$ alkyl optionally substituted by $R^{10A}$. In some of these embodiments, each $R^{W1}$ and $R^{W2}$ is independently $C_1$-$C_6$ alkyl (e.g., methyl).

In some embodiments of the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a) or any variation thereof, or a salt or solvate thereof, X is —$CR^{X1}R^{X2}$—. $R^{X1}$ is hydrogen, $C_1$-$C_6$ alkyl optionally substituted by $R^{10A}$, or taken together with $R^7$, $R^8$, $R^{Y1}$ or $R^{W1}$, where present, to form a $C_1$-$C_6$ alkylene optionally substituted by $R^{10}$, or taken together with $R^{X2}$, $R^{Y1}$, $R^{Y2}$, $R^8$, $R^9$ and the atoms to which they are attached to form a 5-10-membered heteroaryl optionally substituted by $R^{10}$, or taken together with $R^{W1}$, $R^{W2}$, where present, $R^{X2}$, $R^{Y1}$, $R^{Y2}$, $R^8$, $R^9$ and the atoms to which they are attached to form a 5-10-membered heteroaryl optionally substituted by $R^{10}$. $R^{X2}$ is hydrogen or $C_1$-$C_6$ alkyl optionally substituted by $R^{10A}$, or taken together with $R^{X1}$, $R^{Y1}$, $R^{Y2}$, $R^8$, $R^9$ and the atoms to which they are attached to form a 5-10-membered heteroaryl optionally substituted by $R^{10}$, or taken together with $R^{W1}$, $R^{W2}$, where present, $R^{X1}$, $R^{Y1}$, $R^{Y2}$, $R^8$, $R^9$ and the atoms to which they are attached to form a 5-10-membered heteroaryl optionally substituted by $R^{10}$, or taken together with $R^8$ to form a $C_1$-$C_6$ alkylene optionally substituted by $R^{10}$.

In some embodiments, each $R^{X1}$ and $R^{X2}$ is independently hydrogen or $C_1$-$C_6$ alkyl optionally substituted by $R^{10A}$. In some embodiments, each $R^{X1}$ and $R^{X2}$ is independently hydrogen or $C_1$-$C_6$ alkyl (e.g., methyl). In some embodiments, each $R^{X1}$ and $R^{X2}$ is hydrogen. In some embodiments, each $R^{X1}$ and $R^{X2}$ is methyl. In some embodiments, $R^{X1}$ is taken together with $R^7$, $R^8$, $R^{Y1}$ or $R^{W1}$, where present, to form a $C_1$-$C_6$ alkylene optionally substituted by $R^{10}$.

In some embodiments of the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a) or any variation thereof, or a salt or solvate thereof, Y is —$CR^{Y1}R^{Y2}$—. $R^{Y1}$ is hydrogen, $C_1$-$C_6$ alkyl optionally substituted by $R^{10A}$, or taken together with $R^7$, $R^8$, $R^{X1}$ or $R^{W1}$, where present, to form a $C_1$-$C_6$ alkylene optionally substituted by $R^{10}$, or taken together with $R^{Y2}$, $R^8$, $R^9$ and the atoms to which they are attached to form a 5-10-membered heteroaryl optionally substituted by $R^{10}$, or taken together with $R^{X1}$, $R^{X2}$, $R^{Y2}$, $R^8$, $R^9$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y2}$, $R^8$, $R^9$ and the atoms to which they are attached to form a 5-10-membered heteroaryl optionally substituted by $R^{10}$. $R^{Y2}$ is hydrogen, $C_1$-$C_6$ alkyl optionally substituted by $R^{10A}$, or taken together with $R^{Y1}$, $R^8$, $R^9$ and the atoms to which they are attached to form a 5-10-membered heteroaryl optionally substituted by $R^{10}$, or taken together with $R^{X1}$, $R^{X2}$, $R^{Y1}$, $R^8$, $R^9$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y1}$, $R^8$, $R^9$ and the atoms to which they are attached to form a 5-10-membered heteroaryl optionally substituted by $R^{10}$, or taken together with $R^8$ to form a $C_1$-$C_6$ alkylene optionally substituted by $R^{10}$.

In some embodiments, each $R^{Y1}$ and $R^{Y2}$ is independently hydrogen or $C_1$-$C_6$ alkyl optionally substituted by $R^{10}$. In some embodiments, each $R^{Y1}$ and $R^{Y2}$ is independently hydrogen or $C_1$-$C_6$ alkyl (e.g., methyl). In some embodiments, each $R^{Y1}$ and $R^{Y2}$ is hydrogen. In some embodiments, each $R^{Y1}$ and $R^{Y2}$ is methyl. In some embodiments, $R^{Y1}$ is taken together with $R^7$, $R^8$, $R^{X1}$ or $R^{W1}$, where present, to form a $C_1$-$C_6$ alkylene optionally substituted by $R^{10}$.

In some embodiments, $R^7$ and $R^{Y1}$ are taken together to form a $C_1$-$C_6$ alkylene optionally substituted by $R^{10}$. In some embodiments, $R^7$ and $R^{Y1}$ are taken together to form a $C_1$-$C_6$ alkylene. In some embodiments, $R^7$ and $R^{Y1}$ are taken together to form a $C_1$-$C_4$ alkylene optionally substituted by $R^{10}$. In some embodiments, $R^7$ and $R^{Y1}$ are taken together to form a $C_1$-$C_4$ alkylene. In some embodiments, $R^7$ and $R^{Y1}$ are taken together to form a methylene (—$CH_2$—) or ethylene (—$CH_2CH_2$—).

In some embodiments, $R^7$ and $R^{X1}$ are taken together to form a $C_1$-$C_6$ alkylene optionally substituted by $R^{10}$. In some embodiments, $R^7$ and $R^{X1}$ are taken together to form a $C_1$-$C_6$ alkylene. In some embodiments, $R^7$ and $R^{X1}$ are taken together to form a $C_1$-$C_4$ alkylene optionally substituted by $R^{10}$. In some embodiments, $R^7$ and $R^{X1}$ are taken together to form a $C_1$-$C_4$ alkylene. In some embodiments, $R^7$ and $R^{X1}$ are taken together to form a methylene (—$CH_2$—) or ethylene (—$CH_2CH_2$—).

In some embodiments, $R^8$ and $R^{X1}$ are taken together to form a $C_1$-$C_6$ alkylene optionally substituted by $R^{10}$. In some embodiments, $R^8$ and $R^{X1}$ are taken together to form a $C_1$-$C_6$ alkylene. In some embodiments, $R^8$ and $R^{X1}$ are taken together to form a $C_1$-$C_4$ alkylene optionally substituted by $R^{10}$. In some embodiments, $R^8$ and $R^{X1}$ are taken together to form a $C_4$-$C_4$ alkylene. In some embodiments, $R^8$ and $R^{X1}$ are taken together to form a methylene (—$CH_2$—) or ethylene (—$CH_2CH_2$—).

In some embodiments, $R^8$ and $R^{Y1}$ are taken together to form a $C_1$-$C_6$ alkylene optionally substituted by $R^{10}$. In some embodiments, $R^8$ and $R^{Y1}$ are taken together to form a $C_1$-$C_6$ alkylene. In some embodiments, $R^8$ and $R^{Y1}$ are taken together to form a $C_1$-$C_4$ alkylene optionally substituted by $R^{10}$. In some embodiments, $R^8$ and $R^{Y1}$ are taken together to form a $C_1$-$C_4$ alkylene. In some embodiments, $R^8$ and $R^{Y1}$ are taken together to form a propylene (—$CH_2CH_2CH_2$—) or ethylene (—$CH_2CH_2$—).

In some embodiments, $R^8$ and $R^{W1}$ are taken together to form a $C_1$-$C_6$ alkylene optionally substituted by $R^{10}$. In some embodiments, $R^8$ and $R^{W1}$ are taken together to form a $C_1$-$C_6$ alkylene. In some embodiments, $R^8$ and $R^{W1}$ are taken together to form a $C_1$-$C_4$ alkylene optionally substituted by $R^{10}$. In some embodiments, $R^8$ and $R^{W1}$ are taken together to form a $C_1$-$C_4$ alkylene. In some embodiments, $R^8$ and $R^{W1}$ are taken together to form a methylene (—$CH_2$—) or ethylene (—$CH_2CH_2$—).

In some embodiments, $R^{Y1}$ and $R^{W1}$ are taken together to form a $C_1$-$C_6$ alkylene optionally substituted by $R^{10}$. In some embodiments, $R^{Y1}$ and $R^{W1}$ are taken together to form a $C_1$-$C_6$ alkylene. In some embodiments, $R^{Y1}$ and $R^{W1}$ are taken together to form a $C_1$-$C_4$ alkylene optionally substituted by $R^{10}$. In some embodiments, $R^{Y1}$ and $R^{W1}$ are taken together to form a $C_1$-$C_4$ alkylene. In some embodiments, $R^{Y1}$ and $R^{W1}$ are taken together to form a methylene (—$CH_2$—) or ethylene (—$CH_2CH_2$—).

In some embodiments, $R^{Y1}$, $R^{Y2}$, $R^8$ and $R^9$ are taken together with the atoms to which they are attached to form a 5-10-membered heteroaryl optionally substituted by $R^{10}$. In some embodiments, $R^{Y1}$, $R^{Y2}$, $R^8$ and $R^9$ are taken together with the atoms to which they are attached to form a 5- or 6-membered heteroaryl (e.g., 4-imidazolyl or 2-pyridyl) optionally substituted by $R^{10}$. In some embodiments, $R^{Y1}$, $R^{Y2}$, $R^8$ and $R^9$ are taken together with the atoms to which they are attached to form imidazol-4-yl.

In some embodiments, $R^{X1}$, $R^{X2}$, $R^{Y1}$, $R^{Y2}$, $R_8$, $R_9$ are taken together with the atoms to which they are attached to form a 5-10-membered heteroaryl optionally substituted by $R^{10}$. In some embodiments, $R^{X1}$, $R^{X2}$, $R^{Y1}$, $R^{Y2}$, $R^8$, $R^9$ are taken together with the atoms to which they are attached to form a 5- or 6-membered heteroaryl (e.g., 2-pyridyl) optionally substituted by $R^{10}$. In some embodiments, $R^{X1}$, $R^{X2}$, $R^{Y1}$, $R^{Y2}$, $R^8$, $R^9$ are taken together with the atoms to which they are attached to form pyridin-3-yl.

In some embodiments, $R^{X2}$ is taken together with $R^8$ to form a $C_1$-$C_6$ alkylene optionally substituted by $R^{10}$. In some embodiments, $R^{X2}$ and $R^8$ are taken together to form a $C_1$-$C_4$ alkylene optionally substituted by $R^{10}$. In some embodiments, $R^{X2}$ and $R^8$ are taken together to form a propylene (—$CH_2CH_2CH_2$—), ethylene (—$CH_2CH_2$—), or methylene (—$CH_2$—).

In some embodiments, W is $C_1$-$C_4$ alkylene substituted by $R^{W1}$ and $R^{W2}$, and $R^{W1}$, $R^{W2}$, $R^{X1}$, $R^{X2}$, $R^{Y1}$, $R^{Y2}$, $R^8$, $R^9$ are taken together with the atoms to which they are attached to form a 5-10-membered heteroaryl optionally substituted by $R^{10}$. In some embodiments, $R^{W1}$, $R^{W2}$, $R^{X1}$, $R^{X2}$, $R^{Y1}$, $R^{Y2}$, $R^8$, $R^9$ are taken together with the atoms to which they are attached to form a 5- or 6-membered heteroaryl (e.g., 4-pyridyl) optionally substituted by $R^{10}$. In some embodiments, $R^{W1}$, $R^{W2}$, $R^{X1}$, $R^{X2}$, $R^{Y1}$, $R^{Y2}$, $R^8$, $R^9$ are taken together with the atoms to which they are attached to form pyridin-4-yl. In some embodiments, W is a bond (or absent).

In some embodiments, $R^{W1}$ is taken together with $R^8$ to form a $C_1$-$C_6$ alkylene optionally substituted by $R^{10}$. In some embodiments, $R^{W1}$ and $R^8$ are taken together to form a $C_1$-$C_4$ alkylene optionally substituted by $R^{10}$. In some embodiments, $R^{W1}$ and $R^8$ are taken together to form a propylene (—$CH_2CH_2CH_2$—), ethylene (—$CH_2CH_2$—), or methylene (—$CH_2$—).

In some embodiments, $R^7$ and $R^{Y1}$, $R^{X1}$ or $R^{W1}$, where present, are taken together to form a $C_1$-$C_6$ alkylene substituted by $R^{10}$, and $R^8$ is taken together with $R^{10}$ to form a $C_1$-$C_6$ alkylene, to form a fused bicyclic moiety. In some embodiments, $R^7$ and $R^{Y1}$, $R^{X1}$ or $R^{W1}$, where present, are taken together to form a $C_1$-$C_4$ alkylene substituted by $R^{10}$, and $R^8$ is taken together with $R^{10}$ to form a $C_1$-$C_4$ alkylene. In some embodiments, $R^7$ and $R^{Y1}$, $R^{X1}$ or $R^{W1}$, where present, are taken together to form a methylene or ethylene substituted by $R^{10}$, and $R^8$ is taken together with $R^{10}$ to form a methylene or ethylene. In one embodiment, $R^7$ and $R^{X1}$ are taken together to form an ethylene substituted by $R^{10}$, and $R^8$ is taken together with $R^{10}$ to form a methylene.

In some embodiments, $R^7$ and $R^{X1}$ are taken together to form a $C_1$-$C_6$ alkylene optionally substituted by $R^{10}$, and $R^8$ is taken together with $R^{X2}$ to form a $C_1$-$C_6$ alkylene, to form a spiro bicyclic moiety. In some embodiments, $R^7$ and $R^{X1}$ are taken together to form a $C_1$-$C_4$ alkylene optionally substituted by $R^{10}$, and $R^8$ is taken together with $R^{X2}$ to form a $C_1$-$C_4$ alkylene. In some embodiments, $R^7$ and $R^{X1}$ are taken together to form a methylene or ethylene, and $R^8$ is taken together with $R^{X2}$ to form a methylene or ethylene. In one embodiment, $R^7$ and $R^{X1}$ are taken together to form an ethylene, and $R^8$ and $R^{X2}$ are taken together to form a methylene.

In some embodiments of the compound of formula (A-I), (I), (Ia), (I°), (I°a), (II), (IIa), (III), (IIIa), (IV), (IV-a), (V), (V-a), (VI), (VI-a), (VII), (VII-a), (VIII), (VIII-a), or any variation thereof, or a salt or solvate thereof, the —N($R^7$)—W—X—Y—N($R^8$)$R^9$ moiety or the —[N($R^7$)—W—X—Y]$_m$—N($R^8$)$R^9$ moiety, where applicable, is selected from the group consisting of:

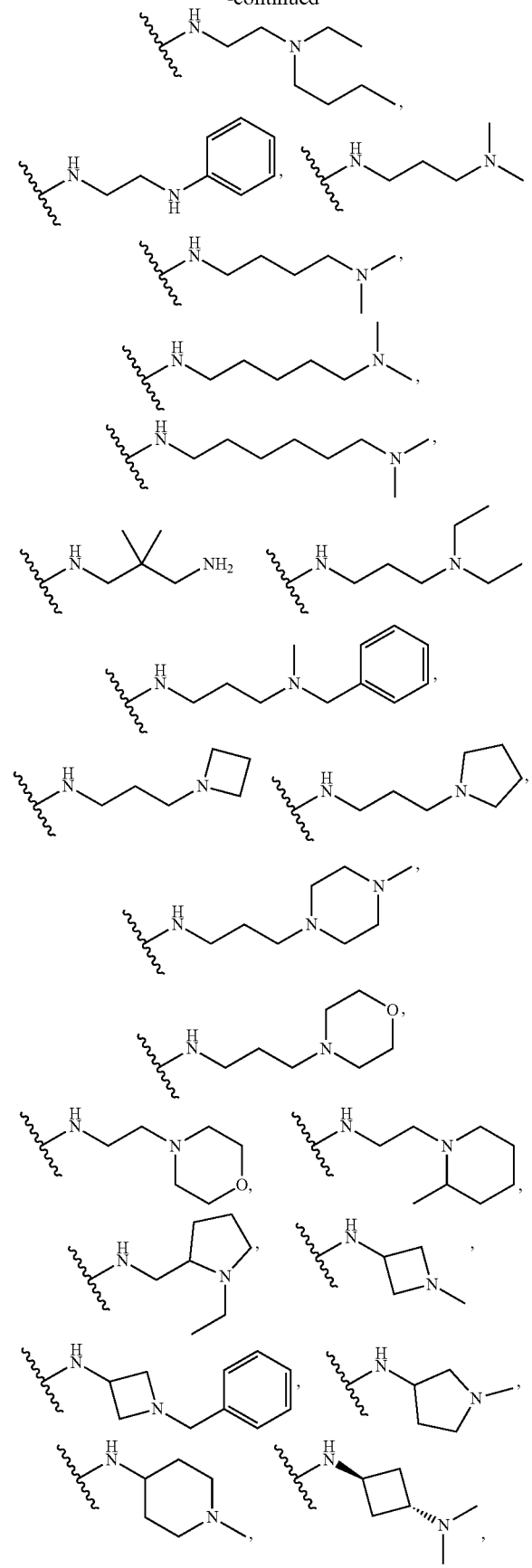

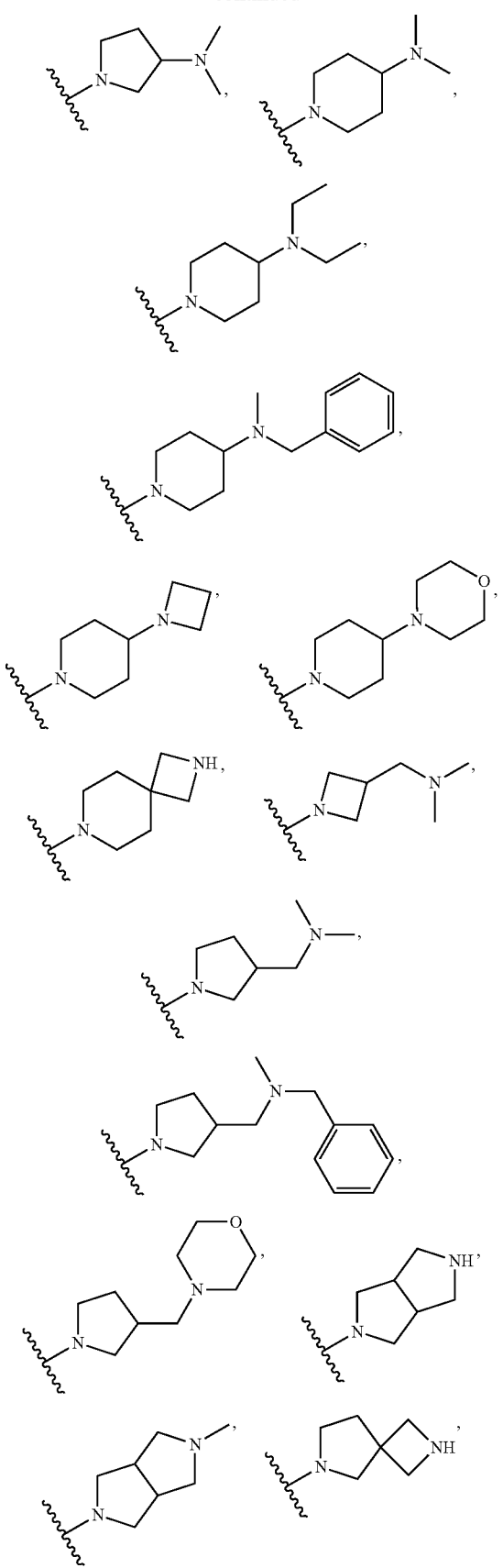
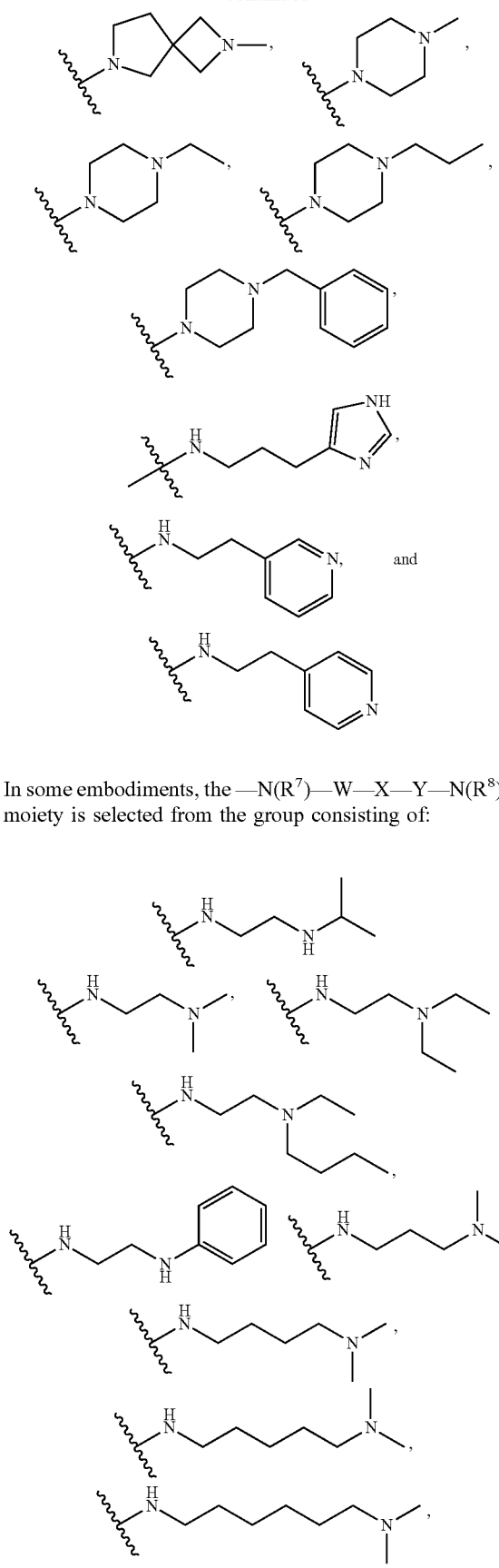
In some embodiments, the —N(R⁷)—W—X—Y—N(R⁸)R⁹ moiety is selected from the group consisting of:

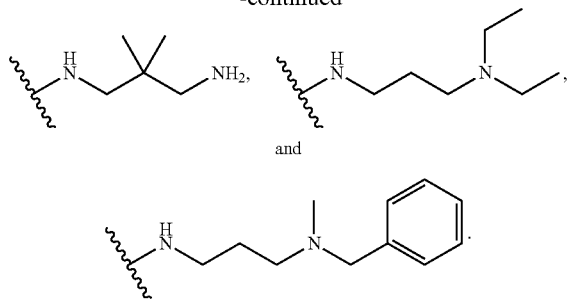

In some embodiments, the —N(R$^7$)—W—X—Y—N(R$^8$)R$^9$ moiety is selected from the group consisting of:

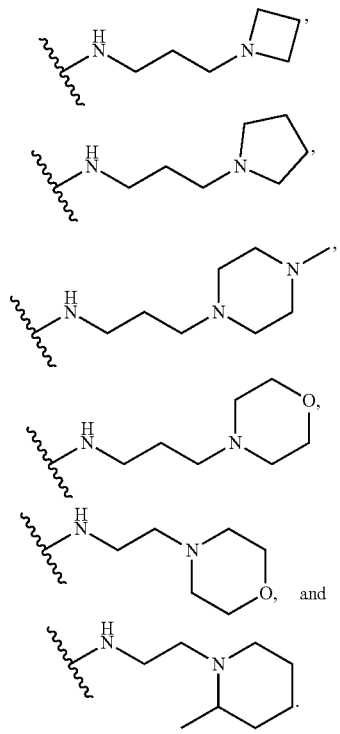

In some embodiments, the —N(R$^7$)—W—X—Y—N(R$^8$)R$^9$ moiety is

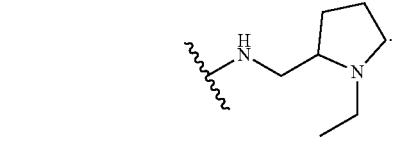 [SMILES: *NCC1CCCN1CC]

In some embodiments, the —N(R$^7$)—W—X—Y—N(R$^8$)R$^9$ moiety is selected from the group consisting of:

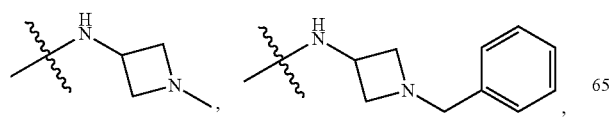

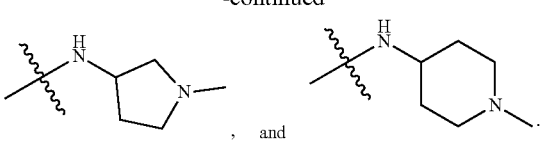

In some embodiments, the —N(R$^7$)—W—X—Y—N(R$^8$)R$^9$ moiety is

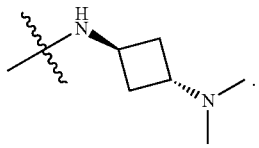 [SMILES: *N[C@H]1C[C@H](N(C)C)C1]

In some embodiments, the —N(R$^7$)—W—X—Y—N(R$^8$)R$^9$ moiety is selected from the group consisting of:

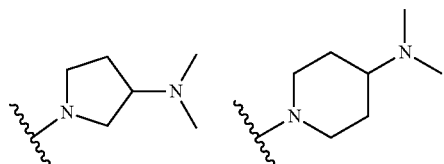

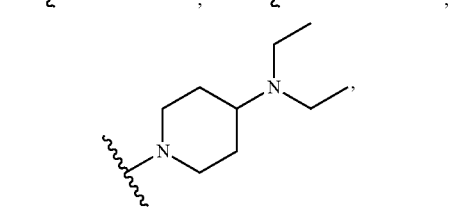

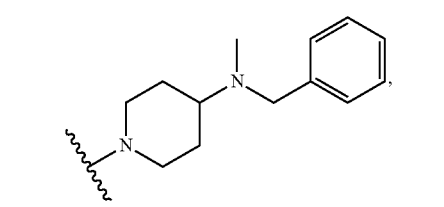

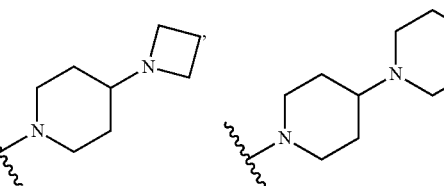

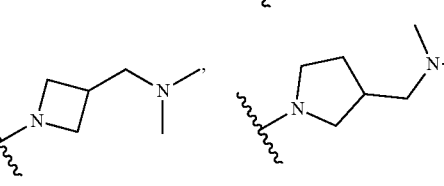

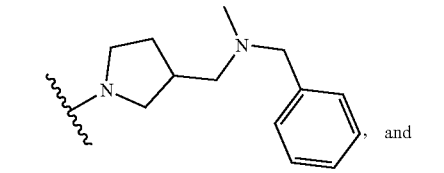

-continued

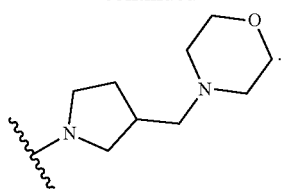

In some embodiments, the —N(R$^7$)—W—X—Y—N(R$^8$)R$^9$ moiety is selected from the group consisting of:

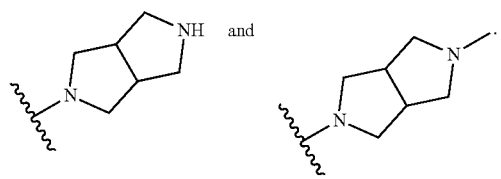

In some embodiments, the —N(R$^7$)—W—X—Y—N(R$^8$)R$^9$ moiety is selected from the group consisting of:

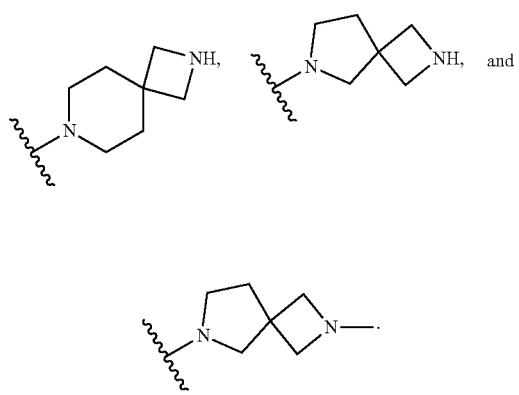

In some embodiments, the —N(R$^7$)—W—X—Y—N(R$^8$)R$^9$ moiety is selected from the group consisting of:

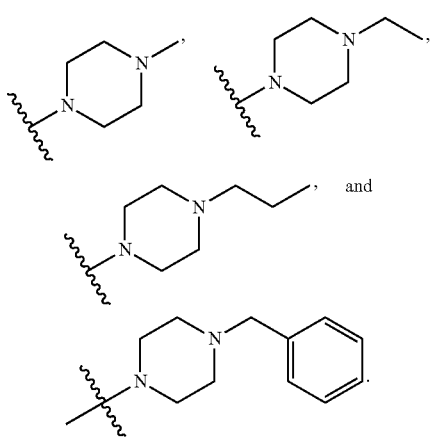

In some embodiments, the —N(R$^7$)—W—X—Y—N(R$^8$)R$^9$ moiety is selected from the group consisting of:

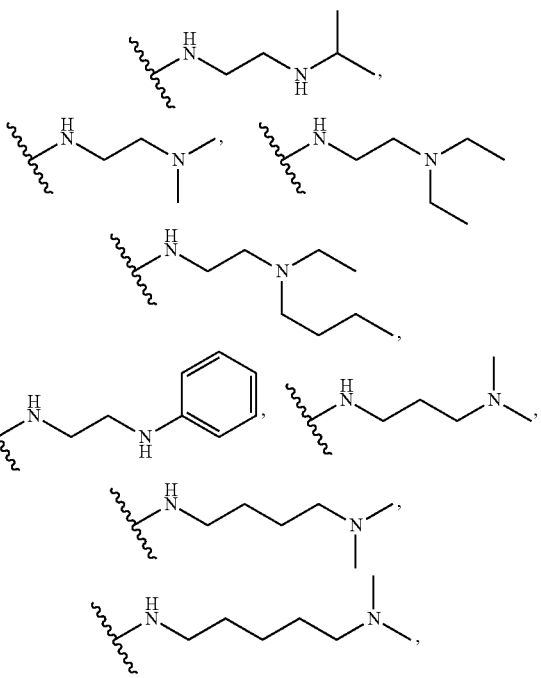

In some embodiments, the —[N(R$^7$)—W—X—Y]$_m$—N(R$^8$)R$^9$ moiety, where k is 0, is

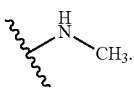

It is intended and understood that each and every variation of ring A$^1$, A$^2$, A$^3$, A$^4$, A$^5$; i, j, U and V described herein, may be combined with each and every variation of R$^1$, R$^3$, R$^6$, R$^7$, R$^8$, R$^9$, W, X, Y, Z, m and n described herein, the same as if each and every combination is individually and specifically described. For example, in some embodiments, A$^1$ is N, A$^2$ is CR$^2$, A$^3$ is N, A$^4$ is N, A$^5$ is N; i is 2, is 1; U is a bond; V is a bond or ethylene (—CH$_2$CH$_2$—); R$^1$ is phenyl optionally substituted by R$^{10A}$ (e.g., 4-methylphenyl or 4-chlorophenyl); R$^2$ is hydrogen or C$_1$-C$_6$ alkyl (e.g., methyl); R$^3$ is hydrogen or C$_1$-C$_6$ alkyl (e.g., methyl), n is 0, 1 or 2; each R$^6$ is independently C$_1$-C$_6$ alkyl, Z is C, m is 1, and the —N(R$^7$)—W—X—Y—N(R$^8$)R$^9$ moiety is selected from the group consisting of:

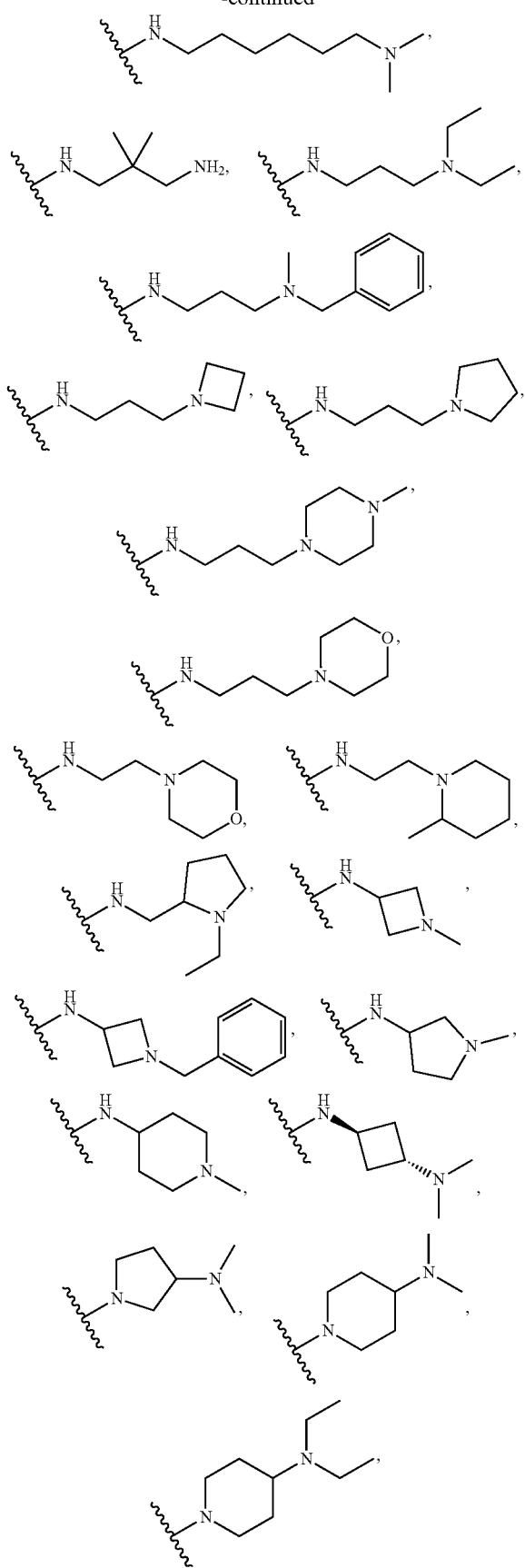
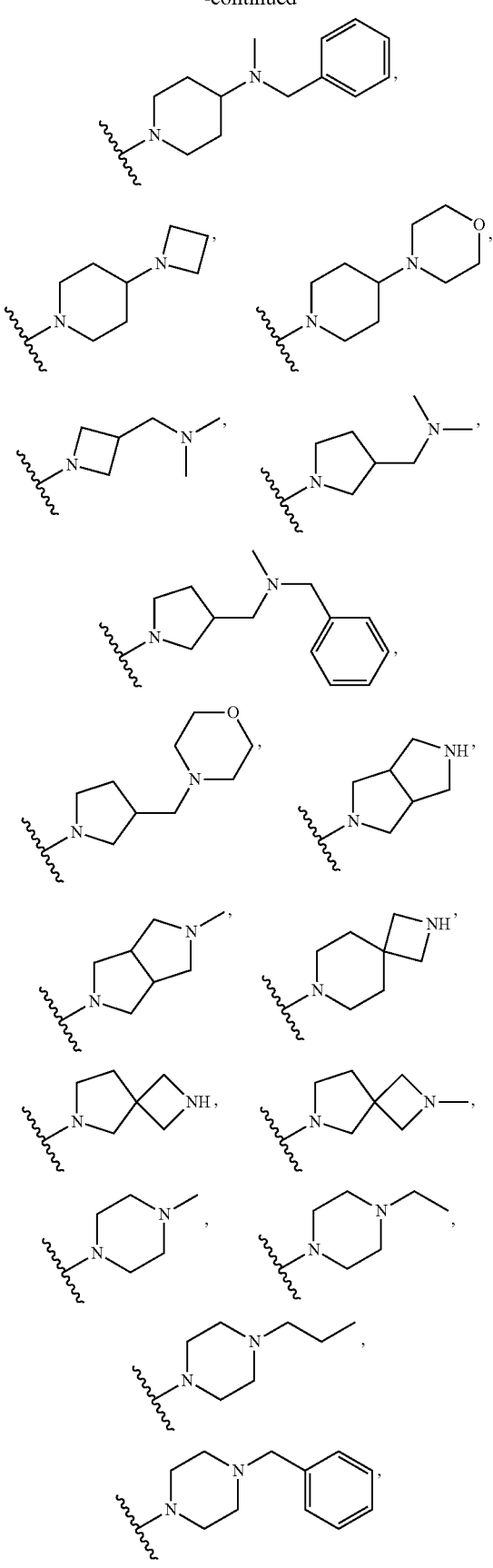

-continued

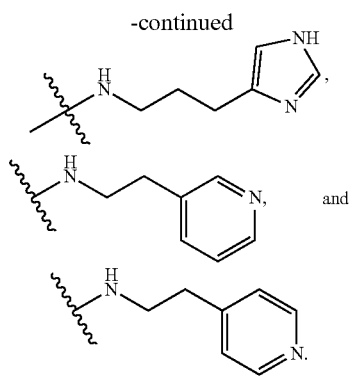

and

In some of these embodiments, $R^1$ is phenyl optionally substituted by $C_1$-$C_6$ alkyl or halo. In some of these embodiments, $R^2$ is hydrogen or methyl. In some of these embodiments, $R^2$ is trifluoromethyl. In some of these embodiments, $R^2$ is phenyl. In some of these embodiments, $R^3$ is hydrogen or methyl. In some of these embodiments, $R^3$ is $CF_3$. In some of these embodiments, $R^3$ is halo (e.g., chloro or iodo). In some of these embodiments, $R^3$ is phenyl. In some of these embodiments, V is a bond. In some of these embodiments, V is a bond. In some of these embodiments, n is 0.

When a group or moiety is optionally substituted by $R^{10}$ or $R^{10A}$, unless otherwise specified, the group or moiety may be unsubstituted or substituted by one or more (e.g., 1, 2, 3, 4 or 5) applicable substituents independently selected from the groups listed for $R^{10}$ or $R^{10A}$. In one embodiment, a group or moiety optionally substituted by $R^{10}$ or $R^{10A}$ has one substituent selected from the groups listed for $R^{10}$ or $R^{10A}$. In another embodiment, a group or moiety optionally substituted by $R^{10}$ or $R^{10A}$ has two substituents independently selected from the groups listed for $R^{10}$ or $R^{10A}$. In another embodiment, a group or moiety optionally substituted by $R^{10}$ or $R^{10A}$ has three substituents independently selected from the groups listed for $R^{10}$ or $R^{10A}$. In another embodiment, a group or moiety optionally substituted by $R^{10}$ or $R^{10A}$ has four substituents independently selected from the groups listed for $R^{10}$ or $R^{10A}$. In some embodiments, a group or moiety optionally substituted by $R^{10}$ or $R^{10A}$ has 1 to 2, 1 to 3, 1 to 4 or 1 to 5 substituents independently selected from the groups listed for $R^{10}$ or $R^{10A}$.

In some embodiments, each optional substituent $R^{10}$ is independently $C_1$-$C_6$ alkyl, $C_2$-$C_6$ alkenyl, $C_2$-$C_6$ alkynyl, $C_3$-$C_8$ cycloalkyl, 3-12-membered heterocyclyl, 5-10-membered heteroaryl, $C_6$-$C_{14}$ aryl, halogen, —CN, —$OR^{11}$, —$SR^{11}$, —$NR^{12}R^{13}$, —$NO_2$, —C=NH($OR^{11}$), —C(O)$R^{11}$, —OC(O)$R^{11}$, —C(O)$OR^{11}$, —C(O)$NR^{12}R^{13}$, —$NR^1$C(O)$R^{12}$, —$NR^1$C(O)$OR^{12}$, —$NR^{11}$C(O)$NR^{12}R^{13}$, —S(O)$R^{11}$, —S(O)$_2R^{11}$, —$NR^{11}$S(O)$R^{12}$, —$NR^{11}$S(O)$_2R^{12}$, —S(O)$NR^{12}R^{13}$, —S(O)$_2NR^{12}R^{13}$, or —P(O)($OR^{12}$)($OR^{13}$); wherein the $C_1$-$C_6$ alkyl, $C_2$-$C_6$ alkenyl, $C_2$-$C_6$ alkynyl, $C_3$-$C_8$ cycloalkyl, 3-12-membered heterocyclyl, 5-10-membered heteroaryl and $C_6$-$C_{14}$ aryl of $R^{10}$ are independently optionally substituted by halogen, —CN, oxo, —$OR^{14}$, —$SR^{14}$, —$NR^{14}R^{15}$, —C(O)$R^{14}$, —C(O)$OR^{14}$, —S(O)$R^{14}$, —S(O)$_2R^{14}$, —P(O)($OR^{14}$)($OR^{15}$), 3-12-membered heterocyclyl, 5-10-membered heteroaryl, $C_6$-$C_{14}$ aryl, $C_3$-$C_8$ cycloalkyl, or $C_1$-$C_6$ alkyl optionally substituted by oxo, —OH or halogen.

In some embodiments, each optional substituent $R^{10}$ is independently $C_1$-$C_6$ alkyl, $C_3$-$C_6$ cycloalkyl, 3-12-membered heterocyclyl, 5-10-membered heteroaryl, $C_6$-$C_{14}$ aryl, halogen, —CN, —$OR^{11}$, —$NR^{12}R^{13}$, —$NO_2$, or —C(O)$R^{11}$, wherein the $C_1$-$C_6$ alkyl, $C_3$-$C_8$ cycloalkyl, 3-12-membered heterocyclyl, 5-10-membered heteroaryl and $C_6$-$C_{14}$ aryl of $R^{10}$ are independently optionally substituted by halogen, —CN, oxo, or —$OR^{14}$. In some embodiments, each optional substituent $R^{10}$ is independently halogen (e.g., F or $C_1$); —$OR^{11}$ (e.g., $OCH_3$); or $C_1$-$C_6$ alkyl (e.g., methyl) optionally substituted by halogen, —CN, oxo, —$OR^{14}$.

In some embodiments, $R^{10}$ is taken together with $R^8$ to form a $C_1$-$C_6$ alkylene. In some embodiments, $R^{10}$ is taken together with $R^8$ to form a $C_1$-$C_4$ alkylene. In some embodiments, $R^{10}$ is taken together with $R^8$ to form a propylene (—$CH_2CH_2CH_2$—), ethylene (—$CH_2CH_2$—), or methylene (—$CH_2$—).

In some embodiments, each $R^{10A}$ is independently oxo or any variation detailed herein for $R^{10}$. In some embodiments, each $R^{10A}$ is independently $C_1$-$C_6$ alkyl, $C_2$-$C_6$ alkenyl, $C_2$-$C_6$ alkynyl, $C_3$-$C_8$ cycloalkyl, 3-12-membered heterocyclyl, 5-10-membered heteroaryl, $C_6$-$C_{14}$ aryl, halogen, —CN, —$OR^{11}$, —$SR^{11}$, —$NR^{12}R^{13}$, —$NO_2$, —C=NH($OR^{11}$), —C(O)$R^{11}$, —OC(O)$R^{11}$, —C(O)$OR^{11}$, —C(O)$NR^{12}R^{13}$, —$NR^{11}$C(O)$R^{12}$, —$NR^{11}$C(O)$OR^{12}$, —$NR^{11}$C(O)$NR^{12}R^{13}$, —S(O)$R^{11}$, —S(O)$_2R^{11}$, —$NR^{11}$S(O)$R^{12}$, —$NR^1$S(O)$_2R^{12}$, —S(O)$NR^{12}R^{13}$, —S(O)$_2NR^{12}R^{13}$, —P(O)($OR^{12}$)($OR^{13}$); wherein the $C_1$-$C_6$ alkyl, $C_2$-$C_6$ alkenyl, $C_2$-$C_6$ alkynyl, $C_3$-$C_8$ cycloalkyl, 3-12-membered heterocyclyl, 5-10-membered heteroaryl and $C_6$-$C_{14}$ aryl of $R^{10A}$ are independently optionally substituted by halogen, —CN, oxo, —$OR^{14}$, —$SR^{14}$, —NR 14$R^{15}$, —C(O)$R^{14}$, —C(O)$OR^{14}$, —S(O)$R^{14}$, —S(O)$_2R^{14}$, —P(O)($OR^{14}$)($OR^{15}$), 3-12-membered heterocyclyl, 5-10-membered heteroaryl, $C_6$-$C_{14}$ aryl, $C_3$-$C_8$ cycloalkyl, or $C_1$-$C_6$ alkyl optionally substituted by oxo, —OH or halogen.

In some embodiments, each optional substituent $R^{10A}$ is independently oxo, $C_1$-$C_6$ alkyl, $C_3$-$C_8$ cycloalkyl, 3-12-membered heterocyclyl, 5-10-membered heteroaryl, $C_6$-$C_{14}$ aryl, halogen, —CN, —$OR^{11}$, —$NR^{12}R^{13}$, —$NO_2$, or —C(O)$R^{11}$, wherein the $C_1$-$C_6$ alkyl, $C_3$-$C_8$ cycloalkyl, 3-12-membered heterocyclyl, 5-10-membered heteroaryl and $C_6$-$C_{14}$ aryl of $R^{10A}$ are independently optionally substituted by halogen, —CN, oxo, or —$OR^{14}$. In some embodiments, each optional substituent $R^{10A}$ is independently oxo, halogen (e.g., F or $C_1$); —$OR^{11}$ (e.g., $OCH_3$); or $C_1$-$C_6$ alkyl (e.g., methyl) optionally substituted by halogen, —CN, oxo, —$OR^{14}$.

In some embodiments, $R^{11}$, $R^{12}$ and $R^{13}$ are each independently hydrogen or $C_1$-$C_6$ alkyl. In some embodiments, $R^{11}$ is hydrogen. In some embodiments, $R^{12}$ and $R^{13}$ are each hydrogen.

In some embodiments, $R^{14}$ and $R^{15}$ are each independently hydrogen or $C_1$-$C_6$ alkyl.

All variations referring to formula (I), where applicable, may apply equally to any of formula (A-I), (Ia), (I⁰), (I⁰a), (I⁰a-1), (I⁰a-2), (II), (IIa), (IIa-1), (IIa-1a), (IIa-1a-1), (IIa-1a-2), (IIa-1a-3), (IIa-1b), (IIa-1b-1), (IIa-1b-2), (IIa-1b-3), (IIa-1c), (IIa-1c-1), (IIa-1d), (IIa-1d-1), (IIa-1d-2), (IIa-1d-3), (IIa-1e), (IIa-1e-1), (IIa-1e-2), (IIa-1e-3), (IIa-1f), (IIa-1f-1), (IIa-1f-2), (IIa-1f-3), (III), (IIIa), (IV), (IV-a), (IV-a-1), (IV-a-2), (V), (V-a), (V-a-1), (V-a-2), (VI), (VI-a), (VI-a-1), (VI-a-2), (VII), (VII-a), (VII-a-1), (VII-a-2), (VIII), (VIII-a), (VIII-a-1), and (VIII-a-2) the same as if each and every variation were specifically and individually listed. Similarly, all variations referring to formula (I), where applicable, apply equally to all formulations and variations detailed herein, as well as to all methods of use detailed herein.

Representative compounds are listed in Table 1.

TABLE 1

| Compound No. | Structure | Chemical Name [1] |
| --- | --- | --- |
| 1 | 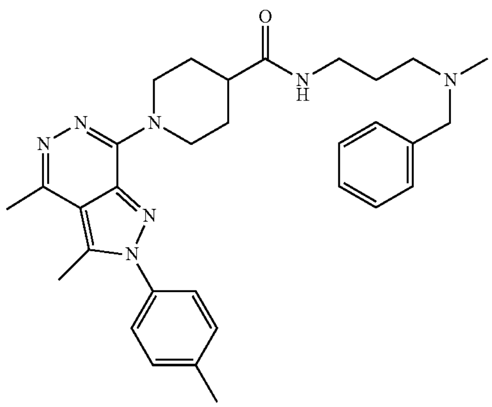 | N-(3-(benzyl(methyl)amino)propyl)-1-(3,4-dimethyl-2-(p-tolyl)-2H-pyrazolo[3,4-d]pyridazin-7-yl)piperidine-4-carboxamide |
| 2 | 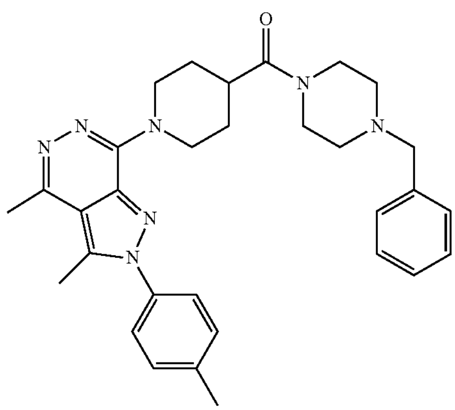 [SMILES: Cc1ccc(-n2nc3c(N4CCC(C(=O)N5CCN(Cc6ccccc6)CC5)CC4)nnc(C)c3c2C)cc1] | (4-benzylpiperazin-1-yl)(1-(3,4-dimethyl-2-(p-tolyl)-2H-pyrazolo[3,4-d]pyridazin-7-yl)piperidin-4-yl)methanone |
| 3 | 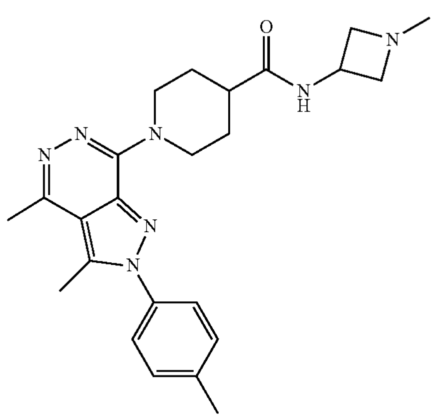 | 1-(3,4-dimethyl-2-(p-tolyl)-2H-pyrazolo[3,4-d]pyridazin-7-yl)-N-(1-methylazetidin-3-yl)piperidine-4-carboxamide |

TABLE 1-continued

| Compound No. | Structure | Chemical Name [1] |
|---|---|---|
| 4 | 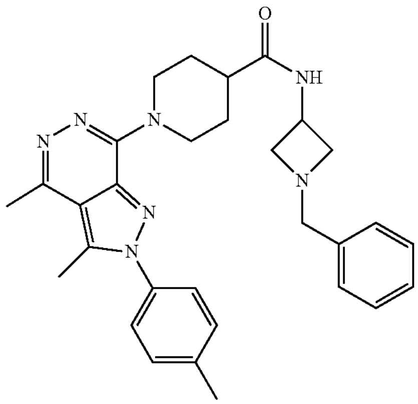 [SMILES: Cc1ccc(-n2nc3c(N4CCC(C(=O)NC5CN(Cc6ccccc6)C5)CC4)nnc(C)c3c2C)cc1] | N-(1-benzylazetidin-3-yl)-1-(3,4-dimethyl-2-(p-tolyl)-2H-pyrazolo[3,4-d]pyridazin-7-yl)piperidine-4-carboxamide |
| 5 | 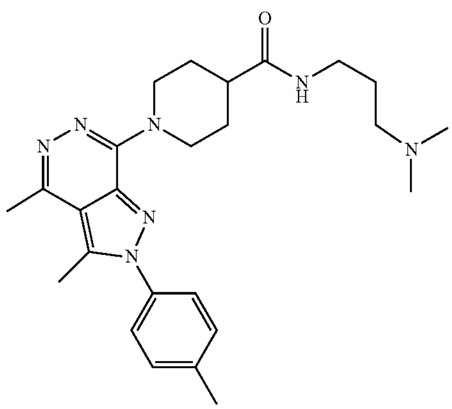 | 1-(3,4-dimethyl-2-(p-tolyl)-2H-pyrazolo[3,4-d]pyridazin-7-yl)-N-(3-(dimethylamino)propyl)piperidine-4-carboxamide |
| 6 | 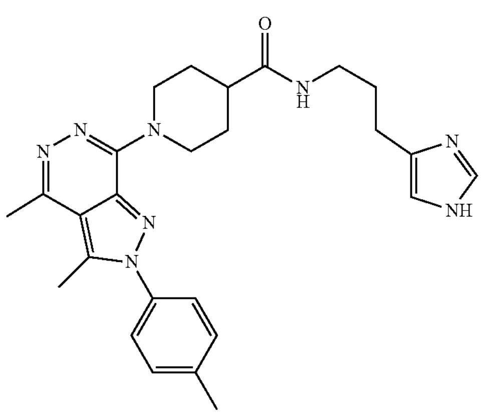 [SMILES: Cc1ccc(-n2nc3c(N4CCC(C(=O)NCCCc5c[nH]cn5)CC4)nnc(C)c3c2C)cc1] | N-(3-(1H-imidazol-4-yl)propyl)-1-(3,4-dimethyl-2-(p-tolyl)-2H-pyrazolo[3,4-d]pyridazin-7-yl)piperidine-4-carboxamide |

TABLE 1-continued

| Compound No. | Structure | Chemical Name [1] |
|---|---|---|
| 7 | 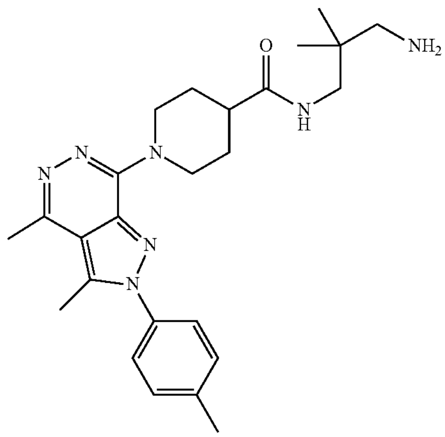 [SMILES: Cc1ccc(-n2nc3c(N4CCC(C(=O)NCC(C)(C)CN)CC4)nnc(C)c3c2C)cc1] | N-(3-amino-2,2-dimethylpropyl)-1-(3,4-dimethyl-2-(p-tolyl)-2H-pyrazolo[3,4-d]pyridazin-7-yl)piperidine-4-carboxamide |
| 8 | 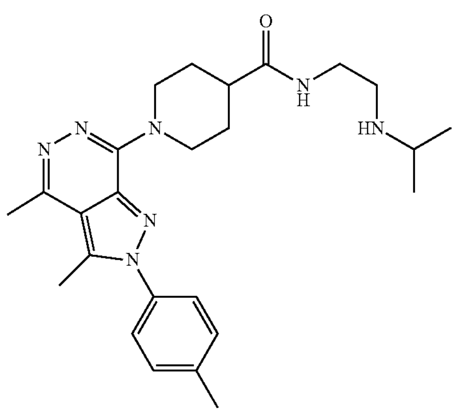 [SMILES: Cc1ccc(-n2nc3c(N4CCC(C(=O)NCCNC(C)C)CC4)nnc(C)c3c2C)cc1] | 1-(3,4-dimethyl-2-(p-tolyl)-2H-pyrazolo[3,4-d]pyridazin-7-yl)-N-(2-(isopropylamino)ethyl)piperidine-4-carboxamide |
| 9 | 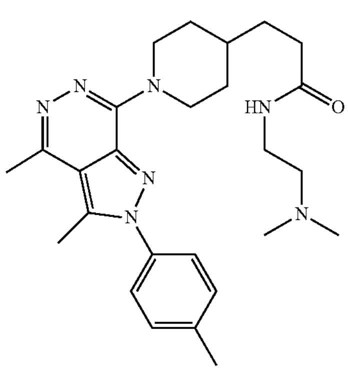 [SMILES: Cc1ccc(-n2nc3c(N4CCC(CCC(=O)NCCN(C)C)CC4)nnc(C)c3c2C)cc1] | 3-(1-(3,4-dimethyl-2-(p-tolyl)-2H-pyrazolo[3,4-d]pyridazin-7-yl)piperidin-4-yl)-N-(2-(dimethylamino)ethyl)propanamide |

TABLE 1-continued

| Compound No. | Structure | Chemical Name [1] |
|---|---|---|
| 10 | 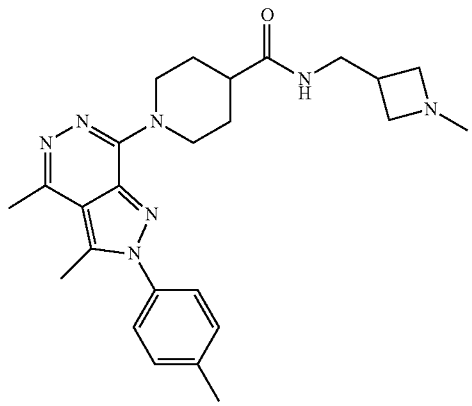 | 1-(3,4-dimethyl-2-(p-tolyl)-2H-pyrazolo[3,4-d]pyridazin-7-yl)-N-((1-methylazetidin-3-yl)methyl)piperidine-4-carboxamide |
| 11 | 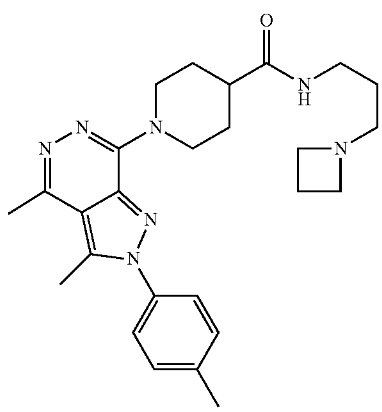 [SMILES: Cc1ccc(-n2nc3c(N4CCC(C(=O)NCCCN5CCC5)CC4)nnc(C)c3c2C)cc1] | N-(3-(azetidin-1-yl)propyl)-1-(3,4-dimethyl-2-(p-tolyl)-2H-pyrazolo[3,4-d]pyridazin-7-yl)piperidine-4-carboxamide |
| 12 | 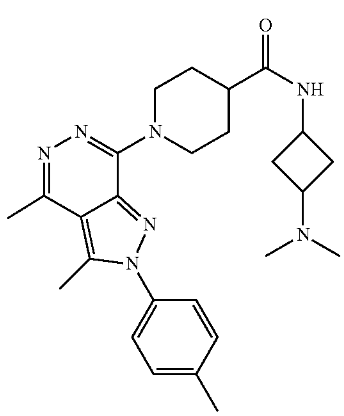 | 1-(3,4-dimethyl-2-(p-tolyl)-2H-pyrazolo[3,4-d]pyridazin-7-yl)-N-(3-(dimethylamino)cyclobutyl)piperidine-4-carboxamide |

TABLE 1-continued

| Compound No. | Structure | Chemical Name [1] |
|---|---|---|
| 12a | 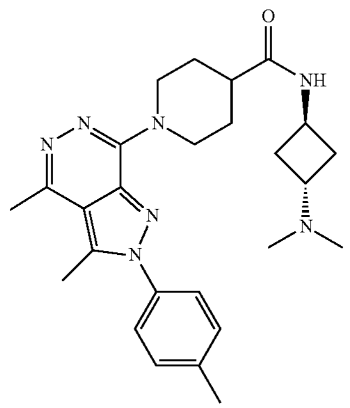 | 1-(3,4-dimethyl-2-(p-tolyl)-2H-pyrazolo[3,4-d]pyridazin-7-yl)-N-((1r,3r)-3-(dimethylamino)cyclobutyl)piperidine-4-carboxamide |
| 12b | 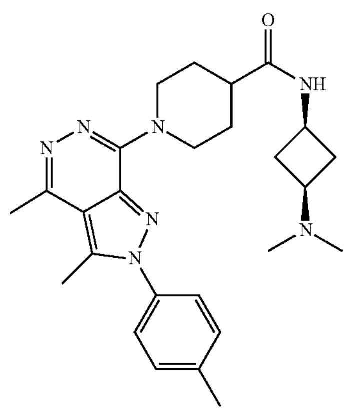 | 1-(3,4-dimethyl-2-(p-tolyl)-2H-pyrazolo[3,4-d]pyridazin-7-yl)-N-((1s,3s)-3-(dimethylamino)cyclobutyl)piperidine-4-carboxamide |
| 13 | 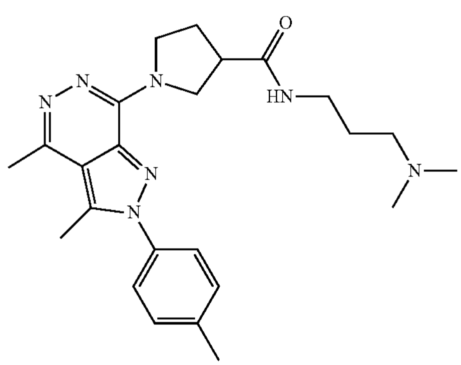 | 1-(3,4-dimethyl-2-(p-tolyl)-2H-pyrazolo[3,4-d]pyridazin-7-yl)-N-(3-(dimethylamino)propyl)pyrrolidine-3-carboxamide |
| 13a | 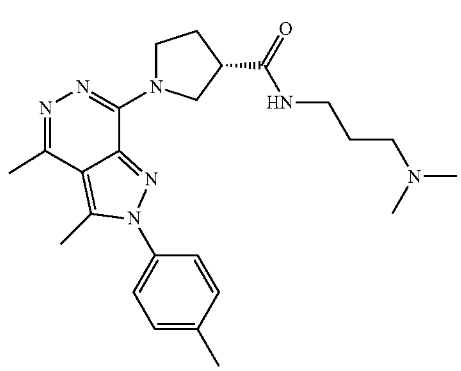 | (S)-1-(3,4-dimethyl-2-(p-tolyl)-2H-pyrazolo[3,4-d]pyridazin-7-yl)-N-(3-(dimethylamino)propyl)pyrrolidine-3-carboxamide |

TABLE 1-continued

| Compound No. | Structure | Chemical Name [1] |
|---|---|---|
| 13b | 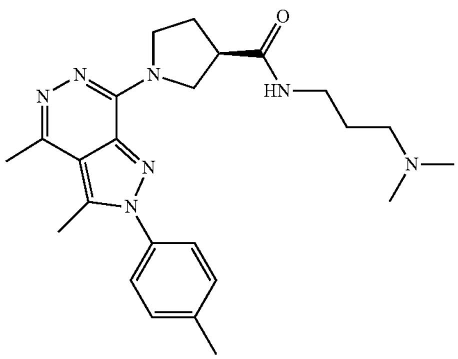 | (R)-1-(3,4-dimethyl-2-(p-tolyl)-2H-pyrazolo[3,4-d]pyridazin-7-yl)-N-(3-(dimethylamino)propyl)pyrrolidine-3-carboxamide |
| 15 | 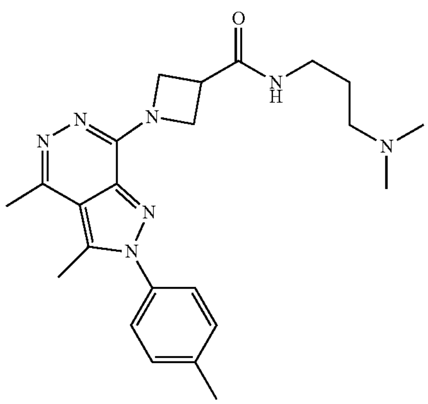 | 1-(3,4-dimethyl-2-(p-tolyl)-2H-pyrazolo[3,4-d]pyridazin-7-yl)-N-(3-(dimethylamino)propyl)azetidine-3-carboxamide |
| 16 | 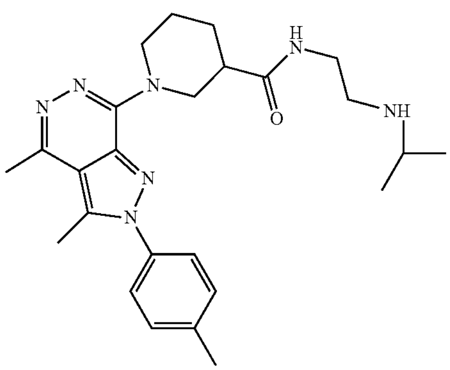 [SMILES: Cc1ccc(-n2nc3c(N4CCCC(C(=O)NCCNC(C)C)C4)nnc(C)c3c2C)cc1] | 1-(3,4-dimethyl-2-(p-tolyl)-2H-pyrazolo[3,4-d]pyridazin-7-yl)-N-(2-(isopropylamino)ethyl)piperidine-3-carboxamide |
| 16a | 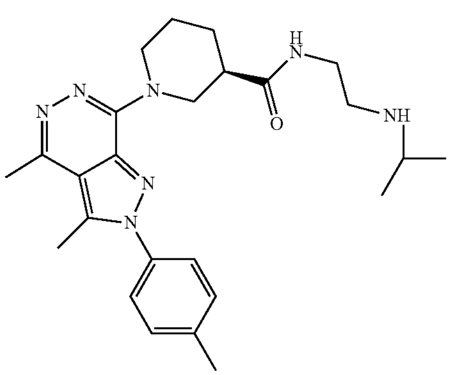 [SMILES: Cc1ccc(-n2nc3c(N4CCC[C@@H](C(=O)NCCNC(C)C)C4)nnc(C)c3c2C)cc1] | (R)-1-(3,4-dimethyl-2-(p-tolyl)-2H-pyrazolo[3,4-d]pyridazin-7-yl)-N-(2-(isopropylamino)ethyl)piperidine-3-carboxamide |

TABLE 1-continued

| Compound No. | Structure | Chemical Name [1] |
|---|---|---|
| 16b | 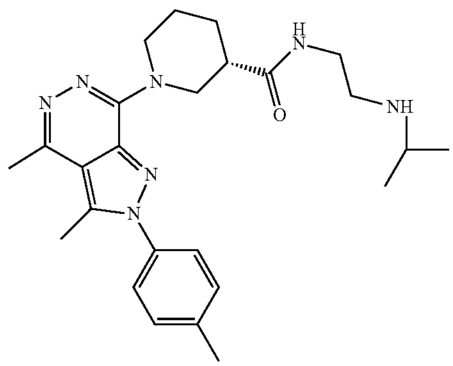 [SMILES: Cc1ccc(-n2nc3c(N4CCC[C@H](C(=O)NCCNC(C)C)C4)nnc(C)c3c2C)cc1] | (S)-1-(3,4-dimethyl-2-(p-tolyl)-2H-pyrazolo[3,4-d]pyridazin-7-yl)-N-(2-(isopropylamino)ethyl)piperidine-3-carboxamide |
| 17 | 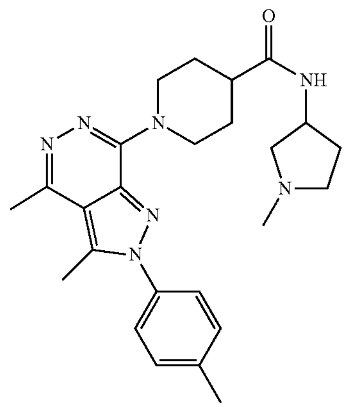 [SMILES: Cc1ccc(-n2nc3c(N4CCC(C(=O)NC5CCN(C)C5)CC4)nnc(C)c3c2C)cc1] | 1-(3,4-dimethyl-2-(p-tolyl)-2H-pyrazolo[3,4-d]pyridazin-7-yl)-N-(1-methylpyrrolidin-3-yl)piperidine-4-carboxamide |
| 17a | 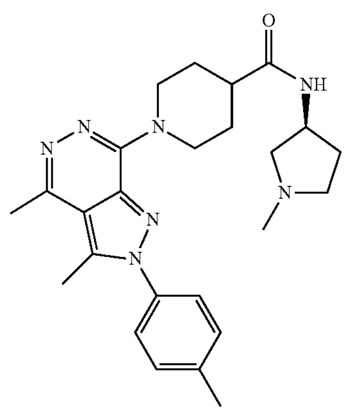 [SMILES: Cc1ccc(-n2nc3c(N4CCC(C(=O)N[C@H]5CCN(C)C5)CC4)nnc(C)c3c2C)cc1] | (S)-1-(3,4-dimethyl-2-(p-tolyl)-2H-pyrazolo[3,4-d]pyridazin-7-yl)-N-(1-methylpyrrolidin-3-yl)piperidine-4-carboxamide |
| 17b | 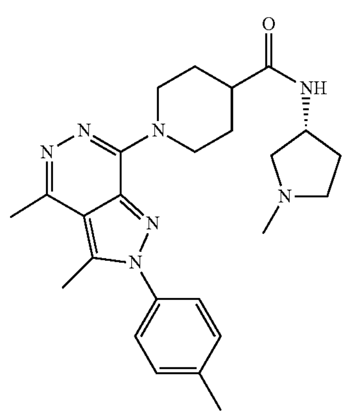 [SMILES: Cc1ccc(-n2nc3c(N4CCC(C(=O)N[C@@H]5CCN(C)C5)CC4)nnc(C)c3c2C)cc1] | (R)-1-(3,4-dimethyl-2-(p-tolyl)-2H-pyrazolo[3,4-d]pyridazin-7-yl)-N-(1-methylpyrrolidin-3-yl)piperidine-4-carboxamide |

TABLE 1-continued

| Compound No. | Structure | Chemical Name [1] |
|---|---|---|
| 18 | 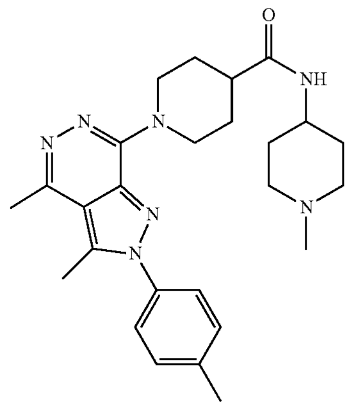 [SMILES: Cc1ccc(-n2nc3c(N4CCC(C(=O)NC5CCN(C)CC5)CC4)nnc(C)c3c2C)cc1] | 1-(3,4-dimethyl-2-(p-tolyl)-2H-pyrazolo[3,4-d]pyridazin-7-yl)-N-(1-methylpiperidin-4-yl)piperidine-4-carboxamide |
| 19 | 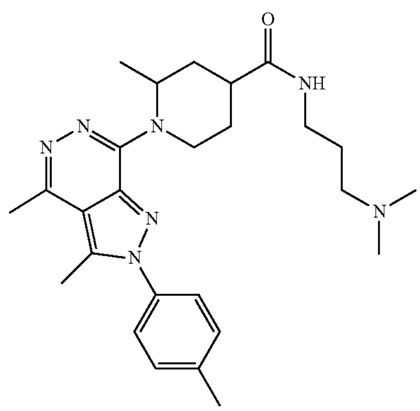 | 1-(3,4-dimethyl-2-(p-tolyl)-2H-pyrazolo[3,4-d]pyridazin-7-yl)-N-(3-(dimethylamino)propyl)-2-methylpiperidine-4-carboxamide |
| 19a | 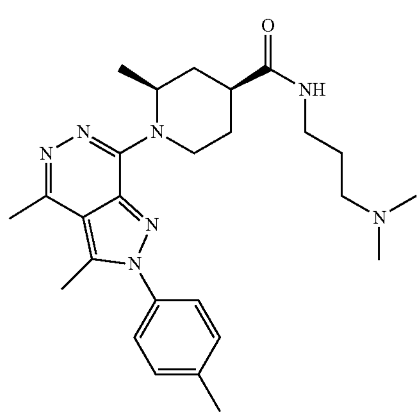 | (2S,4S)-1-(3,4-dimethyl-2-(p-tolyl)-2H-pyrazolo[3,4-d]pyridazin-7-yl)-N-(3-(dimethylamino)propyl)-2-methylpiperidine-4-carboxamide |

TABLE 1-continued

| Compound No. | Structure | Chemical Name[1] |
|---|---|---|
| 19b | 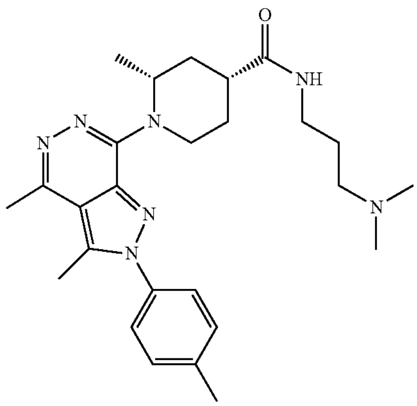 | (2R,4R)-1-(3,4-dimethyl-2-(p-tolyl)-2H-pyrazolo[3,4-d]pyridazin-7-yl)-N-(3-(dimethylamino)propyl)-2-methylpiperidine-4-carboxamide |
| 19c | 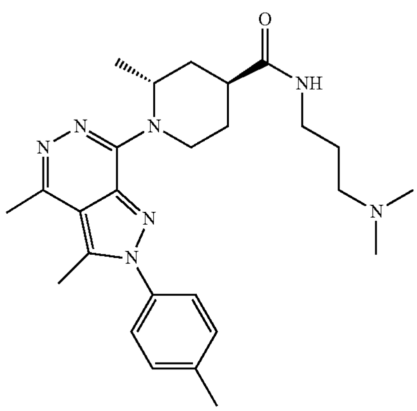 | (2R,4S)-1-(3,4-dimethyl-2-(p-tolyl)-2H-pyrazolo[3,4-d]pyridazin-7-yl)-N-(3-(dimethylamino)propyl)-2-methylpiperidine-4-carboxamide |
| 19d | 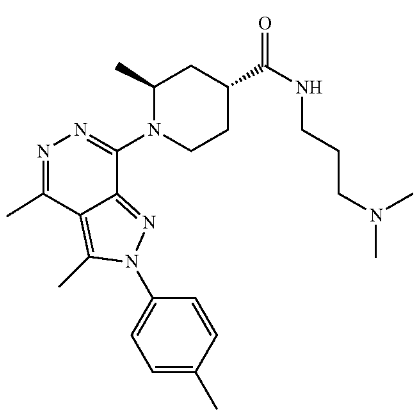 | (2S,4R)-1-(3,4-dimethyl-2-(p-tolyl)-2H-pyrazolo[3,4-d]pyridazin-7-yl)-N-(3-(dimethylamino)propyl)-2-methylpiperidine-4-carboxamide |

TABLE 1-continued

| Compound No. | Structure | Chemical Name [1] |
|---|---|---|
| 20 | 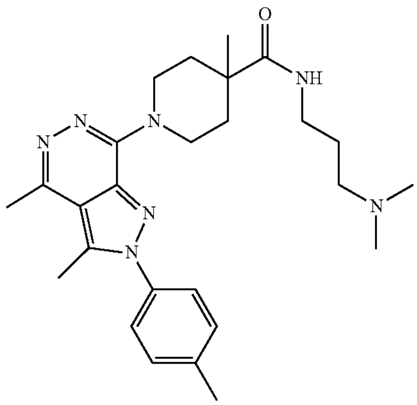 | 1-(3,4-dimethyl-2-(p-tolyl)-2H-pyrazolo[3,4-d]pyridazin-7-yl)-N-(3-(dimethylamino)propyl)-4-methylpiperidine-4-carboxamide |
| 21 | 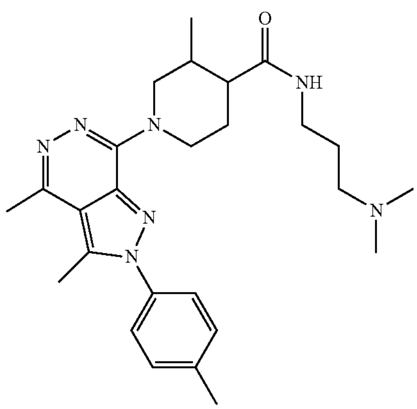 | 1-(3,4-dimethyl-2-(p-tolyl)-2H-pyrazolo[3,4-d]pyridazin-7-yl)-N-(3-(dimethylamino)propyl)-3-methylpiperidine-4-carboxamide |
| 21a | 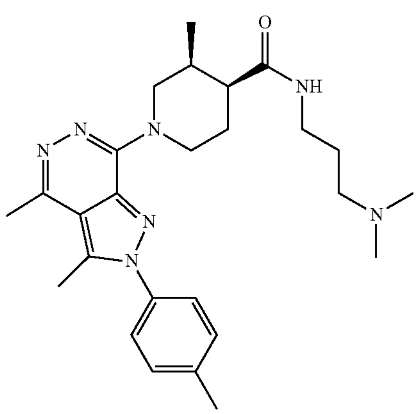 | (3S,4S)-1-(3,4-dimethyl-2-(p-tolyl)-2H-pyrazolo[3,4-d]pyridazin-7-yl)-N-(3-(dimethylamino)propyl)-3-methylpiperidine-4-carboxamide |

TABLE 1-continued

| Compound No. | Structure | Chemical Name [1] |
|---|---|---|
| 21b | 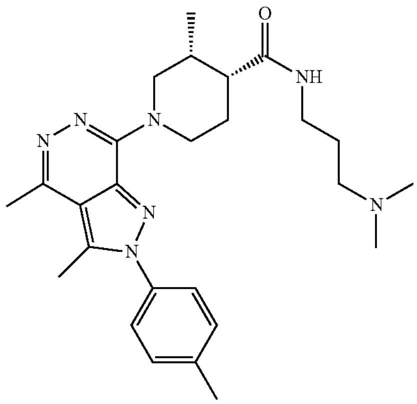 | (3R,4R)-1-(3,4-dimethyl-2-(p-tolyl)-2H-pyrazolo[3,4-d]pyridazin-7-yl)-N-(3-(dimethylamino)propyl)-3-methylpiperidine-4-carboxamide |
| 21c | 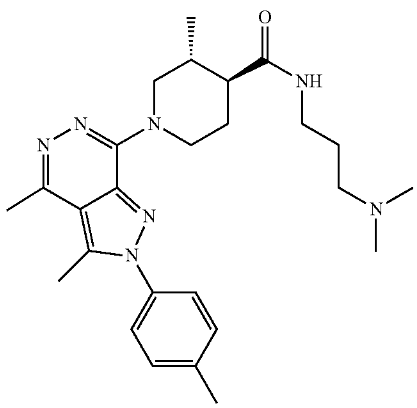 | (3R,4S)-1-(3,4-dimethyl-2-(p-tolyl)-2H-pyrazolo[3,4-d]pyridazin-7-yl)-N-(3-(dimethylamino)propyl)-3-methylpiperidine-4-carboxamide |
| 21d | 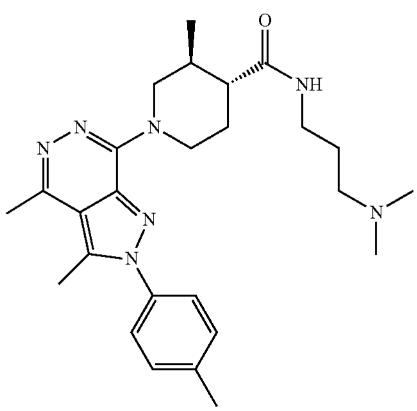 | (3S,4R)-1-(3,4-dimethyl-2-(p-tolyl)-2H-pyrazolo[3,4-d]pyridazin-7-yl)-N-(3-(dimethylamino)propyl)-3-methylpiperidine-4-carboxamide |
| 22 | 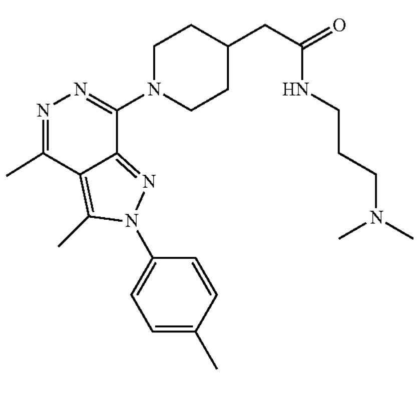 | 2-(1-(3,4-dimethyl-2-(p-tolyl)-2H-pyrazolo[3,4-d]pyridazin-7-yl)piperidin-4-yl)-N-(3-(dimethylamino)propyl)acetamide |

TABLE 1-continued

| Compound No. | Structure | Chemical Name [1] |
|---|---|---|
| 23 | 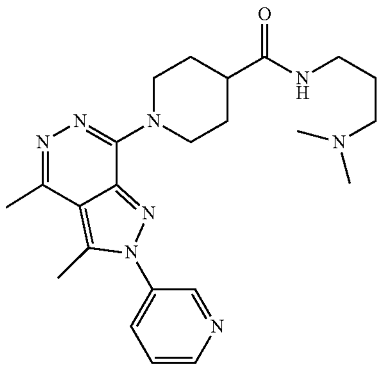 [SMILES: Cc1nnc(N2CCC(C(=O)NCCCN(C)C)CC2)c2nn(-c3cccnc3)c(C)c12] | 1-(3,4-dimethyl-2-(pyridin-3-yl)-2H-pyrazolo[3,4-d]pyridazin-7-yl)-N-(3-(dimethylamino)propyl)piperidine-4-carboxamide |
| 24 | 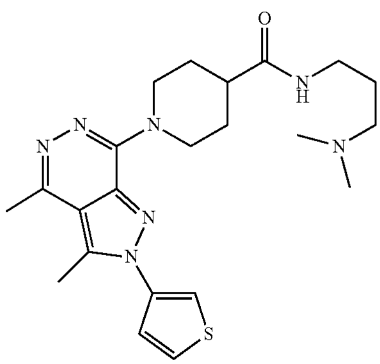 [SMILES: Cc1nnc(N2CCC(C(=O)NCCCN(C)C)CC2)c2nn(-c3ccsc3)c(C)c12] | 1-(3,4-dimethyl-2-(thiophen-3-yl)-2H-pyrazolo[3,4-d]pyridazin-7-yl)-N-(3-(dimethylamino)propyl)piperidine-4-carboxamide |
| 25 | 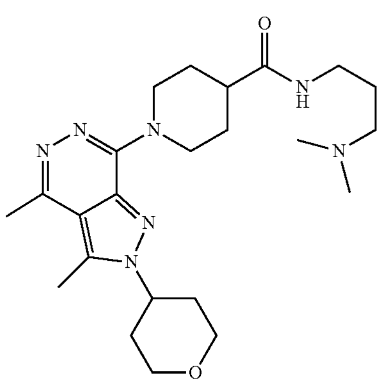 [SMILES: Cc1nnc(N2CCC(C(=O)NCCCN(C)C)CC2)c2nn(C3CCOCC3)c(C)c12] | 1-(3,4-dimethyl-2-(tetrahydro-2H-pyran-4-yl)-2H-pyrazolo[3,4-d]pyridazin-7-yl)-N-(3-(dimethylamino)propyl)piperidine-4-carboxamide |

TABLE 1-continued

| Compound No. | Structure | Chemical Name [1] |
|---|---|---|
| 26 | 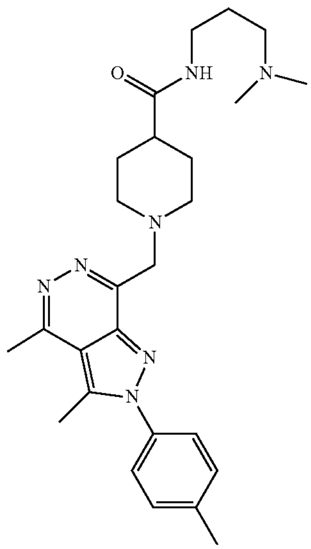 | 1-((3,4-dimethyl-2-(p-tolyl)-2H-pyrazolo[3,4-d]pyridazin-7-yl)methyl)-N-(3-(dimethylamino)propyl)piperidine-4-carboxamide |
| 27 | 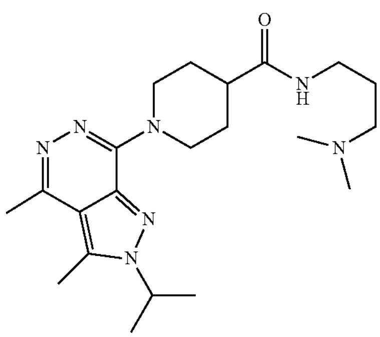 [SMILES: Cc1nnc(N2CCC(C(=O)NCCCN(C)C)CC2)c2nn(C(C)C)c(C)c12] | N-(3-(dimethylamino)propyl)-1-(2-isopropyl-3,4-dimethyl-2H-pyrazolo[3,4-d]pyridazin-7-yl)piperidine-4-carboxamide |
| 28 | 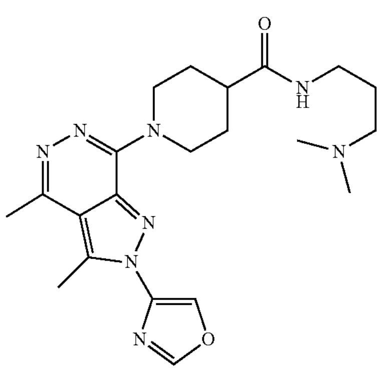 [SMILES: Cc1nnc(N2CCC(C(=O)NCCCN(C)C)CC2)c2nn(-c3cocn3)c(C)c12] | 1-(3,4-dimethyl-2-(oxazol-4-yl)-2H-pyrazolo[3,4-d]pyridazin-7-yl)-N-(3-(dimethylamino)propyl)piperidine-4-carboxamide |

TABLE 1-continued

| Compound No. | Structure | Chemical Name [1] |
|---|---|---|
| 29 | 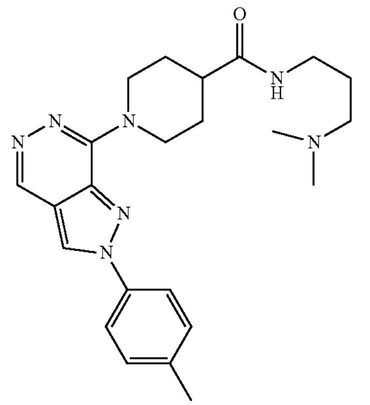 [SMILES: Cc1ccc(-n2cc3cnnc(N4CCC(C(=O)NCCCN(C)C)CC4)c3n2)cc1] | N-(3-(dimethylamino)propyl)-1-(2-(p-tolyl)-2H-pyrazolo[3,4-d]pyridazin-7-yl)piperidine-4-carboxamide |
| 31 | 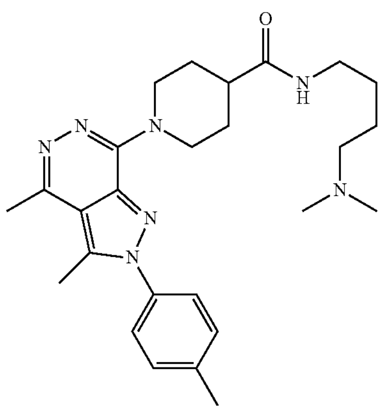 | 1-(3,4-dimethyl-2-(p-tolyl)-2H-pyrazolo[3,4-d]pyridazin-7-yl)-N-(4-(dimethylamino)butyl)piperidine-4-carboxamide |
| 32 | 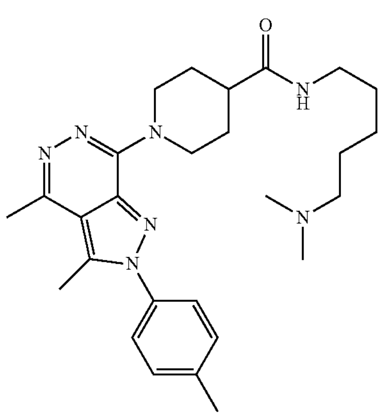 [SMILES: Cc1ccc(-n2nc3c(N4CCC(C(=O)NCCCCCN(C)C)CC4)nnc(C)c3c2C)cc1] | 1-(3,4-dimethyl-2-(p-tolyl)-2H-pyrazolo[3,4-d]pyridazin-7-yl)-N-(5-(dimethylamino)pentyl)piperidine-4-carboxamide |

TABLE 1-continued

| Compound No. | Structure | Chemical Name [1] |
|---|---|---|
| 34 | 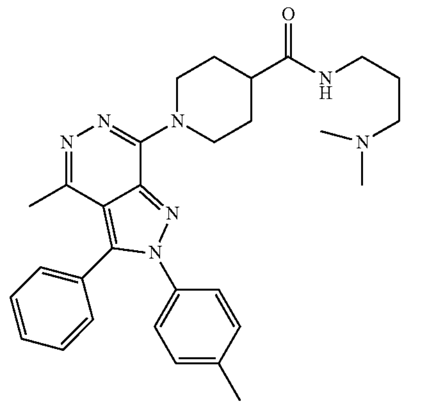 [SMILES: Cc1ccc(-n2nc3c(N4CCC(C(=O)NCCCN(C)C)CC4)nnc(C)c3c2-c2ccccc2)cc1] | N-(3-(dimethylamino)propyl)-1-(4-methyl-3-phenyl-2-(p-tolyl)-2H-pyrazolo[3,4-d]pyridazin-7-yl)piperidine-4-carboxamide |
| 35 | 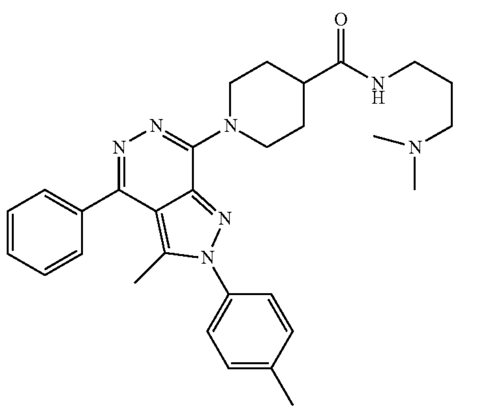 [SMILES: Cc1ccc(-n2nc3c(N4CCC(C(=O)NCCCN(C)C)CC4)nnc(-c4ccccc4)c3c2C)cc1] | N-(3-(dimethylamino)propyl)-1-(3-methyl-4-phenyl-2-(p-tolyl)-2H-pyrazolo[3,4-d]pyridazin-7-yl)piperidine-4-carboxamide |
| 36 | 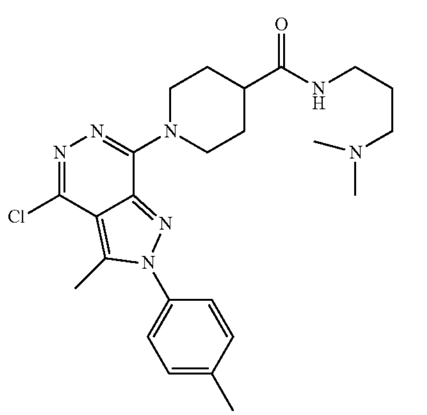 [SMILES: Cc1ccc(-n2nc3c(N4CCC(C(=O)NCCCN(C)C)CC4)nnc(Cl)c3c2C)cc1] | 1-(4-chloro-3-methyl-2-(p-tolyl)-2H-pyrazolo[3,4-d]pyridazin-7-yl)-N-(3-(dimethylamino)propyl)piperidine-4-carboxamide |

TABLE 1-continued

| Compound No. | Structure | Chemical Name [1] |
|---|---|---|
| 37 | 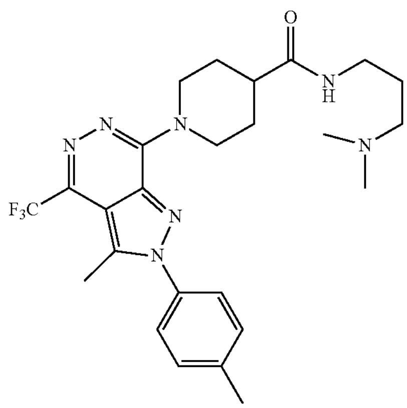 [SMILES: Cc1ccc(-n2nc3c(N4CCC(C(=O)NCCCN(C)C)CC4)nnc(C(F)(F)F)c3c2C)cc1] | N-(3-(dimethylamino)propyl)-1-(3-methyl-2-(p-tolyl)-4-(trifluoromethyl)-2H-pyrazolo[3,4-d]pyridazin-7-yl)piperidine-4-carboxamide |
| 38 | 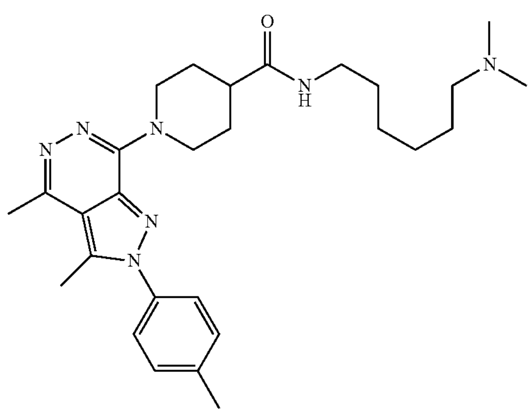 | 1-(3,4-dimethyl-2-(p-tolyl)-2H-pyrazolo[3,4-d]pyridazin-7-yl)-N-(6-(dimethylamino)hexyl)piperidine-4-carboxamide |
| 40 | 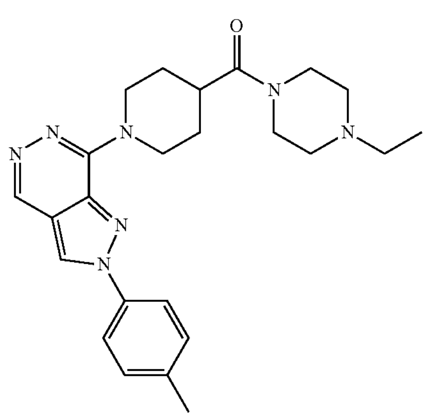 [SMILES: CCN1CCN(C(=O)C2CCN(c3nncc4cn(-c5ccc(C)cc5)nc34)CC2)CC1] | (4-ethylpiperazin-1-yl)(1-(2-(p-tolyl)-2H-pyrazolo[3,4-d]pyridazin-7-yl)piperidin-4-yl)methanone |

TABLE 1-continued

| Compound No. | Structure | Chemical Name |
|---|---|---|
| 41 | 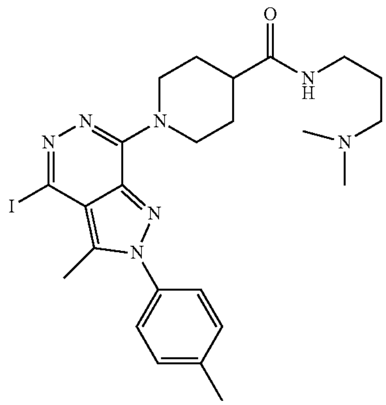 [SMILES: Cc1ccc(-n2nc3c(N4CCC(C(=O)NCCCN(C)C)CC4)nnc(I)c3c2C)cc1] | N-(3-(dimethylamino)propyl)-1-(4-iodo-3-methyl-2-(p-tolyl)-2H-pyrazolo[3,4-d]pyridazin-7-yl)piperidine-4-carboxamide |
| 42 | 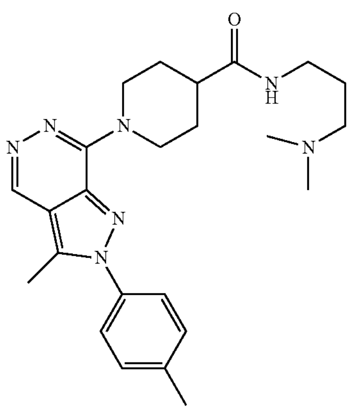 [SMILES: Cc1ccc(-n2nc3c(N4CCC(C(=O)NCCCN(C)C)CC4)nncc3c2C)cc1] | N-(3-(dimethylamino)propyl)-1-(3-methyl-2-(p-tolyl)-2H-pyrazolo[3,4-d]pyridazin-7-yl)piperidine-4-carboxamide |
| 43 | 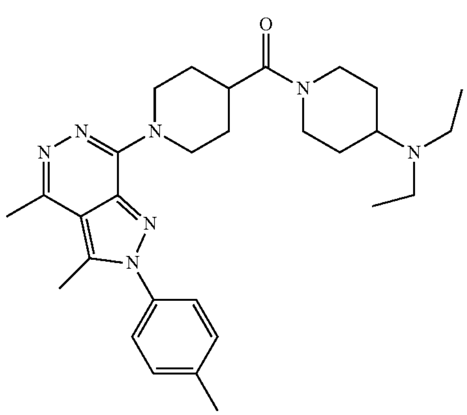 [SMILES: CCN(CC)C1CCN(C(=O)C2CCN(c3nnc(C)c4c(C)n(-c5ccc(C)cc5)nc34)CC2)CC1] | (4-(diethylamino)piperidin-1-yl)(1-(3,4-dimethyl-2-(p-tolyl)-2H-pyrazolo[3,4-d]pyridazin-7-yl)piperidin-4-yl)methanone |

TABLE 1-continued

| Compound No. | Structure | Chemical Name [1] |
|---|---|---|
| 44 | 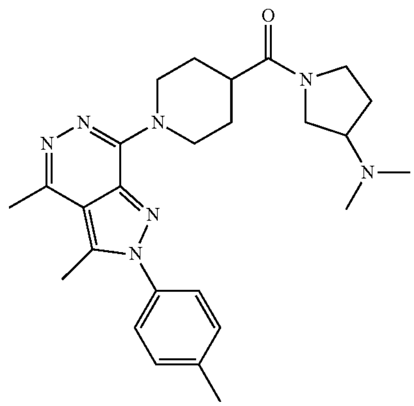 | (1-(3,4-dimethyl-2-(p-tolyl)-2H-pyrazolo[3,4-d]pyridazin-7-yl)piperidin-4-yl)(3-(dimethylamino)pyrrolidin-1-yl)methanone |
| 44a | 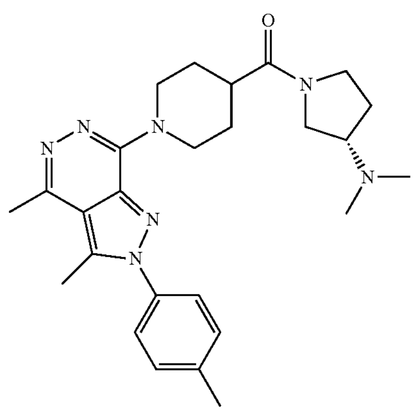 | (S)-(1-(3,4-dimethyl-2-(p-tolyl)-2H-pyrazolo[3,4-d]pyridazin-7-yl)piperidin-4-yl)(3-(dimethylamino)pyrrolidin-1-yl)methanone |
| 44b | 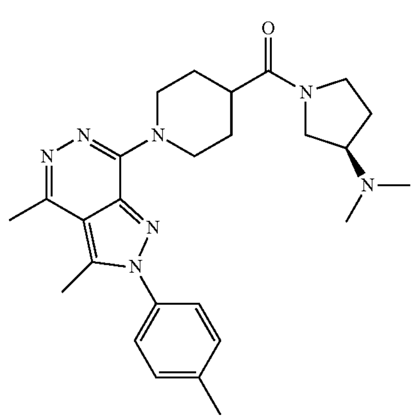 | (R)-(1-(3,4-dimethyl-2-(p-tolyl)-2H-pyrazolo[3,4-d]pyridazin-7-yl)piperidin-4-yl)(3-(dimethylamino)pyrrolidin-1-yl)methanone |

TABLE 1-continued

| Compound No. | Structure | Chemical Name [1] |
|---|---|---|
| 45 | 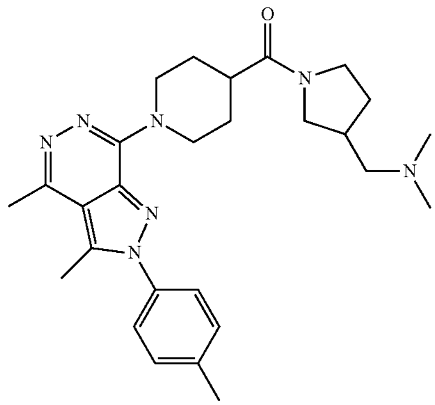 | (1-(3,4-dimethyl-2-(p-tolyl)-2H-pyrazolo[3,4-d]pyridazin-7-yl)piperidin-4-yl)(3-((dimethylamino)methyl)pyrrolidin-1-yl)methanone |
| 45a | 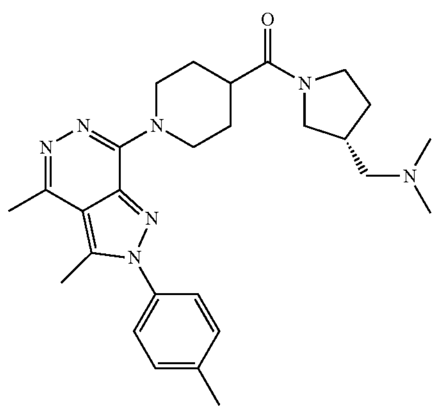 | (R)-(1-(3,4-dimethyl-2-(p-tolyl)-2H-pyrazolo[3,4-d]pyridazin-7-yl)piperidin-4-yl)(3-((dimethylamino)methyl)pyrrolidin-1-yl)methanone |
| 45b | 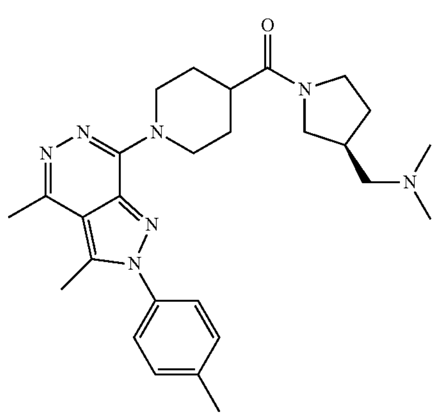 | (S)-(1-(3,4-dimethyl-2-(p-tolyl)-2H-pyrazolo[3,4-d]pyridazin-7-yl)piperidin-4-yl)(3-((dimethylamino)methyl)pyrrolidin-1-yl)methanone |

TABLE 1-continued

| Compound No. | Structure | Chemical Name [1] |
|---|---|---|
| 46 | 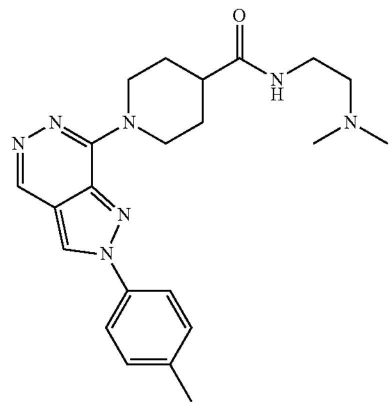 [SMILES: Cc1ccc(-n2cc3cnnc(N4CCC(C(=O)NCCN(C)C)CC4)c3n2)cc1] | N-(2-(dimethylamino)ethyl)-1-(2-(p-tolyl)-2H-pyrazolo[3,4-d]pyridazin-7-yl)piperidine-4-carboxamide |
| 47 | 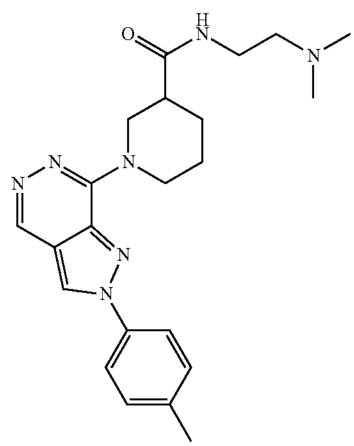 [SMILES: Cc1ccc(-n2cc3cnnc(N4CCCC(C(=O)NCCN(C)C)C4)c3n2)cc1] | N-(2-(dimethylamino)ethyl)-1-(2-(p-tolyl)-2H-pyrazolo[3,4-d]pyridazin-7-yl)piperidine-3-carboxamide |
| 47a | 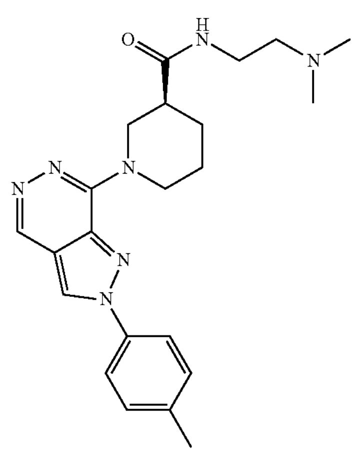 [SMILES: Cc1ccc(-n2cc3cnnc(N4CCC[C@H](C(=O)NCCN(C)C)C4)c3n2)cc1] | (S)-N-(2-(dimethylamino)ethyl)-1-(2-(p-tolyl)-2H-pyrazolo[3,4-d]pyridazin-7-yl)piperidine-3-carboxamide |

TABLE 1-continued

| Compound No. | Structure | Chemical Name [1] |
|---|---|---|
| 47b | 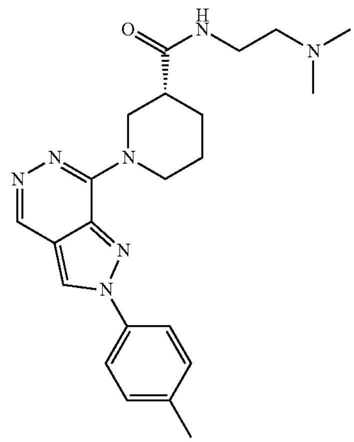 [SMILES: Cc1ccc(-n2cc3cnnc(N4CCC[C@@H](C(=O)NCCN(C)C)C4)c3n2)cc1] | (R)-N-(2-(dimethylamino)ethyl)-1-(2-(p-tolyl)-2H-pyrazolo[3,4-d]pyridazin-7-yl)piperidine-3-carboxamide |
| 48 | 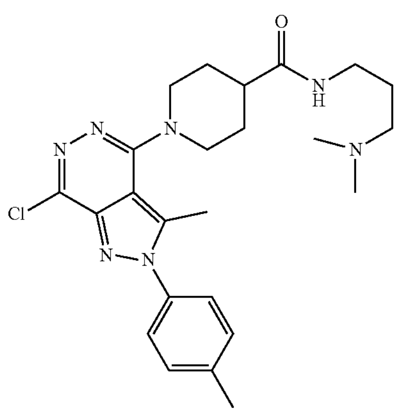 [SMILES: Cc1ccc(-n2nc3c(Cl)nnc(N4CCC(C(=O)NCCCN(C)C)CC4)c3c2C)cc1] | 1-(7-chloro-3-methyl-2-(p-tolyl)-2H-pyrazolo[3,4-d]pyridazin-4-yl)-N-(3-(dimethylamino)propyl)piperidine-4-carboxamide |
| 49 | 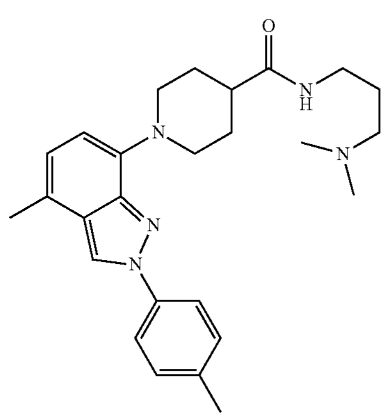 [SMILES: Cc1ccc(-n2cc3c(C)ccc(N4CCC(C(=O)NCCCN(C)C)CC4)c3n2)cc1] | N-(3-(dimethylamino)propyl)-1-(4-methyl-2-(p-tolyl)-2H-indazol-7-yl)piperidine-4-carboxamide |

TABLE 1-continued

| Compound No. | Structure | Chemical Name [1] |
|---|---|---|
| 50 | 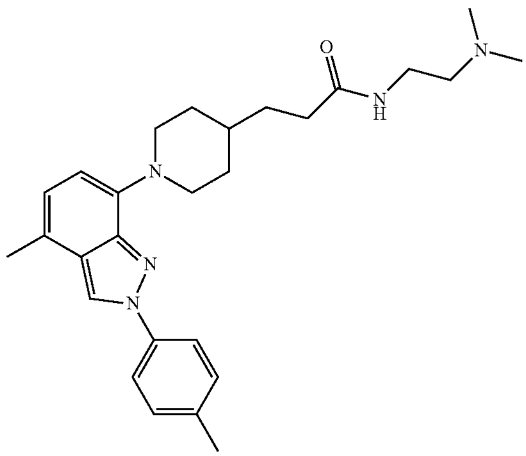 | N-(2-(dimethylamino)ethyl)-3-(1-(4-methyl-2-(p-tolyl)-2H-indazol-7-yl)piperidin-4-yl)propanamide |
| 51 | 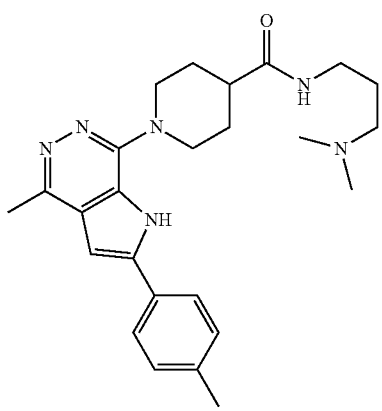 [SMILES: Cc1ccc(-c2cc3c(C)nnc(N4CCC(C(=O)NCCCN(C)C)CC4)c3[nH]2)cc1] | N-(3-(dimethylamino)propyl)-1-(4-methyl-2-(p-tolyl)-1H-pyrrolo[2,3-d]pyridazin-7-yl)piperidine-4-carboxamide |
| 52 | 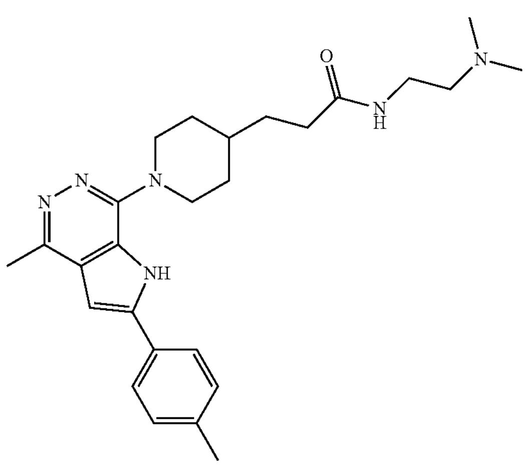 | N-(2-(dimethylamino)ethyl)-3-(1-(4-methyl-2-(p-tolyl)-1H-pyrrolo[2,3-d]pyridazin-7-yl)piperidin-4-yl)propanamide |

TABLE 1-continued

| Compound No. | Structure | Chemical Name [1] |
|---|---|---|
| 53 | 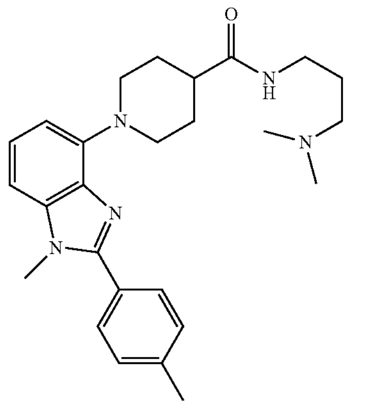 [SMILES: Cc1ccc(-c2nc3c(N4CCC(C(=O)NCCCN(C)C)CC4)cccc3n2C)cc1] | N-(3-(dimethylamino)propyl)-1-(1-methyl-2-(p-tolyl)-1H-benzo[d]imidazol-4-yl)piperidine-4-carboxamide |
| 54 | 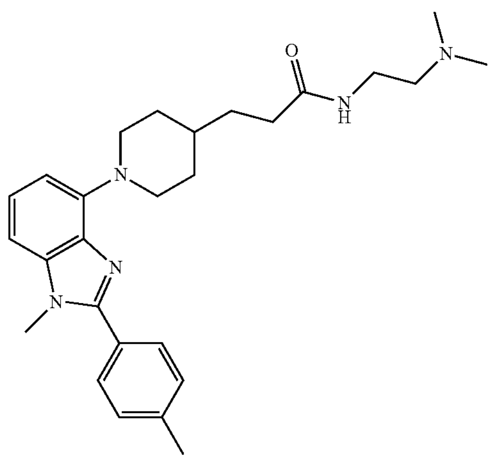 [SMILES: Cc1ccc(-c2nc3c(N4CCC(CCC(=O)NCCN(C)C)CC4)cccc3n2C)cc1] | N-(2-(dimethylamino)ethyl)-3-(1-(1-methyl-2-(p-tolyl)-1H-benzo[d]imidazol-4-yl)piperidin-4-yl)propanamide |
| 55 | 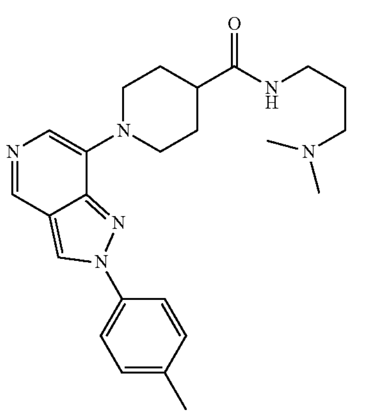 [SMILES: Cc1ccc(-n2cc3cncc(N4CCC(C(=O)NCCCN(C)C)CC4)c3n2)cc1] | N-(3-(dimethylamino)propyl)-1-(2-(p-tolyl)-2H-pyrazolo[4,3-c]pyridin-7-yl)piperidine-4-carboxamide |

TABLE 1-continued

| Compound No. | Structure | Chemical Name [1] |
|---|---|---|
| 56 | 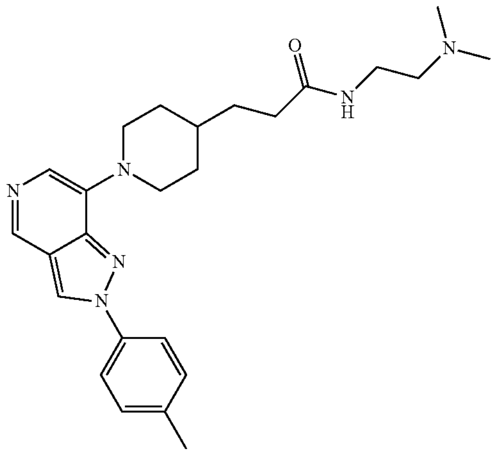 [SMILES: Cc1ccc(-n2cc3cncc(N4CCC(CCC(=O)NCCN(C)C)CC4)c3n2)cc1] | N-(2-(dimethylamino)ethyl)-3-(1-(2-(p-tolyl)-2H-pyrazolo[4,3-c]pyridin-7-yl)piperidin-4-yl)propanamide |

[1] Chemical names are generated using the ChemBioDraw ® Ultra version 14.0.0.117 software.

Additional representative compounds are listed in Table 1-A.

TABLE 1-A

| Compound No. | Structure | Chemical Name [1] |
|---|---|---|
| 57 | 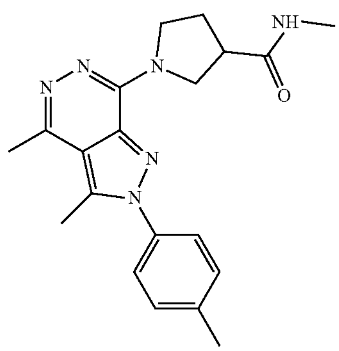 | 1-(3,4-dimethyl-2-(p-tolyl)-2H-pyrazolo[3,4-d]pyridazin-7-yl)-N-methylpyrrolidine-3-carboxamide |
| 58 | 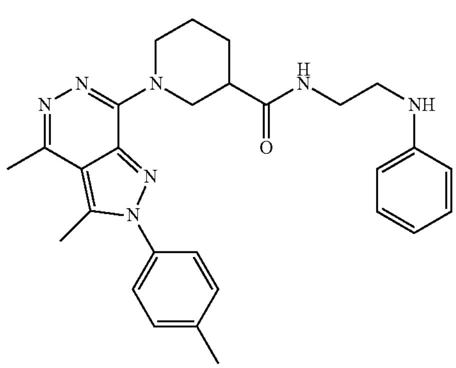 [SMILES: Cc1ccc(-n2nc3c(N4CCCC(C(=O)NCCNc5ccccc5)C4)nnc(C)c3c2C)cc1] | 1-(3,4-dimethyl-2-(p-tolyl)-2H-pyrazolo[3,4-d]pyridazin-7-yl)-N-(2-(phenylamino)ethyl)piperidine-3-carboxamide |

TABLE 1-A-continued

| Compound No. | Structure | Chemical Name [1] |
|---|---|---|
| 59 | 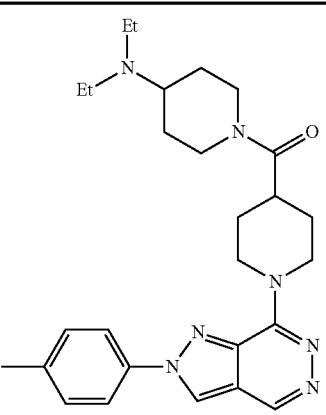 | (4-(diethylamino)piperidin-1-yl)(1-(2-(p-tolyl)-2H-pyrazolo[3,4-d]pyridazin-7-yl)piperidin-4-yl)methanone |
| 60 | 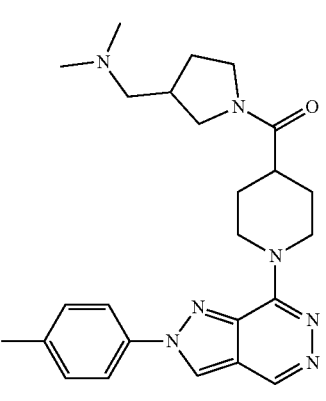 [SMILES: Cc1ccc(-n2cc3cnnc(N4CCC(C(=O)N5CCC(CN(C)C)C5)CC4)c3n2)cc1] | (3-((dimethylamino)methyl)pyrrolidin-1-yl)(1-(2-(p-tolyl)-2H-pyrazol[3,4-d]pyridazin-7-yl)piperidin-4-yl)methanone |
| 61 | 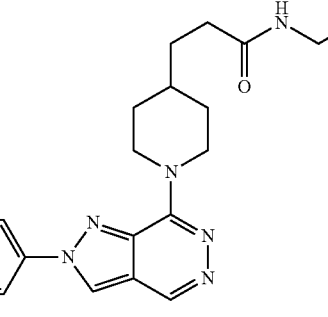 | N-(2-(dimethylamino)ethyl)-3-(1-(2-(p-tolyl)-2H-pyrazolo[3,4-d]pyridazin-7-yl)piperidin-4-yl)propanamide |
| 62 | 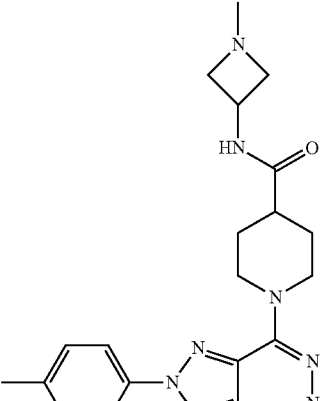 | N-(1-methylazetidin-3-yl)-1-(2-(p-tolyl)-2H-pyrazolo[3,4-d]pyridazin-7-yl)piperidine-4-carboxamide |

TABLE 1-A-continued

| Compound No. | Structure | Chemical Name [1] |
|---|---|---|
| 63 | 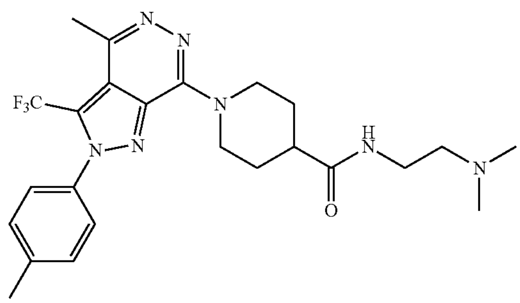 [SMILES: Cc1ccc(-n2nc3c(N4CCC(C(=O)NCCN(C)C)CC4)nnc(C)c3c2C(F)(F)F)cc1] | N-(2-(dimethylamino)ethyl)-1-(4-methyl-2-(p-tolyl)-3-(trifluoromethyl)-2H-pyrazolo[3,4-d]pyridazin-7-yl)piperidine-4-carboxamide |
| 64 | 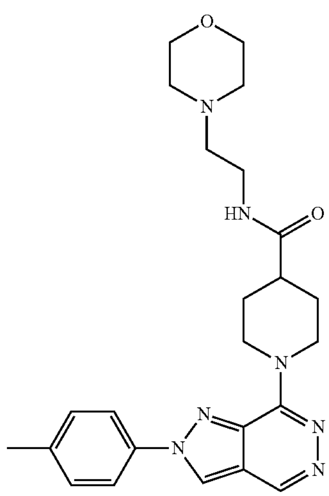 [SMILES: Cc1ccc(-n2cc3cnnc(N4CCC(C(=O)NCCN5CCOCC5)CC4)c3n2)cc1] | N-(2-morpholinoethyl)-1-(2-(p-tolyl)-2H-pyrazolo[3,4-d]pyridazin-7-yl)piperidine-4-carboxamide |
| 65 | 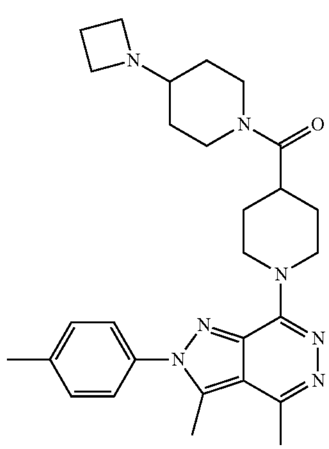 [SMILES: Cc1ccc(-n2nc3c(N4CCC(C(=O)N5CCC(N6CCC6)CC5)CC4)nnc(C)c3c2C)cc1] | (4-(azetidin-1-yl)piperidin-1-yl)(1-(3,4-dimethyl-2-(p-tolyl)-2H-pyrazolo[3,4-d]pyridazin-7-yl)piperidin-4-yl)methanone |

TABLE 1-A-continued

| Compound No. | Structure | Chemical Name [1] |
|---|---|---|
| 66 | 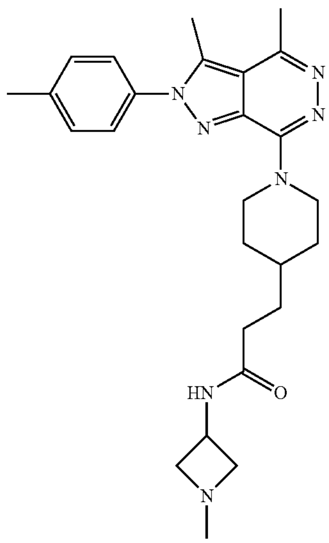 [SMILES: Cc1ccc(-n2nc3c(N4CCC(CCC(=O)NC5CN(C)C5)CC4)nnc(C)c3c2C)cc1] | 3-(1-(3,4-dimethyl-2-(p-tolyl)-2H-pyrazolo[3,4-d]pyridazin-7-yl)piperidin-4-yl)-N-(1-methylazetidin-3-yl)propanamide |
| 67 | 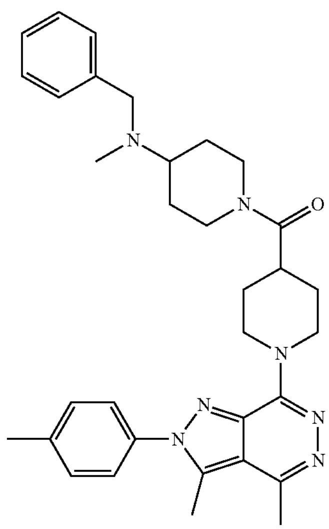 [SMILES: Cc1ccc(-n2nc3c(N4CCC(C(=O)N5CCC(N(C)Cc6ccccc6)CC5)CC4)nnc(C)c3c2C)cc1] | (4-(benzyl(methyl)amino)piperidin-1-yl)(1-(3,4-dimethyl-2-(p-tolyl)-2H-pyrazolo[3,4-d]pyridazin-7-yl)piperidin-4-yl)methanone |
| 68 | 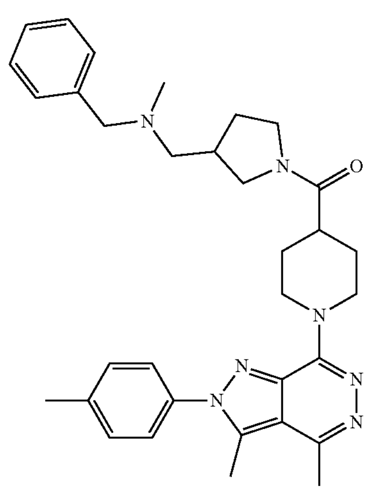 [SMILES: Cc1ccc(-n2nc3c(N4CCC(C(=O)N5CCC(CN(C)Cc6ccccc6)C5)CC4)nnc(C)c3c2C)cc1] | (3-((benzyl(methyl)amino)methyl)pyrrolidin-1-yl)(1-(3,4-dimethyl-2-(p-tolyl)-2H-pyrazolo[3,4-d]pyridazin-7-yl)piperidin-4-yl)methanone |

TABLE 1-A-continued

| Compound No. | Structure | Chemical Name [1] |
|---|---|---|
| 69 | 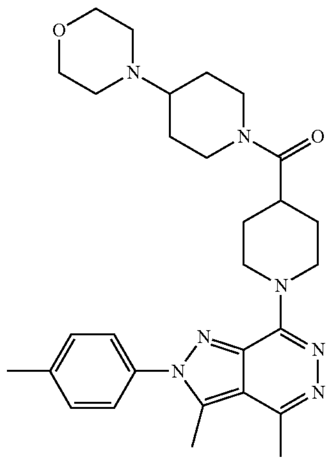 [SMILES: Cc1ccc(-n2nc3c(N4CCC(C(=O)N5CCC(N6CCOCC6)CC5)CC4)nnc(C)c3c2C)cc1] | (1-(3,4-dimethyl-2-(p-tolyl)-2H-pyrazolo[3,4-d]pyridazin-7-yl)piperidin-4-yl)(4-morpholinopiperidin-1-yl)methanone |
| 70 | 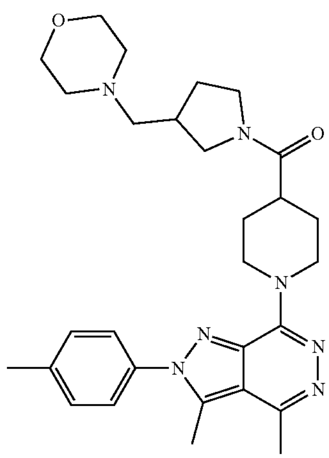 [SMILES: Cc1ccc(-n2nc3c(N4CCC(C(=O)N5CCC(CN6CCOCC6)C5)CC4)nnc(C)c3c2C)cc1] | (1-(3,4-dimethyl-2-(p-tolyl)-2H-pyrazolo[3,4-d]pyridazin-7-yl)piperidin-4-yl)(3-(morpholinomethyl)pyrrolidin-1-yl)methanone |
| 71 | 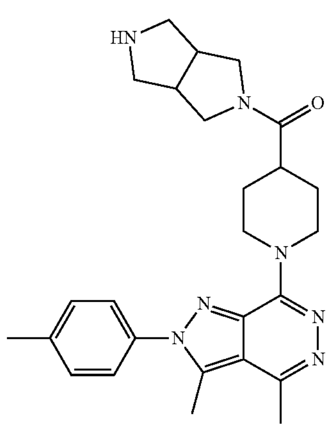 [SMILES: Cc1ccc(-n2nc3c(N4CCC(C(=O)N5CC6CNCC6C5)CC4)nnc(C)c3c2C)cc1] | (1-(3,4-dimethyl-2-(p-tolyl)-2H-pyrazolo[3,4-d]pyridazin-7-yl)piperidin-4-yl)(hexahydropyrrolo[3,4-c]pyrrol-2(1H)-yl)methanone |

TABLE 1-A-continued
| Compound No. | Structure | Chemical Name [1] |
|---|---|---|
| 72 | 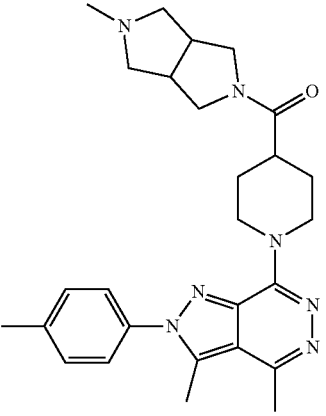 [SMILES: Cc1ccc(-n2nc3c(N4CCC(C(=O)N5CC6CN(C)CC6C5)CC4)nnc(C)c3c2C)cc1] | (1-(3,4-dimethyl-2-(p-tolyl)-2H-pyrazolo[3,4-d]pyridazin-7-yl)piperidin-4-yl)(5-methylhexahydropyrrolo[3,4-c]pyrrol-2(1H)-yl)methano |
| 73 | 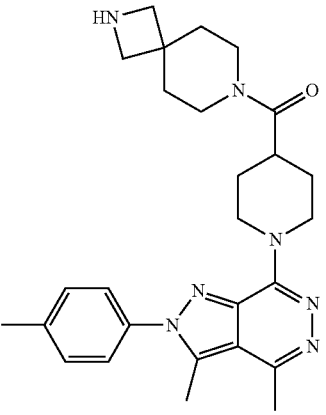 [SMILES: Cc1ccc(-n2nc3c(N4CCC(C(=O)N5CCC6(CC5)CNC6)CC4)nnc(C)c3c2C)cc1] | (1-(3,4-dimethyl-2-(p-tolyl)-2H-pyrazolo[3,4-d]pyridazin-7-yl)piperidin-4-yl)(2,7-diazaspiro[3.5]nonan-7-yl)methanone |
| 74 | 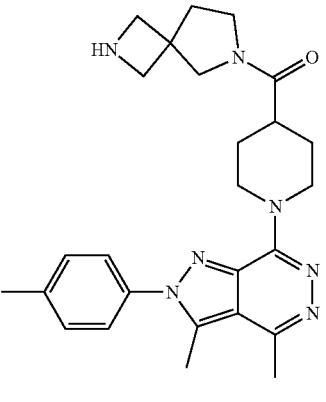 [SMILES: Cc1ccc(-n2nc3c(N4CCC(C(=O)N5CCC6(CNC6)C5)CC4)nnc(C)c3c2C)cc1] | (1-(3,4-dimethyl-2-(p-tolyl)-2H-pyrazolo[3,4-d]pyridazin-7-yl)piperidin-4-yl)(2,6-diazaspiro[3.4]octan-6-yl)methanone |

TABLE 1-A-continued

| Compound No. | Structure | Chemical Name [1] |
|---|---|---|
| 75 | 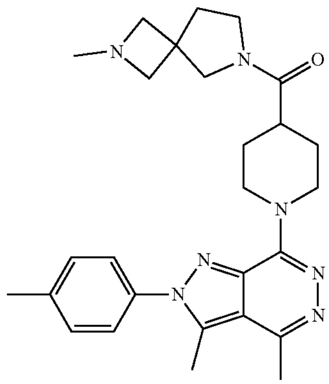 [SMILES: Cc1ccc(-n2nc3c(N4CCC(C(=O)N5CCC6(CN(C)C6)C5)CC4)nnc(C)c3c2C)cc1] | (1-(3,4-dimethyl-2-(p-tolyl)-2H-pyrazolo[3,4-d]pyridazin-7-yl)piperidin-4-yl)(2-methyl-2,6-diazaspiro[3.4]octan-6-yl)methanone |
| 76 | 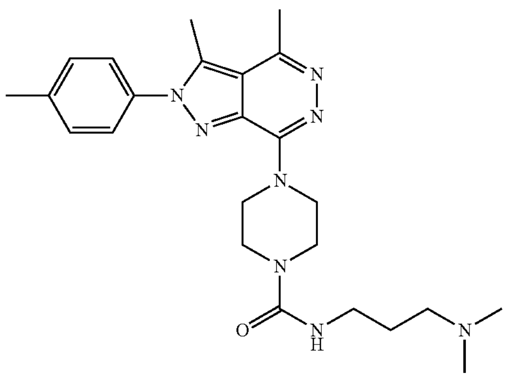 | 4-(3,4-dimethyl-2-(p-tolyl)-2H-pyrazolo[3,4-d]pyridazin-7-yl)-N-(3-(dimethylamino)propyl)piperazine-1-carboxamide |

[1] Chemical names are generated using the ChemBioDraw ® Ultra version 16.0.0.82 (68) software.

Additional compounds of the present disclosure are listed in Table 2.

TABLE 2

| Compound No. | Structure |
|---|---|
| 2-1 | 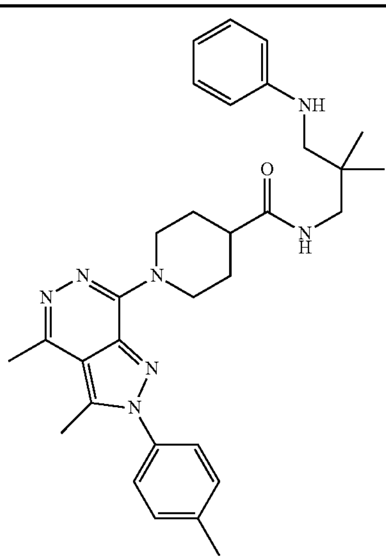 |
| 2-2 | |

TABLE 2-continued
| Compound No. | Structure |
|---|---|
| 2-3 | 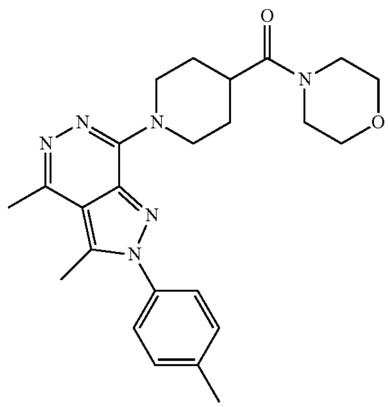 [SMILES: Cc1ccc(-n2nc3c(N4CCC(C(=O)N5CCOCC5)CC4)nnc(C)c3c2C)cc1] |
| 2-4 | 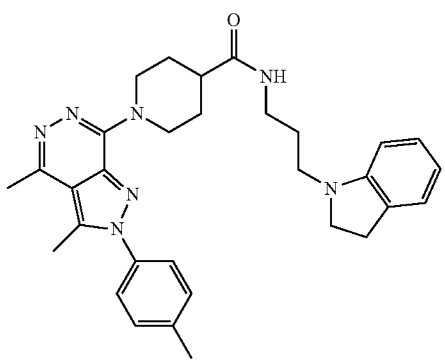 [SMILES: Cc1ccc(-n2nc3c(N4CCC(C(=O)NCCCN5CCc6ccccc65)CC4)nnc(C)c3c2C)cc1] |
| 2-5 | 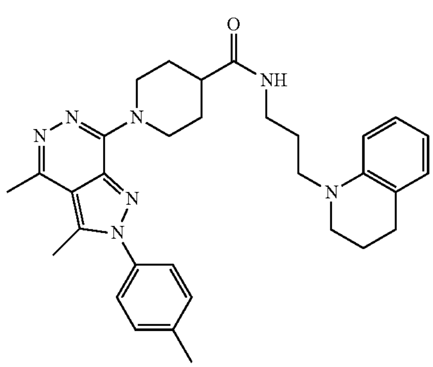 [SMILES: Cc1ccc(-n2nc3c(N4CCC(C(=O)NCCCN5CCCc6ccccc65)CC4)nnc(C)c3c2C)cc1] |
| 2-6 | 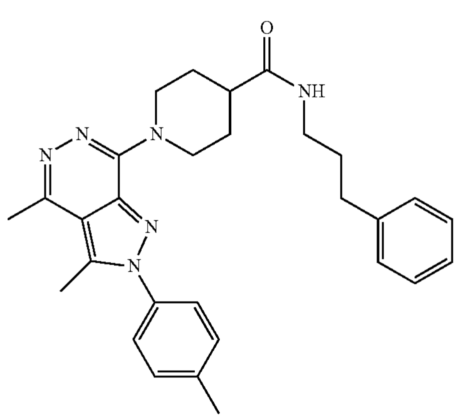 [SMILES: Cc1ccc(-n2nc3c(N4CCC(C(=O)NCCCc5ccccc5)CC4)nnc(C)c3c2C)cc1] |
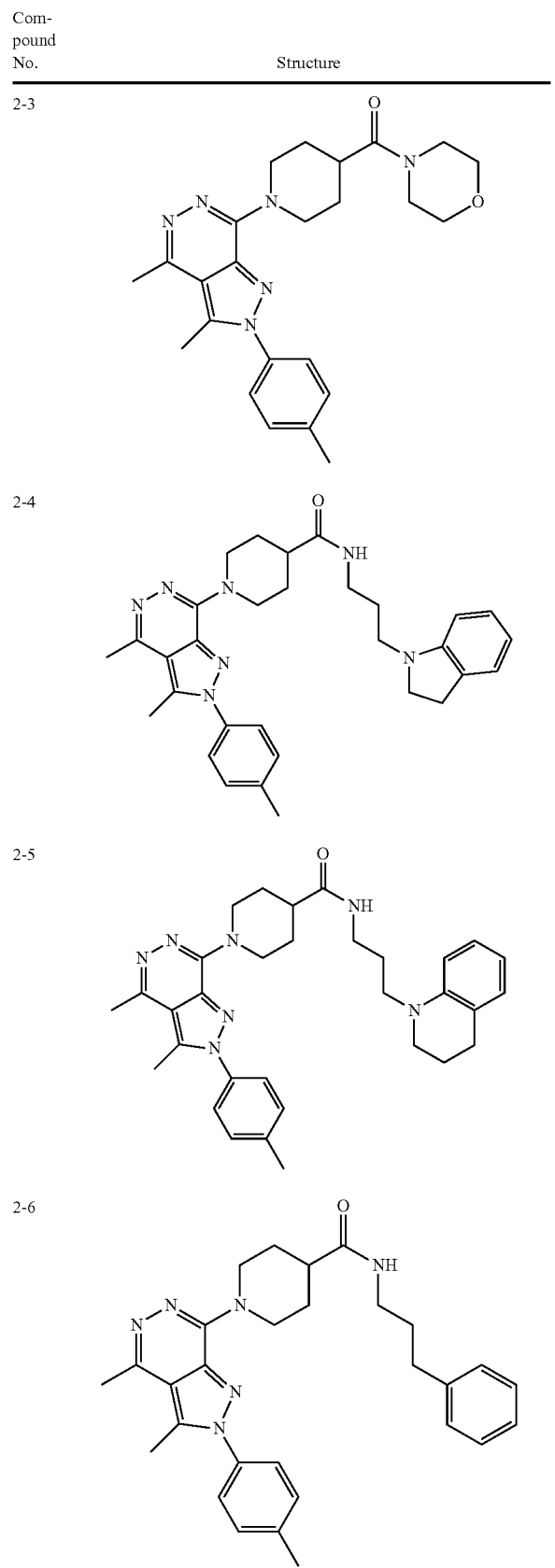
TABLE 2-continued
| Compound No. | Structure |
|---|---|
| 2-7 | 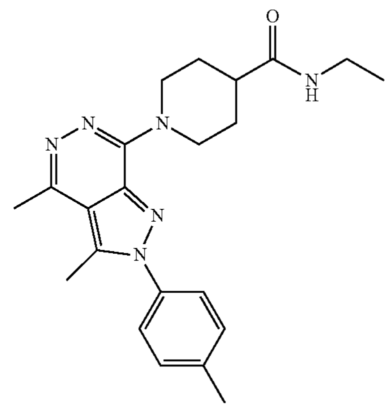 [SMILES: CCNC(=O)C1CCN(c2nnc(C)c3c(C)n(-c4ccc(C)cc4)nc23)CC1] |
| 2-8 | 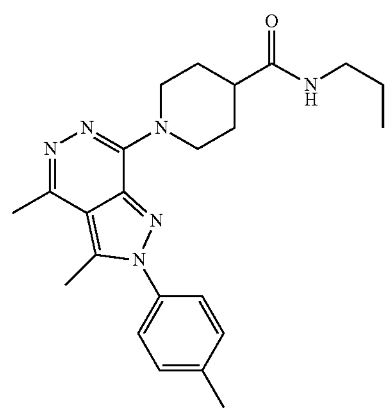 [SMILES: CCCNC(=O)C1CCN(c2nnc(C)c3c(C)n(-c4ccc(C)cc4)nc23)CC1] |
| 2-9 | 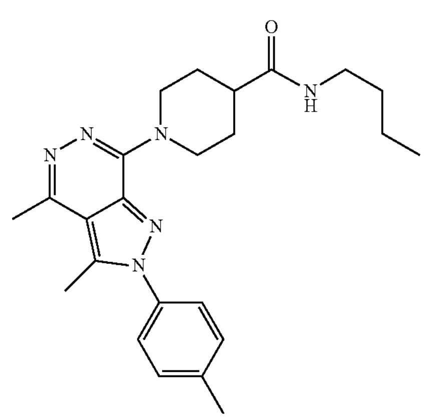 [SMILES: CCCCNC(=O)C1CCN(c2nnc(C)c3c(C)n(-c4ccc(C)cc4)nc23)CC1] |
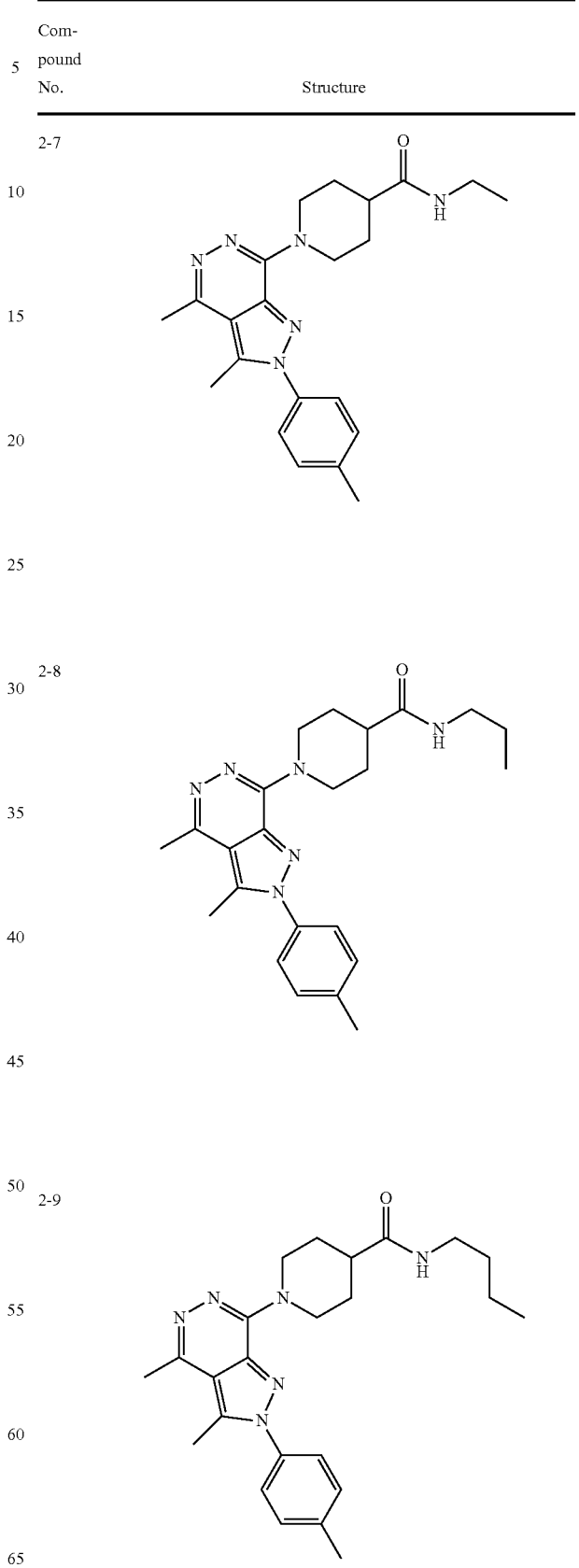

TABLE 2-continued

| Compound No. | Structure |
|---|---|
| 2-10 | (structure: 3,4-dimethyl-2-(p-tolyl)-2H-pyrazolo[3,4-d]pyridazin-7-yl piperidine-4-carboxamide with N-pentyl) |
| 2-11 | (structure: 3,4-dimethyl-2-(p-tolyl)-2H-pyrazolo[3,4-d]pyridazin-7-yl piperidine-4-carboxamide with N-hexyl) |
| 2-12 | (structure: 3,4-dimethyl-2-(p-tolyl)-2H-pyrazolo[3,4-d]pyridazin-7-yl piperidine-4-carboxamide with N-(5-phenylpentyl)) |

Certain compounds of Table 1X are listed in Table 3, with their chemical structure drawings and chemical names.

TABLE 3

| Compound No. | Structure | Chemical Name [1] |
|---|---|---|
| 7x | (structure) | N-(3-(diethylamino)propyl)-1-(3,4-dimethyl-2-phenyl-2H-pyrazolo[3,4-d]pyridazin-7-yl)piperidine-4-carboxamide |

TABLE 3-continued

| Compound No. | Structure | Chemical Name [1] |
|---|---|---|
| 9x | 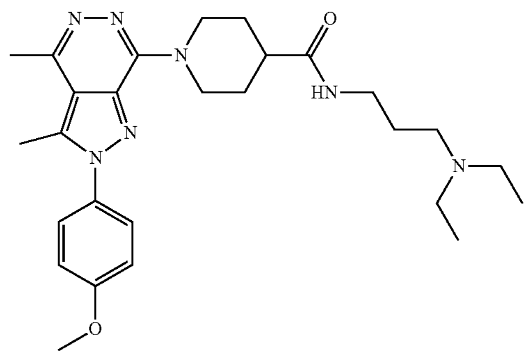 [SMILES: CCN(CC)CCCNC(=O)C1CCN(c2nnc(C)c3c(C)n(-c4ccc(OC)cc4)nc23)CC1] | N-(3-(diethylamino)propyl)-1-(2-(4-methoxyphenyl)-3,4-dimethyl-2H-pyrazolo[3,4-d]pyridazin-7-yl)piperidine-4-carboxamide |
| 17x | 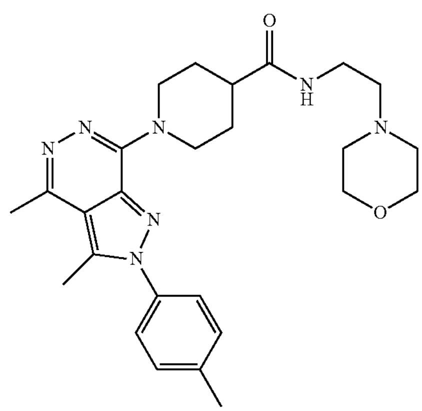 [SMILES: Cc1ccc(-n2nc3c(N4CCC(C(=O)NCCN5CCOCC5)CC4)nnc(C)c3c2C)cc1] | 1-(3,4-dimethyl-2-(p-tolyl)-2H-pyrazolo[3,4-d]pyridazin-7-yl)-N-(2-morpholinoethyl)piperidine-4-carboxamide |
| 19x | 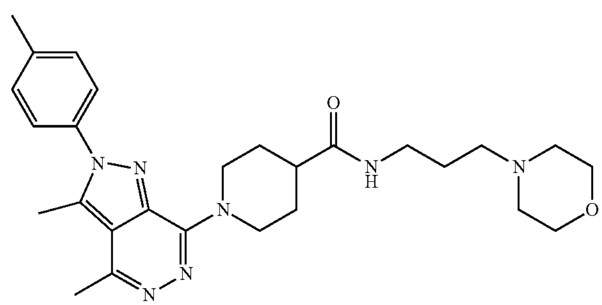 [SMILES: Cc1ccc(-n2nc3c(N4CCC(C(=O)NCCCN5CCOCC5)CC4)nnc(C)c3c2C)cc1] | 1-(3,4-dimethyl-2-(p-tolyl)-2H-pyrazolo[3,4-d]pyridazin-7-yl)-N-(3-morpholinopropyl)piperidine-4-carboxamide |
| 20x | 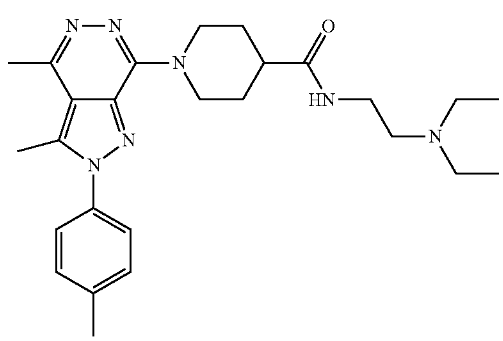 [SMILES: CCN(CC)CCNC(=O)C1CCN(c2nnc(C)c3c(C)n(-c4ccc(C)cc4)nc23)CC1] | N-(2-(diethylamino)ethyl)-1-(3,4-dimethyl-2-(p-tolyl)-2H-pyrazolo[3,4-d]pyridazin-7-yl)piperidine-4-carboxamide |

TABLE 3-continued

| Compound No. | Structure | Chemical Name [1] |
|---|---|---|
| 21x | 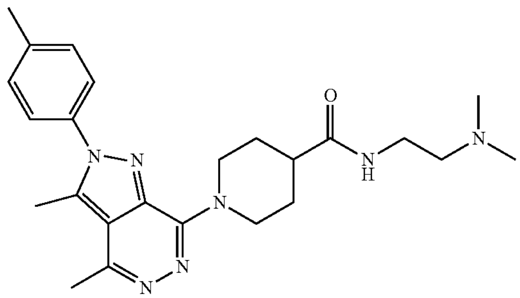 [SMILES: Cc1ccc(-n2nc3c(N4CCC(C(=O)NCCN(C)C)CC4)nnc(C)c3c2C)cc1] | 1-(3,4-dimethyl-2-(p-tolyl)-2H-pyrazolo[3,4-d]pyridazin-7-yl)-N-(2-(dimethylamino)ethyl)piperidine-4-carboxamide |
| 24x | 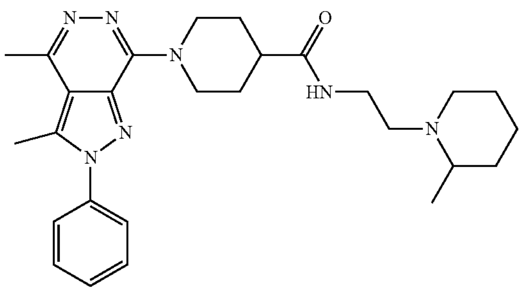 [SMILES: Cc1nnc(N2CCC(C(=O)NCCN3CCCCC3C)CC2)c2nn(-c3ccccc3)c(C)c12] | 1-(3,4-dimethyl-2-phenyl-2H-pyrazolo[3,4-d]pyridazin-7-yl)-N-(2-(2-methylpiperidin-1-yl)ethyl)piperidine-4-carboxamide |
| 25x | 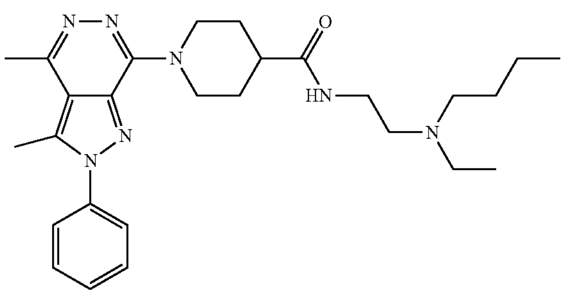 [SMILES: CCCCN(CC)CCNC(=O)C1CCN(c2nnc(C)c3c(C)n(-c4ccccc4)nc23)CC1] | N-(2-(butyl(ethyl)amino)ethyl)-1-(3,4-dimethyl-2-phenyl-2H-pyrazolo[3,4-d]pyridazin-7-yl)piperidine-4-carboxamide |
| 31x | 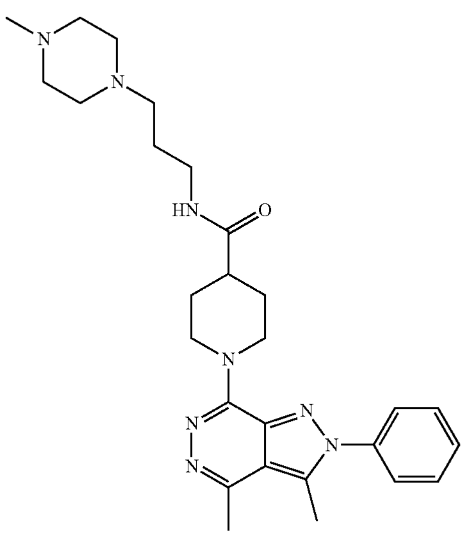 [SMILES: Cc1nnc(N2CCC(C(=O)NCCCN3CCN(C)CC3)CC2)c2nn(-c3ccccc3)c(C)c12] | 1-(3,4-dimethyl-2-phenyl-2H-pyrazolo[3,4-d]pyridazin-7-yl)-N-(3-(4-methylpiperazin-1-yl)propyl)piperidine-4-carboxamide |

TABLE 3-continued

| Compound No. | Structure | Chemical Name [1] |
|---|---|---|
| 32x | 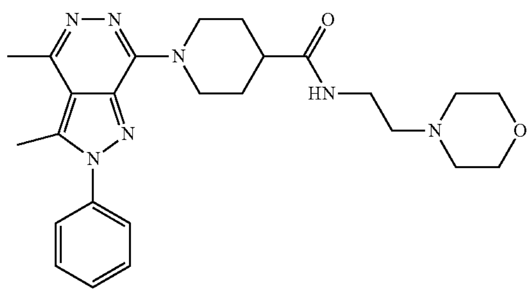 [SMILES: Cc1nnc(N2CCC(C(=O)NCCN3CCOCC3)CC2)c2nn(-c3ccccc3)c(C)c12] | 1-(3,4-dimethyl-2-phenyl-2H-pyrazolo[3,4-d]pyridazin-7-yl)-N-(2-morpholinoethyl)piperidine-4-carboxamide |
| 33x | 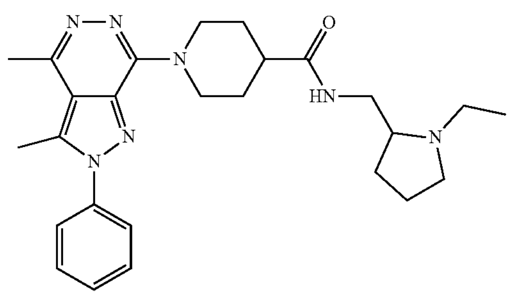 [SMILES: CCN1CCCC1CNC(=O)C1CCN(c2nnc(C)c3c(C)n(-c4ccccc4)nc23)CC1] | 1-(3,4-dimethyl-2-phenyl-2H-pyrazolo[3,4-d]pyridazin-7-yl)-N-((1-ethylpyrrolidin-2-yl)methyl)piperidine-4-carboxamide |
| 45x | 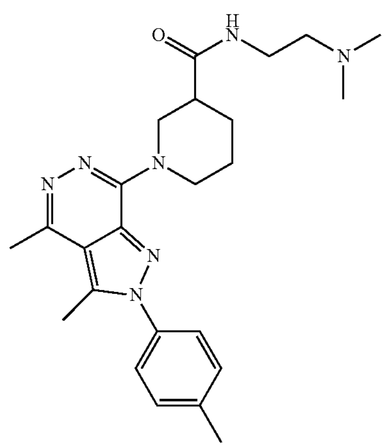 | 1-(3,4-dimethyl-2-(p-tolyl)-2H-pyrazolo[3,4-d]pyridazin-7-yl)-N-(2-(dimethylamino)ethyl)piperidine-3-carboxamide |
| 49x | 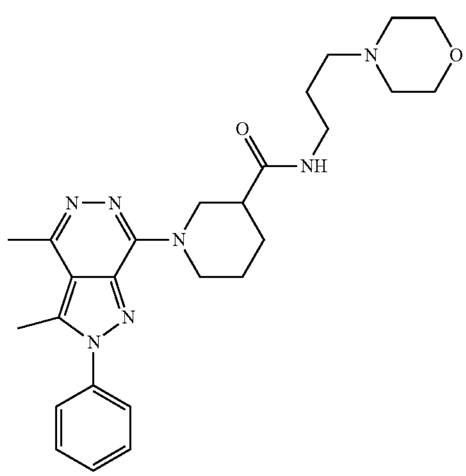 [SMILES: Cc1nnc(N2CCCC(C(=O)NCCCN3CCOCC3)C2)c2nn(-c3ccccc3)c(C)c12] | 1-(3,4-dimethyl-2-phenyl-2H-pyrazolo[3,4-d]pyridazin-7-yl)-N-(3-morpholinopropyl)piperidine-3-carboxamide |

TABLE 3-continued

| Compound No. | Structure | Chemical Name [1] |
|---|---|---|
| 51x | 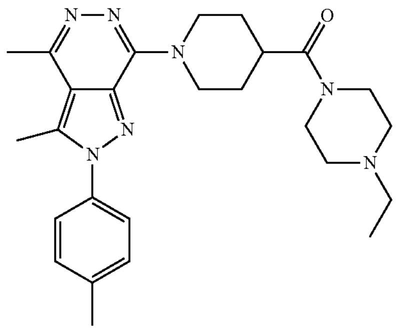 [SMILES: CCN1CCN(C(=O)C2CCN(c3nnc(C)c4c(C)n(-c5ccc(C)cc5)nc34)CC2)CC1] | (1-(3,4-dimethyl-2-(p-tolyl)-2H-pyrazolo[3,4-d]pyridazin-7-yl)piperidin-4-yl)(4-ethylpiperazin-1-yl)methanone |
| 54x | 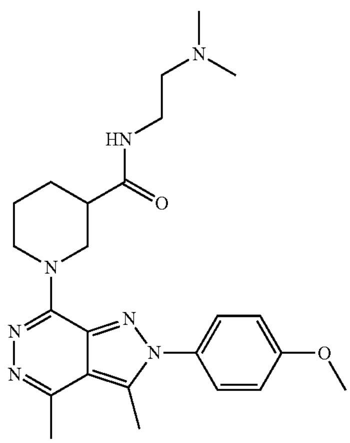 [SMILES: COc1ccc(-n2nc3c(N4CCCC(C(=O)NCCN(C)C)C4)nnc(C)c3c2C)cc1] | N-(2-(dimethylamino)ethyl)-1-(2-(4-methoxyphenyl)-3,4-dimethyl-2H-pyrazolo[3,4-d]pyridazin-7-yl)piperidine-3-carboxamide |
| 59x | 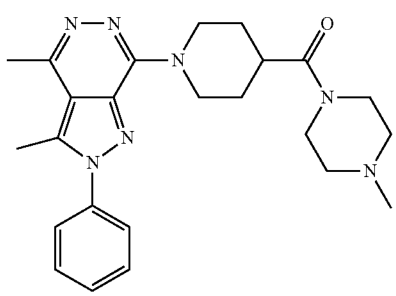 | (1-(3,4-dimethyl-2-phenyl-2H-pyrazolo[3,4-d]pyridazin-7-yl)piperidin-4-yl)(4-methylpiperazin-1-yl)methanone |
| 63x | 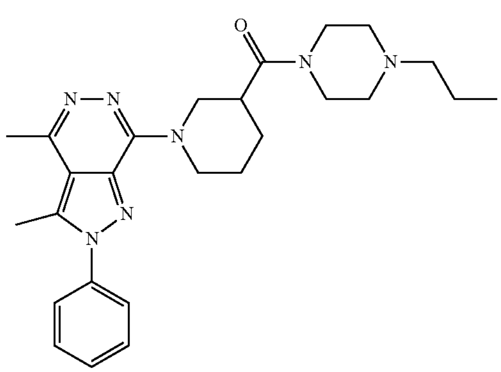 [SMILES: CCCN1CCN(C(=O)C2CCCN(c3nnc(C)c4c(C)n(-c5ccccc5)nc34)C2)CC1] | (1-(3,4-dimethyl-2-phenyl-2H-pyrazolo[3,4-d]pyridazin-7-yl)piperidin-3-yl)(4-propylpiperazin-1-yl)methanone |

TABLE 3-continued

| Compound No. | Structure | Chemical Name [1] |
|---|---|---|
| 64x | 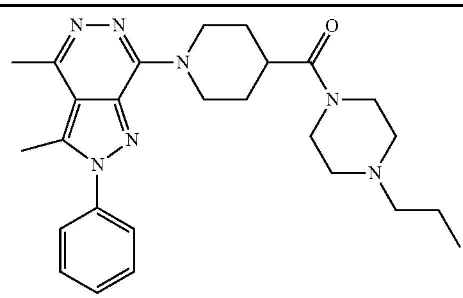 | (1-(3,4-dimethyl-2-phenyl-2H-pyrazolo[3,4-d]pyridazin-7-yl)piperidin-4-yl)(4-propylpiperazin-1-yl)methanone |

[1] Chemical names are generated using the ChemBioDraw® Ultra version 14.0.0.117 or 16.0.0.82 (68) software.

In some embodiments, provided is a compound selected from Compound Nos. 1-56 in Table 1 or Compound Nos. 57-76 in Table 1-A, or a salt thereof. In some embodiments, the compound is selected from the group consisting of one or more of Compound Nos. 1-56 in Table 1, or a salt thereof. In some embodiments, the compound is selected from the group consisting of one or more of Compound Nos. 1-47 in Table 1, or a salt thereof. In some embodiments, provided is a compound selected from Compound Nos. 1, 2, 3, 4, 5, 6, 7, 8, 9, 10, 11, 12, 12a, 12b, 13, 13a, 13b, 15, 16, 16a, 16b, 17, 17a, 17b, 18, 19, 19a, 19b, 19c, 19d, 20, 21, 21a, 21b, 21c, 21d, 22, 23, 24, 25, 26, 27, 28, 29, 31, 32, 34, 35, 36, 37, 38, 40, 41, 42, 43, 44, 44a, 44b, 45, 45a, 45b, 46, 47, 47a, 47b, 48, 49, 50, 51, 52, 53, 54, 55 and 56 in Table 1, or a salt thereof. In some embodiments, the compound is selected from the group consisting of Compound Nos. 1, 2, 3, 4, 5, 6, 7, 8, 9, 10, 11, 12, 12a, 12b, 13, 13a, 13b, 15, 16, 16a, 16b, 17, 17a, 17b, 18, 19, 19a, 19b, 19c, 19d, 20, 21, 21a, 21b, 21c, 21d, 22, 23, 24, 25, 26, 27, 28, 29, 31, 32, 34, 35, 36, 37, 38, 40, 41, 42, 43, 44, 44a, 44b, 45, 45a, 45b, 46, 47, 47a and 47b in Table 1, or a salt thereof. In some embodiments, the compound is selected from the group consisting of one or more of Compound Nos. 57-76 in Table 1-A, or a salt thereof. In some embodiments, provided is a compound selected from the group consisting of Compound Nos. 57, 58, 59, 60, 61, 62, 63, 64, 65, 66, 67, 68, 69, 70, 71, 72, 73, 74, 75, and 76 in Table 1-A, or a salt thereof.

The invention also includes all salts of compounds referred to herein, such as pharmaceutically acceptable salts. The invention also includes any or all of the stereochemical forms, including any enantiomeric or diastereomeric forms, and any tautomers or other forms of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. It is also understood that prodrugs, solvates and metabolites of the compounds are embraced by this disclosure. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization, and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Compounds of the formula ($I^0a$) can be prepared according to Scheme 1, wherein $R^6$, i, j, n and V are as detailed herein for formula ($I^0a$); $R^D$ is $R^1$ as detailed herein for formula ($I^0a$) or a protected form thereof; $R^C$ is $R^2$ as detailed herein for formula ($I^0a$) or a protected form thereof; $R^B$ is $R^3$ as detailed herein for formula ($I^0a$) or a protected form thereof; and $R^A$ is the —N(R$^7$)—W—X—Y—N(R$^8$)R$^9$ moiety as detailed herein for formula (I$^0$a) or a protected form thereof. In some embodiments, $R^D$ is $R^1$ as detailed herein for formula (I$^0$a). In one variation, $R^D$ is phenyl or p-tolyl. In some embodiments, $R^C$ is $R^2$ as detailed herein for formula (I$^0$a). In some embodiments, $R^B$ is $R^3$ as detailed herein for formula (I$^0$a). In some embodiments, $R^A$ is the —N(R$^7$)—W—X—Y—N(R$^8$)R$^9$ moiety as detailed herein for formula (I$^0$a).

Scheme 1

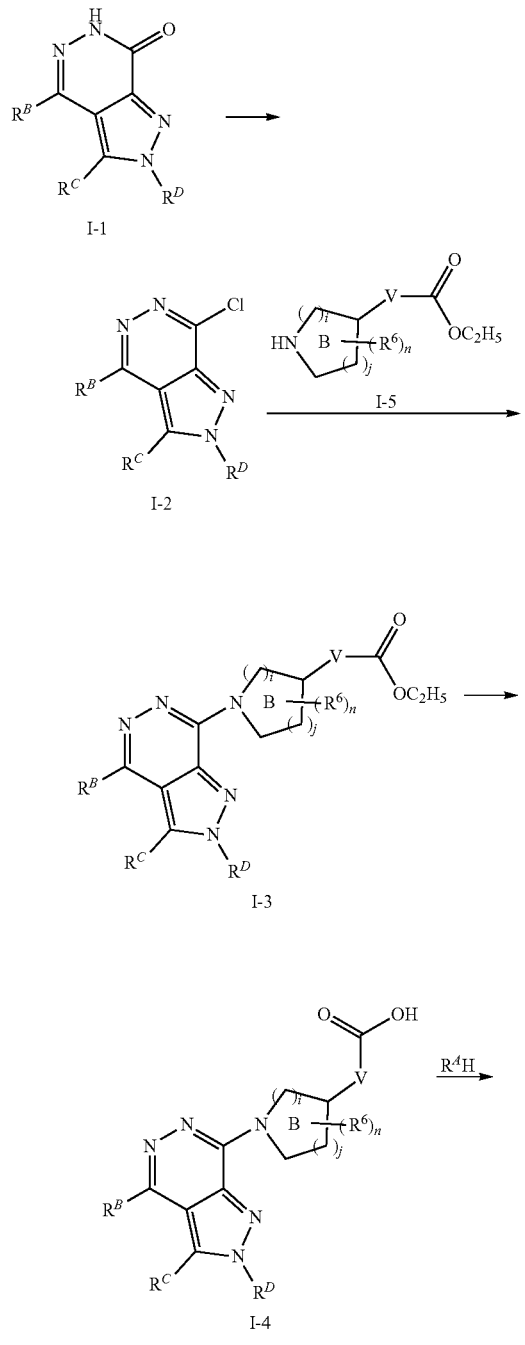

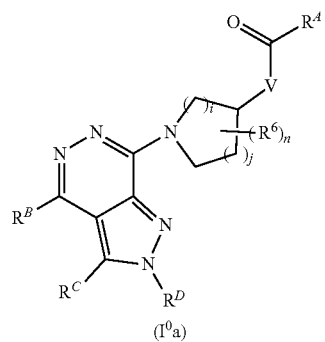

(I$^0$a)

Chlorination of a compound of Formula I-1 using a chlorinating agent (e.g., POCl$_3$) gives rise to a compound of Formula I-2. Displacement of the 7-chloro group in the compound of Formula I-2 with an azacyclic ester of Formula I-5 yields a compound of Formula I-3, which can be converted to a compound of Formula I-4 by hydrolysis using a base (e.g., lithium hydroxide) in an aqueous solution. Amide coupling of a compound of Formula I-4 and amine RAH using a peptide coupling agent (e.g., EDCI or HATU) provides a compounds of Formula (I$^0$a).

Compounds of the formula (Ia) where U is methylene can be prepared according to Scheme 2, wherein R$^6$, i, j, n and V are as detailed herein for formula (Ia); $R^D$ is $R^1$ as detailed herein for formula (Ia) or a protected form thereof; $R^C$ is $R^2$ as detailed herein for formula (Ia) or a protected form thereof; $R^B$ is $R^3$ as detailed herein for formula (Ia) or a protected form thereof; and $R^A$ is the —N(R$^7$)—W—X—Y—N(R$^8$)R$^9$ moiety as detailed herein for formula (Ia) or a protected form thereof. In some embodiments, $R^D$ is $R^1$ as detailed herein for formula (Ia). In one variation, $R^D$ is phenyl or p-tolyl. In some embodiments, $R^C$ is $R^2$ as detailed herein for formula (Ia). In some embodiments, $R^B$ is $R^3$ as detailed herein for formula (Ia). In some embodiments, $R^A$ is the —N(R$^7$)—W—X—Y—N(R$^8$)R$^9$ moiety as detailed herein for formula (Ia).

Scheme 2

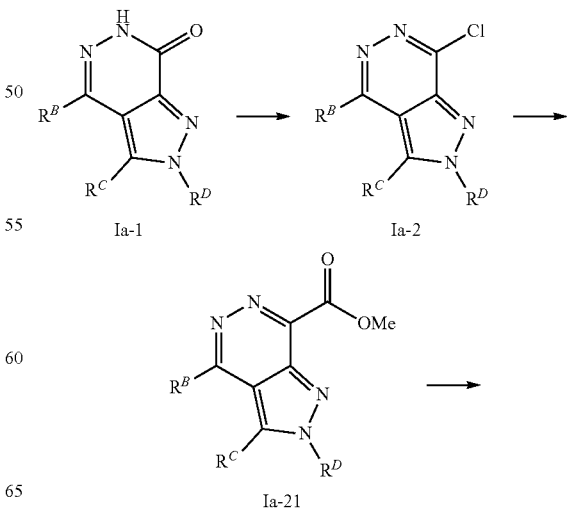

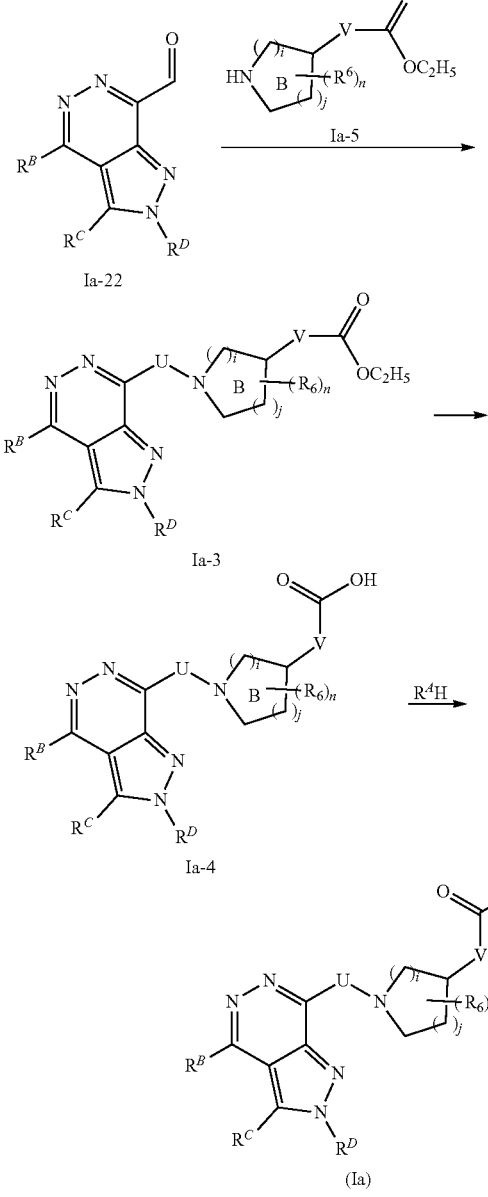

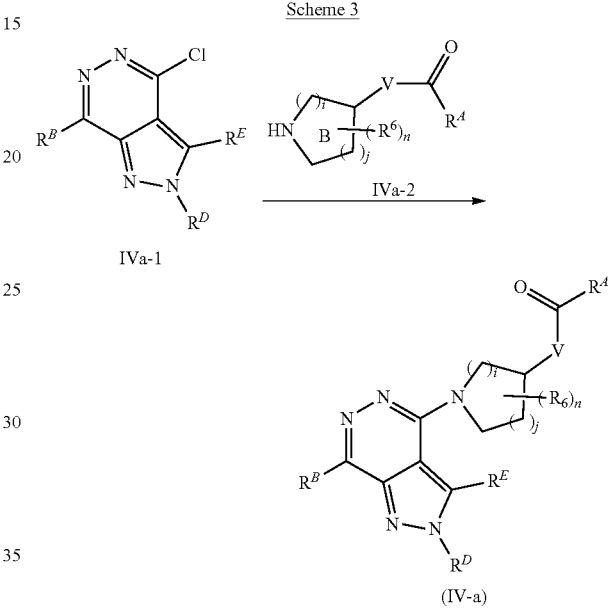

Chlorination of a compound of Formula Ia-1 using a chlorinating agent (e.g., POCl₃) gives rise to a compound of Formula Ia-2. Carboxylation at the 7-position followed by reduction gives the 7-carboxyaldehyde of Formula Ia-22. Coupling of the 7-carboxyaldehyde of Formula Ia-22 with an azacyclic ester of Formula I-5 (e.g., via reductive amination) yields a compound of Formula Ia-3 where U is methylene, which can be converted to a compound of Formula Ia-4 by hydrolysis using a base (e.g., lithium hydroxide) in an aqueous solution. Amide coupling of a compound of Formula Ia-4 and amine R^AH using a peptide coupling agent (e.g., EDCI or HATU) provides a compound of Formula (Ia).

Compounds of formula (IV-a) can be prepared according to Scheme 3, wherein $R^6$, i, j and n are as detailed herein for formula (IV-a); $R^D$ is $R^1$ as detailed herein for formula (IV-a) or a protected form thereof; $R^B$ is $R^3$ as detailed herein for formula (IV-a) or a protected form thereof; $R^E$ is $R^{30}$ as detailed herein for formula (IV-a) or a protected form thereof; and $R^A$ is the —N(R⁷)—W—X—Y—N(R⁸)R⁹ moiety as detailed herein for formula (IV-a) or a protected form thereof. In some embodiments, $R^D$ is $R^1$ as detailed herein for formula (IV-a). In one variation, $R^D$ is phenyl or p-tolyl. In some embodiments, $R^B$ is $R^3$ as detailed herein for formula (IV-a). In one variation, $R^B$ is a halogen (e.g., chloro). In some embodiments, $R^E$ is $R^{30}$ as detailed herein for formula (IV-a). In one variation, $R^E$ is methyl. In some embodiments, $R^A$ is the —N(R⁷)—W—X—Y—N(R⁸)R⁹ moiety as detailed herein for formula (IV-a).

Scheme 3

Coupling of a compound of Formula IVa-1 with a compound of Formula IVa-2 in the presence of a base (e.g. TEA) provides a compound of Formula (IV-a).

Compounds of formula (VII-a) can be prepared according to Scheme 4, wherein $R^6$, i, j and n are as detailed herein for formula (VII-a); $R^D$ is $R^1$ as detailed herein for formula (VII-a) or a protected form thereof; $R^C$ is $R^{2a}$ as detailed herein for formula (VII-a) or a protected form thereof; $R^B$ is $R^3$ as detailed herein for formula (VII-a) or a protected form thereof; $R^F$ is $R^4$ as detailed herein for formula (VII-a) or a protected form thereof; $R^G$ is $R^5$ as detailed herein for formula (VII-a) or a protected form thereof; and $R^A$ is the —N(R⁷)—W—X—Y—N(R⁸)R⁹ moiety as detailed herein for formula (VII-a) or a protected form thereof. In some embodiments, $R^D$ is $R^1$ as detailed herein for formula (VII-a). In one variation, $R^D$ is phenyl or p-tolyl. In some embodiments, $R^C$ is $R^{2a}$ as detailed herein for formula (VII-a). In one variation, $R^C$ is a $C_1$-$C_6$ alkyl (e.g., methyl). In some embodiments, $R^B$ is $R^3$ as detailed herein for formula (VII-a). In one variation, $R^B$ is hydrogen. In some embodiments, $R^F$ is $R^4$ as detailed herein for formula (VII-a). In one variation, $R^F$ is hydrogen. In some embodiments, $R^G$ is $R^5$ as detailed herein for formula (VII-a). In one variation, $R^G$ is hydrogen. In some embodiments, $R^A$ is the —N(R⁷)—W—X—Y—N(R⁸)R⁹ moiety as detailed herein for formula (VII-a).

Scheme 4

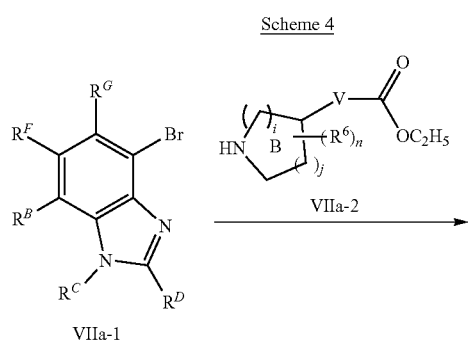

VIIa-1

VIIa-2

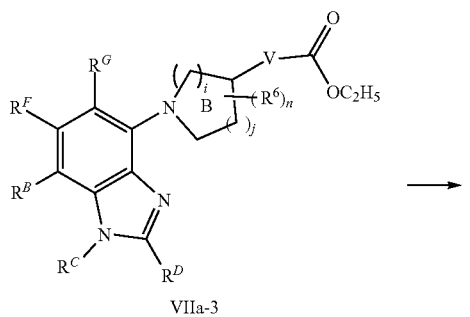

VIIa-3

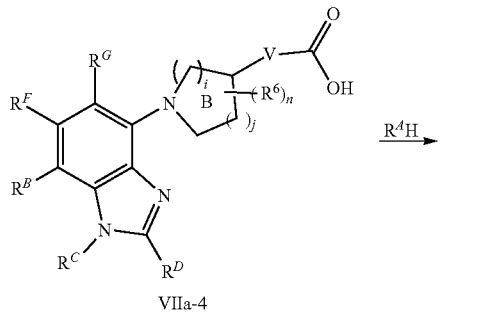

VIIa-4

R^A H

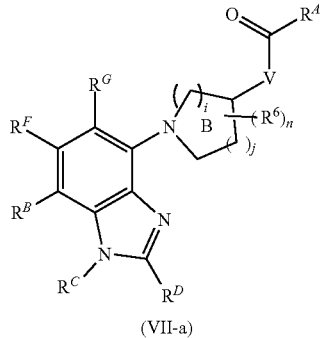

(VII-a)

Coupling of a compound of Formula VIIa-1 with an azacyclic ester of Formula VIIa-2 (e.g., in the presence of a palladium catalyst) yields a compound of Formula VIIa-3, which can be converted to a compound of Formula VIIa-4 by hydrolysis using a base (e.g., lithium hydroxide). Amide coupling of a compound of Formula VIIa-4 and amine R$^A$H using a peptide coupling agent (e.g., EDCI) provides a compound of Formula (VII-a).

Compounds of formula (VIII-a) can be prepared according to Scheme 5, wherein R$^6$, i, j and n are as detailed herein for formula (VIII-a); R$^D$ is R$^1$ as detailed herein for formula (VIII-a) or a protected form thereof; R$^C$ is R$^2$ as detailed herein for formula (VIII-a) or a protected form thereof; R$^B$ is R$^3$ as detailed herein for formula (VIII-a) or a protected form thereof; R$^G$ is R$^5$ as detailed herein for formula (VIII-a) or a protected form thereof; and R$^A$ is the —N(R$^7$)—W—X—Y—N(R$^8$)R$^9$ moiety as detailed herein for formula (VIII-a) or a protected form thereof. In some embodiments, R$^D$ is R$^1$ as detailed herein for formula (VIII-a). In one variation, R$^D$ is phenyl or p-tolyl. In some embodiments, R$^C$ is R$^2$ as detailed herein for formula (VIII-a). In one variation, R$^C$ is hydrogen. In some embodiments, R$^B$ is R$^3$ as detailed herein for formula (VIII-a). In one variation, R$^B$ is hydrogen. In some embodiments, R$^G$ is R$^5$ as detailed herein for formula (VIII-a). In one variation, R$^G$ is hydrogen. In some embodiments, R$^A$ is the —N(R$^7$)—W—X—Y—N(R$^8$)R$^9$ moiety as detailed herein for formula (VIII-a).

Scheme 5

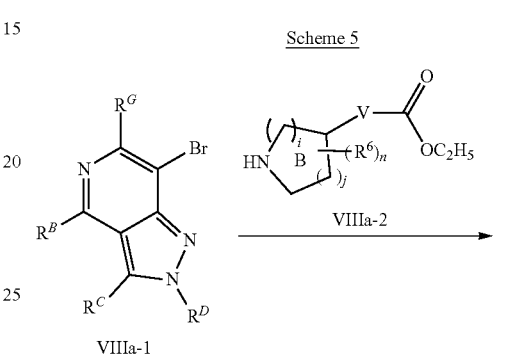

VIIIa-1

VIIIa-2

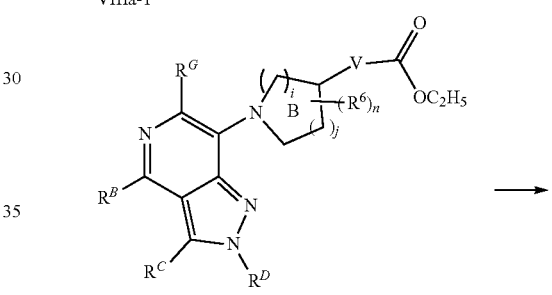

VIIIa-3

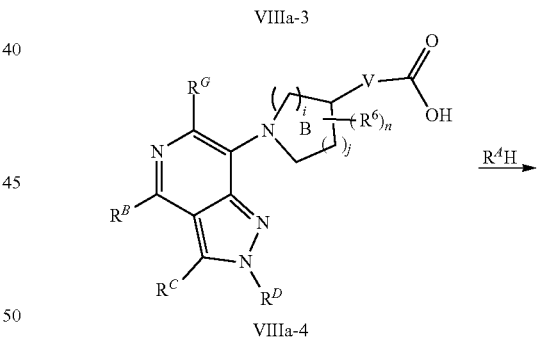

VIIIa-4

R$^A$H

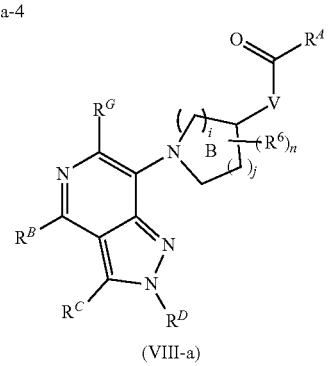

(VIII-a)

Coupling of a compound of Formula VIIIa-1 with an azacyclic ester of Formula VIIIa-2 (e.g., in the presence of a palladium catalyst) yields a compound of Formula VIIIa-3, which can be converted to a compound of Formula VIIIa-4 by hydrolysis using a base (e.g., lithium hydroxide). Amide coupling of a compound of Formula VIIIa-4 and amine RAH using a peptide coupling agent (e.g., HATU) provides a compound of Formula (VIII-a).

Pharmaceutical Compositions and Formulations

Pharmaceutical compositions of any of the compounds detailed herein are embraced by this invention, for example, a compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof detailed herein, or a salt or solvate thereof. Thus, the invention includes pharmaceutical compositions comprising a compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof detailed herein, or a pharmaceutically acceptable salt thereof and a pharmaceutically acceptable excipient. In some embodiments, the compound is selected from Compound Nos. 1-56 in Table 1, or a salt (e.g., a pharmaceutically acceptable salt) or solvate thereof. In some embodiments, the compound is selected from Compound Nos. 57-76 in Table 1-A, or a salt (e.g., a pharmaceutically acceptable salt) or solvate thereof. In some embodiments, the compound includes a compound listed in Table 1X, or a salt or solvate thereof. In some embodiments, the compound does not include a compound listed in Table 1X, and salts and solvates thereof. In some embodiments, the compound is a compound listed in Table 3, or a salt (e.g., a pharmaceutically acceptable salt) or solvate thereof. In some embodiments, the compound is selected from the group consisting of Compound Nos. 7x, 9x, 17x, 19x, 20x, 21x, 24x, 25x, 31x, 32x, 33x, 45x, 49x, 51x, 54x, 59x, 63x, 64x, and salts and solvates thereof.

In one aspect, the pharmaceutically acceptable salt is an acid addition salt, such as a salt formed with an inorganic or organic acid.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. For example, a composition of a substantially pure compound selected from a compound of Table 1 intends a composition that contains no more than 35% impurity, wherein the impurity denotes a compound other than the compound or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1% of the (R) form of the compound.

In one variation, the compounds herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable excipient. In another variation, methods of administering a compound are provided. The purified forms, pharmaceutical compositions and methods of administering the compounds are suitable for any compound or form thereof detailed herein.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable excipients to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable excipient, such as those mentioned above. Depending on the therapeutic form of the system (e.g., transdermal patch vs. oral tablet), the excipient may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington: The Science and Practice of Pharmacy*, Lippincott Williams & Wilkins, 21$^{st}$ ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions. Examples of excipients, which may be used for the preparation of such compositions, are lactose, corn starch or its derivatives, talc, stearate or its salts, etc. Acceptable excipients for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 1, 5, 10, 20, 50, 100, 250 or 500 mg tablet.

Compositions comprising a compound provided herein are also described. In one variation, the composition comprises a compound and a pharmaceutically acceptable excipient. In another variation, a composition of substantially pure compound is provided.

Methods of Use

Compounds and compositions of the present disclosure, such as a pharmaceutical composition comprising a compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof detailed herein, or a pharmaceutically acceptable salt thereof and a pharmaceutically acceptable excipient, are suitable for a plurality of uses involving inhibiting one or both of a toll-like receptor 8 (TLR8)-dependent response and a toll-like receptor 9 (TLR9)-dependent response in an individual in need thereof. The individual in need may have an immunological disorder such as an autoimmune disease or an inflammatory disease. In some instances, the individual in need may have a chronic or an acute pathogen infection. In other instance, the individual may have cancer. In particular, the pharmaceutical compositions of the present disclosure comprising a compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof detailed herein, or a pharmaceutically acceptable salt thereof, are suitable for inhibiting an immune response in an individual in need thereof. The individual of the present disclosure is a mammalian subject. Mammalian subjects include but are not limited to humans, nonhuman primates, rodents, pets, and farm animals. The pharmaceutical composition is administered to the individual in an amount effective to achieve a specific outcome.

A. Inhibition of an Immune Response and Treatment of Cancer

Provided herein are methods of inhibiting an immune response in an individual comprising administering to the individual an amount of a compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof detailed herein, or a pharmaceutically acceptable salt thereof, effective to inhibit the immune response in the individual. In some embodiments, the compound is present in a pharmaceutical composition comprising a pharmaceutically acceptable excipient. The individual of the methods of the present disclosure is a mammal, which in some embodiments is a human while in other embodiments is a nonhuman primate or a rodent. "Inhibiting" an immune response refers to decreasing the immune response of mammalian leukocytes (e.g., peripheral blood mononuclear cells, monocytes, B cells, plasmacytoid dendritic cells, etc.). In some embodiments, immune responses inhibited include inhibition of cytokine production, inhibition of cell maturation and/or inhibition of cell proliferation. In some embodiments, inhibiting an immune response comprises one or more of the group consisting of: inhibiting tumor necrosis factor-alpha production; inhibiting interleukin-1beta production; inhibiting interleukin-6 production; and inhibiting interferon-alpha production. In some embodiments, the compound is selected from Compound Nos. 1-56 in Table 1, or a pharmaceutically acceptable salt thereof. In some embodiments, the compound is selected from Compound Nos. 1-47 in Table 1, or a pharmaceutically acceptable salt thereof. In some embodiments, the compound is selected from Compound Nos. 57-76 in Table 1-A, or a pharmaceutically acceptable salt thereof. In some embodiments, the compound includes a compound listed in Table 1X, or a pharmaceutically acceptable salt thereof. In some embodiments, the compound does not include a compound listed in Table 1X, and pharmaceutically acceptable salts thereof. In some embodiments, the compound includes a compound listed in Table 3, or a pharmaceutically acceptable salt thereof.

In some embodiments, the immune response comprises one or both of a TLR8-dependent immune response and a TLR9-dependent immune response, and the pharmaceutical composition is administered in an amount effective to inhibit one or both of the TLR8-dependent immune response and the TLR9-dependent immune response in the individual. In some preferred embodiments, the immune response comprises a TLR8-dependent immune response and the pharmaceutical composition is administered in an amount effective to inhibit the TLR8-dependent immune response in the individual. In some preferred embodiments, the immune response comprises a TLR9-dependent immune response and the pharmaceutical composition is administered in an amount effective to inhibit the TLR9-dependent immune response in the individual. In some embodiments, the pharmaceutical composition is administered in an amount effective to inhibit the TLR8-dependent immune response but not a TLR9-dependent immune response in the individual. In other embodiments, the pharmaceutical composition is administered in an amount effective to inhibit the TLR9-dependent immune response but not a TLR8-dependent immune response in the individual.

The present disclosure provides methods of inhibiting an immune response, particularly those associated with an immunological disorder. The present disclosure also provides methods for ameliorating symptoms associated with the immunological disorder. The methods of the present disclosure for inhibiting one or both of a TLR8-dependent and a TLR9-dependent immune response can be practiced in vitro, ex vivo or in vivo. In some embodiments, a mammalian (e.g., human, nonhuman primate, rodent, etc.) cell is contacted with a compound of formula (I), or any variation thereof, e.g., a compound of formula (A-I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or a compound selected from Compound Nos. 1-56 in Table 1 or Compound Nos. 57-76 in Table 1-A, or a pharmaceutically acceptable salt thereof, in an amount effective to inhibit a response by the cell that contributes to an immune response (e.g., secretion of a cytokine by the cell).

Inhibition of one or both of a TLR8-dependent and a TLR9-dependent response may be useful for treating and/or preventing a variety of pathological conditions (e.g., immunological disorders) that are responsive to cytokines. Pathological conditions for which a compound of formula (A-I) or (I), or any variation thereof, e.g., a compound of formula (Ia), (I$^0$), (I$^0$a), (II), (IIa), (III), (IIIa), (IV), (IV-a), (V), (V-a), (VI), (VI-a), (VII), (VII-a), (VIII), (VIII-a), or a compound selected from Compound Nos. 1-56 in Table 1 or Compound Nos. 57-76 in Table 1-A, or a pharmaceutically acceptable salt thereof, may be used as treatments include, but are not limited to autoimmune diseases, inflammatory diseases, chronic pathogen stimulation, acute pathogen stimulation, and cancer. Provided herein are methods of treating or preventing an immunological disorder in an individual comprising administering to the individual an effective amount of an compound of formula (A-I) or (I), or any variation thereof, e.g., a compound of formula (Ia), (I⁰), (I⁰a), (II), (IIa), (III), (IIIa), (IV), (IV-a), (V), (V-a), (VI), (VI-a), (VII), (VII-a), (VIII), (VIII-a), or a compound selected from Compound Nos. 1-56 in Table 1 or Compound Nos. 57-76 in Table 1-A, or a pharmaceutically acceptable salt thereof. Further, provided are methods for ameliorating symptoms associated with an immunological disorder comprising administering an effective amount of compound of formula (A-I) or (I), or any variation thereof, e.g., a compound of formula (Ia), (I⁰), (I⁰a), (II), (IIa), (III), (IIIa), (IV), (IV-a), (V), (V-a), (VI), (VI-a), (VII), (VII-a), (VIII), (VIII-a), or a compound selected from Compound Nos. 1-56 in Table 1 or Compound Nos. 57-76 in Table 1-A, or a pharmaceutically acceptable salt thereof, to an individual having the disorder. Methods are also provided for preventing or delaying development of an immunological disorder, comprising administering an effective amount of compound of formula (A-I) or (I), or any variation thereof, e.g., a compound of formula (Ia), (I⁰), (I⁰a), (II), (IIa), (III), (IIIa), (IV), (IV-a), (V), (V-a), (VI), (VI-a), (VII), (VII-a), (VIII), (VIII-a), or a compound selected from Compound Nos. 1-56 in Table 1 or Compound Nos. 57-76 in Table 1-A, or a pharmaceutically acceptable salt thereof, to an individual having the disorder.

Provided herein are methods of inhibiting an immune response in an individual, comprising administering to the individual a compound of formula (A-I) or (I), or any variation thereof, e.g., a compound of formula (Ia), (I⁰), (I⁰a), (II), (IIa), (III), (IIIa), (IV), (IV-a), (V), (V-a), (VI), (VI-a), (VII), (VII-a), (VIII), (VIII-a), or a compound selected from Compound Nos. 1-56 in Table 1 or Compound Nos. 57-76 in Table 1-A, or a pharmaceutically acceptable salt thereof, in an amount effective to inhibit the immune response in the individual. In some embodiments, the immune response is associated with an autoimmune disease. In further embodiments, inhibiting the immune response ameliorates one or more symptoms of the autoimmune disease. In still further embodiments, inhibiting the immune response treats the autoimmune disease. In yet further embodiments, inhibiting the immune response prevents or delays development of the autoimmune disease. In some embodiments, the autoimmune disease is selected from the group consisting of systemic lupus erythematosus, type I diabetes mellitus, multiple sclerosis, rheumatoid arthritis, inflammatory bowel disease, Sjogren's syndrome, scleroderma and dermatomyositis. In some embodiments, the inflammatory bowel disease is selected from the group consisting of Crohn's disease and ulcerative colitis.

The present disclosure provides methods of treating or preventing an autoimmune disease in an individual, comprising administering to the individual an effective amount of a compound of formula (A-I) or (I), or any variation thereof, e.g., a compound of formula (Ia), (I⁰), (I⁰a), (II), (IIa), (III), (IIIa), (IV), (IV-a), (V), (V-a), (VI), (VI-a), (VII), (VII-a), (VIII), (VIII-a), or a compound selected from Compound Nos. 1-56 in Table 1 or Compound Nos. 57-76 in Table 1-A, or a pharmaceutically acceptable salt thereof. Autoimmune diseases are characterized by the production of antibodies that react with self antigens of the individual and/or by the presence of immune effector cells that react to cells of the individual displaying peptides derived from the self antigens.

In some aspects, the autoimmune disease affects a major organ of the individual, such as the heart, kidney or liver. Autoimmune diseases of the heart include for instance, autoimmune myocarditis, which is also referred to as autoimmune cardiomyopathy and Coxsackie myocarditis. Autoimmune diseases of the kidney include but are not limited to lupus nephritis and anti-glomerular basement membrane nephritis, the latter which is also known as Goodpastures syndrome and glomerulonephritis type I. Autoimmune diseases of the liver include for instance, autoimmune hepatitis and primary biliary cirrhosis.

In further aspects, the autoimmune disease affects the skin of the individual. Autoimmune diseases of the skin include but are not limited to alopecia areata, autoimmune urticaria, dermatitis herpetiformis, pemphigus vulgaris, psoriasis, systemic scleroderma, the latter of which is also known as systemic sclerosis and scleroderma.

In additional aspects, the autoimmune disease affects one or more glands of the individual. Autoimmune diseases that affect endocrine glands include for instance, Addison's disease, autoimmune polyendocrine syndrome type 1 (Whitaker's syndrome), type 2 (Schmidt syndrome), and type 3, autoimmune pancreatitis, diabetes mellitus type 1, autoimmune thyroiditis (Hashimoto's thyroiditis), and Graves' disease. Autoimmune diseases that affect exocrine glands include for example, Sjogren's syndrome.

In some aspects, the autoimmune disease affects the digestive system of the individual. Autoimmune diseases of the digestive system include but are not limited to celiac disease, Crohn' disease and ulcerative colitis. Crohn' disease and ulcerative colitis are two types of inflammatory bowel disease.

In further aspects, the autoimmune disease affects blood of the individual. Autoimmune diseases of the blood include for instance antiphospholipid syndrome (Hughes syndrome), autoimmune hemolytic anemia, autoimmune lymphoproliferative syndrome (Canale-Smith syndrome), idiopathic thrombocytopenia purpura, and pernicious anemia.

In additional aspects, the autoimmune disease affects connective tissue or is systemic or otherwise affects multiple tissues of the individual. Such autoimmune diseases include but are not limited to mixed connective tissue disease, psoriatic arthritis, relapsing polychondritis, rheumatoid arthritis, systemic lupus erythematosus, and undifferentiated connective tissue disease.

In some aspects, the autoimmune disease affects muscle of the individual. Autoimmune diseases of muscle include for instance, dermatomyositis, myasthenia gravis, and polymyositis.

In further aspects the autoimmune disease affects the nervous system of the individual. Autoimmune diseases of the nervous system include but are not limited to acute disseminated encephalomyelitis, Guillain Barre syndrome, Hashimoto's encephalopathy, and multiple sclerosis.

In additional aspects, the autoimmune disease affects the eyes or ears of the individual. Autoimmune uveitis is an exemplary autoimmune disease of the eye. Autoimmune inner ear disease is an exemplary autoimmune disease of the ear.

In some aspects, the autoimmune disease affects the vascular system. Autoimmune diseases of the vascular system include for instance Behcet's disease, giant cell arteritis, and vasculitis.

Autoimmune diseases include, without limitation, rheumatoid arthritis, autoimmune pancreatitis, systemic lupus erythematosus (SLE), type I diabetes mellitus, multiple sclerosis (MS), antiphospholipid syndrome (APS), sclerosing cholangitis, systemic onset arthritis, scleroderma, Sjogren's disease, vitiligo, polymyositis, pemphigus vulgaris, pemphigus foliaceus, inflammatory bowel disease (IBD) including Crohn's disease and ulcerative colitis, autoimmune hepatitis, hypopituitarism, graft-versus-host disease, autoimmune skin diseases, uveitis, pernicious anemia, and hypoparathyroidism. Autoimmune diseases may also include, without limitation, polyangitis overlap syndrome, Kawasaki's disease, sarcoidosis, glomerulonephritis, and cryopathies. In some aspects, the autoimmune disease is selected from the group consisting of arthritis, pancreatitis, mixed connective tissue disease, lupus, antiphospholipid syndrome, systemic onset arthritis, and irritable bowel syndrome. In other aspects, the autoimmune disease is selected from the group consisting of systemic lupus erythematosus, rheumatoid arthritis, autoimmune skin disease, and multiple sclerosis. In other aspects, the autoimmune disease is selected from the group consisting of pancreatitis, glomerulonephritis, pyelitis, sclerosing cholangitis, and type I diabetes. In some aspects, the autoimmune disease is rheumatoid arthritis. In some aspects, the autoimmune disease is autoimmune pancreatitis. In some aspects, the autoimmune disease is glomerulonephritis. In some aspects, the autoimmune disease is pyelitis. In some aspects, the autoimmune disease is sclerosing cholangitis. In some aspects the autoimmune disorder is psoriasis. In some aspects, the autoimmune disease is rheumatoid arthritis. In some aspects, the autoimmune disease is type I diabetes mellitus. In some aspects, the autoimmune disease is associated with RNA-containing immune complexes. In some aspects, the autoimmune disease is Sjogren's disease. In further embodiments, the autoimmune disease is selected from the group consisting of type I diabetes mellitus, multiple sclerosis, systemic lupus erythematosus, inflammatory bowel disease, rheumatoid arthritis and Sjogren's syndrome.

Provided herein are methods of inhibiting an immune response in an individual, the method comprising administering to the individual a compound of formula (A-I) or (I), or any variation thereof, e.g., a compound of formula (Ia), (I°), (I°a), (II), (IIa), (III), (IIIa), (IV), (IV-a), (V), (V-a), (VI), (VI-a), (VII), (VII-a), (VIII), (VIII-a), or a compound selected from Compound Nos. 1-56 in Table 1 or Compound Nos. 57-76 in Table 1-A, or a pharmaceutically acceptable salt thereof, in an amount effective to inhibit the immune response in the individual. In some variations, the immune response is associated with an inflammatory disease. The term "inflammatory disease" as used herein encompasses immunological disorders lacking known autoimmune or infectious components. In further aspects, inhibiting the immune response ameliorates one or more symptoms of the inflammatory disease. In still further aspects, inhibiting the immune response treats the inflammatory disease. In yet further aspects, inhibiting the immune response prevents or delays development of the inflammatory disease. In some embodiments, the inflammatory disease is selected from the group consisting of pancreatitis, kidney fibrosis, liver fibrosis, chronic kidney disease, alcohol-related fatty liver disease (such as alcohol-related steatohepatitis, and non-alcoholic fatty liver disease (such as nonalcoholic steatohepatitis, also known as NASH). In other embodiments, the inflammatory disease is selected from the group consisting of atherosclerosis, ischemia, ischemic-reperfusion injury, myocardial injury and traumatic tissue injury.

In some aspects, the inflammatory disease is selected from the group consisting of non-rheumatoid arthritis, kidney fibrosis, and liver fibrosis. In some aspects, the inflammatory disease is an interface dermatitis. In some further aspects, the interface dermatitis is selected from the group consisting of lichen planus, lichenoid eruption, lichen planus-like keratosis, lichen striatus, keratosis lichenoides chronica, erythema multiforme, fixed drug eruption, pityriasis lichenoides, phototoxic dermatitis, radiation dermatitis, viral exanthems, dermatomyositis, secondary syphilis, lichen sclerosus et atrophicus, mycosis fungoides, bullous pemphigoid, lichen aureus, porokeratosis, acrodermatitis chronicus atrophicans, and regressing melanoma. In some aspects, the inflammatory disease is a skin disorder such as atopic dermatitis (eczema). In some aspects, the inflammatory disease is a condition such as drug-induced liver and/or pancreas inflammation. In some further aspects, the inflammatory disease is an inflammatory liver disorder. In some other further aspects, the inflammatory disease is an inflammatory pancreatic disorder.

Also provided are methods of inhibiting an immune response associated with chromic or acute pathogen stimulation in an individual, comprising administering to the individual a compound of formula (A-I) or (I), or any variation thereof, e.g., a compound of formula (Ia), (I°), (I°a), (II), (IIa), (III), (IIIa), (IV), (IV-a), (V), (V-a), (VI), (VI-a), (VII), (VII-a), (VIII), (VIII-a), or a compound selected from Compound Nos. 1-56 in Table 1 or Compound Nos. 57-76 in Table 1-A, or a pharmaceutically acceptable salt thereof, in an amount effective to inhibit the immune response in the individual. In some embodiments, the chronic pathogen stimulation is due to parasitic infection. In some embodiments, the acute pathogen stimulation is due to a bacterial infection. In some embodiments, the acute pathogen stimulation is due to sepsis.

Furthermore, methods of treating cancer in an individual with cancer are provided, comprising administering to the individual a compound of formula (A-I) or (I), or any variation thereof, e.g., a compound of formula (Ia), (I°), (I°a), (II), (IIa), (III), (IIIa), (IV), (IV-a), (V), (V-a), (VI), (VI-a), (VII), (VII-a), (VIII), (VIII-a), or a compound selected from Compound Nos. 1-56 in Table 1 or Compound Nos. 57-76 in Table 1-A, or a pharmaceutically acceptable salt thereof, in an amount effective to treat cancer in the individual. In some embodiments, the cancer is dependent upon activation of one or both of TLR8 and TLR9. In some embodiments, the cancer is activated B cell type-diffuse large B cell lymphoma. In other embodiments, the cancer is Waldenstrom's macroglobulinemia. In some embodiments, the cancer is hepatocellular carcinoma (HCC). In some embodiments, cells of the cancer possess an oncogenic mutation in a myeloid differentiation primary response gene 88 (MYD88). In a subset of the embodiments, the oncogenic mutation is selected from the group consisting of L265P, M232T, P258L, and Q143E.

The methods provided herein are suitable for prophylactic treatment, therapeutic treatment, or both. Prophylactic treatment refers to treatment that is initiated prior to observation of symptoms and/or a suspected exposure to a causative agent (e.g., a pathogen or carcinogen) of a condition. Generally, prophylactic treatment may reduce (a) the likelihood that an individual receiving the treatment develops the condition and/or (b) the duration and/or severity of symptoms in the event the subject develops the condition. As used herein, therapeutic treatment refers to treatment initiated after observation of symptoms and/or a suspected exposure to a causative agent of the condition. Generally, therapeutic treatment may reduce the severity and/or duration of symptoms associated with the condition.

As demonstrated herein, compounds of formula (A-I), (I), (Ia), (I°), (I°a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, inhibit TLR8-dependent and/or TLR9-dependent responses. In some embodiments, certain compounds of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, do not inhibit TLR1-dependent, TLR2-dependent, TLR3-dependent, TLR4-dependent, TLR5-dependent, TLR6-dependent, TLR7-dependent, TLR10-dependent, TLR11-dependent, TLR12-dependent and/or TLR13-dependent responses. In some embodiments, certain compounds of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, inhibit TLR8- and TLR9-dependent responses. In some embodiments, certain compounds of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, inhibit TLR8- and/or TLR9-dependent responses, but not TLR7-dependent responses. In some embodiments, the compound inhibits TLR8-dependent responses, but not TLR7-dependent responses. In some embodiments, the compound inhibits TLR9-dependent responses, but not TLR7-dependent responses. In some embodiments, the compound inhibits TLR8- and TLR9-dependent responses, but not TLR7-dependent responses. In other embodiments, certain compounds of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, inhibit TLR8-dependent but not TLR9-dependent responses. In other embodiments, certain compounds of formula (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, inhibit TLR9-dependent but not TLR8-dependent responses. In some embodiments, certain compounds of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, inhibit TLR8-, TLR9- and TLR7-dependent responses. Inhibition of TLR-dependent responses can be determined in vitro, in vivo, and/or ex vivo.

The identification of compounds with dual TLR8 and TLR9 antagonist activity without TLR7 antagonist activity is quite unexpected given the ligand specificity of these receptors: single-stranded RNA for TLR8 as opposed to CpG-containing single-stranded DNA for TLR9. Given that both TLR7 and TLR8 recognize similar single-stranded RNA structures and have the highest degree of sequence homology among TLRs, it is also unexpected that certain LTR8 inhibitors of the present disclosure do not inhibit TLR7.

Certain compounds of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, that inhibit TLR8- and TLR9-dependent responses include but are not limited to Compound Nos. 1, 2, 4, 33, 67, 19x, 51x and 54x.

Certain compounds of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, that inhibit TLR9-dependent but not TLR8-dependent responses include but are not limited to Compound Nos. 5, 22, 29, 43, 45, 45a, 45b, 46, 9x, 17x, 19x, 21x, 24x and 25x.

In some embodiments of any of the methods involving administration of a compound of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, to an individual (e.g., methods of inhibiting an immune response, treating or preventing an immunological disorder (e.g., autoimmune or inflammatory disease, etc.), the compound of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, has a therapeutically acceptable safety profile. The compound of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, may for example, have a therapeutically acceptable histological profile including an acceptably low, if any, toxicity of the liver, kidney, pancreas, or other organs. On occasion, small molecules have been associated with toxicity to certain organs such as the liver, kidney and pancreas. In some embodiments, the compound of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, has a safety profile that is unexpected and advantageous. In some embodiments, a safety profile includes evaluation of toxicity, blood chemistry, complete blood count, histological profile, and/or necrosis (e.g., liver, kidneys and/or heart). In some embodiments, the compound of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, has a therapeutically acceptable level of toxicity. In some embodiments, the therapeutically acceptable safety profile is determined in non-human primates, mice or rats.

In some embodiments of any of the methods involving administration of a compound of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, to an individual (e.g., methods of inhibiting an immune response, treating or preventing an immunological disorder), the compound has therapeutically acceptable pharmacokinetics (PK) or drug metabolism and pharmacokinetics (DMPK). In some embodiments, the therapeutically PK profile is determined in non-human primates, mice or rats.

In one aspect of the methods detailed herein, the methods described exclude use of a compound of Table 1X. In another aspect, the methods described herein include the use of a compound of Table 1X. In some embodiments, the methods described herein include the use of a compound listed in Table 3.

B. Dosage and Mode of Administration

As with all compositions for inhibition of an immune response, the effective amount and method of administration can vary based on the individual, the condition to be treated and other factors evident to one skilled in the art. For treatment of an individual, depending on activity of the agent, manner of administration, purpose of the administration (i.e., prophylactic or therapeutic), nature and severity of the disorder, age and body weight of the individual, different doses may be necessary. Dosages are generally selected by the physician or other health care professional in accordance with a variety of parameters known in the art, such as severity of symptoms, history of the individual and the like. In some embodiments, an effective amount of the compound of formula (A-I), (I), (Ia), (I$^o$), (I$^o$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, is used in the methods described herein.

A suitable dosage range is one that provides the desired inhibition of an immune response (e.g., suppression of tumor necrosis factor-alpha or other cytokine production in response to a TLR8 and/or TLR9 agonist). Generally, dosage is determined by the amount of the compound administered to the individual. An exemplary dosage range of the compound of formula (A-I), (I), (Ia), (I$^0$), (I$^0$a), (II), (IIa), (III), (IIIa), or any variation thereof, or a pharmaceutically acceptable salt thereof, in an amount to be delivered by subject weight is from about 1 to 10000 mcg/kg. In some embodiments, the dosage is greater than about (lower limit) 1, 5, 10, 50, 100, 150, 200, 250, 300, 350, 400, 450 or 500 mcg/kg. In some embodiments, the dosage is less than about (upper limit) 10000, 7500, 5000, 2000, 1000, 900, 800, 700, 600, 500, 450, 400, 350, 300, 250, 200, 150, or 100 mcg/kg. That is, the dosage is anywhere in the range of from about 1 to 10000 mcg/kg in which the lower limit is less than the upper limit. An exemplary dosage range of the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, given in amount to be delivered to a subject is from about 100 to 10000 mcg. In some embodiments, the dosage is greater than about (lower limit) 100, 500, 1000, 1500, 2000, 2500, 3000, 3500 or 4000 mcg. In some embodiments, the dosage is less than about (upper limit) 10000, 7500, 5000, 4500, 4000, 3500, 3000, 2500, 2000, 1500, or 1000 mcg. That is, the dosage is anywhere in the range of from about 100 to 10000 mcg in which the lower limit is less than the upper limit. The absolute amount given to each individual depends on pharmacological properties such as bioavailability, clearance rate and route of administration.

A suitable dosing regimen is one that provides the desired effect in a prophylactic or therapeutic context. The number of doses administered by a chosen route may be one or more than one. Frequency of dosing may range from twice daily, daily, every other day, weekly, bi-weekly, monthly, bi-monthly, or 3 to 12 months between doses.

The pharmaceutical compositions comprising a compound of formula (A-I), (I), (Ia), (I$^0$), (I$^0$a), (II), (IIa), (III), (IIIa), (IV), (IV-a), (V), (V-a), (VI), (VI-a), (VII), (VIII-a), or any variation thereof, or a pharmaceutically acceptable salt thereof, described herein may be administered by systemic (e.g., parenteral or enteral) or local (e.g., topical or intralesional injection) administration. In some embodiments, the pharmaceutical composition is administered orally, topically, or by inhalation. In some embodiments, the pharmaceutical composition is administered parenterally. As described herein, tissues in which unwanted immune activation is occurring or is likely to occur are preferred targets for the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof. Thus, administration of the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, to lymph nodes, spleen, bone marrow, or blood may be desired.

In some embodiments, the pharmaceutical composition comprising a compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, is administered parenterally. Parenteral routes of administration include, but are not limited to, transdermal, transmucosal, nasopharyngeal, pulmonary and direct injection. Parenteral administration by injection may be by any parenteral injection route, including, but not limited to, intravenous (IV), including bolus and infusion (e.g., fast or slow), intraperitoneal (IP), intramuscular (IM), subcutaneous (SC) and intradermal (ID) routes. Transdermal and transmucosal administration may be accomplished by, for example, inclusion of a carrier (e.g., dimethylsulfoxide), by application of electrical impulses (e.g., iontophoresis) or a combination thereof. Compounds of the present disclosure suitable for parenteral administration are generally formulated in United States Pharmacopeia (USP) grade water (e.g., water for injection) and may further comprise pH buffers, salts, bulking agents, preservatives, and other pharmaceutically acceptable excipients. Compounds of the present disclosure for parenteral injection may be formulated in pharmaceutically acceptable sterile isotonic solutions such as saline and phosphate buffered saline for injection.

C. Combination Therapy

The compounds of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, of the present disclosure can be administered in combination with a second therapeutic agent (e.g., one or more additional therapeutic agents). Specifically, the methods described herein may be practiced in combination with other therapies that make up the standard of care for the disorder. In some embodiments, the second therapeutic agent is selected from the group consisting of a nonsteroidal anti-inflammatory drug, a corticosteroid, an antimalarial drug, an immunosuppressive drug, and a biologic. In specific embodiments, the second therapeutic agent is selected from the group consisting of cyclosporine, tacrolimus, prednisolone, hydrocortisone, sirolimus, everolimus, azathioprine, mycophenolic acid, methotrexate, basiliximab, daclizumab, teplizumab, telixizumab, dactinomycin, rituximab, anti-thymocyte globulin, and a combination thereof. The compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, may be administered simultaneously with one or more additional therapeutic agents (simultaneous administration). Alternatively, the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, may be administered sequentially with one or more additional therapeutic agents (sequential administration). In some embodiments, sequential administration includes administering the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, and the one or more additional therapeutic agents within about any of one minutes, five minutes, 30 minutes, one hour, five hours, 24 hours, 48 hours, or a week from each other. In some embodiments, the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, is administered by the same route of administration as the one or more additional therapeutic agents. In some embodiments, the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, is administered by a different route of administration than the one or more additional therapeutic agents.

In some embodiments, a compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, is administered in combination with a corticosteroid. In some embodiments, the corticosteroid is a glucocorticosteroid. In some embodiments, the corticosteroid is a mineralocorticoid. Corticosteroids include, but are not limited to, corticosterone and derivatives, prodrugs, isomers and analogs thereof, cortisone and derivatives, prodrugs, isomers and analogs thereof, aldosterone and derivatives, prodrugs, isomers and analogs thereof, dexamethasone and derivatives, prodrugs, isomers and analogs thereof, prednisone and derivatives, prodrugs, isomers and analogs thereof, fludrocortisones and derivatives, prodrugs, isomers and analogs thereof, hydrocortisone and derivatives, prodrugs, isomers and analogs thereof, hydroxycortisone and derivatives, prodrugs, isomers and analogs thereof, betamethasone and derivatives, prodrugs, isomers and analogs thereof, budesonide and derivatives, prodrugs, isomers and analogs thereof, methylprednisolone and derivatives, prodrugs, isomers and analogs thereof, prednisolone and derivatives, prodrugs, isomers and analogs thereof, triamcinolone and derivatives, prodrugs, isomers and analogs thereof, and the like. In some embodiments, the corticosteroid is fludrocortisone or a derivative, prodrug, isomer or analog thereof. In some embodiments, the corticosteroid is fludrocortisone. In some embodiments, the corticosteroid is hydroxycortisone or a derivative, prodrug, isomer or analog thereof. In some embodiments, the corticosteroid is hydroxycortisone.

In some preferred embodiments, the combination of a compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, with one or more additional therapeutic agents reduces the effective amount (including, but not limited to, dosage volume, dosage concentration, and/or total drug dose administered) of the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, and/or the one or more additional therapeutic agents administered to achieve the same result as compared to the effective amount administered when the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, or the additional therapeutic agent is administered alone. In some embodiments, the combination of a compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, with the additional therapeutic agents reduces the frequency of administrations of the additional therapeutic agent compared to administration of the additional therapeutic agent alone. In some embodiments, the combination of a compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, with the additional therapeutic agent reduces the total duration of treatment compared to administration of the additional therapeutic agent alone. In some embodiments, the combination of an effective amount of the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, with the additional therapeutic agent is more efficacious compared to an effective amount of the compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, or the additional therapeutic agent alone. In certain embodiments, the additional therapeutic agent is a corticosteroid. Thus in some embodiments, the combination of a compound of formula (A-I), (I), (Ia), (I$^0$), (I$^0$a), (II), (IIa), (III), (IIIa), (IV), (IV-a), (V), (V-a), (VI), (VI-a), (VII), (VII-a), (VIII), (VIII-a), or any variation thereof, or a pharmaceutically acceptable salt thereof, with a corticosteroid reduces the effective amount of corticosteroid administered as compared to the corticosteroid administered alone.

In one aspect, provided is a compound of formula (A-I) or (I), or any variation thereof, e.g., a compound of formula (Ia), (I$^0$), (I$^0$a), (II), (IIa), (III), (IIIa), (IV), (IV-a), (V), (V-a), (VI), (VI-a), (VII), (VII-a), (VIII), (VIII-a), or a compound selected from Compound Nos. 1-56 in Table 1 or Compound Nos. 57-76 in Table 1-A, or a pharmaceutically acceptable salt thereof, for use according to a method described herein, such as a method of inhibiting immune response detailed herein, or a method of treating an immunological disorder, inflammatory disorder, or cancer detailed herein.

Also provided is use of a compound of formula (A-I) or (I), or any variation thereof, e.g., a compound of formula (Ia), (I$^0$), (I$^0$a), (II), (IIa), (III), (IIIa), (IV), (IV-a), (V), (V-a), (VI), (VI-a), (VII), (VII-a), (VIII), (VIII-a), or a compound selected from Compound Nos. 1-56 in Table 1 or Compound Nos. 57-76 in Table 1-A, or a pharmaceutically acceptable salt thereof, in the manufacture of a medicament for inhibiting immune response detailed herein, or for the treatment of an immunological disorder, inflammatory disorder, or cancer detailed herein.

Kits

The invention further provides kits for carrying out the methods of the invention, which comprises one or more compounds described herein or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for use according to a method detailed herein, such as a method of for inhibiting immune response, or a method of treating an immunological disorder or cancer.

Kits generally comprise suitable packaging. The kits may comprise one or more containers comprising any compound described herein. Each component (if there is more than one component) can be packaged in separate containers or some components can be combined in one container where cross-reactivity and shelf life permit. One or more components of a kit may be sterile and/or may be contained within sterile packaging.

The kits may be in unit dosage forms, bulk packages (e.g., multi-dose packages) or sub-unit doses. For example, kits may be provided that contain sufficient dosages of a compound as disclosed herein (e.g., a therapeutically effective amount) and/or a second pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

SYNTHETIC EXAMPLES

The chemical reactions in the Synthetic Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

Abbreviations used in the description of the chemistry and in the Examples that follow are: EDCI (1-(3-dimethylaminopropyl)-3-ethylcarbodiimide hydrochloride); $MgCl_2$ (magnesium chloride); $Et_2O$ (diethyl ether); DCM (dichloromethane); DMF (dimethylformamide); DMSO (dimethyl sulfoxide); EtOAc ethyl acetate); EtOH (ethanol); MeCN (acetonitrile); MeOH (methanol); $POCl_3$ (phosphoryl trichloride); $NaHCO_3$ (sodium bicarbonate); MS (mass spectrometry); NMR (nuclear magnetic resonance); RT (room temperature); sat. aq. (saturated aqueous); THF (tetrahydrofuran); TLC (thin layer chromatography); TEA (triethylamine); HATU (2-(3H-[1,2,3]triazolo[4,5-b]pyridin-3-yl)-1,1,3,3-tetramethyl-isouronium hexafluorophosphate); HOBt (1-hydroxybenzotriazole); TFA (trifluoroacetic acid); DMAP (N,N-dimethylpyridin-4-amine).

Example 1

Synthesis of Compound No. 1

N-(3-(benzyl(methyl)amino)propyl)-1-(3,4-dimethyl-2-(p-tolyl)-2H-pyrazolo[3,4-d]pyridazin-7-yl) piperidine-4-carboxamide

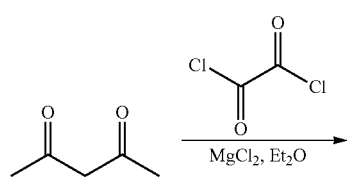

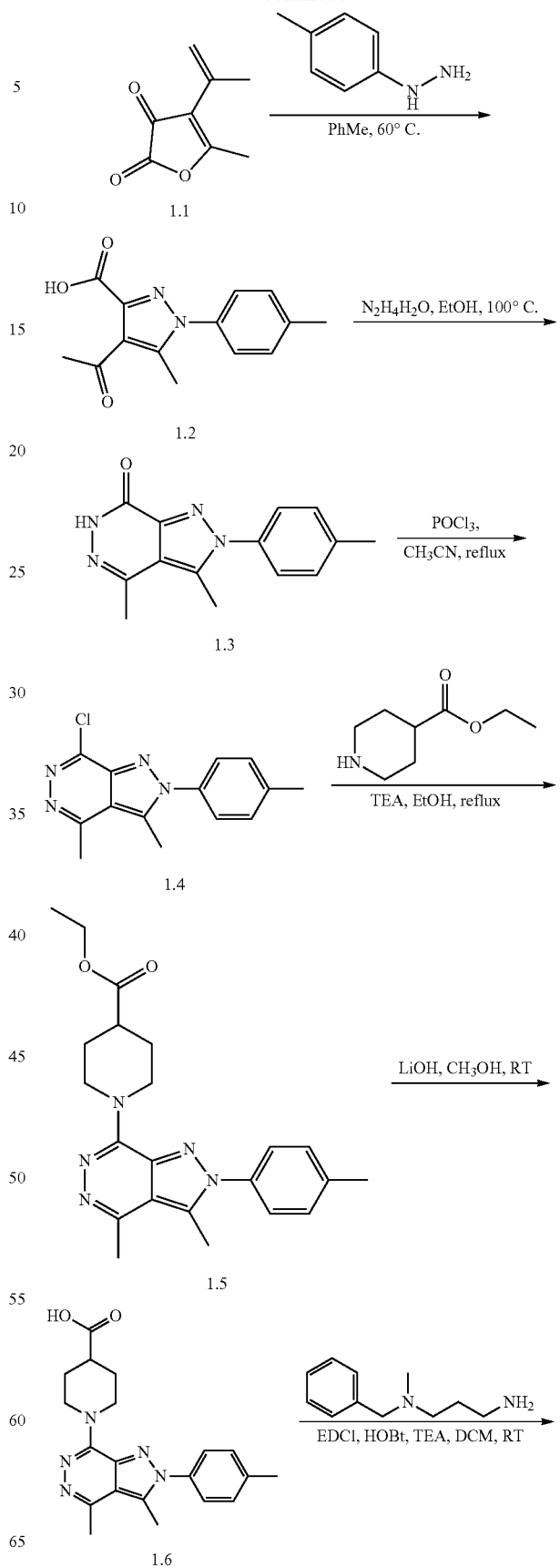

-continued

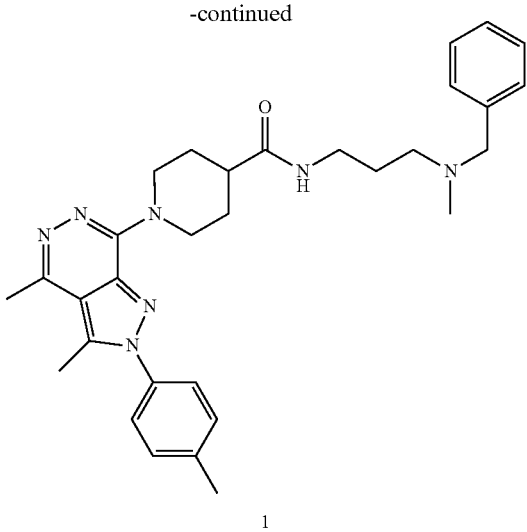

1

Step 1.1: Synthesis of 4-acetyl-5-methylfuran-2,3-dione (1.1)

To a solution of pentane-2,4-dione (20 g, 0.2 mol) and oxalyl dichloride (26.7 g, 0.206 mol) in $Et_2O$ (500 mL) was added $MgCl_2$ (1.90 g, 20 mmol) at RT. It was stirred at the same temperature for 2 h. Then the reaction mixture was concentrated to provide 1.1 (29.2 g, 94.8% yield) as yellow oil, which was used directly for next step.

Step 1.2: Synthesis of 4-acetyl-5-methyl-1-p-tolyl-1H-pyrazole-3-carboxylic acid (1.2)

To a solution of 1.1 (29.2 g, 0.19 mol) in toluene (200 mL) was added p-tolylhydrazine (15.8 g, 0.10 mol) at RT, the mixture was then stirred at 60° C. overnight. Solvent was removed under reduced pressure. The crude product was purified on column chromatography on silica gel (DCM/MeOH=10/1) to get 1.2 (20 g, 40.8% yield) as a yellow solid. LCMS (ESI+) m/z=259.1 (M+H).

Step 1.3: Synthesis of 3,4-dimethyl-2-p-tolyl-2H-pyrazolo[4,3-d]pyridazin-7(6H)-one (1.3)

To a solution of 1.2 (20.0 g, 77.5 mmol) in EtOH (200 mL) was added hydrazine hydrate (19.3 g, 387 mmol) at RT. The reaction mixture was then stirred at 100° C. for 4 h. After that the mixture was cooled to RT and the precipitate was collected by filtration to get 1.3 (15 g, 76.2% yield) as a white solid. LCMS (ESI+) m/z=255.2 (M+H).

Step 1.4: Synthesis of 7-chloro-3,4-dimethyl-2-p-tolyl-2H-pyrazolo[4,3-d]pyridazine (1.4)

To a solution of 1.3 (7.50 g, 29.5 mmol) in MeCN (3 mL) was added $POCl_3$ (13.4 g, 88.5 mmol) at RT. The reaction mixture was then stirred reflux for 2 h. Upon completion, the mixture was concentrated in vacuo and the residue was poured into ice-water. Then its pH was adjusted to 8 with sat. aq. $NaHCO_3$ solution, the aqueous layer was extracted with DCM (70 mL×3). The combined organic layers were washed successively with water (70 mL), brine (70 mL) and then dried over $Na_2SO_4$, filtered and the filtrate was concentrated to afford 1.4 (7.6 g, 94.7% yield) as brown oil. LCMS (ESI+) m/z=273.1 (M+H).

Step 1.5: Synthesis of ethyl 1-(3,4-dimethyl-2-p-tolyl-2H-pyrazolo[4,3-d] pyridazin-7-yl)piperidine-4-carboxylate (1.5)

To a solution of 1.4 (7.60 g, 28 mmol) and ethyl piperidine-4-carboxylate (6.50 g, 42 mmol) in EtOH (50 mL) was added TEA (8.40 g, 84 mmol) at RT. The reaction mixture was stirred reflux for 2 h. Upon completion, solvent was removed under reduced pressure, the residue was diluted with water and extracted with DCM (50 mL×3). The combined organic layers were washed with brine, dried over $Na_2SO_4$, filtered and concentrated to afford 1.5 (5.3 g, 48.1% yield). $^1H$ NMR (400 MHZ, $CDCl_3$) δ 7.40-7.35 (m, 4H), 5.06 (dt, J=13.3, 3.1 Hz, 2H), 4.13 (q, J=7.1 Hz, 2H), 3.26-3.19 (m, 2H), 2.76 (s, 3H), 2.69 (s, 3H), 2.60 (tt, J=11.0, 3.9 Hz, 1H), 2.47 (s, 3H), 2.05-1.98 (m, 2H), 1.86 (ddd, J=13.6, 11.4, 5.7 Hz, 2H), 1.25 (t, J=7.1 Hz, 3H). LCMS (ESI+) m/z=394.2 (M+H).

Step 1.6: Synthesis of 1-(3,4-dimethyl-2-p-tolyl-2H-pyrazolo[4,3-d]pyridazin-7-yl) piperidine-4-carboxylic acid (1.6)

To a solution of 1.5 (5.30 g, 13 mmol) in MeOH (20 mL) was added IN aq. LiOH solution (20 mL) dropwise. The reaction mixture was then stirred at RT for 2 h. MeOH was removed in vacuo and the aqueous layer was adjusted to pH=6 with IN aq. HCl solution, the formed solid was collected by filtration to get 1.6 (3 g, 63.2% yield) as a white solid. LCMS (ESI+) m/z=366.1 (M+H).

Step 1.7: Synthesis of N-(3-(benzyl(methyl)amino) propyl)-1-(3,4-dimethyl-2-(p-tolyl)-2H-pyrazolo[3,4-d]pyridazin-7-yl)piperidine-4-carboxamide (1)

To a solution of 1.6 (100 mg, 0.274 mmol), $N^1$-benzyl-$N^1$-methylpropane-1,3-diamine (73 mg, 0.411 mmol), HOBt (74 mg, 0.548 mmol) and TEA (83 mg, 0.822 mmol) in DCM (4 mL) was added EDCI (105 mg, 0.548 mmol) portion wise under ice-water bath. The reaction mixture was then stirred at RT for 16 h. Upon completion, the reaction mass was diluted with DCM (30 mL) and washed with water (25 mL) and brine (25 mL). The organic layer was dried over $Na_2SO_4$ and concentrated in vacuo. The crude product was purified on prep-HPLC and lyophilized to afford 1 (38 mg, 26.4% yield) as white solid. $^1H$ NMR (400 MHz, $CDCl_3$) δ 7.37 (t, J=9.2 Hz, 4H), 7.32-7.28 (m, 4H), 7.23-7.18 (m, 1H), 6.79 (br, 1H), 5.18 (d, J=13.2 Hz, 2H), 3.47 (s, 2H), 3.32 (q, J=5.2 Hz, 2H), 3.07-3.00 (m, 2H), 2.76 (s, 3H), 2.69 (s, 3H), 2.47 (s, 3H), 2.45 (t, J=6.4 Hz, 2H), 2.29-2.23 (m, 1H), 2.22 (s, 3H), 1.86-1.74 (m, 4H), 1.69-1.64 (m, 2H). LCMS (ESI+) m/z=263.8 (M/2+H).

Example 2

Synthesis of Compound Nos. 2, 3, 4, 5, 7, 8, 9, 13, 15, 17, 18, 22, 31, 32, 2-1, 2-2, 2-3, 2-4, 2-5, 2-6, 2-12, and 21x

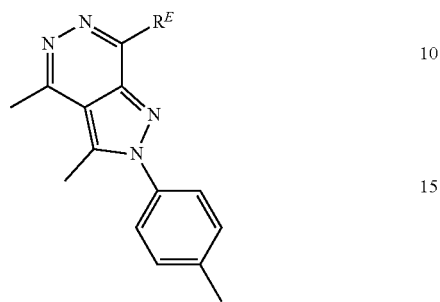

| Compound No. | $R^E$ | $^1$H NMR (400 MHz) (Solvent) δ ppm | LCMS m/z (M + H) |
|---|---|---|---|
| 2 | (piperidine-C(O)-piperazine-CH2-phenyl) | (CDCl$_3$) 7.39-7.34 (m, 4H), 7.33-7.27 (m, 5H), 5.21 (d, J = 13.2 Hz, 2H), 3.64-3.62 (m, 2H), 3.56-3.53 (m, 2H), 3.52 (s, 2H), 3.08 (td, J = 13.1, 2.4 Hz, 2H), 2.79-2.72 (m, 4H), 2.68 (s, 3H), 2.53-2.41 (m, 7H), 2.01-1.91 (m, 2H), 1.81-1.77 (m, 2H). | 524 |
| 3 | (piperidine-C(O)NH-azetidine-N-Me) | (DMSO-d6) δ 8.22 (d, J = 7.5 Hz, 1H), 7.51 (d, J = 8.3 Hz, 2H), 7.44 (d, J = 8.3 Hz, 2H), 5.01 (d, J = 12.9 Hz, 2H), 4.22-4.13 (m, 1H), 3.45 (t, J = 7.2 Hz, 2H), 3.01 (td, J = 12.8, 2.0 Hz, 2H), 2.77-2.73 (m, 2H), 2.67 (s, 3H), 2.66 (s, 3H), 2.45-2.38 (m, 4H), 2.19 (s, 3H), 1.72 (dd, J = 12.8, 3.1 Hz, 2H), 1.59 (ddd, J = 16.0, 12.7, 4.0 Hz, 2H). | 434 |
| 4 | (piperidine-C(O)NH-azetidine-N-Bn) | (CDCl$_3$) 7.39-7.34 (m, 4H), 7.33-7.29 (m, 2H), 7.25-7.23 (m, 3H), 6.04 (d, J = 7.8 Hz, 1H), 5.21 (d, J = 13.4 Hz, 2H), 4.59-4.51 (m, 1H), 3.60-3.57 (m, 4H), 3.12-3.05 (m, 2H), 2.96-2.93 (m, 2H), 2.76 (s, 3H), 2.69 (s, 3H), 2.47 (s, 3H), 2.44-2.36 (m, 1H), 1.93 (dd, J = 12.8, 2.5 Hz, 2H), 1.88-1.81 (m, 2H). | 510 |
| 5 | (piperidine-C(O)NH-CH2CH2CH2-NMe2) | (CD$_3$OD) 7.38-7.33 (m, 4H), 5.09 (d, J = 13.2 Hz, 2H), 3.11 (t, J = 6.9 Hz, 2H), 3.04-2.97 (m, 2H), 2.65 (s, 3H), 2.62 (s, 3H), 2.46-2.41 (m, 1H), 2.39 (s, 3H), 2.27-2.24 (m, 2H), 2.15 (s, 6H), 1.79-1.67 (m, 4H), 1.63-1.56 (m, 2H). | 450 |

-continued

| Compound No. | R$^E$ | $^1$H NMR (400 MHz) (Solvent) δ ppm | LCMS m/z (M + H) |
|---|---|---|---|
| 7 | | (CDCl$_3$) 7.39-7.34 (m, 4H), 5.20 (d, J = 13.2 Hz, 2H), 3.16 (d, J = 5.6 Hz, 2H), 3.13-3.06 (m, 2H), 2.76 (s, 3H), 2.69 (s, 3H), 2.54 (s, 2H), 2.47 (s, 2H), 2.45-2.39 (m, 1H), 1.98 (dd, J = 13.0, 2.8 Hz, 2H), 1.83 (ddd, J = 24.9, 12.4, 4.0 Hz, 2H), 0.87 (s, 6H). | 450 |
| 8 | | (CDCl$_3$) 7.38-7.34 (m, 4H), 6.30 (s, 1H), 5.19 (d, J = 13.3 Hz, 2H), 3.31 (dd, J = 11.4, 5.6 Hz, 2H), 3.12-3.05 (m, 2H), 2.81-2.70 (m, 6H), 2.68 (s, 3H), 2.46 (s, 3H), 2.44-2.38 (m, 1H), 1.96-1.86 (m, 4H), 1.05 (s, 3H), 1.03 (s, 3H). | 450 |
| 9 | | (CDCl$_3$) 7.39-7.35 (m, 4H), 6.05 (s, 1H), 5.15 (d, J = 13.1 Hz, 2H), 3.32 (dd, J = 11.3, 5.4 Hz, 2H), 3.01 (td, J = 13.0, 1.9 Hz, 2H), 2.75 (s, 3H), 2.68 (s, 3H), 2.47 (s, 3H), 2.40 (t, J = 6.0 Hz, 2H), 2.23 (d, J = 10.9 Hz, 8H), 1.78 (d, J = 12.1 Hz, 2H), 1.64-1.59 (m, 3H), 1.44-1.27 (m, 2H). | 464 |
| 13 | | (DMSO-d6) 8.03 (t, J = 5.5 Hz, 1H), 7.51-7.49 (m, 2H), 7.43 (d, J = 8.2 Hz, 2H), 4.12-4.08 (m, 1H), 3.99 (s, 1H), 3.78 (ddd, J = 18.6, 10.4, 7.3 Hz, 2H), 3.07 (dd, J = 12.7, 6.8 Hz, 2H), 3.04-2.98 (m, 1H), 2.65 (s, 3H), 2.63 (s, 3H), 2.42 (s, 3H), 2.16 (dd, J = 14.3, 7.1 Hz, 2H), 2.12-2.01 (m, 8H), 1.56-1.49 (m, 2H). | 436 |
| 15 | | (DMSO-d6) 8.01 (t, J = 5.6 Hz, 1H), 7.50 (d, J = 8.3 Hz, 2H), 7.43 (d, J = 8.4 Hz, 2H), 4.37 (t, J = 8.5 Hz, 2H), 4.32-4.28 (m, 2H), 3.54-3.47 (m, 1H), 3.08 (dd, J = 12.8, 6.8 Hz, 2H), 2.65 (s, 6H), 2.43 (s, 3H), 2.17 (dd, J = 12.9, 5.7 Hz, 2H), 2.09 (s, 6H), 1.56-1.49 (m, 2H). | 422 |
| 17 | | (CD$_3$OD) 7.47-7.42 (m, 4H), 5.18 (d, J = 13.2 Hz, 2H), 4.34-4.27 (m, 1H), 3.12-3.05 (m, 2H), 2.81 (dd, J = 10.1, 7.3 Hz, 1H), 2.74 (s, 3H), 2.71-2.67 (m, 4H), 2.55-2.49 (m, 2H), 2.48 (s, 3H), 2.41 (dd, J = 10.1, 5.0 Hz, 1H), 2.35 (s, 3H), 2.30-2.21 (m, 1H), 1.84-1.75 (m, 4H), 1.72-1.63 (m, 1H). | 448 |

-continued

| Compound No. | R^E | ¹H NMR (400 MHz) (Solvent) δ ppm | LCMS m/z (M + H) |
|---|---|---|---|
| 18 | | (CD₃OD) 7.47-7.42 (m, 4H), 5.18 (d, J = 13.2 Hz, 2H), 3.68-3.60 (m, 1H), 3.14-3.05 (m, 2H), 2.85 (d, J = 11.9 Hz, 2H), 2.75 (s, 3H), 2.71 (s, 3H), 2.55-2.49 (m, 1H), 2.48 (s, 3H), 2.27 (s, 3H), 2.13 (t, J = 11.6 Hz, 2H), 1.87-1.79 (m, 6H), 1.57-1.47 (m, 2H). | 462 |
| 22 | | (DMSO-d6) δ 7.78 (t, J = 5.5 Hz, 1H), 7.50 (d, J = 8.4 Hz, 2H), 7.43 (d, J = 8.2 Hz, 2H), 4.96 (d, J = 12.9 Hz, 2H), 3.06-2.96 (m, 4H), 2.66 (d, J = 1.5 Hz, 6H), 2.43 (s, 3H), 2.16 (t, J = 7.2 Hz, 2H), 2.08 (s, 6H), 1.98(s, 3H), 1.67 (d, J = 11.5 Hz, 2H), 1.53-1.46 (m, 2H), 1.26-1.15 (m, 2H). | 464 |
| 31 | | (DMSO-d6) 7.80 (t, J = 5.5 Hz, 1H), 7.51 (d, J = 8.3 Hz, 2H), 7.44 (d, J = 8.2 Hz, 2H), 5.01 (d, J = 13.0 Hz, 2H), 3.05-2.99 (m, 4H), 2.66 (d, J = 4.0 Hz, 6H), 2.46-2.38 (m, 4H), 2.21-2.17 (m, 2H), 2.11 (s, 6H), 1.74-1.70 (m, 2H), 1.67-1.56 (m, 2H), 1.37 (t, J = 3.2 Hz, 4H). | 464 |
| 32 | | (DMSO-d6) 7.77 (t, J = 5.6 Hz, 1H), 7.51 (d, J = 8.4 Hz, 2H), 7.44 (d, J = 8.1 Hz, 2H), 5.01 (d, J = 13.0 Hz, 2H), 3.04-2.98 (m, 4H), 2.66 (d, J = 3.9 Hz, 6H), 2.44-2.38 (m, 4H), 2.13 (t, J = 7.2 Hz, 2H), 2.07 (s, 6H), 1.72 (dd, J = 12.7, 2.6 Hz, 2H), 1.61 (ddd, J = 15.9, 12.5, 3.8 Hz, 2H), 1.41-1.32 (m, 4H), 1.25-1.18 (m, 2H). | 478 |
| 2-1 | | (CDCl₃) 7.37 (s, 4H), 7.15-7.11 (m, 2H), 6.66-6.62 (m, 3H), 5.88 (t, J = 5.6 Hz, 1H), 5.20 (d, J = 13.2 Hz, 2H), 4.28 (br, 1H), 3.20 (d, J = 6.4 Hz, 2H), 3.12-3.05 (m, 2H), 2.89 (s, 2H), 2.77 (s, 3H), 2.69 (s, 3H), 2.47 (s, 3H), 2.45-2.38 (m, 1H), 1.95-1.77 (m, 4H), 0.95 (s, 6H). | 526 |
| 2-2 | | (DMSO-d6) 7.74 (d, J = 4.5 Hz, 1H), 7.51 (d, J = 8.3 Hz, 2H), 7.43 (d, J = 8.2 Hz, 2H), 5.01 (d, J = 13.1 Hz, 2H), 3.01 (td, J = 12.8, 1.9 Hz, 2H), 2.66 (d, J = 4.2 Hz, 6H), 2.55 (d, J = 4.6 Hz, 3H), 2.43-2.37 (m, 4H), 1.75-1.71 (m, 2H), 1.61 (qd, J = 12.5, 3.8 Hz, 2H). | 379 |

-continued

| Compound No. | R$^E$ | $^1$H NMR (400 MHz) (Solvent) δ ppm | LCMS m/z (M + H) |
|---|---|---|---|
| 2-3 | 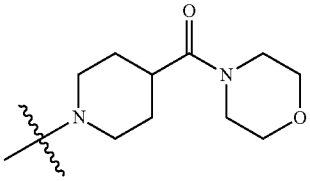 [SMILES: *N1CCC(C(=O)N2CCOCC2)CC1] | (CD$_3$OD) 7.47-7.42 (m, 4H), 5.17 (d, J = 13.2 Hz, 2H), 3.68-3.63 (m, 6H), 3.57 (d, J = 4.6 Hz, 2H), 3.19-3.12 (m, 2H), 3.06-2.99 (m, 1H), 2.74 (s, 3H), 2.70 (s, 3H), 2.47 (s, 3H), 1.88-1.79 (m, 4H). | 435 |
| 2-4 | 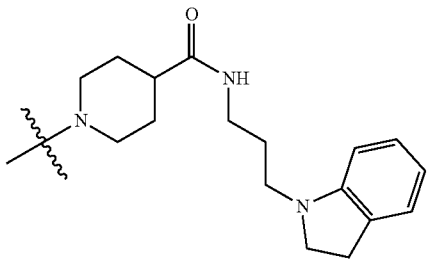 [SMILES: *N1CCC(C(=O)NCCCN2CCc3ccccc32)CC1] | (DMSO-d6) 7.87 (t, J = 5.5 Hz, 1H), 7.51 (d, J = 8.3 Hz, 2H), 7.43 (d, J = 8.1 Hz, 2H), 7.00 (d, J = 6.7 Hz, 1H), 6.95 (t, J = 7.7 Hz, 1H), 6.55-6.51 (m, 1H), 6.45 (d, J = 7.8 Hz, 1H), 5.02 (d, J = 13.1 Hz, 2H), 3.25 (t, J = 8.3 Hz, 2H), 3.12 (dd, J = 12.5, 6.7 Hz, 2H), 3.06-2.99 (m, 4H), 2.85 (t, J = 8.3 Hz, 2H), 2.67 (s, 3H), 2.66 (s, 3H), 2.46-2.43 (m, 4H), 1.75 (d, J = 10.3 Hz, 2H), 1.69-1.58 (m, 4H). | 524 |
| 2-5 | 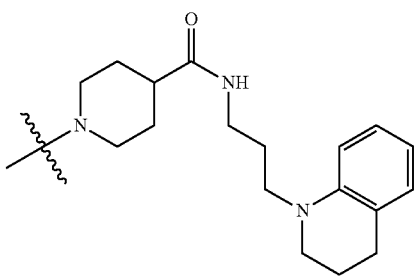 [SMILES: *N1CCC(C(=O)NCCCN2CCCc3ccccc32)CC1] | (CD$_3$OD) 7.46-7.41 (m, 4H), 6.93-6.88 (m, 1H), 6.82 (d, J = 6.9 Hz, 1H), 6.56-6.51 (m, 1H), 6.46-6.42 (m, 1H), 5.17 (d, J = 13.2 Hz, 2H), 3.29-3.21 (m, 6H), 3.12-3.05 (m, 2H), 2.73 (s, 3H), 2.69-2.66 (m, 5H), 2.56-2.48 (m, 1H), 2.47 (s, 3H), 1.93-1.73 (m, 8H). | 538 |
| 2-6 | 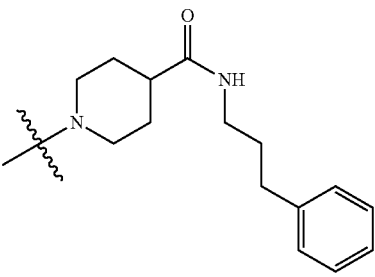 [SMILES: *N1CCC(C(=O)NCCCc2ccccc2)CC1] | (CD$_3$OD) 7.47-7.41 (m, 4H), 7.26-7.22 (m, 2H), 7.18-7.11 (m, 3H), 5.17 (d, J = 13.2 Hz, 2H), 3.18 (t, J = 7.1 Hz, 2H), 3.12-3.05 (m, 2H), 2.73 (s, 3H), 2.70 (s, 3H), 2.62 (t, J = 7.6 Hz, 2H), 2.55-2.50 (m, 1H), 2.47 (s, 3H), 1.85-1.76 (m, 6H). | 483 |
| 2-12 | 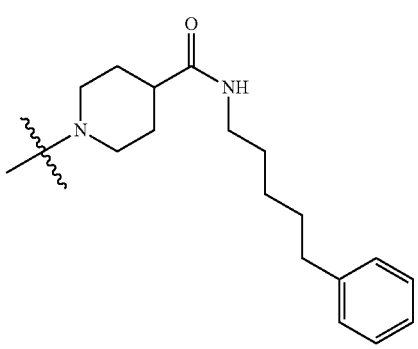 [SMILES: *N1CCC(C(=O)NCCCCCc2ccccc2)CC1] | (DMSO-d6) 7.75 (t, J = 5.6 Hz, 1H), 7.51 (d, J = 8.4 Hz, 2H), 7.43 (d, J = 8.2 Hz, 2H), 7.26-7.21 (m, 2H), 7.17-7.10 (m, 3H), 5.01 (d, J = 13.0 Hz, 2H), 3.03-2.98 (m, 4H), 2.67 (s, 3H), 2.66 (s, 3H), 2.54 (t, J = 7.6 Hz, 2H), 2.43 (s, 3H), 2.41-2.36 (m, 1H), 1.71-1.50 (m, 6H), 1.44-1.36 (m, 2H), 1.28-1.20 (m, 2H). | 511 |

| Compound No. | $R^E$ | ¹H NMR (400 MHz) (Solvent) δ ppm | LCMS m/z (M + H) |
|---|---|---|---|
| 21x | 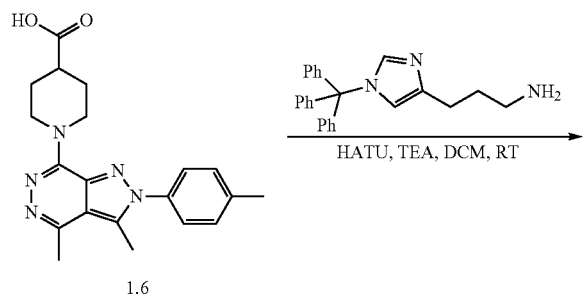 | (DMSO-d6) 7.72 (t, J = 5.5 Hz, 1H), 7.51 (d, J = 8.3 Hz, 2H), 7.43 (d, J = 8.3 Hz, 2H), 5.00 (d, J = 13.0 Hz, 2H), 3.11 (dd, J = 12.6, 6.6 Hz, 2H), 3.01 (t, J = 11.6 Hz, 2H), 2.66 (d, J = 4.0 Hz, 6H), 2.46-2.39 (m, 4H), 2.28-2.20 (m, 2H), 2.12 (s, 6H), 1.72 (d, J = 10.3 Hz, 2H), 1.60 (qd, J = 12.5, 3.6 Hz, 2H). | 436 |

Compound Nos. 6, 11, 33, and 12a were prepared using the appropriate starting materials and reagents according to the same procedures as in Example 1.

Example 3

Synthesis of Compound No. 6

N-(3-(1H-imidazol-4-yl)propyl)-1-(3,4-dimethyl-2-(p-tolyl)-2H-pyrazolo[3,4-d]pyridazin-7-yl)piperidine-4-carboxamide

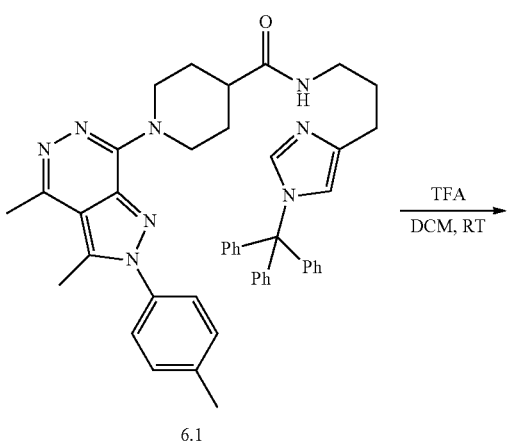

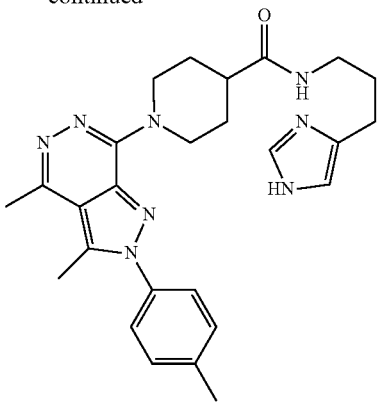

Step 6.1: Synthesis of 1-(3,4-dimethyl-2-p-tolyl-2H-pyrazolo[3,4-d]pyridazin-7-yl)-N-(3-(1-trityl-1H-imidazol-4-yl)propyl)piperidine-4-carboxamide (6.1)

To a solution of 1.6 (100 mg, 0.274 mmol) in DMF (2 mL) were added 3-(1-trityl-1H-imidazol-4-yl)propan-1-amine (151 mg, 0.411 mmol), TEA (83 mg, 0.822 mmol) and HATU (135 mg, 0.356 mmol) successively at RT. The mixture was then stirred at the same temperature for 16 h. Upon completion, the reaction mixture was poured into water (20 mL) and extracted with EtOAc (15 mL×3). The combined organic layers were washed with water (20 mL×2), brine (20 mL), dried over $Na_2SO_4$ and concentrated in vacuo. The residue was purified on column chromatography on silica gel (DCM/MeOH=15/1) to give 6.1 (150 mg, 76.7% yield) as white solid. LCMS (ESI+) m/z=715 (M+H).

Step 6.2: Synthesis of N-(3-(1H-imidazol-4-yl)propyl)-1-(3,4-dimethyl-2-(p-tolyl)-2H-pyrazolo[3,4-d]pyridazin-7-yl)piperidine-4-carboxamide (6)

To a solution of 6.1 (150 mg, 0.210 mmol) in DCM (3 mL) was added TFA (3 mL) dropwise under ice-water bath. The resulting mixture was stirred at RT for 2 h. Upon completion, sat. aq. $NaHCO_3$ solution was added to adjust pH to 8. The aqueous layer was extracted with DCM (20 mL×3). The combined organic layers were dried over $Na_2SO_4$ and concentrated in vacuo. The crude product was purified on prep-HPLC and lyophilized to afford 6 (9 mg, 9.1% yield) as white solid. ¹H NMR (400 MHZ, $CDCl_3$) δ7.48 (s, 1H), 7.37 (s, 4H), 6.76 (s, 1H), 6.18 (br, 1H), 5.19

(d, J=13.6 Hz, 2H), 7.32-7.28 (m, 4H), 7.23-7.18 (m, 1H), 6.79 (br, 1H), 5.18 (d, J=13.2 Hz, 2H), 3.35 (q, J=6.0 Hz, 2H), 3.14-3.07 (m, 2H), 2.77 (s, 3H), 2.70 (s, 3H), 2.61 (t, J=6.0 Hz, 2H), 2.50-2.43 (m, 4H), 1.93-1.78 (m, 6H). LCMS (ESI+) m/z=473.4 (M+H).

Example 4

Synthesis of Compound No. 11

N-(3-(azetidin-1-yl)propyl)-1-(3,4-dimethyl-2-(p-tolyl)-2H-pyrazolo[3,4-d]pyridazin-7-yl)piperidine-4-carboxamide

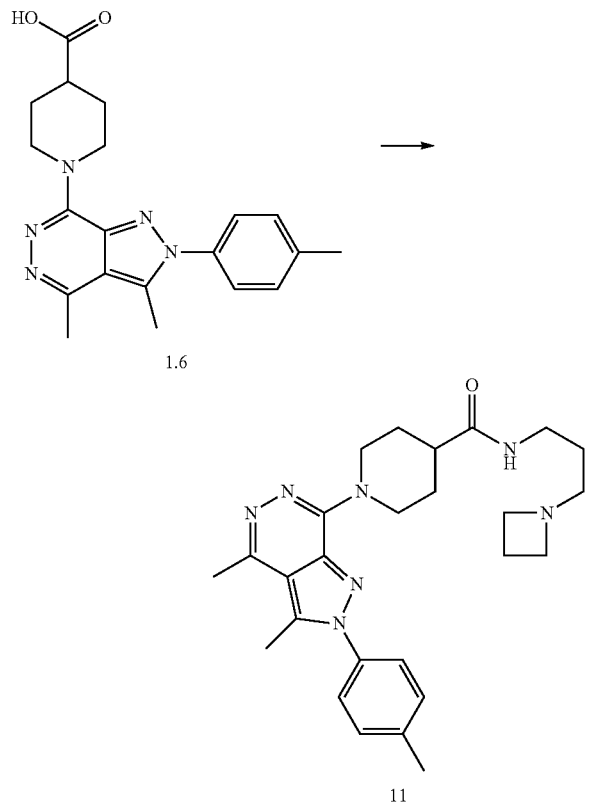

Synthesis of N-(3-(azetidin-1-yl)propyl)-1-(3,4-dimethyl-2-(p-tolyl)-2H-pyrazolo[3,4-d]pyridazin-7-yl)piperidine-4-carboxamide (11)

To a solution of 1.6 (200 mg, 0.548 mmol), 3-bromopropan-1-amine hydrobromide (144 mg, 0.658 mmol), TEA (83 mg, 0.822 mmol) and DMAP (80 mg, 0.658 mmol) in DCM (9 mL) was added EDCI (115 mg, 0.603 mmol) portion wise under ice-water bath. The resulting mixture was stirred at RT for 3 h. Then TEA (110 mg, 1.096 mmol) and azetidine (312 mg, 5.48 mmol) were added successively under ice-water bath. The reaction mixture was stirred at RT for further 16 h. The reaction mass was then diluted with DCM (40 mL) and washed with water (30 mL) and brine (30 mL). The organic layer was dried over $Na_2SO_4$ and concentrated in vacuo. The crude product was purified by prep-HPLC and lyophilized to afford 11 (35 mg, 13.9% yield) as white solid. $^1$H NMR (400 MHZ, $CD_3OD$) δ 7.49-7.44 (m, 4H), 5.19 (d, J=13.2 Hz, 2H), 3.25 (t, J=7.2 Hz, 4H), 3.18 (t, J=6.8 Hz, 2H), 3.14-3.07 (m, 2H), 2.76 (s, 3H), 2.73 (s, 3H), 2.56-2.52 (m, 2H), 2.50 (s, 3H), 2.47 (t, J=8.0 Hz, 2H), 2.14-2.07 (m, 2H), 1.88-1.77 (m, 4H), 1.58-1.50 (m, 2H). LCMS (ESI+) m/z=462.4 (M+H).

Example 5

Synthesis of Compound No. 19x 1-(3,4-dimethyl-2-(p-tolyl)-2H-pyrazolo[3,4-d]pyridazin-7-yl)-N-(3-morpholinopropyl)piperidine-4-carboxamide

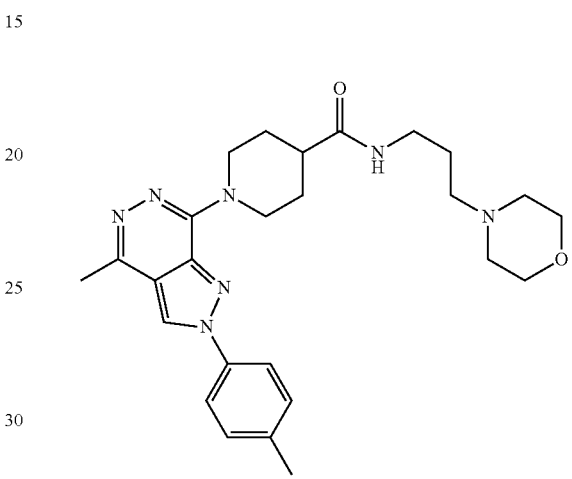

Compound No. 19x was prepared using the appropriate starting materials and reagents according to the same procedures as in Example 4. $^1$H NMR (400 MHZ, DMSO-d6) δ 7.80 (t, J=5.6 Hz, 1H), 7.51 (d, J=8.4 Hz, 2H), 7.44 (d, J=8.1 Hz, 2H), 5.01 (d, J=13.1 Hz, 2H), 3.54 (t, J=4.6 Hz, 4H), 3.07-2.98 (m, 4H), 2.66 (d, J=4.0 Hz, 6H), 2.45-2.38 (m, 4H), 2.30 (br, 4H), 2.24 (t, J=7.2 Hz, 2H), 1.72 (dd, J=12.8, 2.6 Hz, 2H), 1.66-1.59 (m, 2H), 1.56-1.49 (m, 2H). LCMS m/z=492 (M+H).

Example 6

Synthesis of Compound No. 12a 1-(3,4-dimethyl-2-(p-tolyl)-2H-pyrazolo[3,4-d]pyridazin-7-yl)-N-((1r,3r)-3-(dimethylamino)cyclobutyl)piperidine-4-carboxamide

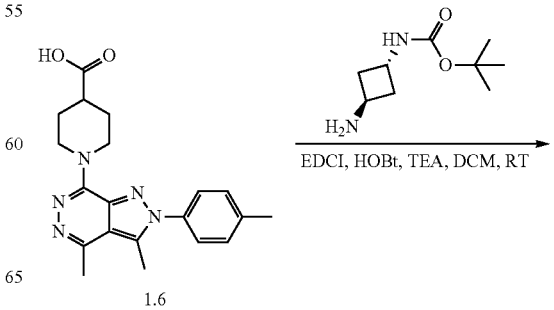

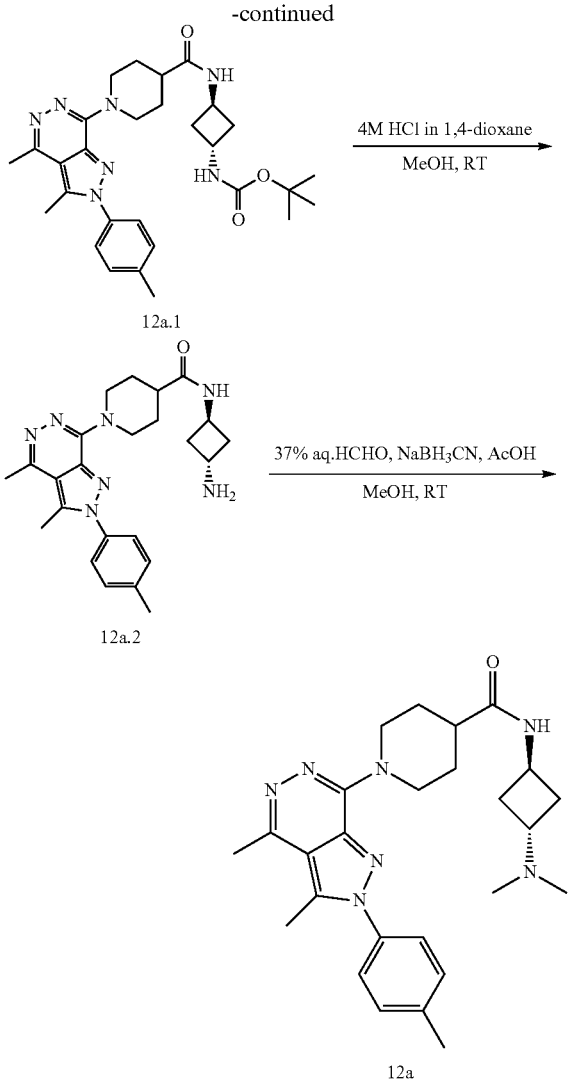

Step 12a.1: Synthesis of tert-butyl (1r, 3r)-3-(1-(3, 4-dimethyl-2-p-tolyl-2H-pyrazolo[3,4-d]pyridazin-7-yl)piperidine-4-carboxamido)cyclobutylcarbamate (12a.1)

To a solution of 1.6 (200 mg, 0.548 mmol), tert-butyl (1r,3r)-3-aminocyclobutylcarbamate (122 mg, 0.658 mmol), HOBt (248 mg, 1.096 mmol) and TEA (166 mg, 1.644 mmol) in DCM (10 mL) was added EDCI (210 mg, 1.096 mmol) portion wise under ice-water bath. The reaction mixture was then stirred at RT for 16 h. Upon completion, the reaction mass was diluted with DCM (50 mL) and washed with water (30 mL) and brine (30 mL). The organic layer was dried over $Na_2SO_4$ and concentrated in vacuo. The crude product was purified on prep-TLC using 9% MeOH/DCM to afford 12a.1 (190 mg, 65.0% yield) as white solid. LCMS (ESI+) m/z=534 (M+H).

Step 12a.2: Synthesis of N-((1r, 3r)-3-aminocyclobutyl)-1-(3,4-dimethyl-2-p-tolyl-2H-pyrazolo[3, 4-d]pyridazin-7-yl)piperidine-4-carboxamide (12a.2)

To a solution of 12a.1 (190 mg, 0.356 mmol) in MeOH (7 mL) was added 4M HCl in 1,4-dioxane (7 mL) dropwise. The mixture was stirred at RT for 2 h. Upon completion, the solvent was removed in vacuo, the residue was dissolved in water, sat. aq. $NaHCO_3$ solution was then added to adjust pH to 8. The aqueous layer was extracted with 10% MeOH/DCM (20 mL×3). The combined organic layers were washed with brine (30 mL), dried over $Na_2SO_4$ and concentrated in vacuo to give 12a.2 (120 mg, 77.8% yield) as pale yellow solid. LCMS (ESI+) m/z=434 (M+H).

Step 12a.3: Synthesis of 1-(3,4-dimethyl-2-(p-tolyl)-2H-pyrazolo[3,4-d]pyridazin-7-yl)-N-((1r,3r)-3-(dimethylamino)cyclobutyl)piperidine-4-carboxamide (12a)

To a solution of 12a.2 (120 mg, 0.277 mmol) in MeOH (6 mL) were added 37% aq. HCHO (4 mL) and a catalytic amount of AcOH. The resulting mixture was stirred at RT for 1 h. After that $NaBH_3CN$ (70 mg, 1.108 mmol) was added portion wise under ice-water bath. The reaction mixture was stirred at RT for further 3 h. The mixture was then partitioned between DCM (40 mL) and water (30 mL), and organic layer was separated, washed with brine (20 mL) and dried over $Na_2SO_4$. The solvent was removed in vacuo, the residue was purified on prep-HPLC and lyophilized to afford 12a (64 mg, 50.1% yield) as white solid. $^1$H NMR (400 MHZ, $CD_3OD$) δ 7.48-7.43 (m, 4H), 5.19 (d, J=13.2 Hz, 2H), 4.22-4.16 (m, 1H), 3.14-3.07 (m, 2H), 2.96-2.89 (m, 1H), 2.75 (s, 3H), 2.72 (s, 3H), 2.59-2.52 (m, 1H), 2.49 (s, 3H), 2.34-2.27 (m, 2H), 2.17 (s, 6H), 2.13-2.06 (m, 2H), 1.86-1.77 (m, 4H). LCMS (ESI+) m/z=462.4 (M+H).

Example 7

Synthesis of Compound No. 29

N-(3-(dimethylamino)propyl)-1-(2-(p-tolyl)-2H-pyrazolo[3,4-d]pyridazin-7-yl)piperidine-4-carboxamide

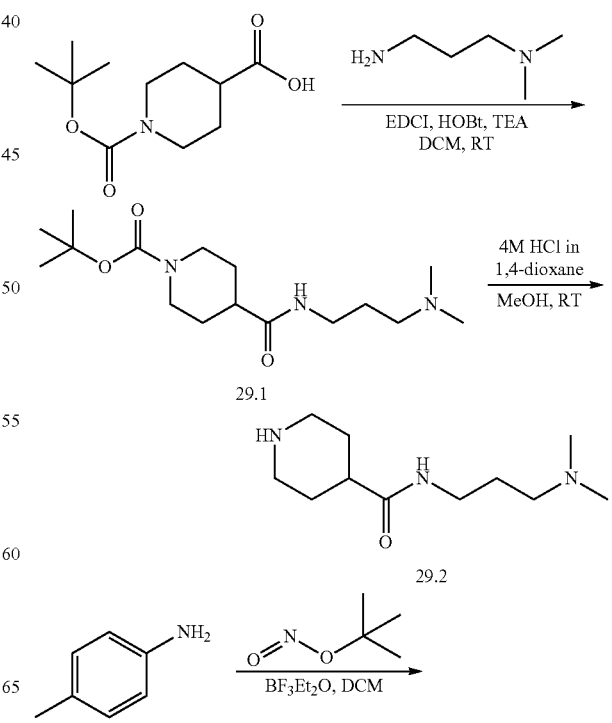

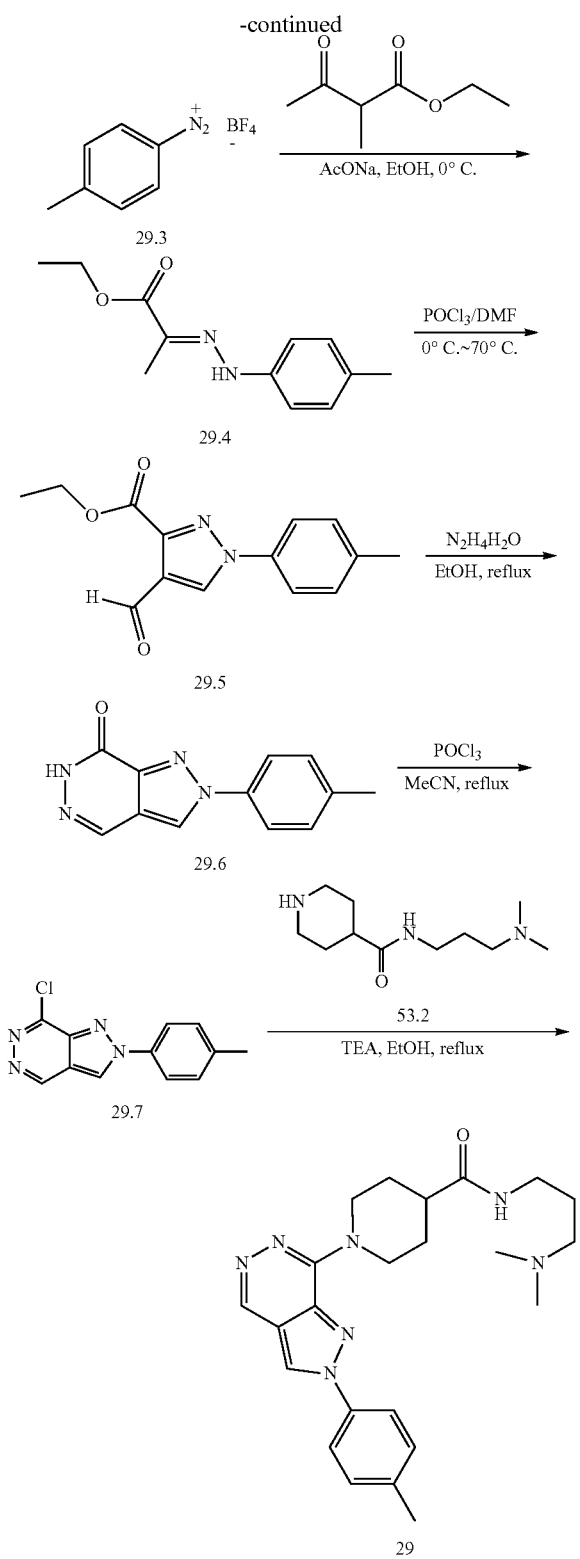

Step 29.1: Synthesis of tert-butyl 4-(3-(dimethylamino)propylcarbamoyl)piperidine-1-carboxylate (29.1)

To a solution of 1-(tert-butoxycarbonyl)piperidine-4-carboxylic acid (10.0 g, 0.044 mol), $N^1,N^1$-dimethylpropane-1,3-diamine (8.91 g, 0.087 mol), HOBt (8.84 g, 0.066 mol) and TEA (13.2 g, 0.131 mol) in DCM (100 mL) was added EDCI (10.9 g, 0.057 mol) portion wise under ice-water bath. The reaction mixture was then stirred at RT for 16 h. Upon completion, the reaction mass was diluted with 10% MeOH/DCM (150 mL) and washed with water (100 mL) and brine (100 mL). The organic layer was dried over $Na_2SO_4$ and concentrated in vacuo. The residue was purified on column chromatography on silica gel (DCM/MeOH=15/1) to afford 29.1 (8.40 g, 61.5% yield) as yellow oil. LCMS (ESI+) m/z=314.2 (M+H).

Step 29.2: Synthesis of N-(3-(dimethylamino)propyl)piperidine-4-carboxamide (29.2)

To a solution of 29.1 (8.40 g, 0.027 mol) in MeOH (35 mL) was added 4M HCl in 1,4-dioxane (33.5 mL) dropwise under ice-water bath. The mixture was stirred at RT for 2 h. Upon completion, the solvent was removed in vacuo, the residue was dissolved in water, sat. aq. $NaHCO_3$ solution was then added to adjust pH to 8. The solvent was removed in vacuo, the residue was triturated with MeOH, filtered and the filtrate was concentrated in vacuo and lyophilized to afford 29.2 (4.60 g, 80.7% yield) as yellow solid. LCMS (ESI+) m/z=214 (M+H).

Step 29.3: Synthesis of 4-methylbenzenediazonium tetrafluoroborate (29.3)

To a stirred solution of $BF_3$-etherate (38 mL, 0.299 mol) in DCM (120 mL) under argon atmosphere was added a solution of p-toluidine (20.0 g, 0.187 mol) in DCM (240 mL) dropwise under ice-salt bath, followed by the addition of a solution of tert-butyl nitrite (23.2 g, 0.224 mol) in DCM (120 mL) dropwise over a 10 min period. After stirred under ice-salt bath for 10 min, the reaction mixture was placed in an ice-water bath for another 1 h. The suspension was then diluted with hexane. The precipitate was filtered and washed with hexane and then diethyl ether. The solid was collected and dried under high vacuum to afford 29.3 (17.0 g) as brown solid which was stored in a −10° C. freezer.

Step 29.4: Synthesis of ethyl 2-(2-p-tolylhydrazono)propanoate (29.4)

A solution of ethyl 2-methyl-3-oxobutanoate (11.9 g, 0.083 mol) and sodium acetate trihydrate (16.9 g, 0.124 mol) in EtOH (220 mL) was cooled in an ice bath. To the solution, while being stirred, 29.3 (17.0 g, 0.083 mol) was added slowly. The reaction mixture was stirred at 0° C. for 4 h. The EtOH was evaporated to half-volume, and the mixture was poured into 400 g of ice-water mixture. The precipitate was collected and triturated with EtOH. The resulting solid was collected by filtration and dried in vacuo to give 29.4 (3.00 g, 16.4% yield) as brown solid. $^1$H NMR (400 MHZ, $CDCl_3$) δ 7.66 (br, 1H), 7.10 (s, 4H), 4.31 (q, J=7.2 Hz, 2H), 2.30 (s, 3H), 2.09 (s, 3H), 1.38 (t, J=7.2 Hz, 3H). LCMS (ESI+) m/z=221.3 (M+H).

Step 29.5: Synthesis of ethyl 4-formyl-1-p-tolyl-1H-pyrazole-3-carboxylate (29.5)

$POCl_3$ (6.26 g, 40.9 mmol) was added to DMF (4.1 mL) in a round-bottomed flask in an ice-cold condition under constant stirring. A solution of 29.4 (3.00 g, 13.6 mmol) in DMF (15 mL) was added to the mixture and stirred for further 1 h, the reaction mixture was then heated to 70° C.

for 4 h. After the reaction, the mixture was poured into 50 g of crushed ice under constant manual stirring. After neutralization with sat.aq.K$_2$CO$_3$ solution, EtOAc (80 mL) was added. The organic phase was separated and the aqueous phase was extracted with EtOAc (80 mL×2). The combined organic layers were washed with water (80 mL) and brine (80 mL), dried and concentrated in vacuo. The crude product was purified by recrystallization from EtOH to afford 29.5 (2.20 g, 62.7% yield) as yellow solid. $^1$H NMR (400 MHZ, CDCl$_3$) δ 10.46 (s, 1H), 8.45 (s, 1H), 7.63 (d, J=8.0 Hz, 2H), 7.30 (d, J=8.0 Hz, 2H), 4.52 (q, J=7.2 Hz, 2H), 2.42 (s, 3H), 1.47 (t, J=7.2 Hz, 3H). LCMS (ESI+) m/z=259.0 (M+H).

Step 29.6: Synthesis of 2-p-tolyl-2H-pyrazolo[4,3-d]pyridazin-7(6H)-one (29.6)

29.5 (1.90 g, 7.36 mmol) and hydrazine hydrate (740 mg, 14.7 mmol) in EtOH (10 mL) was heated to reflux for 16 h. The mixture was then cooled to RT and the precipitate was filtered off and washed with EtOH, dried in vacuo to afford 29.6 (1.40 g, 84.3%) as white solid. $^1$H NMR (400 MHZ, DMSO-d6) δ 12.40 (br, 1H), 9.15 (s, 1H), 8.36 (s, 1H), 7.92 (d, J=8.0 Hz, 2H), 7.42 (d, J=8.0 Hz, 2H), 2.40 (s, 3H). LCMS (ESI+) m/z=227.2 (M+H).

Step 29.7: Synthesis of 7-chloro-2-p-tolyl-2H-pyrazolo[4,3-d]pyridazine (29.7)

To a solution of 29.6 (1.40 g, 6.19 mmol) in MeCN (6 mL) was added POCl$_3$ (2.80 g, 18.6 mmol) at RT. The reaction mixture was then stirred reflux for 2 h. Upon completion, the mixture was concentrated in vacuo and the residue was poured into ice-water. Then its pH was adjusted to 8 with sat. aq. NaHCO$_3$ solution, the aqueous layer was extracted with DCM (40 mL×3). The combined organic layers were washed successively with water (40 mL), brine (40 mL) and then dried over Na$_2$SO$_4$, filtered and the filtrate was concentrated to afford 29.7 (1.20 g, 79.5% yield) as yellow solid. LCMS (ESI+) m/z=245.2 (M+H).

Step 29.8: Synthesis of N-(3-(dimethylamino)propyl)-1-(2-(p-tolyl)-2H-pyrazolo[3,4-d]pyridazin-7-yl)piperidine-4-carboxamide (29)

To a solution of 29.7 (100 mg, 0.410 mmol) and 29.2 (114 mg, 0.533 mmol) in EtOH (8 mL) was added TEA (124 mg, 1.23 mmol) at RT. The reaction mixture was stirred reflux for 16 h. Upon completion, solvent was removed in vacuo, the residue was diluted with water (20 mL) and extracted with 10% MeOH/DCM (20 mL×3). The combined organic layers were washed with brine (20 mL), dried over Na$_2$SO$_4$, filtered and concentrated in vacuo. The residue was purified on prep-HPLC and lyophilized to afford 29 (8 mg, 4.6% yield) as white solid. $^1$H NMR (400 MHz, CD$_3$OD) δ 8.96 (s, 1H), 8.87 (s, 1H), 7.89 (d, J=8.8 Hz, 2H), 7.42 (d, J=8.4 Hz, 2H), 5.37 (d, J=13.2 Hz, 2H), 3.28-3.21 (m, 4H), 2.61 (tt, J=11.4 Hz, 4.0 Hz, 1H), 2.45 (s, 3H), 2.41 (t, J=8.0 Hz, 2H), 2.29 (s, 6H), 1.97-1.82 (m, 4H), 1.76-1.69 (m, 2H). LCMS (ESI+) m/z=422.4 (M+H).

Example 8

Synthesis of Compound No. 53

N-(3-(dimethylamino)propyl)-1-(1-methyl-2-(p-tolyl)-1H-benzo[d]imidazol-4-yl)piperidine-4-carboxamide

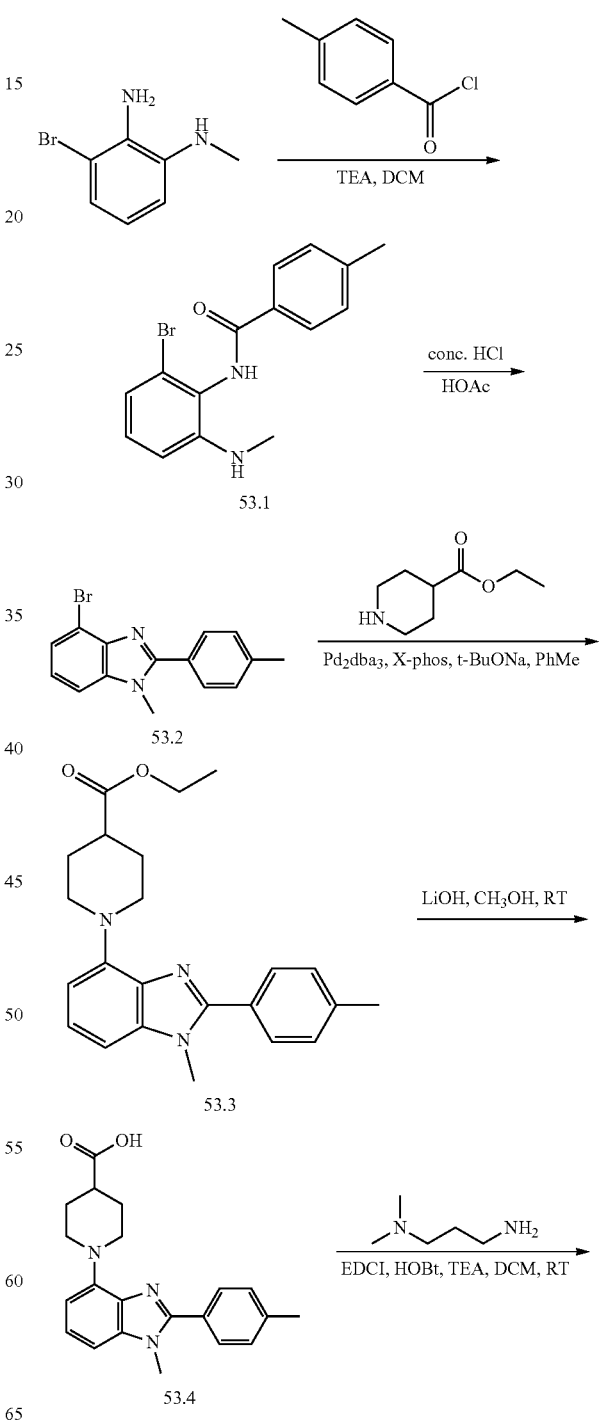

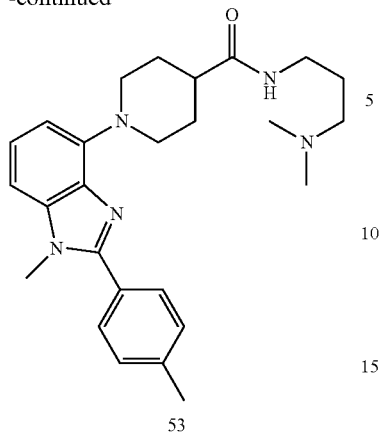

53

Step 53.1: Synthesis of N-(2-bromo-6-(methylamino)phenyl)-4-methylbenzamide (53.1)

To a solution of 3-bromo-$N^1$-methylbenzene-1,2-diamine (2.0 g, 10 mmol) and TEA (2.75 ml, 20 mmol) in DCM (30 mL) was added 4-methylbenzoyl chloride (1.3 g, 8.7 mmol) dropwise under ice-water bath. The reaction mixture was then stirred at RT for 16 h. Then the reaction mixture was concentrated to provide 53.1 (2.7 g, 97.5% yield) as brown oil, which was used directly in next step without further purification.

Step 53.2: Synthesis of 4-bromo-1-methyl-2-p-tolyl-1H-benzo[d]imidazole (53.2)

To a solution of 53.1 (2.7 g, 8.46 mmol) in HOAc (24 mL) was added conc.HCl (0.6 ml) at RT. The reaction mixture was then stirred at RT for 16 h. Upon completion, solvent was removed under reduced pressure. The residue was dissolved in DCM (150 mL) and washed with sat. aq. NaHCO₃ solution (100 mL). The organic layer was dried over Na₂SO₄ and concentrated in vacuo. The crude product was recrystallized with MTBE to provide 53.2 (2.1 g, 82.5% yield) as brown solid. LCMS (ESI+) m/z=301 (M+H).

Step 53.3: Synthesis of ethyl 1-(1-methyl-2-p-tolyl-1H-benzo[d]imidazol-4-yl) piperidine-4-carboxylate (53.3)

To a solution of 53.2 (1.4 g, 4.65 mmol), ethyl piperidine-4-carboxylate (876 mg, 5.58 mmol), X-Phos (887 mg, 1.86 mmol) and NaOt-Bu (625 mg, 6.52 mmol) in PhMe (55 ml) was added Pd₂dba₃ (426 mg, 0.465 mmol) under Ar atmosphere. The resulting mixture was heated to 85° C. for 40 h. The mixture was then concentrated in vacuo. The residue was dissolved in DCM (100 mL) and washed with water (80 mL) and brine (60 mL). The organic layer was dried over Na₂SO₄ and concentrated in vacuo. The residue was purified by column chromatography on silica gel to give 53.3 (400 mg, 23% yield) as yellow solid. LCMS (ESI+) m/z=378 (M+H).

Step 53.4: Synthesis of 1-(1-methyl-2-p-tolyl-1H-benzo[d]imidazol-4-yl)piperidine-4-carboxylic acid (53.4)

To a solution of 53.3 (360 mg, 0.95 mmol) in MeOH (12 mL) was added 1N aq. LiOH solution (3 mL) dropwise. The reaction mixture was then stirred at RT for 2 h. MeOH was removed in vacuo and the aqueous layer was adjusted to pH=6 with 1N aq. HCl solution, the formed solid was collected by filtration to give 53.4 (135 mg, 40.5% yield) as a white solid. LCMS (ESI+) m/z=350 (M+H).

Step 53.5: Synthesis of N-(3-(dimethylamino)propyl)-1-(1-methyl-2-(p-tolyl)-1H-benzo[d]imidazol-4-yl)piperidine-4-carboxamide (53)

To a solution of 53.4 (105 mg, 0.30 mmol), $N^1,N^1$-dimethylpropane-1,3-diamine (46 mg, 0.45 mmol), HOBt (81 mg, 0.60 mmol) and TEA (0.13 ml, 0.90 mmol) in DCM (8 mL) was added EDCI (115 mg, 0.60 mmol) portionwise under ice-water bath. The reaction mixture was then stirred at RT for 16 h. Upon completion, the reaction mass was diluted with DCM (30 mL) and washed with water (25 mL) and brine (25 mL). The organic layer was dried over Na₂SO₄ and concentrated in vacuo. The crude product was purified by prep-HPLC and lyophilized to afford 53 (66 mg, 50.8% yield) as white solid. ¹H NMR (400 MHZ, DMSO-d6) δ 7.81 (t, J=5.5 Hz, 1H), 7.70 (d, J=8.1 Hz, 2H), 7.38 (d, J=7.9 Hz, 2H), 7.12 (t, J=7.9 Hz, 1H), 7.05 (d, J=7.5 Hz, 1H), 6.59 (d, J=7.4 Hz, 1H), 4.37 (d, J=12.0 Hz, 2H), 3.79 (s, 3H), 3.05 (dd, J=12.6, 6.8 Hz, 2H), 2.80-2.67 (m, 2H), 2.41 (s, 3H), 2.32-2.24 (m, 1H), 2.17 (dd, J=15.1, 7.8 Hz, 2H), 2.10 (s, 6H), 1.84-1.69 (m, 4H), 1.56-1.47 (m, 2H). LCMS (ESI+) m/z=434 (M+H).

Example 9

Synthesis of Compound No. 55

N-(3-(dimethylamino)propyl)-1-(2-(p-tolyl)-2H-pyrazolo[4,3-c]pyridin-7-yl)piperidine-4-carboxamide

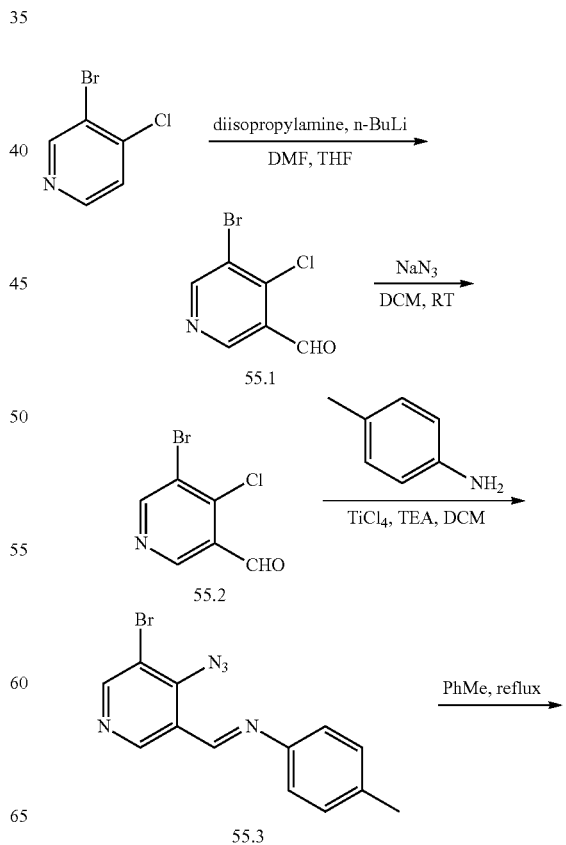

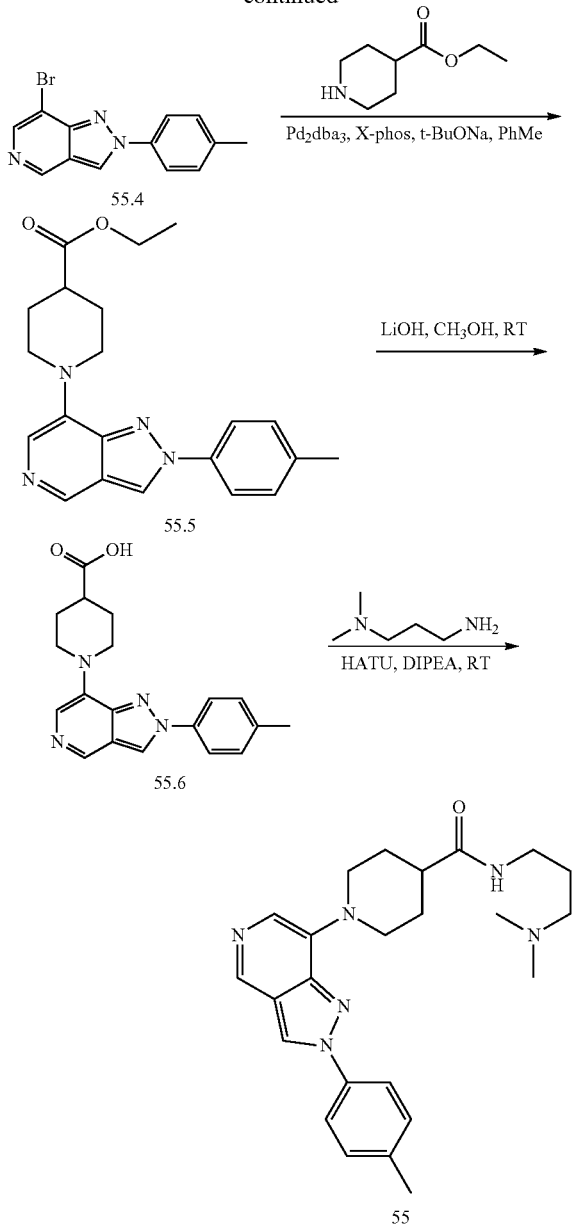

Step 55.1: Synthesis of 5-bromo-4-chloronicotinaldehyde (55.1)

To a solution of diisopropylamine (7.6 g, 74.8 mmol) in THF (66 mL) at −30° C. was added 2.5 M n-BuLi in THF (30 mL). The reaction mixture was stirred for 30 min then cooled to −78° C. A suspension of 3-bromo-4-chloropyridine (12.0 g, 62.4 mmol) in THF (24 mL) was added dropwise over 20 min, then the mixture was stirred at −78° C. for 3.5 h. DMF (5.46 g, 74.8 mmol) was added and the reaction was warmed to RT for 30 min. The reaction mixture was quenched with NH$_4$Cl (360 mL) and extracted with EtOAc (120 mL×3). The combined organic layers were washed with brine (240 mL), dried over Na$_2$SO$_4$ and concentrated in vacuo. The residue was purified by column chromatography on silica gel (PE/EA=15/1) to afford 55.1 (8.0 g, 58% yield) as pale yellow solid. $^1$H NMR (400 MHZ, CDCl$_3$) δ 10.48 (s, 1H), 8.94 (d, J=3.4 Hz, 2H).

Step 55.2: Synthesis of 4-azido-5-bromonicotinaldehyde (55.2)

A mixture of 55.1 (3.0 g, 13.6 mmol) and NaN$_3$ (929 mg, 14.3 mmol) in DMF (9 mL) was stirred at RT overnight. The completion of the reaction was monitored by TLC. The mixture was then quenched with brine (120 mL) and extracted with EtOAc (40 mL×3). The combined organic layers were washed with brine (60 mL), dried over Na$_2$SO$_4$ and concentrated in vacuo to give 55.2 (4.1 g, 100% yield) as pale yellow solid. $^1$H NMR (400 MHZ, CDCl$_3$) δ 10.31 (s, 1H), 8.86 (s, 1H), 8.80 (s, 1H).

Step 55.3: Synthesis of N-((4-azido-5-bromopyridin-3-yl)methylene)-4-methylaniline (55.3)

To a cooled (0° C.) solution of 55.3 (4.1 g, 18.1 mmol), p-toluidine (1.9 g, 18.1 mmol) and TEA (5.5 g, 54.3 mmol) in DCM (80 mL) was added 1.0 M TiCl$_4$ (10.9 mL) dropwise over 20 min. The reaction mixture was stirred for 20 min, warm to RT and then stirred for additional 2 h. The resultant mixture was concentrated to dryness to afford 55.3 (5.7 g) as brown solid, which was used without further purification.

Step 55.4: Synthesis of 7-bromo-2-p-tolyl-2H-pyrazolo[4,3-c]pyridine (55.4)

A solution of 55.3 (5.7 g) in PhMe was heated to reflux overnight. Upon completion, solvent was removed under vacuo. The residue was purified by column chromatography on silica gel to afford 55.4 (2.6 g, 50% yield) as pale yellow solid.

Step 55.5: Synthesis of ethyl 1-(2-p-tolyl-2H-pyrazolo[4,3-c]pyridin-7-yl)piperidine-4-carboxylate (55.5)

To a solution of 55.4 (1.4 g, 5.00 mmol), ethyl piperidine-4-carboxylate (942 mg, 6.00 mmol), X-phos (954 mg, 2.00 mmol) and t-BuONa (672 mg, 7.00 mmol) in PhMe (60 mL) was added Pd$_2$dba$_3$ (458 mg, 0.5 mmol) under Ar atmosphere. The resulting mixture was heated to 85° C. for 20 h. The mixture was then concentrated in vacuo. The residue was dissolved in DCM (100 mL) and washed with water (80 mL) and brine (60 mL). The organic layer was dried over Na$_2$SO$_4$ and concentrated in vacuo. The residue was purified by column chromatography on silica gel (DCM/MeOH=20/1) to afford 55.5 (640 mg, 35% yield) as yellow solid. LCMS (ESI+) m/z=365 (M+H).

Step 55.6: Synthesis of 1-(2-p-tolyl-2H-pyrazolo[4,3-c]pyridin-7-yl)piperidine-4-carboxylic acid (55.6)

To a solution of 55.5 (620 mg, 1.70 mmol) in MeOH (5 mL) was added IN aq. LiOH solution (5.1 mL) dropwise. The reaction mixture was then stirred at RT for 2 h. MeOH was removed in vacuo and the aqueous layer was adjusted to pH=6 with IN aq. HCl solution, the formed solid was collected by filtration to get 55.6 (500 mg, 87% yield) as a yellow solid. LCMS (ESI+) m/z=337 (M+H).

Step 55.7: Synthesis of N-(3-(dimethylamino)propyl)-1-(2-(p-tolyl)-2H-pyrazolo[4,3-c]pyridin-7-yl)piperidine-4-carboxamide (55)

To a solution of 55.6 (100 mg, 0.30 mmol) and N$^1$,N$^1$-dimethylpropane-1,3-diamine (46 mg, 0.45 mmol) in DMF (3 mL) was added DIPEA (116 mg, 0.90 mmol), followed by the addition of HATU (228 mg, 0.60 mmol) portionwise. The reaction mixture was stirred at 30° C. overnight. 10% aq. NaCl (35 mL) solution was added and the mixture was extracted with EtOAc (20 mL×3). The combined organic layers were washed with 10% aq. NaCl (20 mL×2) and brine (20 mL), dried over Na$_2$SO$_4$ and concentrated in vacuo. The residue was purified by prep-HPLC and lyophilized to afford 55 (12 mg, 9.5% yield) as yellow solid. $^1$H NMR (400 MHz, MeOD-d4) δ 9.00 (s, 1H), 8.70 (s, 1H), 7.91 (d, J=8.5 Hz, 2H), 7.57 (s, 1H), 7.41 (d, J=8.5 Hz, 2H), 4.43 (d, J=12.3 Hz, 2H), 3.23 (t, J=6.9 Hz, 2H), 2.92 (td, J=12.1, 2.8 Hz, 2H), 2.49-2.38 (m, 6H), 2.28 (s, 6H), 2.06-1.90 (m, 4H), 1.76-1.68 (m, 2H). LCMS (ESI+) m/z=421.4 (M+H).

Example 10

Synthesis of Compound No. 76

4-(3,4-dimethyl-2-(p-tolyl)-2H-pyrazolo[3,4-d]pyridazin-7-yl)-N-(3-(dimethylamino)propyl)piperazine-1-carboxamide

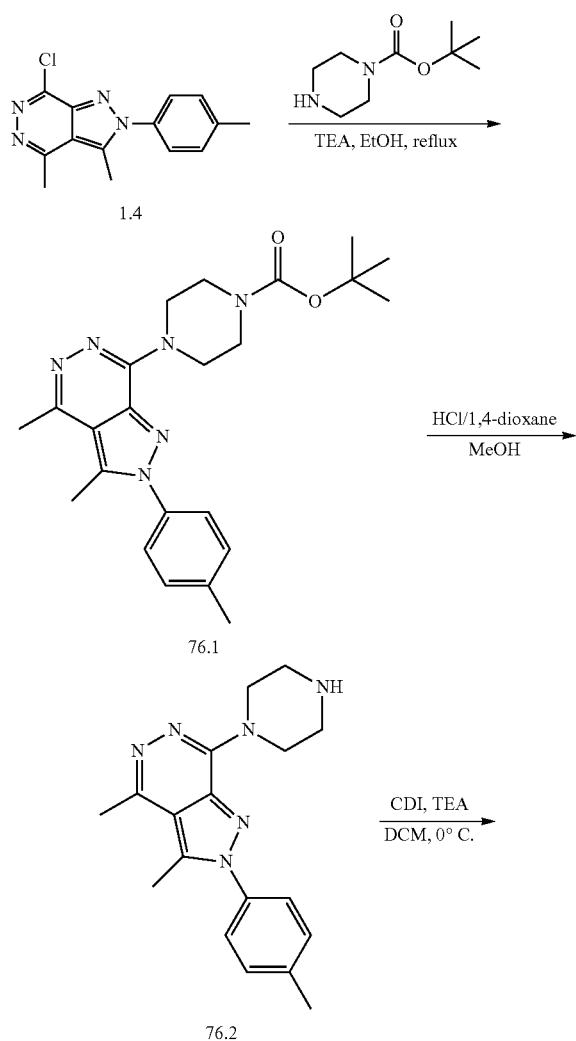

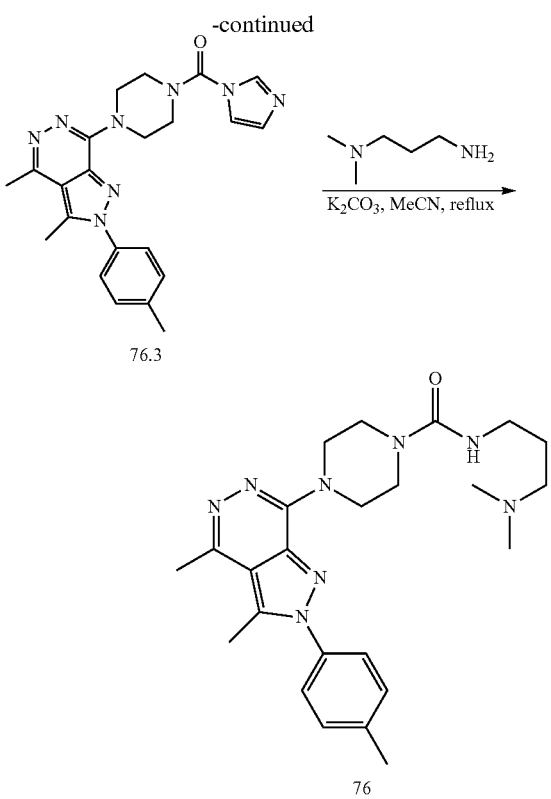

Step 76.1: Synthesis of N-(3-(dimethylamino)propyl)-1-(2-p-tolyl-2H-pyrazolo[4,3-c]pyridine-7-yl)piperidine-4-carboxamide (76.1)

To a solution of 1.4 (300 mg, 1.10 mmol) and tert-butyl piperazine-1-carboxylate (246 mg, 1.32 mmol) in EtOH (20 mL) was added TEA (334 mg, 3.31 mmol). The resulting mixture was heated to reflux overnight. Upon completion, solvent was removed in vacuo, the residue was diluted with water (30 mL) and extracted with 10% MeOH/DCM (30 mL×3). The combined organic layers were washed with brine (20 mL), dried over Na$_2$SO$_4$, filtered and concentrated in vacuo. The residue was purified by column chromatography on silica gel (DCM/MeOH=20/1) to afford 76.1 (440 mg, 95% yield) as yellow solid. LCMS (ESI+) m/z=423 (M+H).

Step 76.2: Synthesis of 3,4-dimethyl-7-(piperazin-1-yl)-2-p-tolyl-2H-pyrazolo[3,4-d]pyridazine (76.2)

To a solution of 76.1 (440 mg, 1.04 mmol) in MeOH (20 mL) was added 4 M HCl in 1,4-dioxane (20 mL) dropwise. The resulting mixture was stirred at RT for 1 h. Solvent was then removed in vacuo, the residue was dissolved with water (10 mL) and then adjusted to pH=8 with satu. aq. Na$_2$CO$_3$ solution. The aqueous phase was extracted with 10% MeOH/DCM (30 mL×3). The combined organic layers were washed with brine (20 mL), dried over Na$_2$SO$_4$ and concentrated in vacuo to afford 76.2 (260 mg, 77.6% yield) as yellow solid. LCMS (ESI+) m/z=323 (M+H).

Step 76.3: Synthesis of (4-(3,4-dimethyl-2-p-tolyl-2H-pyrazolo[3,4-d]pyridazin-7-yl)piperazin-1-yl)(1H-imidazol-1-yl)methanone (76.3)

To a solution of CDI (99 mg, 0.615 mmol) in DCM (10 mL) was added TEA (169 mg, 1.68 mmol), followed by addition of 76.2 (180 mg, 0.559 mmol) portionwise under ice-water bath. The resulting mixture was stirred at the same temperature for 2 h. The mixture was then diluted with DCM (20 mL) and washed with water (15 mL×2). The organic layer was dried over Na₂SO₄ and concentrated in vacuo to afford 76.3 (223 mg, 95% yield) as pale yellow solid. LCMS (ESI+) m/z=417 (M+H).

Step 76.4: Synthesis of 4-(3,4-dimethyl-2-(p-tolyl)-2H-pyrazolo[3,4-d]pyridazin-7-yl)-N-(3-(dimethylamino)propyl)piperazine-1-carboxamide (76)

To a solution of 76.3 (200 mg, 0.481 mmol) in MeCN (15 mL) was added $N^1,N^1$-dimethylpropane-1,3-diamine (980 mg, 9.62 mmol) and K₂CO₃ (265 mg, 1.92 mmol). The reaction mixture was heated to reflux for 48 h. The mixture was then diluted with DCM (45 mL) and washed with water (20 mL) and brine (20 mL). The organic layer was dried over Na₂SO₄ and concentrated in vacuo. The residue was recrystallized in MeCN to afford 76 (45 mg, 21% yield) as white solid. ¹H NMR (400 MHZ, DMSO-d6) δ 7.52 (d, J=8.3 Hz, 2H), 7.44 (d, J=8.2 Hz, 2H), 6.62 (t, J=5.3 Hz, 1H), 3.94-3.92 (m, 4H), 3.43-3.41 (m, 4H), 3.05 (dd, J=12.7, 6.6 Hz, 2H), 2.68 (d, J=5.7 Hz, 6H), 2.43 (s, 3H), 2.19 (t, J=7.1 Hz, 2H), 2.10 (s, 6H), 1.57-1.50 (m, 2H). LCMS (ESI+) m/z=451.3 (M+H).

Example 11

Synthesis of Compound No. 34

N-(3-(dimethylamino)propyl)-1-(4-methyl-3-phenyl-2-(p-tolyl)-2H-pyrazolo[3,4-d]pyridazin-7-yl)piperidine-4-carboxamide

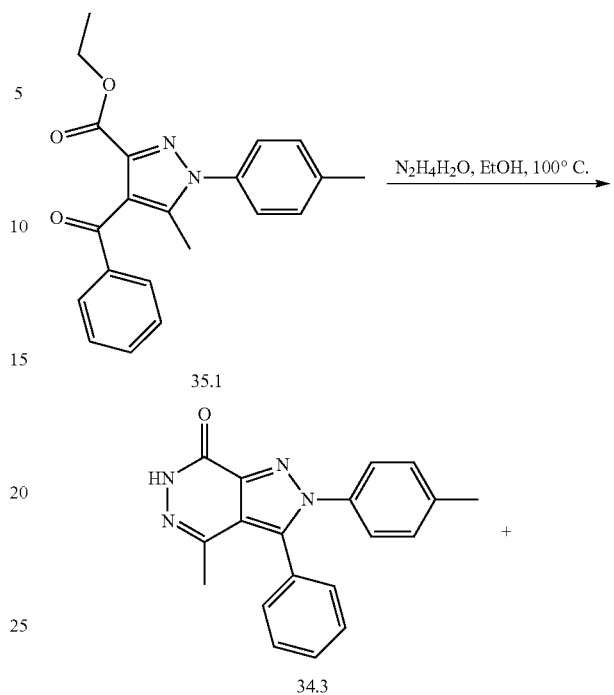

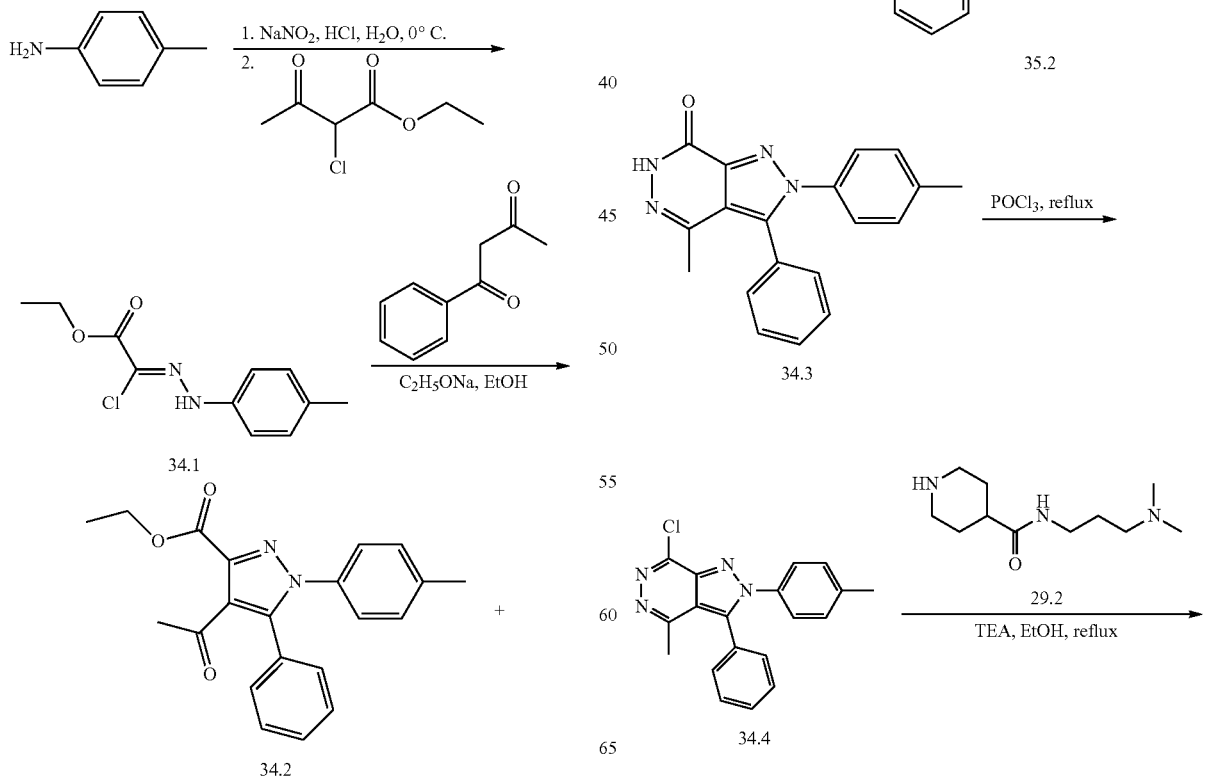

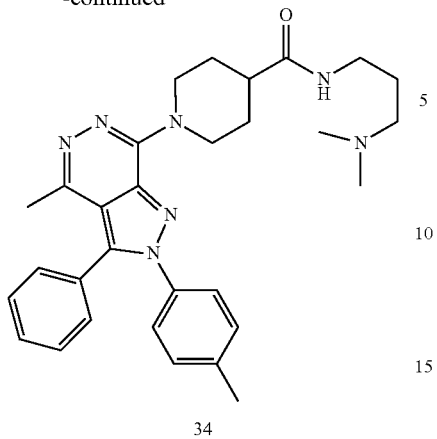

34

Step 34.1: Synthesis of ethyl 2-chloro-2-(2-p-tolylhydrazono)acetate (34.1)

A solution of p-toluidine (10.0 g, 93.5 mmol) in dilute HCl (1:1, 66 mL) was cooled to 0° C., and a cold solution of $NaNO_2$ (7.10 g, 103 mmol) in $H_2O$ (90 mL) was added dropwise over 20 min while maintaining internal solution temperature below 5° C. After addition, the reaction mixture was stirred for further 30 min keeping the internal temperature below 0° ° C. The resulting ice-cold solution was then added dropwise to a pre-cooled (0° C.) solution of ethyl 2-chloro-3-oxobutanoate (15.3 g, 93.5 mmol) and NaOAc (11.5 g, 140 mmol) in $H_2O$/EtOH (1:7, 370 mL). Upon completion of addition, the reaction mixture was stirred for 4 h at the same temperature and then quenched by addition of cold water. The resultant precipitate was filtered and dried in vacuo to give 34.1 (18.0 g, 80.0% yield) as pale yellow solid. $^1H$ NMR (400 MHZ, $CDCl_3$) δ 8.31 (s, 1H), 7.15-7.10 (m, 4H), 4.38 (q, J=7.1 Hz, 2H), 2.31 (s, 3H), 1.40 (t, J=7.1 Hz, 3H). LCMS (ESI+) m/z=241 (M+H).

Step 34.2: Synthesis of ethyl 4-acetyl-5-phenyl-1-p-tolyl-1H-pyrazole-3-carboxylate (34.2) and ethyl 4-benzoyl-5-methyl-1-p-tolyl-1H-pyrazole-3-carboxylate (35.1)

A solution of 1-phenylbutane-1,3-dione (6.75 g, 41.7 mmol) in anhydrous EtOH (40 mL) was added dropwise to a solution of NaOEt (3.12 g, 45.8 mmol) in anhydrous EtOH (25 mL) under ice-water bath. The resulting mixture was heated to 50° C. for 15 min. 34.1 (10.0 g, 41.7 mmol) was added portionwise after the mixture was cooled to RT. The reaction mixture was then stirred at RT for 16 h. Upon completion, the solvent was removed in vacuo, the residue was diluted with DCM (200 mL) and washed with water (100 mL) and brine (100 mL). The organic layer was concentrated in vacuo, the residue was purified by column chromatography on silica gel (PE/EA=5/1) to afford a mixture of 34.2 and 35.1 (7.20 g, 49.6% total yield) as yellow solid. LCMS (ESI+) m/z=349.3 (M+H).

Step 34.3: Synthesis of 4-methyl-3-phenyl-2-p-tolyl-2H-pyrazolo[4,3-d]pyridazin-7(6H)-one (34.3) and 3-methyl-4-phenyl-2-p-tolyl-2H-pyrazolo[4,3-d]pyridazin-7(6H)-one (35.2)

A mixture of 34.2 and 35.1 (2.00 g, 5.75 mmol) was dissolved in EtOH (32 mL) and then hydrazine hydrate (2.88 g, 57.5 mmol) was added to the solution. The reaction mixture was heated to reflux for 16 h. The mixture was then cooled to RT and the precipitate was filtered off, washed with EtOH and dried in vacuo. The residue was purified by prep-HPLC and lyophilized to afford 34.3 (410 mg, 22.6% yield) as white solid and 35.2 (255 mg, 14.0% yield) as white solid. 34.3: $^1H$ NMR (400 MHZ, $CD_3OD$) δ 7.52-7.40 (m, 5H), 7.26-7.24 (m, 2H), 7.18 (d, J=8.2 Hz, 2H), 2.34 (s, 3H), 2.09 (s, 3H). LCMS (ESI+) m/z=317.2 (M+H); 35.2: $^1H$ NMR (400 MHz, $CD_3OD$) δ 7.63-7.60 (m, 2H), 7.55-7.53 (m, 3H), 7.49-7.47 (m, 2H), 7.42 (d, J=8.3 Hz, 2H), 2.46 (s, 3H), 2.18 (s, 3H). LCMS (ESI+) m/z=317.2 (M+H).

Step 34.4: Synthesis of 7-chloro-4-methyl-3-phenyl-2-p-tolyl-2H-pyrazolo[4,3-d]pyridazine (34.4)

A round bottom flask was charged 34.3 (316 mg, 1.00 mmol) and $POCl_3$ (5 mL), the reaction mixture was heated to reflux for 5 h. Upon completion, $POCl_3$ was removed in vacuo, the residue was diluted with water (15 mL) and adjusted PH to 8 with sat. aq. $NaHCO_3$ solution. The aqueous layer was extracted with 10% MeOH/DCM (20 mL×2). The combined organic layers were washed with brine (20 mL), dried over $Na_2SO_4$, filtered and concentrated in vacuo. The residue was purified by column chromatography on silica gel (PE/EA=1/1) to afford 34.4 (300 mg, 89.6% yield) as yellow solid. $^1H$ NMR (400 MHZ, $CD_3OD$) δ 7.56-7.44 (m, 5H), 7.34-7.32 (m, 2H), 7.24 (d, J=8.1 Hz, 2H), 2.46 (s, 3H), 2.37 (s, 3H). LCMS (ESI+) m/z=335.2 (M+H).

Step 34.5: Synthesis of N-(3-(dimethylamino)propyl)-1-(4-methyl-3-phenyl-2-(p-tolyl)-2H-pyrazolo[3,4-d]pyridazin-7-yl)piperidine-4-carboxamide (34)

To a solution of 34.4 (260 mg, 0.778 mmol) and 29.2 (249 mg, 1.17 mmol) in EtOH (10 mL) was added TEA (354 mg, 3.50 mmol) at RT. The reaction mixture was stirred reflux for 16 h. Upon completion, solvent was removed in vacuo, the residue was diluted with water (40 mL) and extracted with 10% MeOH/DCM (30 mL×3). The combined organic layers were washed with brine (40 mL), dried over $Na_2SO_4$, filtered and concentrated in vacuo. The residue was purified on prep-HPLC and lyophilized to afford 34 (89 mg, 22% yield) as yellow solid. $^1H$ NMR (400 MHZ, MeOD-d4) δ 7.51-7.43 (m, 3H), 7.41-7.39 (m, J=6.9, 2H), 7.26 (d, J=7.2 Hz, 2H), 7.19 (d, J=7.5 Hz, 2H), 5.27 (d, J=13.3 Hz, 2H), 3.23-3.13 (m, 4H), 2.59-2.51 (m, 1H), 2.39-2.35 (m, 5H), 2.25 (t, J=3.8 Hz, 9H), 1.90-1.80 (m, 4H), 1.72-1.66 (m, 2H). LCMS (ESI+) m/z=512.4 (M+H).

Compound Nos. 23 and 63 were prepared using the appropriate starting materials and reagents according to the same procedures as in Example 11.

Example 12

Synthesis of Compound Nos. 23 and 63

| Compound No. | Structure | ¹H NMR (400 MHz) (Solvent) δ ppm | LCMS m/z (M + H) |
|---|---|---|---|
| 23 | 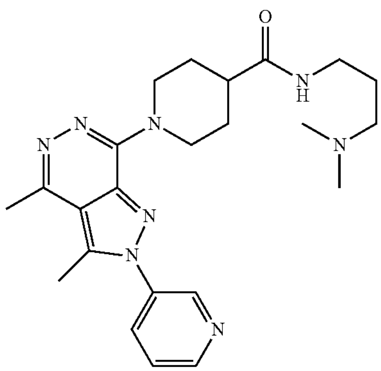 [SMILES: Cc1nnc(N2CCC(C(=O)NCCCN(C)C)CC2)c2nn(-c3cccnc3)c(C)c12] | (DMSO-d6) δ 8.90 (d, J = 2.2 Hz, 1H), 8.81 (dd, J = 4.8, 1.4 Hz, 1H), 8.17 (ddd, J = 8.2, 2.5, 1.5 Hz, 1H), 7.81 (t, J = 5.6 Hz, 1H), 7.73-7.69 (m, 1H), 5.01 (d, J = 13.0 Hz, 2H), 3.06-3.00 (m, 4H), 2.70 (d, J = 10.0 Hz, 6H), 2.46-2.38 (m, 1H), 2.16 (t, J = 7.2 Hz, 2H), 2.09 (s, 6H), 1.73 (dd, J = 12.4, 2.2 Hz, 2H), 1.67-1.57 (m, 2H), 1.53-1.46 (m, 2H). | 437 |
| 63 | 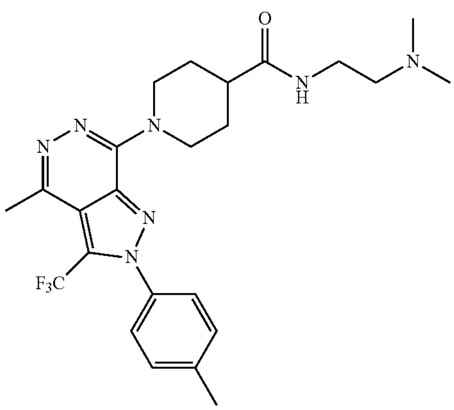 | (DMSO-d6) δ 7.73 (t, J = 5.5 Hz, 1H), 7.57 (d, J = 8.3 Hz, 2H), 7.44 (d, J = 8.1 Hz, 2H), 5.02 (d, J = 13.1 Hz, 2H), 3.15-3.08 (m, 4H), 2.66 (d, J = 1.9 Hz, 3H), 2.48-2.44 (m, 4H), 2.24 (t, J = 6.8 Hz, 2H), 2.12 (s, 6H), 1.76-1.73 (m, 2H), 1.67-1.57 (m, 2H). | 490 |

Example 13

Synthesis of Compound No. 35

N-(3-(dimethylamino)propyl)-1-(3-methyl-4-phenyl-2-(p-tolyl)-2H-pyrazolo[3,4-d]pyridazin-7-yl)piperidine-4-carboxamide

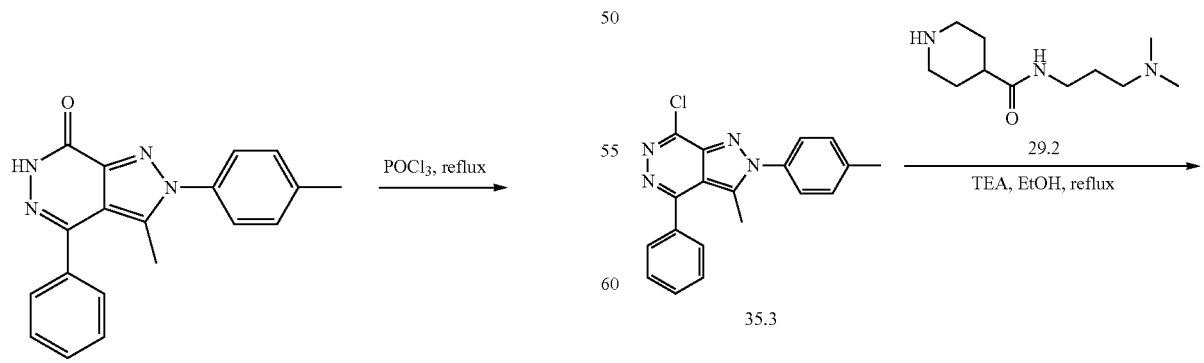

241
-continued

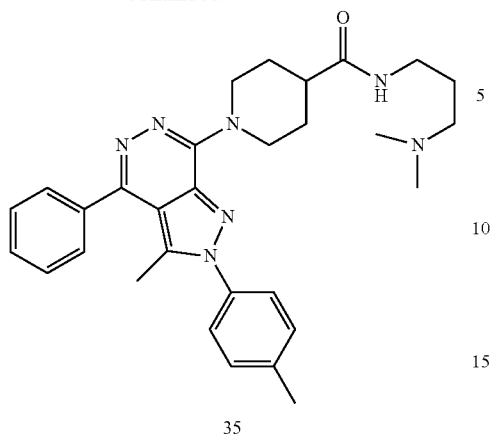

35

Step 35.1: Synthesis of 7-chloro-3-methyl-4-phenyl-2-p-tolyl-2H-pyrazolo[4,3-d]pyridazine (35.3)

A round bottom flask was charged 35.2 (160 mg, 0.506 mmol) and POCl₃ (3 mL), the reaction mixture was heated to reflux for 5 h. Upon completion, POCl₃ was removed in vacuo, the residue was diluted with water (10 mL) and adjusted PH to 8 with sat. aq. NaHCO₃ solution. The aqueous layer was extracted with 10% MeOH/DCM (20 mL×2). The combined organic layers were washed with brine (20 mL), dried over Na₂SO₄, filtered and concentrated in vacuo. The residue was purified by column chromatography on silica gel (PE/EA=1/1) to afford 35.3. (150 mg, 88% yield) as yellow solid. $^1$H NMR (400 MHZ, DMSO-d6) δ 7.79-7.75 (m, 2H), 7.62-7.59 (m, 5H), 7.47 (d, J=8.1 Hz, 2H), 2.44 (s, 3H), 2.31 (s, 3H). LCMS (ESI+) m/z=335 (M+H).

Step 35.2: Synthesis of N-(3-(dimethylamino)propyl)-1-(3-methyl-4-phenyl-2-(p-tolyl)-2H-pyrazolo[3,4-d]pyridazin-7-yl)piperidine-4-carboxamide (35)

To a solution of 35.3 (150 mg, 0.449 mmol) and 29.2 (124 mg, 0.584 mmol) in EtOH (10 mL) was added TEA (136 mg, 1.35 mmol) at RT. The reaction mixture was stirred reflux for 16 h. Upon completion, solvent was removed in vacuo, the residue was diluted with water (20 mL) and extracted with 10% MeOH/DCM (20 mL×3). The combined organic layers were washed with brine (30 mL), dried over Na₂SO₄, filtered and concentrated in vacuo. The residue was purified on prep-HPLC and lyophilized to afford 35 (73 mg, 32% yield) as pale yellow solid. $^1$H NMR (400 MHZ, MeOD) δ 7.63-7.61 (m, 2H), 7.56-7.51 (m, 3H), 7.47 (d, J=8.4 Hz, 2H), 7.42 (d, J=8.2 Hz, 2H), 5.33 (d, J=13.2 Hz, 2H), 3.22-3.15 (m, 4H), 2.62-2.53 (m, 1H), 2.46 (s, 3H), 2.38-2.34 (m, 2H), 2.23 (d, J=12.1 Hz, 9H), 1.90-1.80 (m, 4H), 1.73-1.66 (m, 2H). LCMS (ESI+) m/z=512.3 (M+H).

242

Example 14

Synthesis of Compound Nos. 36 and 48

1-(4-chloro-3-methyl-2-(p-tolyl)-2H-pyrazolo[3,4-d]pyridazin-7-yl)-N-(3-(dimethylamino)propyl)piperidine-4-carboxamide and 1-(7-chloro-3-methyl-2-(p-tolyl)-2H-pyrazolo[3,4-d]pyridazin-4-yl)-N-(3-(dimethylamino)propyl)piperidine-4-carboxamide

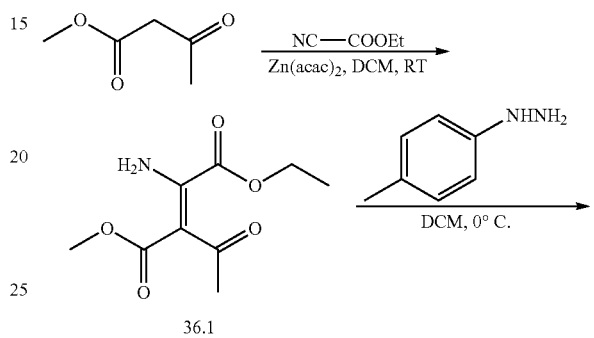

36.1

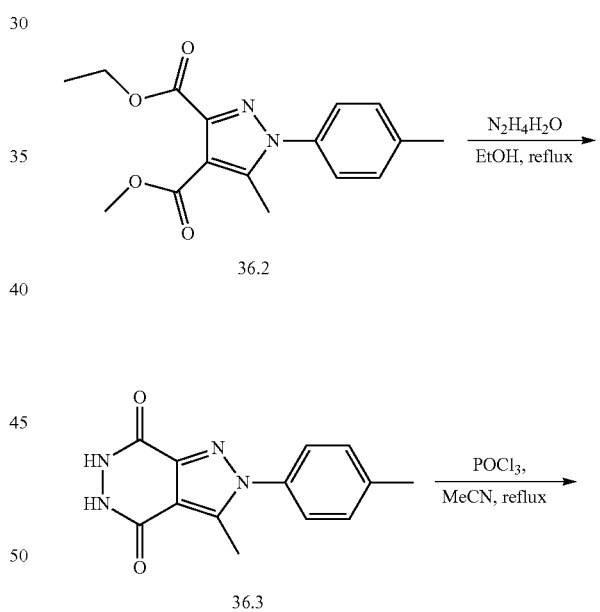

36.2

36.3

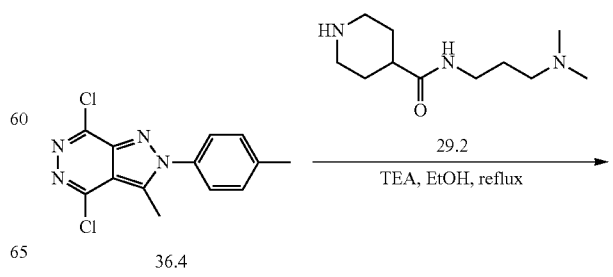

36.4

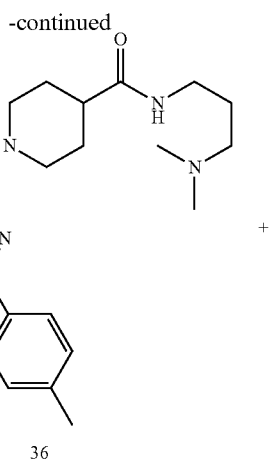

36

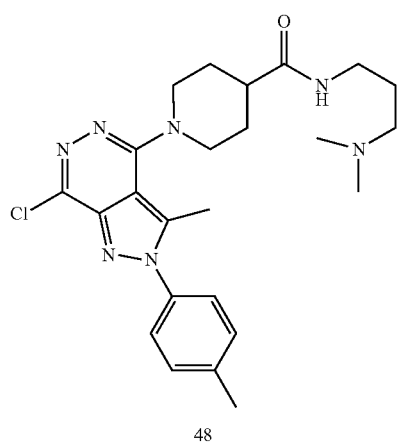

48

Step 36.1: Synthesis of 4-ethyl 1-methyl 2-acetyl-3-aminofumarate (36.1)

To a solution of methyl 3-oxobutanoate (9.8 g, 84.4 mmol) in DCM (20 mL) were added ethyl carbonocyanidate (12.5 g, 126 mmol) and Zn(acac)$_2$ (445 mg, 1.69 mmol). The mixture was stirred at RT under Ar atmosphere overnight. Solvent was then removed under reduced pressure. The residue was treated with EtOAc (30 mL) and the suspension was filtered over celite. The clear filtrate was evaporated in vacuo to give 36.1 (15.8 g, 87% yield) as white solid. LCMS (ESI+) m/z=216 (M+H).

Step 36.2: Synthesis of 3-ethyl 4-methyl 5-methyl-1-p-tolyl-1H-pyrazole-3,4-dicarboxylate (36.2)

To a stirred and cooled (0° C.) solution of 36.1 (19.0 g, 88.4 mmol) in DCM (150 mL) was added a cooled solution of p-tolylhydrazine (16.2 g, 132 mmol) in DCM (180 mL) dropwise over 30 min. The resulting mixture was stirred at the same temperature overnight. The mixture was then diluted with DCM (800 mL) and washed with 0.5 N aq. HCl solution (400 mL), water (400 mL) and brine (400 mL). The organic layer was dried over Na$_2$SO$_4$ and concentrated in vacuo. The residue was recrystallized in EtOH and filtered, the precipitate was collected to give 36.2 (21.0 g, 79% yield) as pale yellow solid. LCMS (ESI+) m/z=303 (M+H).

Step 36.3: Synthesis of 3-methyl-2-p-tolyl-5,6-dihydro-2H-pyrazolo[4,3-d]pyridazine-4,7-dione (36.3)

To a solution of 36.2 (11.1 g, 36.8 mmol) in EtOH (45 mL) was added hydrazine hydrate (18.4 g, 368 mmol) at RT. The reaction mixture was then heated to reflux overnight. After that the mixture was cooled to RT and the precipitate was collected by filtration to get 36.3 (7.77 g, 82.7% yield) as a white solid. LCMS (ESI+) m/z=257 (M+H).

Step 36.4: Synthesis of 4,7-dichloro-3-methyl-2-p-tolyl-2H-pyrazolo[4,3-d]pyridazine (36.4)

To a solution of 36.3 (2.6 g, 10.2 mmol) in MeCN (3 mL) was added POCl$_3$ (7.8 g, 50.8 mmol) at RT. The reaction mixture was then stirred reflux for 2 h. Upon completion, the mixture was concentrated in vacuo and the residue was poured into ice-water. Then its pH was adjusted to 8 with sat. aq. NaHCO$_3$ solution, the aqueous layer was extracted with DCM (50 mL×3). The combined organic layers were washed successively with water (50 mL), brine (50 mL) and then dried over Na$_2$SO$_4$, filtered and the filtrate was concentrated in vacuo. The residue was purified by column chromatography on silica gel (PE/EA=1/1) to afford 36.4 (2.3 g, 76.9% yield) as yellow solid. LCMS (ESI+) m/z=293 (M+H).

Step 36.5: Synthesis of 1-(4-chloro-3-methyl-2-(p-tolyl)-2H-pyrazolo[3,4-d]pyridazin-7-yl)-N-(3-(dimethylamino)propyl)piperidine-4-carboxamide (36) and 1-(7-chloro-3-methyl-2-(p-tolyl)-2H-pyrazolo[3,4-d]pyridazin-4-yl)-N-(3-(dimethylamino)propyl)piperidine-4-carboxamide (48)

To a solution of 36.4 (1.0 g, 3.42 mmol) and 29.2 (650 mg, 3.25 mmol) in EtOH (10 mL) was added TEA (1.0 g, 10.2 mmol) at RT. The reaction mixture was stirred reflux for 2 h. Upon completion, solvent was removed in vacuo, the residue was diluted with water (40 mL) and extracted with 10% MeOH/DCM (30 mL×3). The combined organic layers were washed with brine (40 mL), dried over Na$_2$SO$_4$, filtered and concentrated in vacuo. The residue was purified on prep-HPLC and lyophilized to afford 36 (400 mg, 24.9% yield) as white solid and 48 (120 mg, 7.5%) as white solid. 36: $^1$H NMR (400 MHz, DMSO-d6) δ 7.81 (t, J=5.6 Hz, 1H), 7.56 (d, J=8.3 Hz, 2H), 7.45 (d, J=8.1 Hz, 2H), 5.06 (d, J=13.1 Hz, 2H), 3.14-3.08 (m, 2H), 3.03 (dd, J=12.6, 6.8 Hz, 2H), 2.69 (s, 3H), 2.47-2.43 (m, 4H), 2.16 (t, J=7.2 Hz, 2H), 2.08 (s, 6H), 1.76 (dd, J=12.6, 2.3 Hz, 2H), 1.61 (qd, J=12.6, 3.8 Hz, 2H), 1.53-1.46 (m, 2H). LCMS (ESI+) m/z=470.4 (M+H); 48: $^1$H NMR (400 MHZ, DMSO-d6) δ 7.88 (t, J=5.5 Hz, 1H), 7.61 (d, J=8.3 Hz, 2H), 7.46 (d, J=8.2 Hz, 2H), 3.87 (d, J=12.9 Hz, 2H), 3.07 (dd, J=12.6, 6.8 Hz, 2H), 3.02-2.95 (m, 2H), 2.64 (s, 3H), 2.44 (s, 3H), 2.41-2.35 (m, 1H), 2.19 (t, J=7.1 Hz, 2H), 2.10 (s, 6H), 1.86-1.73 (m, 4H), 1.56-1.49 (m, 2H). LCMS (ESI+) m/z=470.3 (M+H).

Example 15

Synthesis of Compound No. 41

N-(3-(dimethylamino)propyl)-1-(4-iodo-3-methyl-2-(p-tolyl)-2H-pyrazolo[3,4-d]pyridazin-7-yl)piperidine-4-carboxamide

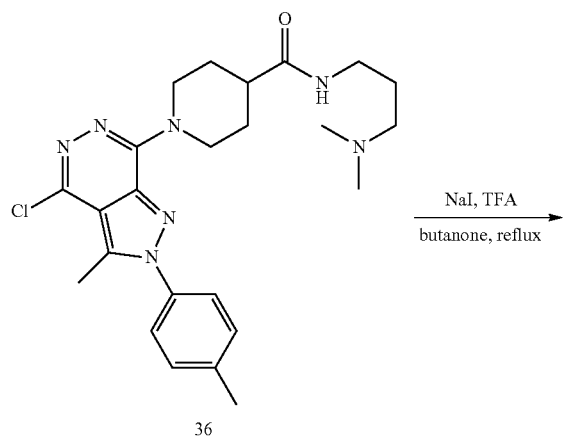

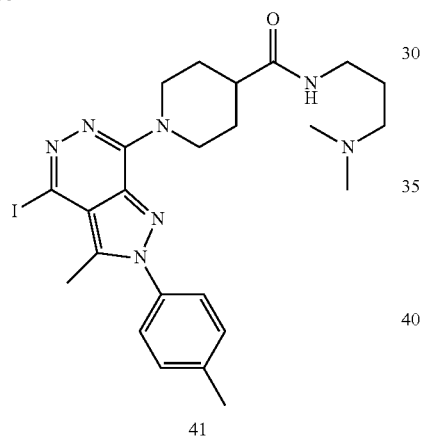

Step 41.1: Synthesis of N-(3-(dimethylamino)propyl)-1-(4-iodo-3-methyl-2-(p-tolyl)-2H-pyrazolo[3,4-d]pyridazin-7-yl)piperidine-4-carboxamide (41)

To a solution of 36 (100 mg, 0.213 mmol) and NaI (640 mg, 4.26 mmol) in butanone (5 mL) was added TFA (122 mg, 1.07 mmol) dropwise under ice-water bath. The resulting mixture was heated to reflux overnight. After that the mixture was cooled to RT and added to sat. aq. NaHCO$_3$ solution slowly under ice-water bath. The mixture was then extracted with 10% MeOH/DCM (40 mL) and the organic layer was washed with aq. NaHSO$_3$ (30 mL), dried over Na$_2$SO$_4$ and concentrated in vacuo. The residue was purified on prep-HPLC and lyophilized to afford 41 (4 mg, 3.3% yield) as yellow solid. $^1$H NMR (400 MHZ, MeOD-d4) δ 7.47-7.42 (m, 4H), 5.23 (d, J=13.3 Hz, 2H), 3.21-3.10 (m, 4H), 2.74 (s, 3H), 2.57-2.50 (m, 1H), 2.48 (s, 3H), 2.36-2.32 (m, 2H), 2.24 (s, 6H), 1.88-1.74 (m, 4H), 1.72-1.64 (m, 2H). LCMS (ESI+) m/z=562.2 (M+H).

Example 16

Synthesis of Compound No. 42

N-(3-(dimethylamino)propyl)-1-(3-methyl-2-(p-tolyl)-2H-pyrazolo[3,4-d]pyridazin-7-yl)piperidine-4-carboxamide

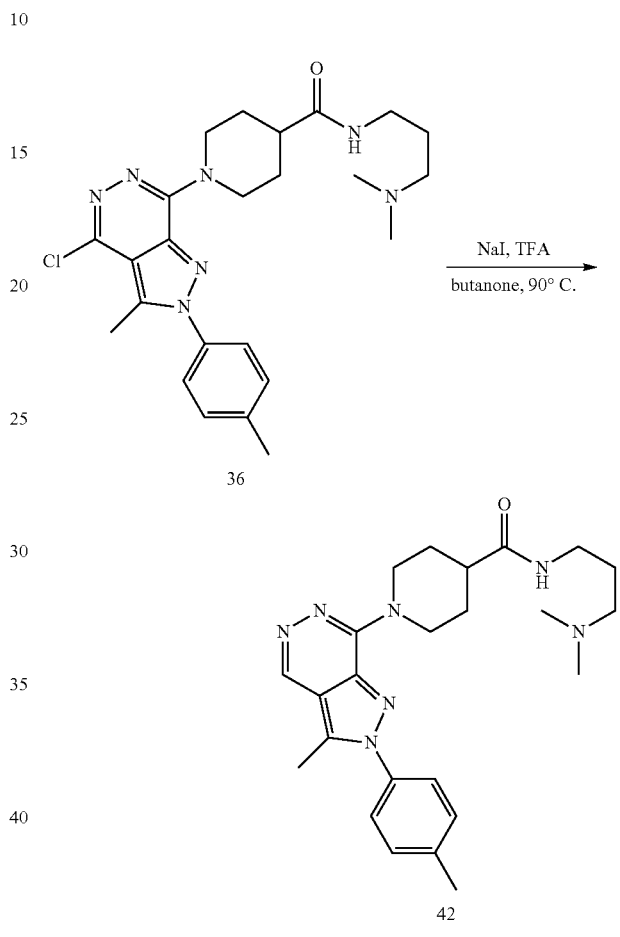

Step 42.1: Synthesis of N-(3-(dimethylamino)propyl)-1-(3-methyl-2-(p-tolyl)-2H-pyrazolo[3,4-d]pyridazin-7-yl)piperidine-4-carboxamide (42)

To a solution of 36 (70 mg, 0.149 mmol) and NaI (448 mg, 2.99 mmol) in butanone (3.5 mL) was added TFA (0.35 mL) dropwise under ice-water bath. The resulting mixture was stirred at 90° C. in a sealed tube overnight. After that the mixture was cooled to RT and added to sat. aq. NaHCO$_3$ solution slowly under ice-water bath. The mixture was then extracted with 10% MeOH/DCM (30 mL) and the organic layer was washed with aq. NaHSO$_3$ (20 mL), dried over Na$_2$SO$_4$ and concentrated in vacuo. The residue was purified on prep-HPLC and lyophilized to afford 42 (13 mg, 20.4% yield) as yellow solid. $^1$H NMR (400 MHZ, MeOD-d4) δ 8.83 (s, 1H), 7.50 (d, J=8.3 Hz, 2H), 7.43 (d, J=8.3 Hz, 2H), 5.28 (d, J=13.4 Hz, 2H), 3.21-3.12 (m, 4H), 2.64 (s, 3H), 2.59-2.51 (m, 1H), 2.47 (s, 3H), 2.38-2.34 (m, 2H), 2.25 (s, 6H), 1.90-1.76 (m, 4H), 1.72-1.65 (m, 2H). LCMS (ESI+) m/z=436.4 (M+H).

Compound Nos. 16, 20, 24, 25, 27, 38, 43-45, 57, 58, 65-75, 15x, 17x, and 45x were prepared using the appropriate starting materials and reagents according to the same procedures as in Example 1.

Example 17

Synthesis of Compound Nos. 16, 20, 24, 25, 27, 38, 43-45, 57, 58, 65-75, 15x, 17x, and 45x

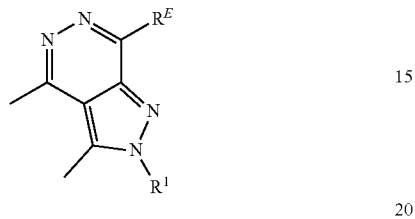

| Compound No. | $R^E$ | $R^1$ | $^1$H NMR (400 MHz) (Solvent) δ ppm | LCMS m/z (M + H) |
|---|---|---|---|---|
| 16 | piperidine-4-carboxamide with N-(2-(isopropylamino)ethyl) | 4-methylphenyl | (MeOD-d4) 7.48-7.43 (m, 4H), 5.01-4.94 (m, 2H), 3.39-3.34 (m, 2H), 3.29-3.21 (m, 2H), 2.93-2.83 (m, 1H), 2.75-2.71 (m, 8H), 2.60 (tt, J = 10.3, 3.8 Hz, 1H), 2.48 (s, 3H), 1.99-1.77 (m, 3H), 1.70-1.59 (m, 1H), 1.08 (d, J = 6.3 Hz, 6H). | 450 |
| 20 | 4-methylpiperidine-4-carboxamide with N-(3-(dimethylamino)propyl) | 4-methylphenyl | (DMSO-d6) 7.74 (t, J = 5.5 Hz, 1H), 7.51 (d, J = 8.3 Hz, 2H), 7.43 (d, J = 8.2 Hz, 2H), 4.38 (dd, J = 9.3, 4.5 Hz, 2H), 3.50 (t, J = 10.3 Hz, 2H), 3.10 (dd, J = 12.5, 6.7 Hz, 2H), 2.65 (d, J = 0.9 Hz, 6H), 2.43 (s, 3H), 2.18 (t, J = 7.1 Hz, 2H), 2.09-2.05 (m, 8H), 1.53 (p, J = 7.0 Hz, 2H), 1.45-1.38 (m, 2H), 1.10 (s, 3H). | 464 |
| 24 | piperidine-4-carboxamide with N-(3-(dimethylamino)propyl) | 3-thienyl | (MeOD-d4) 7.82 (dd, J = 3.2, 1.4 Hz, 1H), 7.69 (dd, J = 5.2, 3.2 Hz, 1H), 7.41 (dd, J = 5.2, 1.4 Hz, 1H), 5.18 (d, J = 13.3 Hz, 2H), 3.20 (t, J = 6.9 Hz, 2H), 3.14-3.07 (m, 2H), 2.79 (s, 3H), 2.74 (s, 3H), 2.56-2.48 (m, 1H), 2.36 (dd, J = 8.6, 6.9 Hz, 2H), 2.25 (s, 6H), 1.88-1.76 (m, 4H), 1.72-1.65 (m, 2H) | 442 |
| 25 | piperidine-4-carboxamide with N-(3-(dimethylamino)propyl) | tetrahydropyran-4-yl | (DMSO-d6) 7.89 (t, J = 5.4 Hz, 1H), 5.06 (t, J = 11.3 Hz, 1H), 4.05 (dd, J = 11.3, 3.5 Hz, 2H), 3.44 (t, J = 12.1 Hz, 4H), 3.08 (dd, J = 12.6, 6.7 Hz, 2H), 2.90 (br, 2H), 2.76 (s, 3H), 2.63 (s, 3H), 2.36 (br, 1H), 2.20 (t, J = 7.2 Hz, 2H), 2.15-2.08 (m, 8H), 1.87-1.77 (m, 6H), 1.57-1.50 (m, 2H). | 444 |

-continued

| Compound No. | R^E | R^1 | ^1H NMR (400 MHz) (Solvent) δ ppm | LCMS m/z (M + H) |
|---|---|---|---|---|
| 27 | | | (MeOD-d4) 5.45-5.35 (m, 1H), 3.59 (d, J = 12.7 Hz, 2H), 3.24 (t, J = 7.0 Hz, 2H), 2.99 (br, 2H), 2.83 (s, 3H), 2.70 (s, 3H), 2.49-2.37 (m, 3H), 2.27 (s, 6H), 2.04-1.96 (m, 4H), 1.76-1.69 (m, 2H), 1.53 (d, J = 6.6 Hz, 6H). | 402 |
| 38 | | | (DMSO-d6) 7.77 (t, J = 5.5 Hz, 1H), 7.51 (d, J = 8.3 Hz, 2H), 7.44 (d, J = 8.3 Hz, 2H), 5.01 (d, J = 12.8 Hz, 2H), 3.05-2.98 (m, 4H), 2.66 (d, J = 3.7 Hz, 6H), 2.43-2.38 (m, 4H), 2.13 (t, J = 14.4 Hz, 1H), 2.07 (s, 6H), 1.73-1.56 (m, 4H), 1.33 (dd, J = 15.0, 9.1 Hz, 4H), 1.27-1.22 (m, 4H). | 492 |
| 43 | | | (DMSO-d6) 7.51 (d, J = 8.3 Hz, 2H), 7.43 (d, J = 8.2 Hz, 2H), 5.01 (t, J = 9.8 Hz, 2H), 4.40 (d, J = 12.6 Hz, 1H), 4.05 (d, J = 13.0 Hz, 1H), 3.12-2.93 (m, 4H), 2.72-2.66 (m, 7H), 2.45 (t, J = 7.8 Hz, 8H), 1.74-1.55 (m, 6H), 1.36-1.27 (m, 6H), 1.20-1.10 (m, 1H), 0.94 (t, J = 7.1 Hz, 6H). | 504 |
| 44 | | | (DMSO-d6) 7.51 (d, J = 8.3 Hz, 2H), 7.43 (d, J = 8.2 Hz, 2H), 5.04 (d, J = 12.9 Hz, 2H), 3.82-3.69 (m, 1H), 3.58-3.44 (m, 1H), 3.24-2.90 (m, 1H), 2.83-2.71 (m, 1H), 2.66 (d, J = 3.6 Hz, 6H), 2.58 (dd, J = 15.1, 7.8 Hz, 1H), 2.43 (s, 3H), 2.17 (s, 3H), 2.13 (s, 3H), 2.09-1.95 (m, 1H), 1.79-1.55 (m, 5H). | 462 |
| 45 | | | (DMSO-d6) 7.51 (d, J = 8.3 Hz, 2H), 7.43 (d, J = 8.3 Hz, 2H), 5.04 (d, J = 13.1 Hz, 2H), 3.70-3.60 (m, 1H), 3.52-3.36 (m, 2H), 3.22-3.15 (m, 1H), 3.07 (dd, J = 22.7, 10.5 Hz, 2H), 2.83-2.73 (m, 1H), 2.66 (d, J = 3.6 Hz, 6H), 2.47-2.37 (m, 4H), 2.32-2.13 (m, 8H), 2.03-1.85 (m, 1H), 1.72-1.42 (m, 5H) | 476 |
| 57 | | | (MeOD) 7.44 (q, J = 8.6 Hz, 4H), 4.27-4.14 (m, 2H), 4.02-3.87 (m, 2H), 3.15-3.07 (m, 1H), 2.75 (s, 3H), 2.70 (d, J = 2.8 Hz, 6H), 2.47 (s, 3H), 2.31-2.16 (m, 2H). | 365 |
| 58 | | | (DMSO-d6) 8.02 (s, 1H), 7.51 (d, J = 7.7 Hz, 2H), 7.41 (d, J = 7.7 Hz, 2H), 7.06 (t, J = 7.2 Hz, 2H), 6.56-6.50 (m, 3H), 5.59 (s, 1H), 4.98 (t, J = 10.3 Hz, 2H), 3.34-3.03 (m, 6H), 2.67 (s, 6H), 2.41-2.33 (m, 4H), 1.89-1.49 (m, 4H). | 484 |

-continued

| Compound No. | R^E | R^1 | ^1H NMR (400 MHz) (Solvent) δ ppm | LCMS m/z (M + H) |
|---|---|---|---|---|
| 65 | (1-piperidinyl-carbonyl-piperidinyl-azetidine structure) | (p-tolyl) | (DMSO-d6) 7.51 (d, J = 8.2 Hz, 2H), 7.43 (d, J = 8.1 Hz, 2H), 5.01 (d, J = 12.8 Hz, 2H), 3.86 (dd, J = 41.0, 12.2 Hz, 2H), 3.19-3.04 (m, 7H), 2.97-2.87 (m, 2H), 2.66 (d, J = 3.2 Hz, 6H), 2.43 (s, 3H), 2.21-2.14 (m, 1H), 1.94-1.87 (m, 2H), 1.67-1.51 (m, 6H), 1.04 (dd, J = 50.8, 10.9 Hz, 2H) | 488 |
| 66 | (piperidinyl-propanamide-N-methylazetidine structure) | (p-tolyl) | (MeOD-d4) δ 7.47-7.42 (m, 4H), 5.11 (d, J = 13.2 Hz, 2H), 4.42-4.35 (m, 1H), 3.68-3.64 (m, 2H), 3.06-2.95 (m, 4H), 2.71 (d, J = 11.3 Hz, 6H), 2.48 (s, 3H), 2.34 (s, 3H), 2.23 (t, J = 7.4 Hz, 2H), 1.81 (d, J = 12.3 Hz, 2H), 1.56 (dd, J = 12.0, 5.0 Hz, 3H), 1.35-1.25 (m, 2H). | 462 |
| 67 | (piperidinyl-carbonyl-piperidinyl-N-methyl-benzyl structure) | (p-tolyl) | (DMSO-d6) 7.51 (d, J = 8.2 Hz, 2H), 7.43 (d, J = 8.2 Hz, 2H), 7.30 (dd, J = 7.0, 5.8 Hz, 4H), 7.24-7.20 (m, 1H), 5.02 (t, J = 10.6 Hz, 2H), 4.43 (d, J = 13.1 Hz, 1H), 4.08 (d, J = 13.3 Hz, 1H), 3.54 (s, 2H), 3.10 (t, J = 12.0 Hz, 2H), 3.03-2.96 (m, 2H), 2.64 (dd, J = 17.2, 3.8 Hz, 7H), 2.44 (d, J = 8.9 Hz, 4H), 2.08 (s, 3H), 1.84-1.59 (m, 6H), 1.44 (dd, J = 22.3, 10.8 Hz, 1H), 1.29 (dd, J = 22.4, 11.0 Hz, 1H). | 552 |
| 68 | (piperidinyl-carbonyl-pyrrolidinyl-N-methyl-benzyl structure) | (p-tolyl) | (MeOD-d4) 7.27-7.21 (m, 4H), 7.12-7.05 (m, 4H), 7.03-6.98 (m, 1H), 4.97 (d, J = 10.4 Hz, 2H), 3.39-3.33 (m, 2H), 3.25-3.12 (m, 3H), 2.98-2.86 (m, 3H), 2.64-2.57 (m, 1H), 2.52 (d, J = 13.2 Hz, 6H), 2.42-2.32 (m, 1H), 2.27 (s, 3H), 2.19-2.09 (m, 2H), 2.05 (d, J = 8.6 Hz, 3H), 1.93-1.79 (m, 1H), 1.63-1.33 (m, 5H). | 552 |
| 69 | (piperidinyl-carbonyl-piperidinyl-morpholine structure) | (p-tolyl) | (DMSO-d6) 7.51 (d, J = 8.3 Hz, 2H), 7.43 (d, J = 8.3 Hz, 2H), 5.01 (s, 2H), 4.36 (d, J = 13.4 Hz, 1H), 4.04 (d, J = 14.0 Hz, 1H), 3.55 (t, J = 4.4 Hz, 4H), 3.12-2.94 (m, 4H), 2.66 (d, J = 3.4 Hz, 6H), 2.56 (d, J = 6.2 Hz, 1H), 2.45-2.33 (m, 8H), 1.84-1.57 (m, 6H), 1.31 (dd, J = 22.4, 10.7 Hz, 1H), 1.16 (dd, J = 21.9, 11.5 Hz, 1H). | 518 |
| 70 | (piperidinyl-carbonyl-pyrrolidinyl-methyl-morpholine structure) | (p-tolyl) | (DMSO-d6) 7.51 (d, J = 7.4 Hz, 2H), 7.43 (d, J = 7.4 Hz, 2H), 5.04 (d, J = 13.2 Hz, 2H), 3.69-3.42 (m, 6H), 3.24-2.91 (m, 4H), 2.70 (d, J = 35.8 Hz, 7H), 2.43-2.24 (m, 10H), 2.02-1.85 (m, 1H), 1.73-1.45 (m, 5H). | 518 |

-continued

| Compound No. | R^E | R^1 | ¹H NMR (400 MHz) (Solvent) δ ppm | LCMS m/z (M + H) |
|---|---|---|---|---|
| 71 | | | (DMSO-d6) 7.51 (d, J = 8.3 Hz, 2H), 7.43 (d, J = 8.3 Hz, 2H), 5.03 (d, J = 12.7 Hz, 2H), 3.76 (dd, J = 10.7, 8.4 Hz, 1H), 3.54-3.45 (m, 2H), 3.18-3.03 (m, 2H), 2.87-2.82 (m, 2H), 2.79-2.73 (m, 2H), 2.66 (d, J = 3.7 Hz, 6H), 2.62-2.53 (m, 2H), 2.43 (s, 3H), 1.71 (d, J = 11.6 Hz, 2H), 1.64-1.54 (m, 2H) | 460 |
| 72 | | | (DMSO-d6) 7.51 (d, J = 8.3 Hz, 2H), 7.43 (d, J = 8.2 Hz, 2H), 5.03 (d, J = 12.0 Hz, 2H), 3.80-3.70 (m, 1H), 3.52 (dd, J = 12.2, 8.8 Hz, 1H), 3.41 (dd, J = 10.8, 4.3 Hz, 2H), 3.19 (dd, J = 12.3, 4.3 Hz, 1H), 3.10-3.03 (m, 2H), 2.90-2.82 (m, 2H), 2.80-2.71 (m, 2H), 2.66 (d, J = 4.1 Hz, 6H), 2.41 (d, J = 10.6 Hz, 6H), 2.24 (s, 3H), 1.70-1.55 (m, 4H). | 474 |
| 73 | | | (MeOD-d4) 7.44 (t, J = 9.2 Hz, 4H), 5.16 (d, J = 13.2 Hz, 2H), 3.59 (dd, J = 11.6, 5.4 Hz, 6H), 3.52 (t, J = 4.8 Hz, 2H), 3.19-3.12 (m, 2H), 3.08-3.01 (m, 1H), 2.72 (dd, J = 12.8, 1.9 Hz, 6H), 2.47 (s, 3H), 1.89-1.87 (m, 2H), 1.83-1.69 (m, 6H). | 474 |
| 74 | | | (MeOD-d4) 7.44 (t, J = 8.8 Hz, 4H), 5.19 (d, J = 13.3 Hz, 2H), 3.84-3.67 (m, 6H), 3.59 (s, 1H), 3.43 (t, J = 7.1 Hz, 1H), 3.19-3.09 (m, 1H), 2.89-2.81 (m, 1H), 2.73 (d, J = 13.6 Hz, 6H), 2.48 (s, 3H), 2.27 (t, J = 6.9 Hz, 1H), 2.13 (t, J = 7.1 Hz, 1H), 1.83-1.81 (m, 4H). | 460 |
| 75 | | | (DMSO-d6) 7.51 (d, J = 7.3 Hz, 2H), 7.43 (d, J = 8.2 Hz, 2H), 5.04 (d, J = 10.7 Hz, 2H), 3.62 (s, 1H), 3.53 (t, J = 6.9 Hz, 1H), 3.33 (s, 1H), 3.25 (t, J = 7.0 Hz, 1H), 3.10-2.98 (m, 6H), 2.77-2.71 (m, 1H), 2.66 (d, J = 3.6 Hz, 6H), 2.43 (s, 3H), 2.20 (d, J = 9.3 Hz, 3H), 2.03 (t, J = 6.8 Hz, 1H), 1.91 (t, J = 7.0 Hz, 1H), 1.71 (d, J = 12.9 Hz, 2H), 1.64-1.54 (m, 2H). | 474 |
| 15x | | | (MeOD-d4) δ 7.47-7.42 (m, 4H), 5.18 (d, J = 13.3 Hz, 2H), 3.21 (t, J = 6.9 Hz, 2H), 3.14-3.06 (m, 2H), 2.74 (s, 3H), 2.71 (s, 3H), 2.57-2.48 (m, 10H), 1.89-1.77 (m, 8H), 1.76-1.69 (m, 2H). | 476 |
| 17x | | | (DMSO-d6) 7.74 (t, J = 5.5 Hz, 1H), 7.51 (d, J = 8.3 Hz, 2H), 7.44 (d, J = 8.2 Hz, 2H), 5.00 (d, J = 13.0 Hz, 2H), 3.54 (t, J = 4.4 Hz, 4H), 3.14 (dd, J = 12.7, 6.5 Hz, 2H), 3.03 (t, J = 11.6 Hz, 2H), 2.66 (d, J = 4.0 Hz, 6H), 2.46-2.41 (m, 4H), 2.34-2.29 (m, 6H), 1.74-1.71 (m, 2H), 1.61 (qd, J = 12.5, 3.4 Hz, 2H). | 478 |

| Compound No. | R^E | R^1 | ^1H NMR (400 MHz) (Solvent) δ ppm | LCMS m/z (M + H) |
|---|---|---|---|---|
| 45x | (piperidine-3-carboxamide with N-(2-(dimethylamino)ethyl) group) | (p-tolyl) | (DMSO-d6) 7.79 (t, J = 5.6 Hz, 1H), 7.51 (d, J = 8.4 Hz, 2H), 7.43 (d, J = 8.2 Hz, 2H), 4.97 (t, J = 11.7 Hz, 2H), 3.19-2.97 (m, 4H), 2.67 (s, 6H), 2.51-2.39 (m, 4H), 2.26-2.19 (m, 2H), 2.10 (s, 6H), 1.85-1.82 (m, 1H), 1.72-1.64 (m, 2H), 1.55-1.44 (m, 1H). | 436 |

Compound Nos. 40, 46, 47, 59-62, and 64 were prepared using the appropriate starting materials and reagents according to the same procedures as in Example 7.

Example 18

Synthesis of Compound Nos. 40, 46, 47, 59-62, and 64

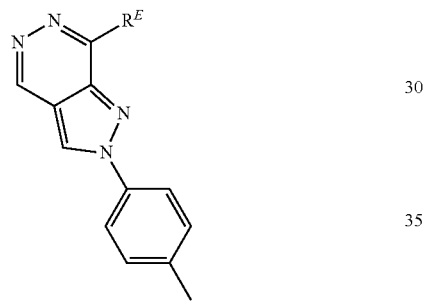

| Compound No. | R^E | ^1H NMR (400 MHz) (Solvent) δ ppm | LCMS m/z (M + H) |
|---|---|---|---|
| 40 | (piperidine-4-carbonyl-4-ethylpiperazine) | (DMSO-d6) 9.23 (s, 1H), 8.93 (s, 1H), 7.95 (d, J = 8.3 Hz, 2H), 7.43 (d, J = 8.3 Hz, 2H), 5.20 (d, J = 13.0 Hz, 2H), 3.57 (s, 2H), 3.44 (s, 2H), 3.23 (t, J = 11.8 Hz, 2H), 3.07-3.01 (m, 1H), 2.40-2.28 (m, 9H), 1.78-1.61 (m, 4H), 1.01 (t, J = 7.1 Hz, 3H). | 434 |
| 46 | (piperidine-4-carboxamide with N-(2-(dimethylamino)ethyl)) | (MeOD-d4) 8.87 (s, 1H), 8.81 (s, 1H), 7.81 (d, J = 8.4 Hz, 2H), 7.35 (d, J = 8.3 Hz, 2H), 5.31 (d, J = 13.3 Hz, 2H), 3.33 (t, J = 4.9 Hz, 2H), 3.23-3.16 (m, 2H), 2.63-2.55 (m, 1H), 2.46 (t, J = 6.9 Hz, 2H), 2.41 (s, 3H), 2.27 (s, 6H), 1.96-1.76 (m, 4H). | 408 |

-continued

| Compound No. | R^E | ¹H NMR (400 MHz) (Solvent) δ ppm | LCMS m/z (M + H) |
|---|---|---|---|
| 47 | *piperidine-N-linked, 3-position C(O)NH-CH₂CH₂-N(CH₃)₂* | (MeOD-d4) 8.91 (s, 1H), 8.83 (s, 1H), 7.85 (d, J = 8.3 Hz, 2H), 7.38 (d, J = 8.2 Hz, 2H), 5.19 (t, J = 10.9 Hz, 2H), 3.43-3.26 (m, 2H), 2.61-2.52 (m, 1H), 2.43 (d, J = 9.5 Hz, 5H), 2.31-2.24 (m, 8H), 2.02-1.85 (m, 3H), 1.72-1.62 (m, 1H). | 408 |
| 59 | *piperidine-N-linked, 4-C(O)-piperidine-4-N(Et)₂* | (MeOD-d4) 8.95 (s, 1H), 8.86 (s, 1H), 7.88 (d, J = 8.5 Hz, 2H), 7.41 (d, J = 8.2 Hz, 2H), 5.35 (t, J = 12.9 Hz, 2H), 4.61 (d, J = 13.3 Hz, 1H), 4.25 (d, J = 13.7 Hz, 1H), 3.27-3.11 (m, 4H), 2.89-2.84 (m, 1H), 2.67-2.57 (m, 5H), 2.44 (s, 3H), 1.99-1.82 (m, 6H), 1.54-1.44 (m, 1H), 1.41-1.31 (m, 1H), 1.09 (t, J = 7.2 Hz, 6H). | 476 |
| 60 | *piperidine-N-linked, 4-C(O)-pyrrolidine-3-CH₂N(CH₃)₂* | (DMSO-d6) 9.22 (s, 1H), 8.93 (d, J = 0.8 Hz, 1H), 7.95 (d, J = 8.2 Hz, 2H), 7.43 (d, J = 8.3 Hz, 2H), 5.23 (d, J = 12.7 Hz, 2H), 3.74-3.64 (m, 1H), 3.53-3.33 (m, 2H), 3.26-3.17 (m, 3H), 2.88-2.80 (m, 1H), 2.42-2.27 (m, 4H), 2.24-2.10 (m, 8H), 2.05-1.86 (m, 1H), 1.81-1.44 (m, 5H). | 448 |
| 61 | *piperidine-N-linked, 4-CH₂CH₂C(O)NH-CH₂CH₂N(CH₃)₂* | (MeOD-d4) 8.86 (s, 1H), 8.76 (s, 1H), 7.81 (d, J = 8.5 Hz, 2H), 7.34 (d, J = 8.2 Hz, 2H), 5.24 (d, J = 13.2 Hz, 2H), 3.28-3.25 (m, 2H), 3.09 (t, J = 11.8 Hz, 2H), 2.40 (dd, J = 13.7, 6.9 Hz, 5H), 2.21 (d, J = 11.9 Hz, 8H), 1.83 (d, J = 12.4 Hz, 2H), 1.61-1.52 (m, 3H), 1.34-1.24 (m, 2H). | 436 |
| 62 | *piperidine-N-linked, 4-C(O)NH-azetidine-N-CH₃* | (MeOD-d4) 8.86 (s, 1H), 8.80 (s, 1H), 7.80 (d, J = 8.5 Hz, 2H), 7.34 (d, J = 8.2 Hz, 2H), 5.30 (d, J = 13.3 Hz, 2H), 4.39 (p, J = 7.1 Hz, 1H), 3.67 (td, J = 7.1, 1.6 Hz, 2H), 3.22-3.15 (m, 2H), 3.01 (td, J = 7.1, 1.6 Hz, 2H), 2.58 (tt, J = 11.3, 4.0 Hz, 1H), 2.40 (s, 3H), 2.35 (s, 3H), 1.92-1.77 (m, 4H). | 406 |
| 64 | *piperidine-N-linked, 4-C(O)NH-CH₂CH₂-morpholine* | (DMSO-d6) 9.22 (s, 1H), 8.93 (s, 1H), 7.95 (d, J = 8.5 Hz, 2H), 7.77 (t, J = 5.7 Hz, 1H), 7.43 (d, J = 8.2 Hz, 2H), 5.18 (d, J = 13.2 Hz, 2H), 3.55 (t, J = 4.4 Hz, 4H), 3.22-3.13 (m, 4H), 2.40-2.31 (m, 10H), 1.81 (dd, J = 13.1, 1.9 Hz, 2H), 1.72-1.62 (m, 2H). | 450 |

BIOLOGICAL EXAMPLES

Example B1—Inhibition of Human TLR7 in Human Plasmacytoid Dendritic Cells

Inhibition of human TLR7 was tested using human plasmacytoid dendritic cells. When placed in cell culture, engagement of TLR7 with an agonist leads to expression and release of cytokines into the media. Antagonist (inhibitory) activity indicates that test compounds can permeate into intact cells.

Materials: Buffy coats from anonymized, healthy human donors. CD304 (BDCA-4/Neuropilin-1) MicroBead Kit (Milteny Cat. No. 130-090-532). Heat inactivated influenza virus (ATCC Cat No. VR-95). Human interferon-alpha ELISA kit (Mabtech Cat. No. 3425-1H-20).

Assay procedures: Human plasmacytoid dendritic cells were plated into 96 well plates at approximately 30,000 cells per well. Test compounds were serially diluted and added to the plates. Immediately after adding test compounds, the TLR7 agonist (heat inactivated influenza virus) was added to a final multiplicity of infection of 2. Cells were incubated for 24 hours at 37° C. A portion of the media supernatant was analyzed for the presence of interferon-alpha using an ELISA kit. The amount of interferon-alpha produced is a reflection of the amount of TLR7-dependent receptor activity. The $IC_{50}$ values (the concentration at which 50% of the TLR7-dependent receptor activity is reduced) were calculated based upon the TLR7-dependent receptor activity over a range of different test compound concentrations. Selected compounds of the present invention were tested and the activities ($IC_{50}$) are summarized in Table B1-1.

TABLE B1-1

| Compound No. | Human TLR7 $IC_{50}$ (µM) |
|---|---|
| 1 | 2.967 |
| 2 | 9.934 |
| 4 | 3.36 |
| 5 | 2.23 |
| 6 | >10 |
| 9 | >10 |
| 2-1 | >10 |

Example B2—Inhibition of Human TLR8 in Human Monocytes

Inhibition of human TLR8 was demonstrated using human monocytes. When placed in cell culture, engagement of TLR8 with an agonist leads to expression and release of cytokines into the media. Antagonist (inhibitory) activity indicates that test compounds can permeate into intact cells.

Materials: Buffy coats from anonymized, healthy human donors. CD14 microbeads (Milteny Cat. No. 130-050-201). TLR8 agonist, (5'-M2UGCUGCUUGUG-/glycerol/-GU-GUUCGUCGUM2-5' with M2-C6-linker, ORN8L, RNA oligonucleotide (Chem Genes Corp.). Human TNF-alpha ELISA kit (Mabtech Cat. No. 3510-1H-20). Human interleukin (IL)-1 beta ELISA kit (Mabtech Cat. No. 3415-1H-20).

Assay procedures: Following isolation of monocytes from buffy coats, human monocytes were plated into 96 well plates at approximately 200,000 cells per well. Test compounds were serially diluted and added to the plates. Immediately after adding test compounds, the TLR8 agonist (ORN8L, RNA oligonucleotide) was added to a final concentration of 100 µg/mL. Cells were incubated for 24 hours at 37° ° C. A portion of the media supernatant was analyzed for the presence of TNF-alpha and/or IL-1 beta using ELISA kits. The amount of TNF-alpha or IL-1 beta produced is a reflection of the amount of TLR8-dependent receptor activity. The $IC_{50}$ values (the concentration at which 50% of the TLR8-dependent receptor activity is reduced) were calculated based upon the TLR8-dependent receptor activity over a range of different test compound concentrations. Selected compounds of the present invention were tested and the activities ($IC_{50}$) are summarized in Table B2-1.

TABLE B2-1

| Compound No. | Human TLR8 $IC_{50}$ (µM) TNF-a | IL-1b |
|---|---|---|
| 1 | 0.62 | 0.74 |
| 2 | 0.67 | 0.90 |
| 3 | >10 | >10 |
| 4 | 0.77 | 1.01 |
| 5 | >10 | >10 |
| 6 | 6.68 | >10 |
| 7 | >10 | >10 |
| 8 | >10 | >10 |
| 9 | 1.22 | 5.02 |
| 11 | >10 | >10 |
| 12a | >10 | >10 |
| 13* | >10 | >10 |
| 15 | >10 | >10 |
| 16* | 20 | NT |
| 17* | >10 | >10 |
| 18 | >10 | >10 |
| 22 | >10 | >10 |
| 23 | 20 | NT |
| 24 | 20 | NT |
| 25 | 20 | NT |
| 27 | 20 | NT |
| 29 | >10 | 1.61 |
| 31 | 2.68 | NT |
| 32 | >10 | >10 |
| 34 | 20 | NT |
| 35 | 20 | NT |
| 36 | 7.68 | NT |
| 38 | 20 | NT |
| 40 | 0.226 | NT |
| 41 | 20 | NT |
| 42 | 20 | NT |
| 43 | 20 | NT |
| 44* | 20 | NT |
| 45* | 20 | NT |
| 46 | 20 | NT |
| 47* | 2.616 | NT |
| 48 | 20 | NT |
| 53 | 20 | NT |
| 7x | >10 | >10 |
| 9x | >10 | >10 |
| 15x | 4.6 | NT |
| 17x | 20 | NT |
| 19x | 0.74 | 0.74 |
| 20x | 4.86 | 5.04 |
| 21x | >10 | >10 |
| 24x* | >10 | >10 |
| 25x | 4.85 | 4.54 |
| 31x | >10 | >10 |
| 32x | >10 | >10 |
| 33x* | >10 | >10 |
| 45x* | 20 | NT |
| 49x* | 3.56 | 3.94 |
| 51x | 0.23 | 0.33 |
| 54x* | 0.29 | 0.74 |
| 59x | 2.04 | 2.11 |
| 63x* | 1.12 | 1.01 |
| 64x | 0.90 | 0.66 |
| 2-1 | 9.77 | 9.92 |
| 2-2 | 20 | NT |
| 2-3 | >10 | >10 |
| 2-4 | >10 | >10 |

TABLE B2-1-continued

| Compound No. | Human TLR8 IC$_{50}$ (μM) | |
|---|---|---|
| | TNF-a | IL-1b |
| 2-5 | >10 | >10 |
| 2-6 | >10 | >10 |
| 2-12 | >10 | >10 |

*Denotes compounds that were tested as racemic mixtures.
NT = not tested

Additional selected compounds of the present invention were tested and the activities (IC$_{50}$) are summarized in Table B2-1A.

TABLE B2-1A

| Compound No. | Human TLR8 IC50 (μM) | |
|---|---|---|
| | TNF-a | IL-1b |
| 57 | 20 | NT |
| 58* | 20 | NT |
| 59 | 0.77 | NT |
| 60* | 0.98 | NT |
| 61 | 4.85 | NT |
| 62 | 3.84 | NT |
| 63 | 20 | NT |
| 64 | 20 | NT |
| 65 | 1.85 | NT |
| 66 | 20.00 | NT |
| 67 | 0.48 | NT |
| 68* | 1.18 | NT |
| 69 | 3.84 | NT |
| 70* | 5.12 | NT |
| 71 | 20 | NT |
| 72 | 9.17 | NT |
| 73 | 20 | NT |
| 74 | 20 | NT |
| 75 | 20 | NT |
| 76 | 11.73 | NT |

*Denotes compounds that were tested as racemic mixtures.
NT = not tested

Example B3—Inhibition of Human TLR9 in Human B Cells

Inhibition of human TLR9 was demonstrated using human B cells. When placed in cell culture, engagement of TLR9 with an agonist leads to expression and release of cytokines into the media. Antagonist (inhibitory) activity indicates that test compounds can permeate into intact cells.

Materials: Buffy coats from anonymized, healthy human donors. CD19 microbeads (Miltenyi Cat. No. 130-050-301). TLR9 agonist, 1018 ISS, CpG-containing DNA oligonucleotide. Human interleukin (IL)-6 ELISA kit (Mabtech Cat. No. 3460-1H-20).

Assay procedures: Following isolation of monocytes from buffy coats, human B cells were plated into 96 well plates at approximately 300,000 cells per well. Test compounds were serially diluted and added to the plates. Test compounds were typically assayed using a concentration range from about 0.01 μM to about 10 μM. Certain test compounds were further assayed in an expanded dilution series using a compound concentration range from about 0.001 μM to about 30 μM. Immediately after adding test compounds, the TLR9 agonist (1018 ISS, CpG-containing DNA oligonucleotide) was added to a final concentration of 1 μM. Cells were incubated for 48 hours at 37° C. A portion of the media supernatant was analyzed for the presence of IL-6 using ELISA kits. The amount of IL-6 produced is a reflection of the amount of TLR9-dependent receptor activity. The IC$_{50}$ values (the concentration at which 50% of the TLR9-dependent receptor activity is reduced) were calculated based upon the TLR9-dependent receptor activity over a range of different test compound concentrations.

Selected compounds of the present invention were tested and the activities (IC$_{50}$) are summarized in Table B3-1.

TABLE B3-1

| Compound No. | Human TLR9 IC$_{50}$ (μM) |
|---|---|
| 1 | 0.040 |
| 2 | 0.242 |
| 3 | 0.143 |
| 4 | 0.093 |
| 5 | 0.040 |
| 6 | 0.154 |
| 7 | 0.360 |
| 8 | 0.308 |
| 9 | 0.003 |
| 11 | 0.379 |
| 12a | 0.071 |
| 13* | 0.292 |
| 15 | 0.250 |
| 16* | 0.046 |
| 17* | 0.083 |
| 18 | 0.137 |
| 20 | 0.018; 0.024** |
| 22 | 0.031 |
| 23 | >10 |
| 24 | 0.400 |
| 25 | >10 |
| 27 | >10 |
| 29 | 0.007 |
| 31 | 0.086 |
| 32 | 0.055 |
| 34 | 0.251 |
| 35 | 3.710 |
| 36 | 1.150 |
| 38 | 0.040 |
| 40 | 0.026 |
| 41 | 0.793 |
| 42 | 0.133 |
| 43 | 0.001; 0.013** |
| 44* | 0.202 |
| 45* | 0.001; 0.014** |
| 46 | 0.002; 0.0** |
| 47* | 0.027 |
| 48 | 10.800 |
| 53 | 2.228 |
| 55 | 0.007; 0.009** |
| 7x | 0.368 |
| 9x | 0.040 |
| 15x | 0.408 |
| 17x | 0.017 |
| 19x | 0.018 |
| 20x | 0.003 |
| 21x | 0.004 |
| 24x* | 0.032 |
| 25x | 0.041 |
| 31x | 0.211 |
| 32x | 0.341 |
| 33x* | 0.070 |
| 45x* | 0.009 |
| 49x* | 0.029 |
| 51x | 0.006 |
| 54x* | 0.004 |
| 59x | 0.059 |
| 63x* | 0.018 |
| 64x | 0.013 |
| 2-1 | 4.647 |
| 2-2 | 3.770 |
| 2-3 | >10 |
| 2-4 | >10 |
| 2-5 | >10 |

TABLE B3-1-continued

| Compound No. | Human TLR9 IC$_{50}$ (μM) |
|---|---|
| 2-6 | >10 |
| 2-12 | 0.427 |

*Denotes compounds that were tested as racemic mixtures.
**Denotes data from expanded dilution series.

Additional selected compounds of the present invention were tested and the activities (IC$_{50}$) are summarized in Table B3-1A.

TABLE B3-1A

| Compound No. | Human TLR9 IC$_{50}$ (μM) |
|---|---|
| 57* | 9.373 |
| 58* | 4.818 |
| 59 | 0.006 |
| 60* | 0.002 |
| 61 | 0.009 |
| 62 | 0.021 |
| 63 | 5.580 |
| 64 | 0.557 |
| 65 | 0.010 |
| 66 | 0.182 |
| 67 | 0.049 |
| 68* | 0.085 |
| 69 | 0.253 |
| 70* | 0.150 |
| 71 | 0.588 |
| 72 | 0.012 |
| 73 | 1.141 |
| 74 | 2.589 |
| 75 | 0.025 |
| 76 | 0.118 |

*Denotes compounds that were tested as racemic mixtures.

Example B4—Inhibition of Mouse TLR9 in Mouse Acute Challenge Model

Inhibition of mouse TLR9 was demonstrated in vivo using an acute challenge model in mice. When administered a CpG-containing DNA oligonucleotide, mice respond in an acute manner with release of cytokines into the peripheral blood within 6 hours. The addition of an inhibitor against TLR9 will attenuate the response to the DNA oligonucleotide agonist, which can be measured through a reduction in serum cytokines. Demonstration of antagonist (inhibitory) activity indicates that test compounds can distribute systemically, are stable in blood and are not immediately metabolized to inactive metabolites. Additionally, antagonist (inhibitory) activity indicates that test compounds can permeate intact cells.

Materials: Balb/c mice (Charles River). TLR9 agonist 1018 ISS, CpG-containing DNA oligonucleotide. Mouse interleukin (IL)-12p40 ELISA kit (BD Pharmingen Cat. No. 551219 and 554476).

Assay procedures: Mice were injected by the intravenous or intra-peritoneal routes with test compound at 5 mg/kg. Following injection of test compound, mice were injected with a TLR9 agonist (a CpG-containing DNA oligonucleotide) by the intra-peritoneal route to a final dose of approximately 2.5 mg/kg. Four hours following administration of the DNA oligonucleotide, blood was collected and processed to serum. The serum was tested for the presence of IL-12 using an ELISA kit. The amount of IL-12 produced is a reflection of the amount of TLR9-dependent receptor activity. The activity of the test compound, presented as percent inhibition of agonist alone, is presented in FIG. 1.

Example B4-a—Inhibition of Mouse TLR9 in Mouse Acute Challenge Model Over Time

Inhibition of mouse TLR9 over a 24 hour time period was demonstrated in vivo using an acute challenge model in mice. When administered a CpG-containing DNA oligonucleotide, mice respond in an acute manner with release of cytokines into the peripheral blood within 6 hours. The addition of an inhibitor against TLR9 will attenuate the response to the DNA oligonucleotide agonist, which can be measured through a reduction in serum cytokines. Demonstration of antagonist (inhibitory) activity indicates that test compounds can distribute systemically, are stable in blood and are not immediately metabolized to inactive metabolites. Additionally, antagonist (inhibitory) activity indicates that test compounds can permeate intact cells.

Materials: Balb/c mice (Charles River). TLR9 agonist 1018 ISS, CpG-containing DNA oligonucleotide. Mouse interleukin (IL)-12p40 ELISA kit (BD Pharmingen Cat. No. 551219 and 554476).

Figure 2:
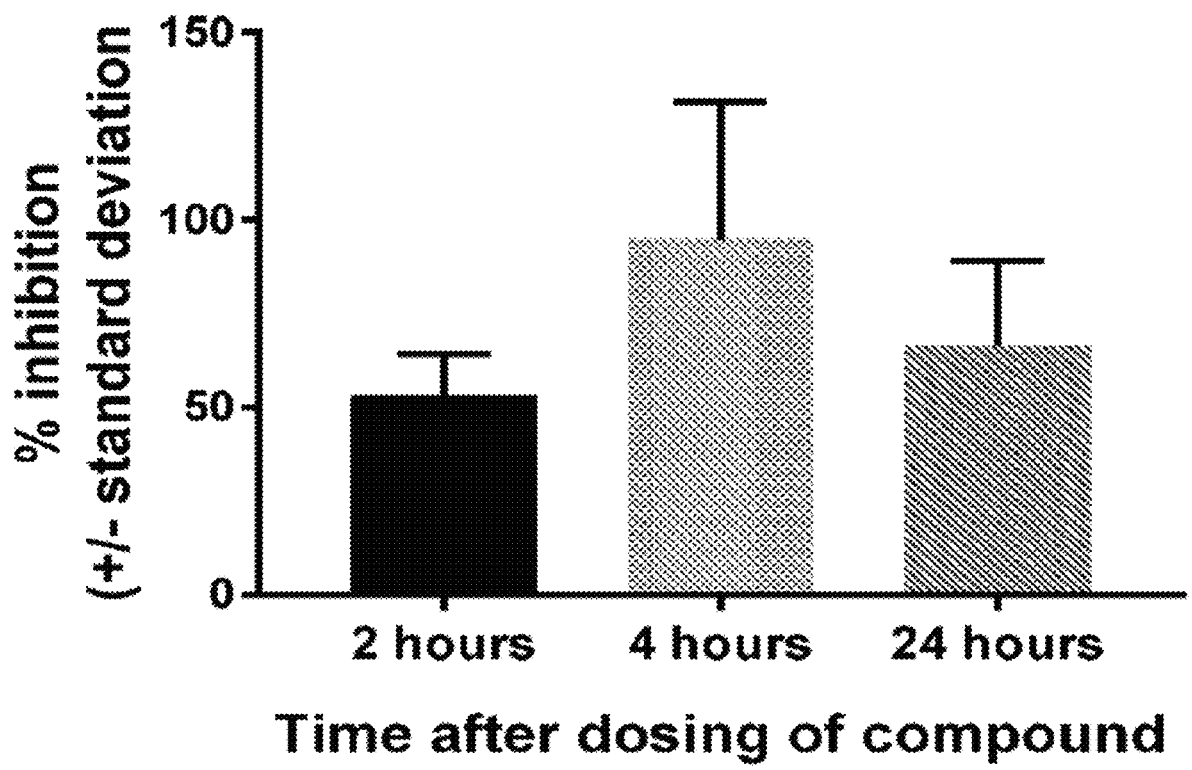
FIG. 2 shows inhibition of TLR9 activity in mice over time following intra-peritoneal injection of Compound No. 5 at 5 mg/Kg.

Assay procedures: Mice were injected by the intra-peritoneal dosing route with test compound at 5 mg/kg. Following injection of test compound, mice were injected with a TLR9 agonist (a CpG-containing DNA oligonucleotide) by the intra-peritoneal route to a final dose of approximately 2.5 mg/kg. Two, four and twenty-four hours following administration of the DNA oligonucleotide, blood was collected from mice and processed to serum. The serum was tested for the presence of IL-12 using an ELISA kit. The amount of IL-12 produced is a reflection of the amount of TLR9-dependent receptor activity. The activity of the test compound, presented as percent inhibition of agonist alone, is presented in FIG. 2.

Example B5—Receptor Specificity

Representative compounds were tested for antagonist activity against related toll-like receptor family members and other nucleic acid intracellular signaling receptors in primary human leukocytes. The compounds were Compound Nos. 5 and 9, and they were tested for their ability to inhibit human RIG-I, TLR-2, TLR-4, and TLR-5. With one exception, neither compound was able to inhibit these receptors greater than 50% at 10 μM. The one exception was Compound No. 9, which had an IC$_{50}$ of 8.3 μM against RIG-I.

Example B6—Plasma Stability

The stability of compounds in human plasma was tested. Human plasma was spiked with compound to final concentration of 90% plasma and 2 μM compound. Samples were incubated for 0, 5, 15, 30, 45 and 60 minutes at 37° C. The reaction was stopped by the addition of acetonitrile. An aliquot of the stopped reaction was mixed with ultra-pure water (Millipore, ZMQS50F01) and analyzed by liquid chromatography/electrospray ionization mass spectroscopy. Selected compounds of the present invention were tested and the stability values are summarized in Table B6-1.

TABLE B6-1

| Compound No. | T$_{1/2}$ (minute) |
|---|---|
| 1 | 224.4 |
| 3 | 207.0 |
| 5 | 1071.0 |

Example B7—Metabolic Stability

The stability of compounds in human liver microsomes was tested. Human liver microsomes (from BD Gentest) were spiked with compounds to a final liver microsomal protein concentration of 0.5 mg/mL and a final compound concentration of 1.5 μM. Samples were incubated for 0, 5, 15, 30, 45 minutes at 37° C. The reaction was stopped by the addition of acetonitrile. An aliquot of the stopped reaction was mixed with ultra-pure water (Millipore, ZMQS50F01) and analyzed by liquid chromatography/electrospray ionization mass spectroscopy. Selected compounds of the present invention were tested and the stability values are summarized in Table B7-1.

TABLE B7-1

| Compound No. | $T_{1/2}$ (minute) | $Cl_{int}$ (mL/min/kg) |
|---|---|---|
| 1 | 5.0 | 347.0 |
| 3 | 383.8 | 4.5 |
| 5 | 800.9 | 2.2 |

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:
1. A method of inhibiting the production of a cytokine in a subject in need thereof, comprising:
administering to the subject a therapeutically effective amount of a compound of formula (I), or a pharmaceutically acceptable salt or solvate thereof:

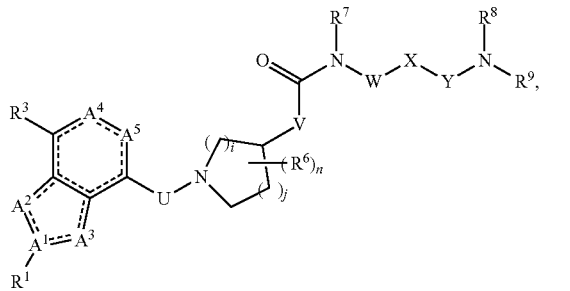

(I)

wherein:
$A^1$ is C or N;
$A^2$ is $CR^2$, N, or $NR^{2a}$;
$A^3$ is $CR^{30}$, N, or $NR^{3a}$;
$A^4$ is N or $CR^4$;
$A^5$ is N or $CR^5$;
provided that two, three, or four of $A^1$, $A^2$, $A^3$, $A^4$, and $A^5$ are N; wherein the dashed lines indicate partial or delocalized bonds in an aromatic ring;
i and j are independently 0, 1, or 2;
$R^1$ is $C_1$-$C_6$ alkyl, $C_3$-$C_8$ cycloalkyl, $C_6$-$C_{14}$ aryl, 5-10-membered heteroaryl, or 3-12-membered heterocyclyl; wherein the $C_1$-$C_6$ alkyl, $C_3$-$C_8$ cycloalkyl, $C_6$-$C_{14}$ aryl, 5-10-membered heteroaryl, and 3-12-membered heterocyclyl are independently optionally substituted by $R^{10A}$;
each $R^2$, $R^3$, $R^{30}$, $R^4$, and $R^5$ is independently hydrogen, halogen, $C_1$-$C_6$ alkyl, $C_3$-$C_8$ cycloalkyl, $C_6$-$C_{14}$ aryl, 5-10-membered heteroaryl, or 3-12-membered heterocyclyl; wherein the $C_1$-$C_6$ alkyl, $C_3$-$C_8$ cycloalkyl, $C_6$-$C_{14}$ aryl, 5-10-membered heteroaryl, and 3-12-membered heterocyclyl are independently optionally substituted by $R^{10A}$;
each $R^{2a}$ and $R^{3a}$ is independently hydrogen, $C_1$-$C_6$ alkyl, $C_3$-$C_8$ cycloalkyl, $C_6$-$C_{14}$ aryl, 5-10-membered heteroaryl, or 3-12-membered heterocyclyl; wherein the $C_1$-$C_6$ alkyl, $C_3$-$C_8$ cycloalkyl, $C_6$-$C_{14}$ aryl, 5-10-membered heteroaryl, and 3-12-membered heterocyclyl are independently optionally substituted by $R^{10A}$;
each $R^6$, where present, is independently $C_1$-$C_6$ alkyl optionally substituted by $R^{10A}$;
n is 0, 1, 2, 3, or 4;
U is a bond or methylene optionally substituted by $R^{10}$;
V is a bond or $C_1$-$C_2$ alkylene optionally substituted by $R^{10}$;
W is a bond or $C_1$-$C_4$ alkylene optionally substituted by one or both of $R^{W1}$ and $R^{W2}$;
X is $-CR^{X1}R^{X2}-$;
Y is $-CR^{Y1}R^{Y2}-$;
$R^7$ is hydrogen, $C_1$-$C_6$ alkyl, or taken together with $R^8$ to form an ethylene optionally substituted by $R^{10}$, or taken together with $R^{Y1}$, $R^{X1}$, or $R^{W1}$, where present, to form a $C_1$-$C_6$ alkylene optionally substituted by $R^{10}$;
$R^8$ is hydrogen, $C_1$-$C_6$ alkyl optionally substituted by $R^{10}$, $C_6$-$C_{14}$ aryl, 5-10-membered heteroaryl, or taken together with $R^7$ to form an ethylene optionally substituted by $R^{10}$, or taken together with $R^{Y1}$, $R^{Y2}$, $R^{X1}$, $R^{X2}$, or $R^{W1}$, where present, to form a $C_1$-$C_6$ alkylene optionally substituted by $R^{10}$, or taken together with $R^{10}$, where present, to form a $C_1$-$C_6$ alkylene, or taken together with $R^9$ and the nitrogen atom to which they are attached to form a 3-12-membered heterocyclyl optionally substituted by $R^{10}$ or a 5-10-membered heteroaryl optionally substituted by $R^{10}$, or taken together with $R^{Y1}$, $R^{Y2}$, $R^9$ and the atoms to which they are attached to form a 5-10-membered heteroaryl optionally substituted by $R^{10}$, or taken together with $R^{X1}$, $R^{X2}$, $R^{Y1}$, $R^{Y2}$, $R^9$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y1}$, $R^{Y2}$, $R^9$ and the atoms to which they are attached to form a 5-10-membered heteroaryl optionally substituted by $R^{10}$;
$R^9$ is hydrogen, $C_1$-$C_6$ alkyl optionally substituted by $R^{10}$, or taken together with $R^8$ and the nitrogen atom to which they are attached to form a 3-12-membered heterocyclyl optionally substituted by $R^{10}$ or a 5-10-membered heteroaryl optionally substituted by $R^{10}$, or taken together with $R^{Y1}$, $R^{Y2}$, $R^8$ and the atoms to which they are attached to form a 5-10-membered heteroaryl optionally substituted by $R^{10}$, or taken together with $R^{X1}$, $R^{X2}$, $R^{Y1}$, $R^{Y2}$, $R^8$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y1}$, $R^{Y2}$, $R^8$ and the atoms to which they are attached to form a 5-10-membered heteroaryl optionally substituted by $R^{10}$;
$R^{W1}$, where present, is $C_1$-$C_6$ alkyl optionally substituted by $R^{10A}$, or taken together with $R^7$, $R^8$, $R^{X1}$, or $R^{Y1}$ to form a $C_1$-$C_6$ alkylene optionally substituted by $R^{10}$, or taken together with $R^{W2}$, $R^{X1}$, $R^{X2}$, $R^{Y1}$, $R^{Y2}$, $R^8$, $R^9$ and the atoms to which they are attached to form a 5-10-membered heteroaryl optionally substituted by $R^{10}$;

$R^{W2}$, where present, is $C_1$-$C_6$ alkyl optionally substituted by $R^{10A}$, or taken together with $R^{W1}$, $R^{X1}$, $R^{X2}$, $R^{Y1}$, $R^{Y2}$, $R^8$, $R^9$ and the atoms to which they are attached to form a 5-10-membered heteroaryl optionally substituted by $R^{10}$;

$R^{X1}$ is hydrogen, $C_1$-$C_6$ alkyl optionally substituted by $R^{10A}$, or taken together with $R^7$, $R^8$, $R^{Y1}$, or $R^{W1}$, where present, to form a $C_1$-$C_6$ alkylene optionally substituted by $R^{10}$, or taken together with $R^{X2}$, $R^{Y1}$, $R^{Y2}$, $R^8$, $R^9$ and the atoms to which they are attached to form a 5-10-membered heteroaryl optionally substituted by $R^{10}$, or taken together with $R^{W1}$, $R^{W2}$, where present, $R^{X2}$, $R^{Y1}$, $R^{Y2}$, $R^8$, $R^9$ and the atoms to which they are attached to form a 5-10-membered heteroaryl optionally substituted by $R^{10}$;

$R^{X2}$ is hydrogen or $C_1$-$C_6$ alkyl optionally substituted by $R^{10A}$, or taken together with $R^{X1}$, $R^{Y1}$, $R^{Y2}$, $R^8$, $R^9$ and the atoms to which they are attached to form a 5-10-membered heteroaryl optionally substituted by $R^{10}$, or taken together with $R^{W1}$, $R^{W2}$, where present, $R^{X1}$, $R^{Y1}$, $R^{Y2}$, $R^8$, $R^9$ and the atoms to which they are attached to form a 5-10-membered heteroaryl optionally substituted by $R^{10}$, or taken together with $R^8$ to form a $C_1$-$C_6$ alkylene optionally substituted by $R^{10}$;

$R^{Y1}$ is hydrogen, $C_1$-$C_6$ alkyl optionally substituted by $R^{10A}$, or taken together with $R^7$, $R^8$, $R^{X1}$, or $R^{W1}$, where present, to form a $C_1$-$C_6$ alkylene optionally substituted by $R^{10}$, or taken together with $R^{Y2}$, $R^8$, $R^9$ and the atoms to which they are attached to form a 5-10-membered heteroaryl optionally substituted by $R^{10}$, or taken together with $R^{X1}$, $R^{X2}$, $R^{Y2}$, $R^8$, $R^9$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y2}$, $R^8$, $R^9$ and the atoms to which they are attached to form a 5-10-membered heteroaryl optionally substituted by $R^{10}$;

$R^{Y2}$ is hydrogen, $C_1$-$C_6$ alkyl optionally substituted by $R^{10A}$, or taken together with $R^{Y1}$, $R^8$, $R^9$ and the atoms to which they are attached to form a 5-10-membered heteroaryl optionally substituted by $R^{10}$, or taken together with $R^{X1}$, $R^{X2}$, $R^{Y1}$, $R^8$, $R^9$ and the atoms to which they are attached to form a 5-10-membered heteroaryl optionally substituted by $R^{10}$, or taken together with $R^{W1}$, $R^{W2}$, where present, $R^{X1}$, $R^{X2}$, $R^{Y1}$, $R^8$, $R^9$ and the atoms to which they are attached to form a 5-10-membered heteroaryl optionally substituted by $R^{10}$, or taken together with $R^8$ to form a $C_1$-$C_6$ alkylene optionally substituted by $R^{10}$;

each $R^{10}$ is independently $C_1$-$C_6$ alkyl, $C_2$-$C_6$ alkenyl, $C_2$-$C_6$ alkynyl, $C_3$-$C_8$ cycloalkyl, 3-12-membered heterocyclyl, 5-10-membered heteroaryl, $C_6$-$C_{14}$ aryl, halogen, —CN, —$OR^{11}$, —$SR^{11}$, —$NR^{12}R^{13}$, —$NO_2$, —C=$NH(OR^{11})$, —C(O) $R^{11}$, —OC(O) $R^{11}$, —C(O) $OR^{11}$, —C(O) $NR^{12}R^{13}$, —$NR^{11}$C(O) $R^{12}$, —$NR^{11}$C(O) $OR^{12}$, —$NR^{11}$C(O) $NR^{12}R^{13}$, —S(O) $R^{11}$, —S(O)$_2R^{11}$, —$NR^{11}$S(O) $R^{12}$, —$NR^{11}$S(O)$_2R^{12}$, —S(O) $NR^{12}R^{13}$, —S(O)$_2NR^{12}R^{13}$, or —P(O) $(OR^{12})$ $(OR^{13})$; wherein the $C_1$-$C_6$ alkyl, $C_2$-$C_6$ alkenyl, $C_2$-$C_6$ alkynyl, $C_3$-$C_8$ cycloalkyl, 3-12-membered heterocyclyl, 5-10-membered heteroaryl and $C_6$-$C_{14}$ aryl of $R^{10}$ are independently optionally substituted by halogen, —CN, oxo, —$OR^{14}$, —$SR^{14}$, —$NR^{14}R^{15}$, —C(O) $R^{14}$, —C(O) $OR^{14}$, —S(O) $R^{14}$, —S(O)$_2R^{14}$, —P(O) $(OR^{14})$ $(OR^{15})$, 3-12-membered heterocyclyl, 5-10-membered heteroaryl, $C_6$-$C_{14}$ aryl, $C_3$-$C_8$ cycloalkyl, or $C_1$-$C_6$ alkyl optionally substituted by oxo, —OH or halogen, or taken together with $R^8$ to form a $C_1$-$C_6$ alkylene;

each $R^{10A}$ is independently oxo or $R^{10}$;

$R^{11}$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl, or 3-6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl, and 3-6-membered heterocyclyl of $R^{11}$ are independently optionally substituted by halogen, oxo, —CN, —$OR^{16}$, —$NR^{16}R^{17}$, —P(O) $(OR^{16})$ $(OR^{17})$, or $C_1$-$C_6$ alkyl optionally substituted by halogen, —OH or oxo;

$R^{12}$ and $R^{13}$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl, or 3-6 membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl, and 3-6 membered heterocyclyl of $R^{12}$ and $R^{13}$ are independently optionally substituted by halogen, oxo, —CN, —$OR^{16}$, —$NR^{16}R^{17}$ or $C_1$-$C_6$ alkyl optionally substituted by halogen, —OH or oxo;

or $R^{12}$ and $R^{13}$ are taken together with the atom to which they attached to form a 3-6 membered heterocyclyl optionally substituted by halogen, oxo, —$OR^{16}$, —$NR^{16}R^{17}$, or $C_1$-$C_6$ alkyl optionally substituted by halogen, oxo, or—OH;

$R^{14}$ and $R^{15}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^{14}$ and $R^{15}$ are taken together with the atom to which they attached to form a 3-6 membered heterocyclyl optionally substituted by halogen, oxo, or $C_1$-$C_6$ alkyl optionally substituted by halogen or oxo; and $R^{16}$ and $R^{17}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^{16}$ and $R^{17}$ are taken together with the atom to which they attached to form a 3-6 membered heterocyclyl optionally substituted by halogen, oxo, or $C_1$-$C_6$ alkyl optionally substituted by oxo or halogen;

provided that when $R^8$ and $R^9$ are taken together with the nitrogen atom to which they are attached to form a 5-10-membered heteroaryl optionally substituted by $R^{10}$, and the 5-10-membered heteroaryl is a fused ring heteroaryl comprising an aryl moiety fused to a heterocycle containing the nitrogen atom to which $R^8$ and $R^9$ are attached, the aryl moiety is not adjacent to the nitrogen atom to which $R^8$ and $R^9$ are attached.

2. The method of claim 1, wherein at least one applies:
(a) $A^1$ is N, $A^2$ is $CR^2$ and $A^3$ is N;
(b) $A^1$ is C, $A^2$ is $CR^2$ or $NR^{2a}$ and $A^3$ is NH;
(c) $A^4$ is N and $A^5$ is N;
(d) $A^4$ is N and $A^5$ is $CR^5$;
(e) $A^4$ is $CR^4$ and $A^5$ is $CR^5$.

3. The method of claim 1, wherein at least one applies:
(a) $R^{2a}$ is $C_1$-$C_6$ alkyl;
(b) $R^4$ is hydrogen;
(c) $R^5$ is hydrogen.

4. The method of claim 1, wherein the compound is at least one of the following:

(a) the compound of formula (Ia):

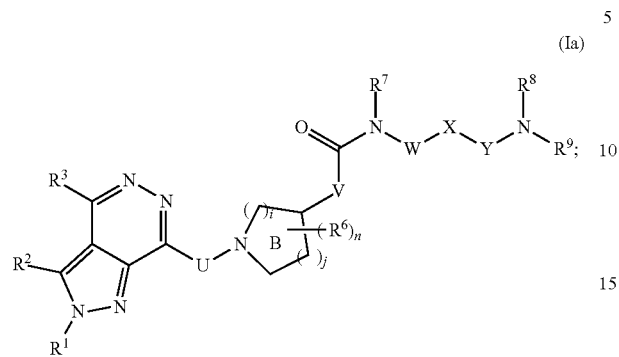

(b) the compound of formula (II):

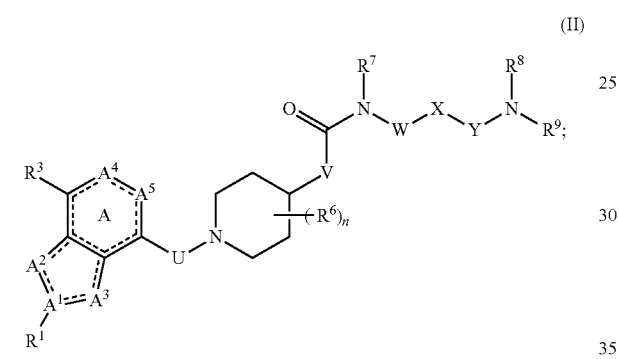

(c) the compound of formula (IIa):

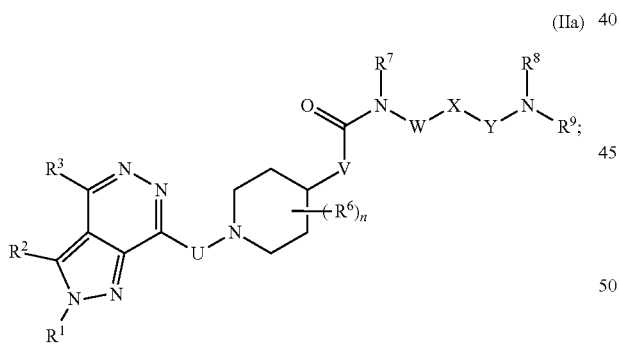

(d) the compound of formula (III):

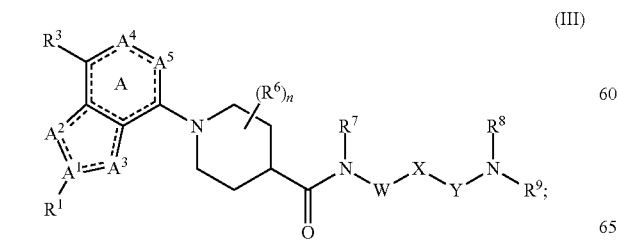

and (e) the compound of formula (IIIa):

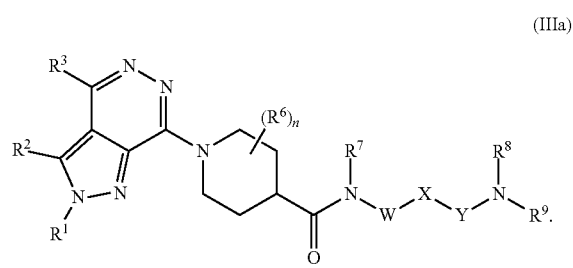

5. The method of claim 1, wherein i is 2 and j is 1 or 2; or wherein i is 1 and j is 2; or wherein i is 1 and j is 1; or wherein i is 1 and j is 0; or wherein i is 0 and j is 0.

6. The method of claim 1, wherein at least one applied:
(a) U is a bond;
(b) V is a bond;
(c) V is ethylene (—CH$_2$CH$_2$—).

7. The method of claim 1, wherein: n is 0; or n is 1 or 2 and each R$^6$ is independently C$_1$-C$_6$ alkyl optionally substituted by R$^{10A}$.

8. The method of claim 1, wherein R$^1$ is phenyl optionally substituted by R$^{10A}$.

9. The method of claim 1, wherein at least one applies:
(a) R$^2$ is C$_1$-C$_6$ alkyl;
(b) R$^3$ is C$_1$-C$_6$ alkyl;
(c) R$^7$ is hydrogen or C$_1$-C$_6$ alkyl;
(d) W is a bond;
(e) W is C$_1$-C$_4$ alkylene optionally substituted by one or both of R$^{W1}$ and R$^{W2}$;
(f) each of R$^{X1}$ and R$^{X2}$ is independently hydrogen or C$_1$-C$_6$ alkyl;
(g) each of R$^{Y1}$ and R$^{Y2}$ is independently hydrogen or C$_1$-C$_6$ alkyl;
(h) R$^8$ is hydrogen or C$_1$-C$_6$ alkyl;
(i) R$^9$ is hydrogen or C$_1$-C$_6$ alkyl optionally substituted by R$^{10}$;
(j) R$^8$ and R$^9$ are taken together with the nitrogen atom to which they are attached to form a 3-12-membered heterocyclyl optionally substituted by R$^{10}$ or a 5-10-membered heteroaryl optionally substituted by R$^{10}$;
(k) R$^{Y1}$, R$^{Y2}$, R$^8$ and R$^9$ are taken together with the atoms to which they are attached to form a 5-10-membered heteroaryl optionally substituted by R$^{10}$;
(l) R$^{X1}$ and R$^8$ are taken together to form a methylene (—CH$_2$—);
(m) R$^{Y1}$ and R$^8$ are taken together to form a propylene (—CH$_2$CH$_2$CH$_2$—);
(n) R$^{X1}$, R$^{X2}$, R$^{Y1}$, R$^{Y2}$, R$^8$, R$^9$ are taken together with the atoms to which they are attached to form a 5-10-membered heteroaryl optionally substituted by R$^{10}$;
(o) R$^7$ and R$^8$ are taken together to form an ethylene optionally substituted by R$^{10}$.

10. The method of claim 1, wherein the —N(R$^7$)—W—X—Y—N(R$^8$) R$^9$ moiety is selected from the group consisting of:

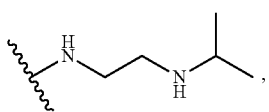

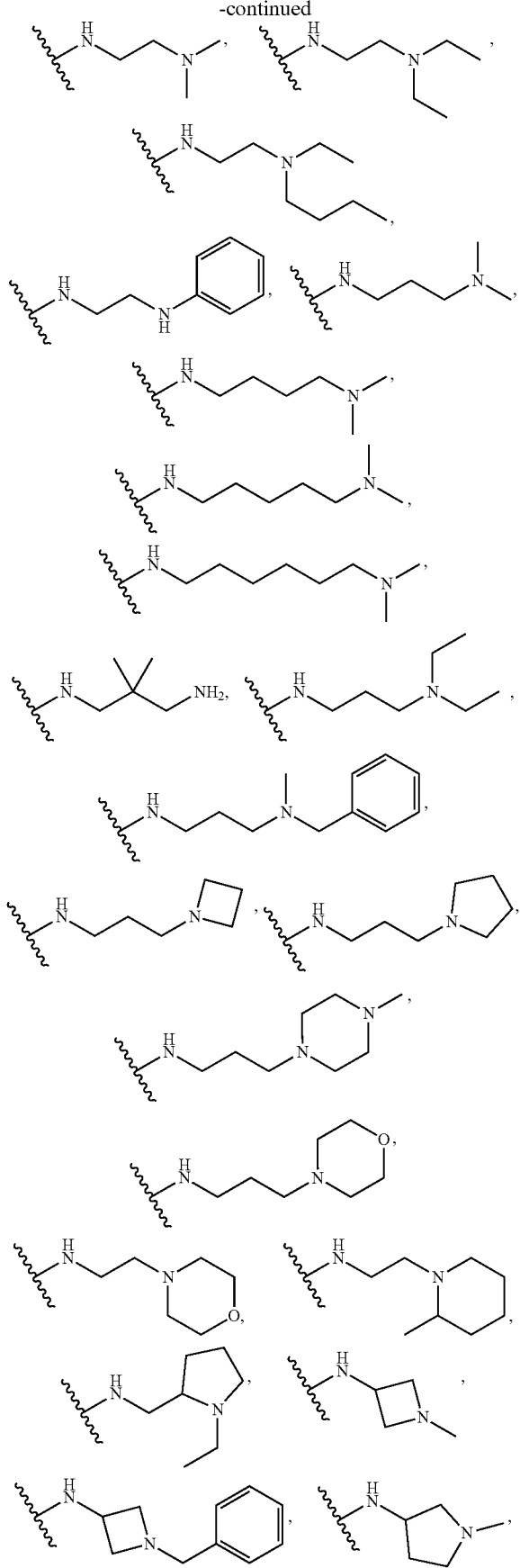
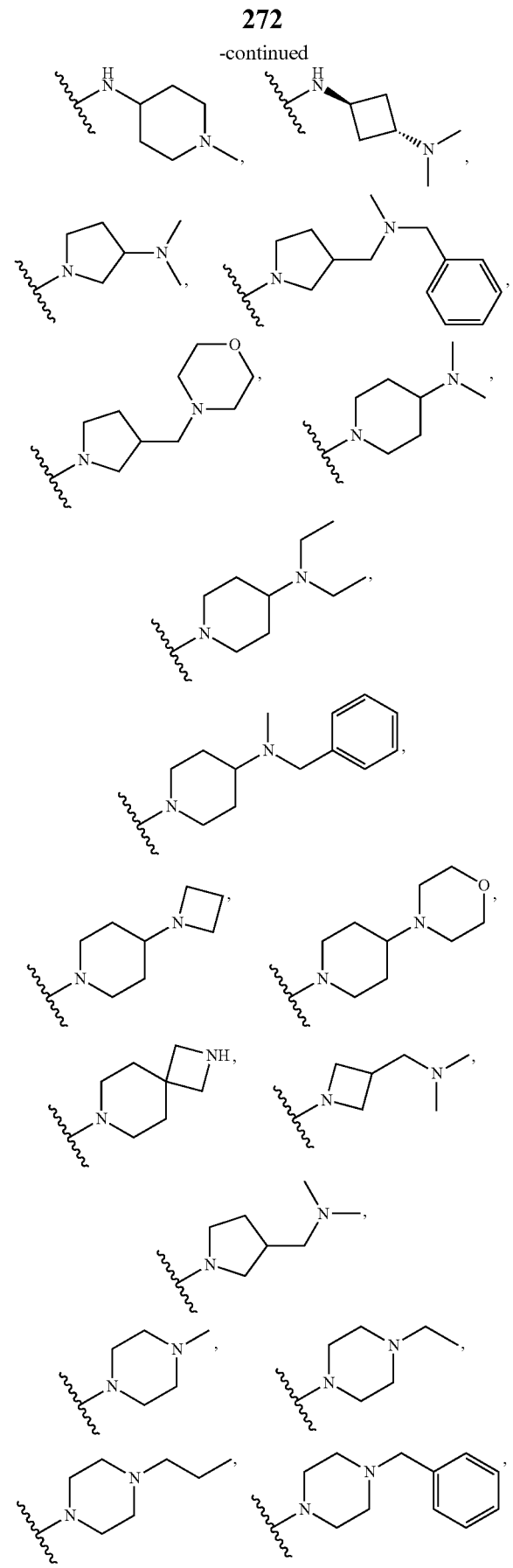

-continued
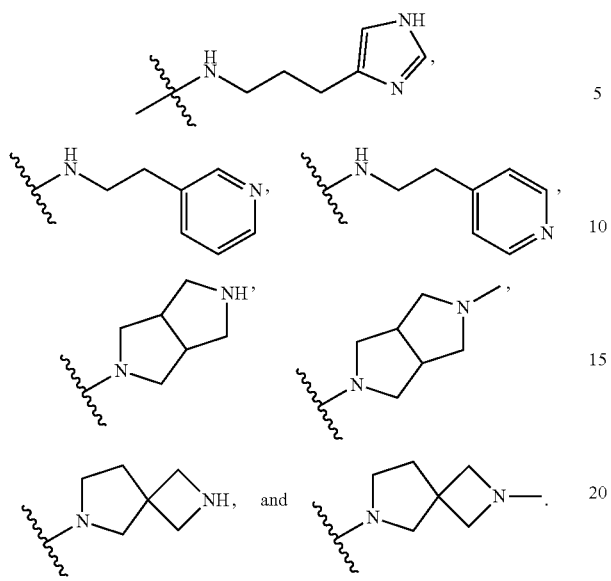
11. The method of claim 1, wherein the compound is at least one of:
(a) the compound of formula (IIa-1a-2):
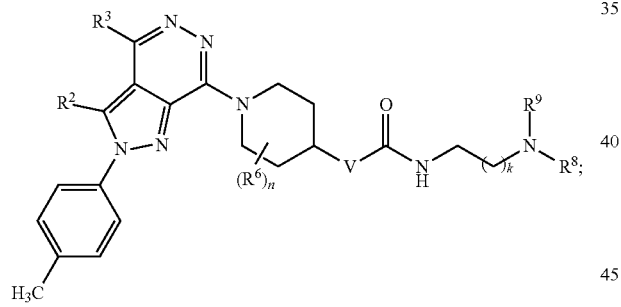
(IIa-1a-2)
(b) the compound of formula (IIa-1b-2):
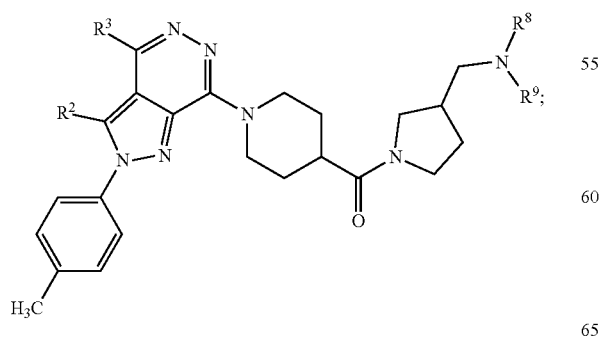
(IIa-1b-2)
(c) the compound of formula (IIa-1c-1):
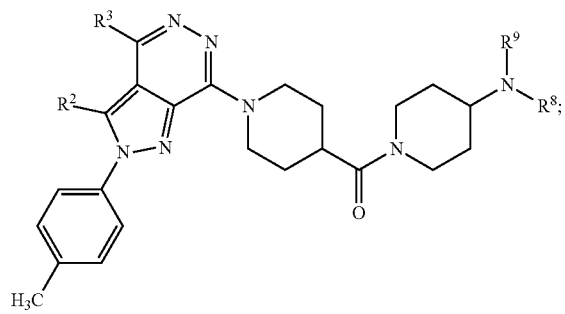
(IIa-1c-1)
(d) the compound of formula (IIa-1d-2):
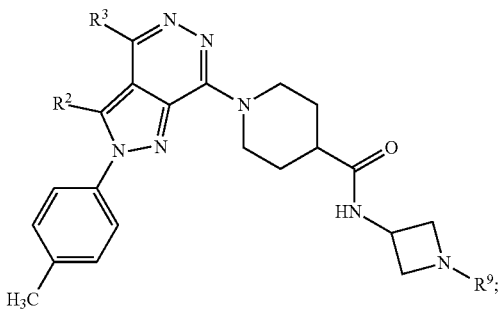
(IIa-1d-2)
(e) the compound of formula (IIa-1e-2):
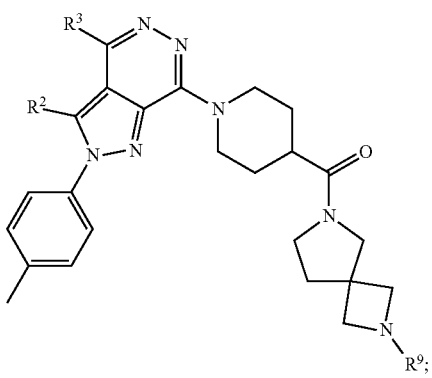
(IIa-1e-2)

(f) the compound of formula (IIa-1f-2):

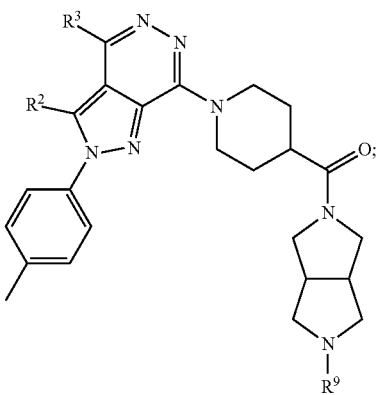

(IIa-1f-2)

(g) the compound of formula (VIII-a-2):

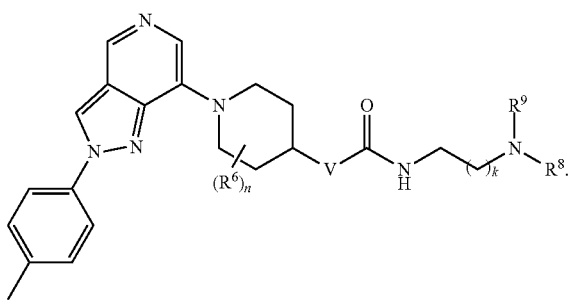

(VIII-a-2)

12. The method of claim 11, or a salt or solvate thereof, wherein at least one applies:

(a) V is a bond;

(b) V is $C_1$-$C_2$ alkylene;

(c) $R^2$ and $R^3$ are independently hydrogen or $C_1$-$C_6$ alkyl;

(d) k is 1 or 2;

(e) n is 1 and $R^6$ is $C_1$-$C_6$ alkyl;

(f) n is 0;

(g) $R^8$ and $R^9$ are independently $C_1$-$C_6$ alkyl optionally substituted by $R^{10}$;

(h) $R^8$ and $R^9$ are taken together with the nitrogen atom to which they are attached to form a 3-12-membered heterocyclyl;

(i) $R^{10}$ is $C_6$-$C_{14}$ aryl.

13. The method of claim 1, wherein the cytokine is tumor necrosis factor-alpha.

14. The method of claim 1, wherein the cytokine is interleukin-1 beta.

15. The method of claim 1, wherein the cytokine is interleukin-6.

16. The method of claim 1, wherein the cytokine is interferon-alpha.

17. The method of claim 1, wherein the cytokine is selected from the group consisting of tumor necrosis factor-alpha, interleukin-1 beta, interleukin-6, and interferon-alpha.

* * * * *